United States Patent [19]

Tjian et al.

[11] Patent Number: 5,534,410
[45] Date of Patent: Jul. 9, 1996

[54] TATA-BINDING PROTEIN ASSOCIATED FACTORS DRUG SCREENS

[75] Inventors: Robert Tjian, Berkeley; Lucio Comai, El Corrito, both of Calif.; Brian D. Dynlacht, Charlestown, Mass.; Timothy Hoey, San Francisco, Calif.; Siegfried Ruppert; Naoko Tanese, both of Berkeley, Calif.; Edith Wang, San Francisco, Calif.; Robert O. J. Weinzierl, Berkely, Calif.

[73] Assignee: The Regents of the University of California, Oakland, Calif.

[21] Appl. No.: 188,582

[22] Filed: Jan. 28, 1994

Related U.S. Application Data

[63] Continuation-in-part of Ser. No. 87,119, Jun. 30, 1993, abandoned, which is a continuation-in-part of Ser. No. 13,412, Jan. 28, 1993, abandoned.

[51] Int. Cl.$^6$ ............................ C12Q 1/68; G01N 33/53
[52] U.S. Cl. .................................................. 435/6; 435/7.1
[58] Field of Search ........................................ 435/6, 7.1

[56] References Cited

PUBLICATIONS

Gambari et al., International Journal of Pharmaceutics (1991), vol. 72: pp. 251–258.
Haigh et al., Nature (1990), vol. 344; pp. 257–259.
Simon et al., PNAS (USA) (1990), vol. 87: pp. 513–517.
Comai et al., "The TATA–Binding Protein and Associated Factors Are Integral Components of the RNA Polymerase I Transcription Factor, SL1", Cell 68:965–976 (1992).
Dynlacht et al., "Isolation of Coactivators Associated with the TATA–Binding Protein That Mediate Transcriptional Activation", Cell 66:563–576 (1991).
Dynlacht et al., "The dTAF$_{11}$80 Subunit of Drosophila TFIID Contains β–transducin Repeats", Nature 363:176–179 (1993.
Gill and Tjian, "Eukaryotic Coactivators Associated with the TATA Box Binding Protein", Current Opinion in Genetics and Development 2:236–242 (1992).
Goodrich et al., "Drosophila TAF$_{22}$40 Interacts with Both a VP16 Activation Domain and the Basal Transcription Factor TFIIB", Cell 75:519–530 (1993).
Hoey et al., "Isolation and Characterization of the Drosphila Gene Encoding the TATA Box Binding Protein, TF11D", Cell 61:1179–1186 (1990).
Hoey et al., "Molecular Cloning and Functional Analysis of Drosophila TAF110 Reveal Properties Expected of Coactivators", Cell 72:247–260 (1993).
Pugh and Tjian, "Diverse Transcriptional Functions of the Multisubunit Eukaryotic TFllD Complex", Journal of Biological Chemistry 267(2):679–682 (1992).
Pugh and Tjian, "Transcription from a TATA–less Promoter Requires a Multisubunit TFllD Complex", Genes & Development 5:1935–1945 (1991).
Pugh and Tijan, "Mechanism of Transcriptional Activation by Sp1: Evidence for Coactivators", Cell 61:1187–1197 (1990).
Ruppert et al., "Cloning and Expression of Human TAF$_{11}$250: a TBP–associated Factor Implicated in Cell–cycle Regulation", Nature 362:175–179 (1993).
Sekiguchi et al., "The Human CCG1 Gene, Essential for Progression of the G$_1$ Phase, Encodes a 210–Kilodalton Nuclear DNA–binding Protein", Molecular and Cellular Biology 11(6):3317–3325 (1991).
Taggart et al., "The TATA–binding Protein and Associated Factors are Components of Pol III Transcription Factor TFIIIB", Cell 71:1015–1028 (1992).
Takada et al., "Identification of Human TF11D Components and Direct Interaction Between a 250–kDA Polypeptide and the TATA Box–binding Protein" (TF11D$_1$), Proc. Natl. Acad. Sci. USA 89:11809–11813 (1992).
Tanese et al., "Coactivators for a Proline–rich Activator Purified From the Multisubunit Human TFllD Complex", Genes & Development 5:2212–2224 (1991).
Timmers and Sharp, "The Mammalian TFIID Protein is Present in Two Functionally Distinct Complexes", Genes & Development 5:1946–1956 (1991).
Verrijzer et al., "Drosophila TAF$_{11}$150: Similarity to Yeast Gene TSM–1 and Specific Binding to core Promoter DNA", Science 264:933–941 (1994).
Wang and Tjian, "Promoter–selective Transcriptional Defect in Cell cycle Mutant ts13 Rescued by hTAF$_{11}$250", Science 263:811–814 (1994).
Weinzierl et al, "Largest Subunit of Drosophila Transcription Factor IID Directs Assembly of a Complex Containing TBP and a Coactivator", Nature 362:511–517 (1993).
Weinzierl et al., "Cloning and Expressin of Drosophila TAF$_{11}$6 and Human TAF$_{11}$70 Reveal Conserved Interactions with Other Subunits of TFllD", The EMBO Journal 12(13):5303–5309 (193).
Yokomori et al., "Drosophila TFllA–L is Processed into Two Subunits that are Associated with the TBP/TAF Complex", Genes & Development 7:2235–2245 (1993).
Yokomori et al, "Molecular Cloning and Characterization of dTAF$_{11}$30α and DTAF$_{11}$30β; Two Small Subunits of Drosophila TFllD" Genes & Development 7:2587–2597 (193).

Primary Examiner—Mindy Fleisher
Assistant Examiner—Terry A. McKelvey
Attorney, Agent, or Firm—Richard Aron Osman

[57] ABSTRACT

TATA-binding protein associated factors, TAFs, nuclear proteins involved in RNA polymerase I, II, and III transcription, and nucleic acids encoding TAFs are disclosed. The disclosed methods and compositions find use in developing pharmaceuticals, diagnosis and therapy.

20 Claims, No Drawings

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 4615 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 538..3300

( x i ) SEQUENCE DESCRIPTION: SEQ ID NO:1:

```
CAACTCGTCC   GTACCTCGGC   GGTCCGTAAA   CAATATTTAC   TCGGTTTTCG   GCTAAATCGC      60

CAGAGAAACG   CAACGGGAAA   TCGTTTAAAA   TGCGCCCCAG   TGCACCGAGT   TTGAACGCAA     120

AATGAATTGA   ATGCTCAACA   ATCAGTCCGT   GCGAGCACGC   GCGAGTGTGT   GTGTGCGCAG     180

GAAAACCCGC   CGATCGGGAA   AAGTGTAGAA   AGGCTTAGCG   GCGCAAACAA   AAGGCAGCGA     240

ATTAGCGAGA   TAACACACAC   GCGACAACGA   CTGCAACGGA   TGCGCCAGGA   GAAAGGCCGA     300

CGACAGTGAC   GGCAAAGGCG   AGTGCGAGTG   AGCCAGCGCA   GCACCAATTC   AGCGGAGCAC     360
```

| | | | | | | | | | | | | | | |
|---|---|---|---|---|---|---|---|---|---|---|---|---|---|---|
| CCGCTTTTTT | GGCCAAGTTC | GCTTCTGGAG | CGCACAGCAT | GCAACAACTC | CGCCAACACC | | | | | | | | | 420 |
| AACACAGGAT | GTGCGCAACT | AGTTGATCGG | AACAGGATCG | CTCGCCCACA | CCAACACACA | | | | | | | | | 480 |
| GAAGTCAGTG | GAATAGGAGA | AACACACTCG | CCAATAACAT | AAACACCACA | CAGCACG | | | | | | | | | 537 |

```
ATG  AAC  ACC  AGC  CAG  ACA  GCT  GCC  GGC  AAT  CGC  ATC  ACC  TTC  ACC  AGC        585
Met  Asn  Thr  Ser  Gln  Thr  Ala  Ala  Gly  Asn  Arg  Ile  Thr  Phe  Thr  Ser
 1             5                        10                       15

CAG  CCG  CTG  CCC  AAT  GGC  ACC  ATC  AGC  ATA  GCC  GGC  AAT  CCC  GGC  GCG        633
Gln  Pro  Leu  Pro  Asn  Gly  Thr  Ile  Ser  Ile  Ala  Gly  Asn  Pro  Gly  Ala
              20                        25                       30

GTC  ATC  TCC  ACG  GCC  CAG  CTA  CCG  AAT  ACC  ACC  ACC  ATC  AAG  ACG  ATC        681
Val  Ile  Ser  Thr  Ala  Gln  Leu  Pro  Asn  Thr  Thr  Thr  Ile  Lys  Thr  Ile
              35                        40                       45

CAG  GCG  GGG  ATC  GGT  GGT  CAG  CAT  CAG  GGA  CTT  CAG  CAG  GTG  CAT  CAT        729
Gln  Ala  Gly  Ile  Gly  Gly  Gln  His  Gln  Gly  Leu  Gln  Gln  Val  His  His
 50                        55                       60

GTC  CAA  CAG  CAG  CAG  CAG  TCG  CAA  CAG  CAA  CAA  CAG  CAG  CAA  CAG  CAG        777
Val  Gln  Gln  Gln  Gln  Gln  Ser  Gln  Gln  Gln  Gln  Gln  Gln  Gln  Gln  Gln
 65                        70                       75                       80

ACG  CAA  TCC  GCC  GGT  CAA  CCG  CTG  CTC  AAT  TCA  ATG  CTG  CCG  GCT  GGC        825
Thr  Gln  Ser  Ala  Gly  Gln  Pro  Leu  Leu  Asn  Ser  Met  Leu  Pro  Ala  Gly
                   85                        90                       95

GTG  GTG  GTG  GGC  ATG  CGC  CAA  CAG  GCG  CCG  TCA  CAG  CAG  CAG  CAG  AAG        873
Val  Val  Val  Gly  Met  Arg  Gln  Gln  Ala  Pro  Ser  Gln  Gln  Gln  Gln  Lys
                   100                       105                      110

AAT  GTG  CCC  ACC  AAC  CCG  CTC  AGT  CGC  GTG  GTG  ATC  AAC  TCC  CAC  ATG        921
Asn  Val  Pro  Thr  Asn  Pro  Leu  Ser  Arg  Val  Val  Ile  Asn  Ser  His  Met
                   115                       120                      125

GCG  GGC  GTG  AGA  CCG  CAG  AGT  CCA  TCG  ATA  ACT  TTA  AGC  ACA  CTT  AAT        969
Ala  Gly  Val  Arg  Pro  Gln  Ser  Pro  Ser  Ile  Thr  Leu  Ser  Thr  Leu  Asn
     130                       135                      140

ACG  GGT  CAG  ACC  CCG  GCA  TTG  CTG  GTC  AAG  ACG  GAT  AAC  GGA  TTC  CAG       1017
Thr  Gly  Gln  Thr  Pro  Ala  Leu  Leu  Val  Lys  Thr  Asp  Asn  Gly  Phe  Gln
 145                       150                      155                      160

CTG  TTG  CGC  GTG  GGC  ACG  ACG  ACG  GGT  CCG  CCG  ACG  GTG  ACA  CAG  ACT       1065
Leu  Leu  Arg  Val  Gly  Thr  Thr  Thr  Gly  Pro  Pro  Thr  Val  Thr  Gln  Thr
                   165                       170                      175

ATA  ACC  AAC  ACC  AGC  AAT  AAC  AGC  AAC  ACG  ACA  AGC  ACC  ACA  AAC  CAT       1113
Ile  Thr  Asn  Thr  Ser  Asn  Asn  Ser  Asn  Thr  Thr  Ser  Thr  Thr  Asn  His
                   180                       185                      190

CCC  ACA  ACC  ACA  CAG  ATC  CGT  CTG  CAA  ACT  GTG  CCG  GCT  GCA  GCT  TCT       1161
Pro  Thr  Thr  Thr  Gln  Ile  Arg  Leu  Gln  Thr  Val  Pro  Ala  Ala  Ala  Ser
                   195                       200                      205

ATG  ACC  AAC  ACG  ACC  GCC  ACC  AGC  AAC  ATC  ATT  GTC  AAT  TCG  GTG  GCA       1209
Met  Thr  Asn  Thr  Thr  Ala  Thr  Ser  Asn  Ile  Ile  Val  Asn  Ser  Val  Ala
     210                       215                      220

AGC  AGT  GGA  TAT  GCA  AAC  TCT  TCG  CAG  CCG  CCG  CAT  CTG  ACG  CAA  CTA       1257
Ser  Ser  Gly  Tyr  Ala  Asn  Ser  Ser  Gln  Pro  Pro  His  Leu  Thr  Gln  Leu
 225                       230                      235                      240

AAT  GCG  CAG  GCG  CCA  CAA  CTG  CCG  CAG  ATT  ACG  CAG  ATT  CAA  ACA  ATA       1305
Asn  Ala  Gln  Ala  Pro  Gln  Leu  Pro  Gln  Ile  Thr  Gln  Ile  Gln  Thr  Ile
                   245                       250                      255

CCG  GCC  CAG  CAG  TCT  CAG  CAG  CAG  CAG  GTG  AAC  AAT  GTA  AGC  TCC  GCG       1353
Pro  Ala  Gln  Gln  Ser  Gln  Gln  Gln  Gln  Val  Asn  Asn  Val  Ser  Ser  Ala
                   260                       265                      270

GGA  GGA  ACG  GCA  ACG  GCG  GTC  AGC  AGT  ACG  ACG  GCA  GCG  ACG  ACG  ACG       1401
Gly  Gly  Thr  Ala  Thr  Ala  Val  Ser  Ser  Thr  Thr  Ala  Ala  Thr  Thr  Thr
                   275                       280                      285

CAG  CAG  GGC  AAT  ACC  AAA  GAA  AAG  TGT  CGC  AAG  TTT  CTA  GCC  AAT  TTA       1449
```

```
        Gln Gln Gly Asn Thr Lys Glu Lys Cys Arg Lys Phe Leu Ala Asn Leu
            290                 295                 300

ATC GAA TTG TCG ACA CGG GAA CCG AAG CCG GTG GAG AAG AAC GTG CGC          1497
Ile Glu Leu Ser Thr Arg Glu Pro Lys Pro Val Glu Lys Asn Val Arg
305                 310                 315                 320

ACC CTC ATC CAG GAG CTG GTC AAT GCG AAT GTC GAG CCG GAG GAG TTT          1545
Thr Leu Ile Gln Glu Leu Val Asn Ala Asn Val Glu Pro Glu Glu Phe
                325                 330                 335

TGT GAC CGC CTG GAG CGC TTG CTC AAC GCC AGC CCG CAG CCG TGT TTG          1593
Cys Asp Arg Leu Glu Arg Leu Leu Asn Ala Ser Pro Gln Pro Cys Leu
            340                 345                 350

ATT GGA TTC CTT AAG AAG AGT TTG CCT CTG CTA CGA CAA GCC CTC TAC          1641
Ile Gly Phe Leu Lys Lys Ser Leu Pro Leu Leu Arg Gln Ala Leu Tyr
        355                 360                 365

ACA AAG GAG CTG GTC ATC GAA GGC ATT AAA CCT CCG CCG CAG CAC GTT          1689
Thr Lys Glu Leu Val Ile Glu Gly Ile Lys Pro Pro Pro Gln His Val
370                 375                 380

CTC GGC CTG GCC GGA CTC TCT CAA CAG TTG CCT AAA ATC CAA GCG CAA          1737
Leu Gly Leu Ala Gly Leu Ser Gln Gln Leu Pro Lys Ile Gln Ala Gln
385                 390                 395                 400

ATC CGT CCG ATC GGT CCT AGC CAG ACA ACG ACC ATT GGA CAG ACG CAG          1785
Ile Arg Pro Ile Gly Pro Ser Gln Thr Thr Thr Ile Gly Gln Thr Gln
                405                 410                 415

GTG CGT ATG ATA ACG CCG AAT GCC TTG GGC ACG CCG CGA CCC ACC ATT          1833
Val Arg Met Ile Thr Pro Asn Ala Leu Gly Thr Pro Arg Pro Thr Ile
            420                 425                 430

GGC CAC ACC ACG ATA TCG AAG CAG CCA CCG AAT ATT CGG TTG CCT ACG          1881
Gly His Thr Thr Ile Ser Lys Gln Pro Pro Asn Ile Arg Leu Pro Thr
        435                 440                 445

GCC CCG CGT CTC GTC AAC ACT GGA GGA ATT CGC ACC CAG ATA CCC TCG          1929
Ala Pro Arg Leu Val Asn Thr Gly Gly Ile Arg Thr Gln Ile Pro Ser
450                 455                 460

TTG CAG GTG CCT GGT CAG GCG AAC ATT GTG CAA ATA CGT GGA CCG CAG          1977
Leu Gln Val Pro Gly Gln Ala Asn Ile Val Gln Ile Arg Gly Pro Gln
465                 470                 475                 480

CAT GCT CAG CTG CAG CGT ACT GGA TCG GTC CAG ATC CGG GCC ACC ACT          2025
His Ala Gln Leu Gln Arg Thr Gly Ser Val Gln Ile Arg Ala Thr Thr
                485                 490                 495

CGT CCG CCA AAC AGT GTG CCC ACC GCG AAC AAA CTC ACT GCC GTC AAG          2073
Arg Pro Pro Asn Ser Val Pro Thr Ala Asn Lys Leu Thr Ala Val Lys
            500                 505                 510

GTG GGA CAG ACG CAA ATC AAA GCG ATT ACG CCC AGC CTG CAT CCA CCC          2121
Val Gly Gln Thr Gln Ile Lys Ala Ile Thr Pro Ser Leu His Pro Pro
        515                 520                 525

TCG CTG GCG GCA ATC TCA GGT GGA CCA CCG CCG ACA CCC ACG CTG TCT          2169
Ser Leu Ala Ala Ile Ser Gly Gly Pro Pro Pro Thr Pro Thr Leu Ser
530                 535                 540

GTT TTG TCT ACG TTG AAC TCC GCC TCG ACC ACA ACG CTG CCC ATA CCA          2217
Val Leu Ser Thr Leu Asn Ser Ala Ser Thr Thr Thr Leu Pro Ile Pro
545                 550                 555                 560

TCG TTA CCC ACG GTC CAC CTT CCC CCC GAA GCT CTT CGA GCC CGT GAG          2265
Ser Leu Pro Thr Val His Leu Pro Pro Glu Ala Leu Arg Ala Arg Glu
                565                 570                 575

CAG ATG CAA AAT TCG CTG AAC CAC AAC AGC AAT CAC TTC GAT GCA AAA          2313
Gln Met Gln Asn Ser Leu Asn His Asn Ser Asn His Phe Asp Ala Lys
            580                 585                 590

CTG GTG GAG ATC AAG GCG CCG TCG CTG CAT CCG CCG CAC ATG GAG CGG          2361
Leu Val Glu Ile Lys Ala Pro Ser Leu His Pro Pro His Met Glu Arg
        595                 600                 605

ATC AAC GCA TCT CTC ACA CCG ATT GGA GCC AAG ACG ATG GCA AGG CCG          2409
```

```
Ile Asn Ala Ser Leu Thr Pro Ile Gly Ala Lys Thr Met Ala Arg Pro
    610             615             620

CCG CCT GCG ATC AAC AAG GCG ATA GGG AAA AAG AAA CGC GAC GCC ATG    2457
Pro Pro Ala Ile Asn Lys Ala Ile Gly Lys Lys Lys Arg Asp Ala Met
625             630             635             640

GAA ATG GAC GCC AAA TTG AAC ACA TCG AGC GGA GGA GCG GCG TCC GCT    2505
Glu Met Asp Ala Lys Leu Asn Thr Ser Ser Gly Gly Ala Ala Ser Ala
            645             650             655

GCG AAC TCG TTT TTC CAG CAG AGC TCC ATG TCC TCG ATG TAC GGT GAC    2553
Ala Asn Ser Phe Phe Gln Gln Ser Ser Met Ser Ser Met Tyr Gly Asp
            660             665             670

GAT GAT ATC AAC GAT GTT GCC GCC ATG GGA GGT GTT AAC TTG GCG GAG    2601
Asp Asp Ile Asn Asp Val Ala Ala Met Gly Gly Val Asn Leu Ala Glu
            675             680             685

GAG TCG CAG CGA ATT CTC GGC TGT ACC GAA AAC ATC GGC ACG CAG ATT    2649
Glu Ser Gln Arg Ile Leu Gly Cys Thr Glu Asn Ile Gly Thr Gln Ile
    690             695             700

CGA TCC TGC AAA GAT GAG GTT TTT CTT AAT CTC CCC TCG CTG CAA GCT    2697
Arg Ser Cys Lys Asp Glu Val Phe Leu Asn Leu Pro Ser Leu Gln Ala
705             710             715             720

AGA ATA CGG GCA ATT ACT TCG GAG GCG GGA CTG GAT GAG CCG TCG CAG    2745
Arg Ile Arg Ala Ile Thr Ser Glu Ala Gly Leu Asp Glu Pro Ser Gln
                725             730             735

GAT GTG GCC GTT CTG ATA TCG CAC GCC TGT CAG GAG CGC CTG AAG AAC    2793
Asp Val Ala Val Leu Ile Ser His Ala Cys Gln Glu Arg Leu Lys Asn
            740             745             750

ATC GTT GAG AAG TTG GCT GTG ATA GCG GAG CAC CGC ATT GAT GTC ATC    2841
Ile Val Glu Lys Leu Ala Val Ile Ala Glu His Arg Ile Asp Val Ile
755             760             765

AAG TTG GAT CCA CGC TAT GAG CCC GCC AAG GAT GTG CGC GGT CAG ATC    2889
Lys Leu Asp Pro Arg Tyr Glu Pro Ala Lys Asp Val Arg Gly Gln Ile
770             775             780

AAG TTT CTC GAG GAG CTG GAC AAG GCC GAG CAG AAG CGA CAC GAG GAA    2937
Lys Phe Leu Glu Glu Leu Asp Lys Ala Glu Gln Lys Arg His Glu Glu
785             790             795             800

CTG GAG CGT GAG ATG CTG CTG CGG GCA GCC AAG TCA CGG TCG AGG GTG    2985
Leu Glu Arg Glu Met Leu Leu Arg Ala Ala Lys Ser Arg Ser Arg Val
            805             810             815

GAA GAT CCC GAG CAG GCC AAG ATG AAG GCG AGG GCC AAG GAG ATG CAA    3033
Glu Asp Pro Glu Gln Ala Lys Met Lys Ala Arg Ala Lys Glu Met Gln
            820             825             830

CGC GCC GAA ATG GAG GAG TTG CGT CAA CGA GAT GCC AAT CTG ACG GCG    3081
Arg Ala Glu Met Glu Glu Leu Arg Gln Arg Asp Ala Asn Leu Thr Ala
            835             840             845

CTG CAG GCG ATT GGA CCT CGG AAA AAG CTG AAG CTG GAC GGC GAA ACA    3129
Leu Gln Ala Ile Gly Pro Arg Lys Lys Leu Lys Leu Asp Gly Glu Thr
850             855             860

GTC AGT TCG GGA GCG GGT TCA AGT GGC GGC GGA GTG CTA AGC AGC TCG    3177
Val Ser Ser Gly Ala Gly Ser Ser Gly Gly Gly Val Leu Ser Ser Ser
865             870             875             880

GGA TCT GCG CCG ACG ACG TTA CGG CCT CGC ATA AAA CGT GTG AAC CTG    3225
Gly Ser Ala Pro Thr Thr Leu Arg Pro Arg Ile Lys Arg Val Asn Leu
            885             890             895

CGC GAC ATG CTC TTC TAC ATG GAG CAA GAG CGG GAG TTC TGT CGC AGT    3273
Arg Asp Met Leu Phe Tyr Met Glu Gln Glu Arg Glu Phe Cys Arg Ser
            900             905             910

TCC ATG CTG TTC AAG ACA TAC CTC AAG TGATCGCTGC TGTTGCCCAT          3320
Ser Met Leu Phe Lys Thr Tyr Leu Lys
            915             920

CAATCGCACC GTCTTCTCCT CGCCGATCCT CCTACTCCGT GGACTGTCGT GTTGTTGTTT  3380
```

```
TATACAGCTT  TACGATTTCA  TCCACTTGCA  ATATATTTTA  GCCTCAACTT  TAAATGCGTC      3440
GCGTGTCCCC  TGTTGTTGTT  TCTTTTTAGT  TAGGCGGCTC  TATTTAATTT  CTATTTTTAC      3500
ATTTATTTAC  ATAAATCCTA  AATTCTAATC  GTATTTGATT  TTAAGCCTAA  TTTAAAGCTC      3560
GTTTATTTTT  CCAATAAATT  CTCTGTAAAA  CTTAAACCAA  ACCAATCCAA  AAACAAAACA      3620
AAACCAGAGT  AAACGAAGAG  AATAAAATAA  TAGAGAGGAA  AGTAAAAGAA  GGTAAAAGAG      3680
AGCGCGCAGT  CAGCGGTCGT  TTGATTTGTA  ATTTGTAACA  TAATAATGTT  TGCATCAACT      3740
GCATTGACGG  CCTTATCTAA  ACGATATAAA  CATAATTATT  AATATTTAAT  TATTTAGCTT      3800
AGTTTGTTAA  ACGAAAACGA  ACCATAATTC  CTAGATTTTA  AGTAAAAAGC  AAGGGCGCGT      3860
GAAGAGAAAT  CGAAACCGAA  TTACAGATAA  AGGTTTTTAA  AACCAACTAG  ATCGAAACAA      3920
GTTCAGCAAC  AGCAAAACAA  AAGAACACAT  CAAAAAAAGA  ACCGAAAAAT  ATCCATTTAA      3980
ACATCCATTG  AATTAGGTTT  AGTTGTTTAA  AAAAGATGTA  ATTTTTAATT  ACCCATAATG      4040
TATAAACGGA  AATCAATCGT  TAGGCAAGAC  CACAACAAAC  CCAACAAATT  GTAAATACAT      4100
TCTAGGCTAC  GGTTTTCTA   ATAGATAACT  AGGTAAAAAC  GCAAACGTAA  TTAACAAATT      4160
ATCGATGGCA  AGGAGCGATG  CGAGCGCAGA  CAACTTGGCA  CACCGAAAAA  ATATGTTTTT      4220
ATTAGTGGCG  CTCGTTCATC  CATTAAGAAT  GGCGATTCAT  TAGGCTCCAT  AGATCCATAA      4280
ATCCCCTAAT  CCAATCTGAA  CTACACACAA  AATAGACAAA  TTTTATACAA  TTAGCTCGAT      4340
AAATCTTGTA  AAATAGAGTC  CCGTAAAAAA  TTATAACAAA  TAAATTGACA  ACAATTGATG      4400
TAATTCAGTA  AACCTAAGCA  AAAAGTGAAA  CCATTCTAAG  CAAATTCTTT  GTGTGTAAAA      4460
ATTAATATGA  TAAACAAAAT  GCAGATGCAA  CCGTAAACAG  CGCATAGTTT  GGTAGGCATA      4520
TAACTGAATA  TATATATATT  ATTATTATTA  TGTTTTAACA  TTAAGCAAAA  AAATAAAAGA      4580
AAAAATTGAG  AAAACTTCAA  AAAAAAAAAA  AAAAA                                   4615
```

( 2 ) INFORMATION FOR SEQ ID NO:2:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Thr Ser Gln Thr Ala Ala Gly Asn Arg Ile Thr Phe Thr Ser
 1               5                  10                  15

Gln Pro Leu Pro Asn Gly Thr Ile Ser Ile Ala Gly Asn Pro Gly Ala
            20                  25                  30

Val Ile Ser Thr Ala Gln Leu Pro Asn Thr Thr Thr Ile Lys Thr Ile
        35                  40                  45

Gln Ala Gly Ile Gly Gly Gln His Gln Gly Leu Gln Val His His
    50                  55                  60

Val Gln Gln Gln Gln Gln Ser Gln Gln Gln Gln Gln Gln Gln Gln
65                  70                  75                  80

Thr Gln Ser Ala Gly Gln Pro Leu Leu Asn Ser Met Leu Pro Ala Gly
                85                  90                  95

Val Val Val Gly Met Arg Gln Gln Ala Pro Ser Gln Gln Gln Lys
            100                 105                 110

Asn Val Pro Thr Asn Pro Leu Ser Arg Val Val Ile Asn Ser His Met
        115                 120                 125

Ala Gly Val Arg Pro Gln Ser Pro Ser Ile Thr Leu Ser Thr Leu Asn
```

|     |     |     |     |     |     |     |     |     |     |     |     |     |     |     |
|-----|-----|-----|-----|-----|-----|-----|-----|-----|-----|-----|-----|-----|-----|-----|
|     |     |     | 130 |     |     |     | 135 |     |     |     | 140 |     |     |     |
| Thr 145 | Gly | Gln | Thr | Pro | Ala 150 | Leu | Leu | Val | Lys | Thr 155 | Asp | Asn | Gly | Phe 160 | Gln |
| Leu | Leu | Arg | Val | Gly 165 | Thr | Thr | Thr | Gly | Pro 170 | Pro | Thr | Val | Thr | Gln 175 | Thr |
| Ile | Thr | Asn | Thr 180 | Ser | Asn | Asn | Ser | Asn 185 | Thr | Thr | Ser | Thr | Thr 190 | Asn | His |
| Pro | Thr | Thr 195 | Thr | Gln | Ile | Arg | Leu 200 | Gln | Thr | Val | Pro | Ala 205 | Ala | Ala | Ser |
| Met | Thr 210 | Asn | Thr | Thr | Ala | Thr 215 | Ser | Asn | Ile | Ile | Val 220 | Asn | Ser | Val | Ala |
| Ser 225 | Ser | Gly | Tyr | Ala | Asn 230 | Ser | Ser | Gln | Pro | Pro 235 | His | Leu | Thr | Gln | Leu 240 |
| Asn | Ala | Gln | Ala | Pro 245 | Gln | Leu | Pro | Gln | Ile 250 | Thr | Gln | Ile | Gln | Thr 255 | Ile |
| Pro | Ala | Gln | Gln 260 | Ser | Gln | Gln | Gln | Gln 265 | Val | Asn | Asn | Val | Ser 270 | Ser | Ala |
| Gly | Gly | Thr 275 | Ala | Thr | Ala | Val | Ser 280 | Ser | Thr | Thr | Ala | Ala 285 | Thr | Thr | Thr |
| Gln | Gln | Gly | Asn 290 | Thr | Lys | Glu 295 | Lys | Cys | Arg | Lys | Phe 300 | Leu | Ala | Asn | Leu |
| Ile 305 | Glu | Leu | Ser | Thr | Arg 310 | Glu | Pro | Lys | Pro | Val 315 | Glu | Lys | Asn | Val | Arg 320 |
| Thr | Leu | Ile | Gln | Glu 325 | Leu | Val | Asn | Ala | Asn 330 | Val | Glu | Pro | Glu | Glu 335 | Phe |
| Cys | Asp | Arg | Leu 340 | Glu | Arg | Leu | Leu | Asn 345 | Ala | Ser | Pro | Gln | Pro 350 | Cys | Leu |
| Ile | Gly | Phe 355 | Leu | Lys | Lys | Ser | Leu 360 | Pro | Leu | Leu | Arg | Gln 365 | Ala | Leu | Tyr |
| Thr | Lys 370 | Glu | Leu | Val | Ile | Glu 375 | Gly | Ile | Lys | Pro | Pro 380 | Pro | Gln | His | Val |
| Leu 385 | Gly | Leu | Ala | Gly | Leu 390 | Ser | Gln | Gln | Leu | Pro 395 | Lys | Ile | Gln | Ala | Gln 400 |
| Ile | Arg | Pro | Ile | Gly 405 | Pro | Ser | Gln | Thr | Thr 410 | Thr | Ile | Gly | Gln | Thr 415 | Gln |
| Val | Arg | Met | Ile 420 | Thr | Pro | Asn | Ala | Leu 425 | Gly | Thr | Pro | Arg | Pro 430 | Thr | Ile |
| Gly | His | Thr 435 | Thr | Ile | Ser | Lys | Gln 440 | Pro | Pro | Asn | Ile | Arg 445 | Leu | Pro | Thr |
| Ala | Pro 450 | Arg | Leu | Val | Asn | Thr 455 | Gly | Gly | Ile | Arg | Thr 460 | Gln | Ile | Pro | Ser |
| Leu 465 | Gln | Val | Pro | Gly | Gln 470 | Ala | Asn | Ile | Val | Gln 475 | Ile | Arg | Gly | Pro | Gln 480 |
| His | Ala | Gln | Leu | Gln 485 | Arg | Thr | Gly | Ser | Val 490 | Gln | Ile | Arg | Ala | Thr 495 | Thr |
| Arg | Pro | Pro | Asn 500 | Ser | Val | Pro | Thr | Ala 505 | Asn | Lys | Leu | Thr | Ala 510 | Val | Lys |
| Val | Gly | Gln 515 | Thr | Gln | Ile | Lys | Ala 520 | Ile | Thr | Pro | Ser | Leu 525 | His | Pro | Pro |
| Ser | Leu 530 | Ala | Ala | Ile | Ser | Gly 535 | Gly | Pro | Pro | Thr | Pro 540 | Thr | Leu | Ser |
| Val 545 | Leu | Ser | Thr | Leu | Asn 550 | Ser | Ala | Ser | Thr | Thr 555 | Thr | Leu | Pro | Ile | Pro 560 |

```
Ser  Leu  Pro  Thr  Val  His  Leu  Pro  Pro  Glu  Ala  Leu  Arg  Ala  Arg  Glu
                    565            570                      575

Gln  Met  Gln  Asn  Ser  Leu  Asn  His  Asn  Ser  Asn  His  Phe  Asp  Ala  Lys
               580            585                      590

Leu  Val  Glu  Ile  Lys  Ala  Pro  Ser  Leu  His  Pro  Pro  His  Met  Glu  Arg
          595                      600                 605

Ile  Asn  Ala  Ser  Leu  Thr  Pro  Ile  Gly  Ala  Lys  Thr  Met  Ala  Arg  Pro
     610                      615                 620

Pro  Pro  Ala  Ile  Asn  Lys  Ala  Ile  Gly  Lys  Lys  Arg  Asp  Ala  Met
625                 630                 635                           640

Glu  Met  Asp  Ala  Lys  Leu  Asn  Thr  Ser  Ser  Gly  Gly  Ala  Ala  Ser  Ala
               645                      650                      655

Ala  Asn  Ser  Phe  Phe  Gln  Gln  Ser  Ser  Met  Ser  Ser  Met  Tyr  Gly  Asp
               660                 665                      670

Asp  Asp  Ile  Asn  Asp  Val  Ala  Ala  Met  Gly  Gly  Val  Asn  Leu  Ala  Glu
          675                      680                 685

Glu  Ser  Gln  Arg  Ile  Leu  Gly  Cys  Thr  Glu  Asn  Ile  Gly  Thr  Gln  Ile
     690                 695                      700

Arg  Ser  Cys  Lys  Asp  Glu  Val  Phe  Leu  Asn  Leu  Pro  Ser  Leu  Gln  Ala
705                 710                      715                           720

Arg  Ile  Arg  Ala  Ile  Thr  Ser  Glu  Ala  Gly  Leu  Asp  Glu  Pro  Ser  Gln
               725                      730                      735

Asp  Val  Ala  Val  Leu  Ile  Ser  His  Ala  Cys  Gln  Glu  Arg  Leu  Lys  Asn
               740                      745                      750

Ile  Val  Glu  Lys  Leu  Ala  Val  Ile  Ala  Glu  His  Arg  Ile  Asp  Val  Ile
          755                      760                 765

Lys  Leu  Asp  Pro  Arg  Tyr  Glu  Pro  Ala  Lys  Asp  Val  Arg  Gly  Gln  Ile
770                      775                 780

Lys  Phe  Leu  Glu  Glu  Leu  Asp  Lys  Ala  Glu  Gln  Lys  Arg  His  Glu  Glu
785                 790                      795                           800

Leu  Glu  Arg  Glu  Met  Leu  Leu  Arg  Ala  Ala  Lys  Ser  Arg  Ser  Arg  Val
               805                      810                      815

Glu  Asp  Pro  Glu  Gln  Ala  Lys  Met  Lys  Ala  Arg  Ala  Lys  Glu  Met  Gln
               820                      825                      830

Arg  Ala  Glu  Met  Glu  Glu  Leu  Arg  Gln  Arg  Asp  Ala  Asn  Leu  Thr  Ala
               835                      840                 845

Leu  Gln  Ala  Ile  Gly  Pro  Arg  Lys  Lys  Leu  Lys  Leu  Asp  Gly  Glu  Thr
     850                      855                 860

Val  Ser  Ser  Gly  Ala  Gly  Ser  Ser  Gly  Gly  Val  Leu  Ser  Ser  Ser
865                      870                 875                      880

Gly  Ser  Ala  Pro  Thr  Thr  Leu  Arg  Pro  Arg  Ile  Lys  Arg  Val  Asn  Leu
               885                      890                      895

Arg  Asp  Met  Leu  Phe  Tyr  Met  Glu  Gln  Glu  Arg  Glu  Phe  Cys  Arg  Ser
               900                      905                      910

Ser  Met  Leu  Phe  Lys  Thr  Tyr  Leu  Lys
          915                      920
```

( 2 ) INFORMATION FOR SEQ ID NO:3:

( i ) SEQUENCE CHARACTERISTICS:
        ( A ) LENGTH: 4164 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
TTCGCTGTAC GAGGTACCCG GTCCGAATTC CAAAAGGGCC AACAACTTCA CCCGTGACTT       60
TCTGCAGGTG TTTATTTACC GCCTGTTCTG GAAAAGTCGC GACAACCCGC CCCGCATTCG      120
AATGGACGAT ATAAAACAGG CTTTTCCCGC TCATTCCGAG AGCAGCATCC GCAAGCGTTT      180
AAAGCAGTGC GCTGACTTCA AGCGAACAGG CATGGACTCC AATTGGTGGG TTATAAAGCC      240
AGAGTTTCGC CTTCCATCCG AGGAGGAGAT CCGAGCCATG GTGTCACCTG AGCAGTGTTG      300
CGGTACTTCA GCATGATAGC GGCGGAACAA CGCTTAAAGG ATGCTGGGTA TGGAGAAAAG      360
TTTTTGTTCG CACCTCAGGA AGATGACGAC GAGGAGGCGC AGTGAAAGCT TGACGACGAA      420
GTAAAGGTGG CTCCTTGGAA CACGACTCGC GCATATATCC AAGCCATGCG GGAAAGTGT       480
TTACTCCAGT TGAGTGGTCC AGCCGATCCA ACGGGATGTG GAGAGGGATT TTCATATGTT      540
CGAGTGCCAA ACAAGCCCAC GCAAACCAAG GAGGAGCAAG AGTCGCAGCC TAAACGTTCG      600
GTCACAGGAA CAGATGCAGA TTTGCGTCGT CTGCCACTCC AGCGTGCAAA AGAGCTGTTG      660
CGGCAGTTCA AGGTGCCCGA GGAGGAGATC AAAAAGCTTT CCCGCTGGGA GGTCATTGAC      720
GTGGTGCGCA CCCTGTCCAC AGAAAAGGCC AAGGCCGGTG AAGAGGGAAT GGATAAGTTT      780
TCTCGTGGCA ACCGGTTCTC CATTGCAGAG CATCAGGAGC GTTATAAGGA AGAGTGCCAG      840
CGCATATTCG ATCTGCAAAA CAGAGTGCTG GCCAGCTCTG AGGTGCTGTC CACAGATGAG      900
GCAGAGTCCT CGGCCTCTGA GGAATCTGAT CTCGAAGAAC TTGGCAAGAA TCTTGAGAAC      960
ATGCTGTCAA ACAAGAAAAC CTCGACGCAA TTGTCAAGGG AACGTGAAGA GCTGGAGCGT     1020
CAGGAGTTGC TTCGCCAGCT TGACGAAGAA CACGGCGGAC CAAGTGGTAG TGGAGGAGCC     1080
AAGGGAGCCA AAGGAAAGGA TGATCCGGGA CAGCAAATGC TGGCAACCAA CAACCAGGGC     1140
AGGATCCTTC GCATTACGCG TACCTTTAGA GGTAACGATG GCAAGGAATA TACTCGCGTG     1200
GAGACTGTGC GGCGGCAACC AGTTATCGAC GCCTACATCA AGATTCGCAC CACTAAGGAC     1260
GAGCAGTTCA TCAAGCAGTT CGCAACGCTA GATGAGCAGC AGAAGGAGGA GATGAAGCGC     1320
GAAAAGAGAC GCATTCAGGA GCAGCTACGT CGCATCAAGC GCAACCAGGA GCGCGAACGC     1380
CTGGCGCAGC TGGCCCAGAA CCAGAAGCTT CAGCCAGGTG GCATGCCCAC TTCCTTGGGT     1440
GATCCTAAGA GCTCGGGCGG TCATTCGCAC AAGGAGCGGG ATAGCGGCTA CAAGGAGGTC     1500
AGCCCTTCGC GCAAGAAGTT CAAGCTTAAG CCAGACCTAA AGCTGAAGTG CGGCGCCTGT     1560
GGACAGGTTG GTCACATGCG CACAAACAAA GCCTGTCCCT TGTATTCTGG CATGCAAAGC     1620
AGTCTGTCCC AGTCGAACCC ATCTCTGGCT GACGATTTTG ACGAACAGAG CGAAAAGGAG     1680
ATGACAATGG ATGACGATGA TCTTGTGAAT GTCGATGGCA CCAAAGTAAC GCTCAGCAGT     1740
AAGATTCTCA GCGTCATGGT GGTGATGATG GCAAGCGTC GCAGCGGATC TAGCTCTGGT     1800
TTCACCTTGA AGGTTCCCCG AGATGCGATG GGCAAGAAGA AACGCAGAGT GGGTGGCGAT     1860
CTTCATTGTG ACTATCTGCA GCGACACAAT AAAACGGCCA ATCGCAGGCG CACGGACCCC     1920
GTTGTGGTAC TGTCCTCTAT CCTGGAGATT ATCCATAATG AGCTGCGATC TATGCCAGAT     1980
GTATCGCCAT TCCTGTTCCC GGTAAGCGCA AAAAAGGTTC CCGACTACTA CCGCGTGGTG     2040
ACCAAGCCCA TGGATCTGCA AACGATGAGG GAGTATATCG CCAAAGGCTA ACACGAGTCG     2100
CGAGATGTTC CTCGAGGATC TCAAGCAGAT TGTGGACAAC TCGCTGATCT ACAATGGACC     2160
GCAGAGTGCA TACACCTTGG CTGCCCAACG CATGTTCAGC AGTTGTTTTG AATTGCTCGC     2220
AGAGGCGAAG ACAAACTGAT GCGCCTCGAG AAGGCAATTA CCCGCTGCT GGACGACGAT      2280
GACCAAGTGG CACTCTCCTT TATCTTTGAC AAGCTGCACT CGCAGATTAA GCAATTACCA     2340
```

```
GAGAGCTGGC  CTTTCCTTAA  GCCTGTCAAC  AAGAAACAGG  TTAAGGACTA  CTACACGGTT    2400

ATCAAGCGAC  CCATGGACCT  CGAAACTATC  GGCAAAAACA  TTGAAGCTCA  TCGCTATCAC    2460

AGTCGTGCCG  AGTATCTGGC  TGATATCGAG  TTGATCGCCA  CCAACTGTGA  GCAGTACAAC    2520

GGCAGTGACA  CCCGCTACAC  CAAGTTCTCA  AGAAGATAC   TTGAGTATGC  CCAAACCCAG    2580

TTAATTGAGT  TTTCGGAGCA  CTGCGGCCAG  TTGGAAAATA  ACATAGCTAA  GACGCAGGAG    2640

CGTGCTAGGG  AAAATGCACC  AGAGTTTGAT  GAAGCCTGGG  GCAATGATGA  TTACAACTTT    2700

GACCGTGGCA  GTAGGGCCAG  TTCACCCGGA  GATGACTACA  TCGACGTCGA  GGGTCATGGG    2760

GGGCATGCCT  CCTCATCGAA  CTCTATCCAT  CGCAGCATGG  GCGCCGAGGC  CGGTTCGTCA    2820

CATACGGCGC  CGGCGGTGCG  AAAACCAGCT  CCTCCTGGTC  CTGGTGAGGT  GAAGCGCGGA    2880

AGGGGTAGGC  CCCGCAAGCA  GCGCGACCCC  GTGGAGGAGG  TCAAATCCCA  GAATCCGGTT    2940

AAGCGTGGTC  GGGGGCGTCC  GAGGAAGGAC  AGCCTTGCCT  CAAACATGAG  TCACACGCAA    3000

GCTTACTTCC  TGGATGAAGA  TCTCCAATGC  TCCACAGATG  ACGAGGACGA  CGACGAGGAG    3060

GAGGACTTCC  AGGAGGTCTC  CGAAGACGAG  AACAATGCGG  CGAGCATTTT  AGATCAGGGC    3120

GAACGTATCA  ATGCGCCTGC  CGATGCCATG  GATGGCATGT  TTGACCCCAA  GAACATCAAG    3180

ACAGAGATTG  ACCTAGAGGC  TCACCAGATG  GCAGAGGAGC  CGATCGGCGA  GGATGACAGC    3240

CAGCAGGTGG  CCGAAGCAAT  GGTGCAGTTG  AGTGGCGTGG  GCGGCTACTA  TGCTCAACAG    3300

CAGCAAGATG  AATCCATGGA  TGTGGACCCC  AACTACGATC  CCTCAGATTT  CCTCGCCATG    3360

CACAAGCAGC  GCCAGAGCCT  CGGCGAGCCC  AGCAGCTTGC  AGGGTGCTTT  CACCAACTTC    3420

CTATCGCACG  AGCAGGATGA  TAATGGGCCT  TACAATCCCG  CCGAAGCCAG  CACAAGTGCC    3480

GCTTCCGGTG  CAGACTTAGG  AATGGACGCT  TCAATGGCCA  TGCAAATGGC  GCCGGAAATG    3540

CCTGTCAATA  CCATGAACAA  CGGAATGGGC  ATCGATGATG  ATCTGGATAT  TTCGGAGAGT    3600

GACGAGGAAG  ACGATGGTTC  TCGAGTGCGT  ATCAAAAAGG  AGGTCTTCGA  CGACGGGGAT    3660

TACGCCTTGC  AGCACCAGCA  GATGGGACAG  GCAGCATCGC  AGTCGCAGAT  ATACATGGGG    3720

ATTCGTCCAA  CGAGCCCACG  ACTCTCGACT  ACCAGCAACC  ACCGCAACTG  GACTTCCAAC    3780

AAGTGCAGGA  AATGGAGCAG  TTGCAGCACC  AAGTGATGCC  ACCAATGCAA  TCAGAGCAAC    3840

TGCAGCAGCA  ACAGACGCCG  CAGGAGACAA  TGATTATGCC  TGGACTTTTT  AGTGATAGGG    3900

AATAATTGTT  AGTTGTTAGA  AAATAAAACG  TCGATTTAAT  AATAGGATTG  AGCTTCGCTG    3960

TGAAACAATT  TTATACACTT  TTTACAATGC  ATTGTTTTAA  CGGATTTTGA  AATACTACAA    4020

TATGTTCTCT  GAAAAAATAT  TTCCTTTTCA  TGCCAATATG  TTTTTAATTT  TACACTTTAC    4080

AATTTATGAA  ATCTAATTCA  AAATATGTTT  TTAAAATATA  ATTTTCATAA  CTTTAAATAA    4140

TGCCTAGAAA  AAAAAAAAAA  AAAA                                              4164
```

( 2 ) INFORMATION FOR SEQ ID NO:4:

( i ) SEQUENCE CHARACTERISTICS:
        ( A ) LENGTH: 2359 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 49..2160

( x i ) SEQUENCE DESCRIPTION: SEQ ID NO:4:

```
GATAACAAAA  TAGTACACAA  GTTCCATATA  TTTCAATTTT  CCGCGAAA  ATG AGC CTG     57
```

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  | Met | Ser | Leu |  |
|  |  |  |  |  |  |  |  |  |  |  |  | 1 |  |  |  |

```
                                                                      Met  Ser  Leu
                                                                       1

GAA  GTG  AGC  AAT  ATC  AAC  GGG  GGA  AAC  GGT  ACT  CAA  TTG  TCC  CAC  GAC        105
Glu  Val  Ser  Asn  Ile  Asn  Gly  Gly  Asn  Gly  Thr  Gln  Leu  Ser  His  Asp
      5              10                      15

AAG  CGT  GAG  CTG  CTA  TGC  CTG  CTG  AAA  CTC  ATC  AAA  AAG  TAC  CAG  CTG        153
Lys  Arg  Glu  Leu  Leu  Cys  Leu  Leu  Lys  Leu  Ile  Lys  Lys  Tyr  Gln  Leu
 20                  25                      30                          35

AAG  AGC  ACT  GAG  GAG  CTG  CTC  TGC  CAA  GAG  GCG  AAT  GTG  AGC  AGT  GTG        201
Lys  Ser  Thr  Glu  Glu  Leu  Leu  Cys  Gln  Glu  Ala  Asn  Val  Ser  Ser  Val
                 40                      45                      50

GAA  TTG  TCG  GAA  ATC  AGC  GAA  AGT  GAT  GTT  CAG  CAG  GTG  CTG  GGC  GCA        249
Glu  Leu  Ser  Glu  Ile  Ser  Glu  Ser  Asp  Val  Gln  Gln  Val  Leu  Gly  Ala
             55                      60                          65

GTT  TTG  GGA  GCT  GGC  GAT  GCC  AAC  CGG  GAG  CGG  AAA  CAT  GTC  CAA  TCT        297
Val  Leu  Gly  Ala  Gly  Asp  Ala  Asn  Arg  Glu  Arg  Lys  His  Val  Gln  Ser
         70                      75                      80

CCG  GCG  CAG  GGT  CAT  AAA  CAG  TCC  GCG  GTG  ACG  GAG  GCC  AAT  GCT  GCA        345
Pro  Ala  Gln  Gly  His  Lys  Gln  Ser  Ala  Val  Thr  Glu  Ala  Asn  Ala  Ala
     85                      90                      95

GAG  GAA  CTG  GCC  AAG  TTC  ATC  GAC  GAC  GAC  AGC  TTT  GAT  GCT  CAG  CAC        393
Glu  Glu  Leu  Ala  Lys  Phe  Ile  Asp  Asp  Asp  Ser  Phe  Asp  Ala  Gln  His
100                     105                     110                         115

TAT  GAG  CAG  GCA  TAC  AAG  GAG  CTG  CGC  ACT  TTC  GTT  GAG  GAC  TCC  CTG        441
Tyr  Glu  Gln  Ala  Tyr  Lys  Glu  Leu  Arg  Thr  Phe  Val  Glu  Asp  Ser  Leu
                 120                     125                     130

GAC  ATA  TAC  AAG  CAT  GAG  CTG  TCC  ATG  GTT  CTG  TAC  CCA  ATT  CTG  GTG        489
Asp  Ile  Tyr  Lys  His  Glu  Leu  Ser  Met  Val  Leu  Tyr  Pro  Ile  Leu  Val
             135                     140                         145

CAG  ATC  TAC  TTC  AAG  ATC  CTC  GCC  AGT  GGA  CTA  AGG  GAG  AAG  GCC  AAA        537
Gln  Ile  Tyr  Phe  Lys  Ile  Leu  Ala  Ser  Gly  Leu  Arg  Glu  Lys  Ala  Lys
         150                     155                     160

GAA  TTC  ATT  GAG  AAG  TAC  AAA  TGC  GAT  CTC  GAC  GGC  TAC  TAC  ATA  GAG        585
Glu  Phe  Ile  Glu  Lys  Tyr  Lys  Cys  Asp  Leu  Asp  Gly  Tyr  Tyr  Ile  Glu
165                     170                     175

GGT  CTT  TTC  AAC  CTT  CTT  TTG  CTG  TCT  AAG  CCC  GAG  GAG  CTG  CTG  GAG        633
Gly  Leu  Phe  Asn  Leu  Leu  Leu  Leu  Ser  Lys  Pro  Glu  Glu  Leu  Leu  Glu
180                     185                     190                         195

AAT  GAC  CTC  GTA  GTA  GCC  ATG  GAG  CAG  GAT  AAG  TTT  GTC  ATT  CGC  ATG        681
Asn  Asp  Leu  Val  Val  Ala  Met  Glu  Gln  Asp  Lys  Phe  Val  Ile  Arg  Met
             200                     205                     210

TCC  AGG  GAC  TCG  CAC  TCT  CTG  TTC  AAG  CGA  CAC  ATT  CAG  GAT  CGC  CGG        729
Ser  Arg  Asp  Ser  His  Ser  Leu  Phe  Lys  Arg  His  Ile  Gln  Asp  Arg  Arg
                 215                     220                     225

CAG  GAA  GTG  GTG  GCA  GAT  ATT  GTT  TCC  AAG  TAC  TTG  CAT  TTC  GAC  ACA        777
Gln  Glu  Val  Val  Ala  Asp  Ile  Val  Ser  Lys  Tyr  Leu  His  Phe  Asp  Thr
         230                     235                     240

TAC  GAG  GGC  ATG  GCG  CGC  AAC  AAG  CTG  CAG  TGC  GTC  GCC  ACC  GCG  GGC        825
Tyr  Glu  Gly  Met  Ala  Arg  Asn  Lys  Leu  Gln  Cys  Val  Ala  Thr  Ala  Gly
245                     250                     255

TCG  CAC  CTC  GGA  GAG  GCC  AAG  CGA  CAG  GAC  AAC  AAA  ATG  CGG  GTG  TAC        873
Ser  His  Leu  Gly  Glu  Ala  Lys  Arg  Gln  Asp  Asn  Lys  Met  Arg  Val  Tyr
260                     265                     270                         275

TAC  GGA  CTG  CTC  AAG  GAG  GTG  GAC  TTT  CAG  ACT  CTG  ACC  ACT  CCA  GCG        921
Tyr  Gly  Leu  Leu  Lys  Glu  Val  Asp  Phe  Gln  Thr  Leu  Thr  Thr  Pro  Ala
             280                     285                     290

CCG  GCA  CCA  GAG  GAG  GAG  GAC  GAT  GAT  CCG  GAT  GCC  CCG  GAT  CGT  CCG        969
Pro  Ala  Pro  Glu  Glu  Glu  Asp  Asp  Asp  Pro  Asp  Ala  Pro  Asp  Arg  Pro
                 295                     300                     305

AAA  AAG  AAA  AAG  CCA  AAA  AAG  GAT  CCC  CTG  CTG  TCG  AAA  AAG  TCC  AAG       1017
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Lys | Lys | Lys 310 | Lys | Pro | Lys | Lys | Asp 315 | Pro | Leu | Leu | Ser | Lys 320 | Lys | Ser | Lys |      |
| TCG | GAT | CCG | AAT | GCT | CCA | TCC | ATC | GAC | AGA | ATT | CCC | CTG | CCG | GAA | CTG | 1065 |
| Ser | Asp 325 | Pro | Asn | Ala | Pro | Ser 330 | Ile | Asp | Arg | Ile | Pro 335 | Leu | Pro | Glu | Leu |      |
| AAG | GAT | TCG | GAC | AAG | TTG | CTA | AAG | CTT | AAG | GCT | CTC | AGG | GAA | GCC | AGC | 1113 |
| Lys | Asp 340 | Ser | Asp | Lys | Leu | Leu 345 | Lys | Leu | Lys | Ala | Leu 350 | Arg | Glu | Ala | Ser 355 |      |
| AAG | CGT | TTA | GCC | CTC | AGC | AAG | GAT | CAA | CTG | CCC | TCT | GCC | GTC | TTC | TAC | 1161 |
| Lys | Arg | Leu | Ala | Leu 360 | Ser | Lys | Asp | Gln | Leu 365 | Pro | Ser | Ala | Val | Phe 370 | Tyr |      |
| ACG | GTG | CTT | AAT | TCC | CAT | CAG | GGC | GTA | ACC | TGT | GCC | GAG | ATT | TCA | GAC | 1209 |
| Thr | Val | Leu | Asn 375 | Ser | His | Gln | Gly | Val 380 | Thr | Cys | Ala | Glu | Ile 385 | Ser | Asp |      |
| GAT | TCC | ACG | ATG | TTG | GCC | TGT | GGA | TTT | GGC | GAT | TCT | AGC | GTG | AGG | ATT | 1257 |
| Asp | Ser | Thr 390 | Met | Leu | Ala | Cys | Gly 395 | Phe | Gly | Asp | Ser | Ser 400 | Val | Arg | Ile |      |
| TGG | TCA | TTG | ACG | CCC | GCG | AAG | CTG | CGT | ACG | CTG | AAG | GAT | GCA | GAT | TCC | 1305 |
| Trp | Ser 405 | Leu | Thr | Pro | Ala | Lys 410 | Leu | Arg | Thr | Leu | Lys 415 | Asp | Ala | Asp | Ser |      |
| CTT | CGC | GAA | CTG | GAC | AAG | GAA | TCG | GCG | GAT | ATC | AAT | GTG | CGT | ATG | CTG | 1353 |
| Leu 420 | Arg | Glu | Leu | Asp | Lys 425 | Glu | Ser | Ala | Asp | Ile 430 | Asn | Val | Arg | Met | Leu 435 |      |
| GAT | GAC | CGA | AGT | GGT | GAG | GTA | ACC | AGG | AGC | TTA | ATG | GGT | CAC | ACC | GGA | 1401 |
| Asp | Asp | Arg | Ser | Gly 440 | Glu | Val | Thr | Arg | Ser 445 | Leu | Met | Gly | His | Thr 450 | Gly |      |
| CCC | GTA | TAC | CGC | TGT | GCC | TTT | GCC | CCC | GAG | ATG | AAC | CTG | TTG | CTC | TCA | 1449 |
| Pro | Val | Tyr | Arg 455 | Cys | Ala | Phe | Ala | Pro 460 | Glu | Met | Asn | Leu | Leu 465 | Leu | Ser |      |
| TGT | TCC | GAG | GAC | AGC | ACC | ATA | AGG | CTG | TGG | TCT | CTG | CTC | ACC | TGG | TCC | 1497 |
| Cys | Ser | Glu 470 | Asp | Ser | Thr | Ile | Arg 475 | Leu | Trp | Ser | Leu | Leu 480 | Thr | Trp | Ser |      |
| TGC | GTA | GTC | ACC | TAC | CGC | GGG | CAC | GTT | TAC | CCG | GTG | TGG | GAT | GTT | CGC | 1545 |
| Cys | Val | Val 485 | Thr | Tyr | Arg | Gly | His 490 | Val | Tyr | Pro | Val | Trp 495 | Asp | Val | Arg |      |
| TTT | GCG | CCG | CAT | GGC | TAC | TAT | TTT | GTT | TCT | TGT | TCG | TAC | GAC | AAA | ACT | 1593 |
| Phe 500 | Ala | Pro | His | Gly | Tyr 505 | Tyr | Phe | Val | Ser | Cys 510 | Ser | Tyr | Asp | Lys | Thr 515 |      |
| GCT | CGT | CTG | TGG | GCC | ACG | GAT | TCC | AAT | CAA | GCG | TTG | CGC | GTA | TTC | GTG | 1641 |
| Ala | Arg | Leu | Trp | Ala 520 | Thr | Asp | Ser | Asn | Gln 525 | Ala | Leu | Arg | Val | Phe 530 | Val |      |
| GGT | CAC | TTG | TCG | GAC | GTG | GAT | TGT | GTA | CAA | TTT | CAT | CCC | AAT | TCC | AAT | 1689 |
| Gly | His | Leu | Ser 535 | Asp | Val | Asp | Cys | Val 540 | Gln | Phe | His | Pro | Asn 545 | Ser | Asn |      |
| TAT | GTG | GCC | ACC | GGT | TCT | AGC | GAT | CGC | ACG | GTA | CGC | CTG | TGG | GAC | AAC | 1737 |
| Tyr | Val | Ala | Thr 550 | Gly | Ser | Ser | Asp | Arg 555 | Thr | Val | Arg | Leu | Trp 560 | Asp | Asn |      |
| ATG | ACC | GGT | CAG | TCG | GTA | CGC | CTG | ATG | ACG | GGC | CAC | AAG | GGA | TCG | GTG | 1785 |
| Met | Thr 565 | Gly | Gln | Ser | Val | Arg 570 | Leu | Met | Thr | Gly | His 575 | Lys | Gly | Ser | Val |      |
| AGT | TCT | CTG | GCC | TTC | TCC | GCC | TGC | GGC | CGG | TAT | CTG | GCC | TCG | GGT | TCA | 1833 |
| Ser | Ser | Leu 580 | Ala | Phe | Ser | Ala | Cys 585 | Gly | Arg | Tyr | Leu | Ala 590 | Ser | Gly | Ser 595 |      |
| GTA | GAT | CAC | AAT | ATC | ATC | ATC | TGG | GAT | CTG | TCG | AAC | GGA | TCC | CTG | GTC | 1881 |
| Val | Asp | His | Asn | Ile 600 | Ile | Ile | Trp | Asp | Leu 605 | Ser | Asn | Gly | Ser | Leu 610 | Val |      |
| ACC | ACC | CTG | TTG | AGG | CAC | ACT | AGC | ACT | GTG | ACC | ACG | ATC | ACC | TTT | AGT | 1929 |
| Thr | Thr | Leu | Leu 615 | Arg | His | Thr | Ser | Thr 620 | Val | Thr | Thr | Ile | Thr 625 | Phe | Ser |      |
| CGC | GAT | GGA | ACA | GTC | CTG | GCT | GCA | GCC | GGC | TTG | GAT | AAC | AAT | CTA | ACT | 1977 |

|  |  |  |  |  |  |  |  |  |  |  |  |  |  |  |  |  |
|---|---|---|---|---|---|---|---|---|---|---|---|---|---|---|---|---|
| Arg | Asp | Gly<br>630 | Thr | Val | Leu | Ala | Ala<br>635 | Ala | Gly | Leu | Asp | Asn<br>640 | Asn | Leu | Thr | |

| CTG | TGG | GAC | TTT | CAC | AAG | GTT | ACC | GAA | GAC | TAT | ATC | AGC | AAT | CAC | ATC | 2025 |
|---|---|---|---|---|---|---|---|---|---|---|---|---|---|---|---|---|
| Leu | Trp<br>645 | Asp | Phe | His | Lys | Val<br>650 | Thr | Glu | Asp | Tyr | Ile<br>655 | Ser | Asn | His | Ile | |

| ACT | GTG | TCG | CAC | CAT | CAG | GAT | GAG | AAC | GAC | GAG | GAC | GTC | TAC | CTC | ATG | 2073 |
|---|---|---|---|---|---|---|---|---|---|---|---|---|---|---|---|---|
| Thr<br>660 | Val | Ser | His | His | Gln<br>665 | Asp | Glu | Asn | Asp | Glu<br>670 | Asp | Val | Tyr | Leu | Met<br>675 | |

| CGT | ACT | TTC | CCC | AGC | AAG | AAC | TCG | CCA | TTT | GTC | AGC | CTG | CAC | TTT | ACG | 2121 |
|---|---|---|---|---|---|---|---|---|---|---|---|---|---|---|---|---|
| Arg | Thr | Phe | Pro | Ser<br>680 | Lys | Asn | Ser | Pro | Phe<br>685 | Val | Ser | Leu | His | Phe<br>690 | Thr | |

| CGC | CGA | AAT | CTC | CTG | ATG | TGC | GTG | GGT | CTA | TTC | AAG | AGT | TAGGAGCACA | 2170 |
|---|---|---|---|---|---|---|---|---|---|---|---|---|---|---|
| Arg | Arg | Asn | Leu<br>695 | Leu | Met | Cys | Val | Gly<br>700 | Leu | Phe | Lys | Ser | | |

| GATAAGCTTA | TTTGGTATAC | GTAATGTAGT | GTTAAGGAAT | GCTCGGAATG | TTTAGGATTA | 2230 |
|---|---|---|---|---|---|---|
| ATGTTTTGTA | TTTCGTTTGT | GACCCATCCC | CCCTGAAATG | TCGATTAGTT | GTTTAAGCAT | 2290 |
| AAAAGTGTAA | AGTGCATATA | TGCGCAAGTT | ATCAATAAAT | TTAATTAAT | ATAAAGTCA | 2350 |
| AAAAAAAA | | | | | | 2359 |

(2) INFORMATION FOR SEQ ID NO:5:

(i) SEQUENCE CHARACTERISTICS:
        (A) LENGTH: 704 amino acids
        (B) TYPE: amino acid
        (D) TOPOLOGY: linear (ii) MOLECULE TYPE: protein (xi) SEQUENCE DESCRIPTION: SEQ ID NO:5:

| Met<br>1 | Ser | Leu | Glu | Val<br>5 | Ser | Asn | Ile | Asn | Gly<br>10 | Gly | Asn | Gly | Thr | Gln<br>15 | Leu |
|---|---|---|---|---|---|---|---|---|---|---|---|---|---|---|---|
| Ser | His | Asp | Lys<br>20 | Arg | Glu | Leu | Leu | Cys<br>25 | Leu | Leu | Lys | Leu | Ile<br>30 | Lys | Lys |
| Tyr | Gln | Leu<br>35 | Lys | Ser | Thr | Glu | Glu<br>40 | Leu | Leu | Cys | Gln | Glu<br>45 | Ala | Asn | Val |
| Ser | Ser<br>50 | Val | Glu | Leu | Ser | Glu<br>55 | Ile | Ser | Glu | Ser | Asp<br>60 | Val | Gln | Gln | Val |
| Leu<br>65 | Gly | Ala | Val | Leu | Gly<br>70 | Ala | Gly | Asp | Ala | Asn<br>75 | Arg | Glu | Arg | Lys | His<br>80 |
| Val | Gln | Ser | Pro | Ala<br>85 | Gln | Gly | His | Lys | Gln<br>90 | Ser | Ala | Val | Thr | Glu<br>95 | Ala |
| Asn | Ala | Ala | Glu<br>100 | Glu | Leu | Ala | Lys | Phe<br>105 | Ile | Asp | Asp | Ser | Phe<br>110 | Asp | Asp |
| Ala | Gln | His<br>115 | Tyr | Glu | Gln | Ala | Tyr<br>120 | Lys | Glu | Leu | Arg | Thr<br>125 | Phe | Val | Glu |
| Asp | Ser<br>130 | Leu | Asp | Ile | Tyr | Lys<br>135 | His | Glu | Leu | Ser | Met<br>140 | Val | Leu | Tyr | Pro |
| Ile | Leu<br>145 | Val | Gln | Ile | Tyr | Phe<br>150 | Lys | Ile | Leu | Ala | Ser<br>155 | Gly | Leu | Arg | Glu<br>160 |
| Lys | Ala | Lys | Glu | Phe<br>165 | Ile | Glu | Lys | Tyr | Lys<br>170 | Cys | Asp | Leu | Asp | Gly<br>175 | Tyr |
| Tyr | Ile | Glu | Gly<br>180 | Leu | Phe | Asn | Leu | Leu<br>185 | Leu | Leu | Ser | Lys | Pro<br>190 | Glu | Glu |
| Leu | Leu | Glu<br>195 | Asn | Asp | Leu | Val | Val<br>200 | Ala | Met | Glu | Gln | Asp<br>205 | Lys | Phe | Val |
| Ile | Arg | Met<br>210 | Ser | Arg | Asp | Ser | His<br>215 | Ser | Leu | Phe | Lys | Arg<br>220 | His | Ile | Gln |

```
Asp  Arg  Arg  Gln  Glu  Val  Val  Ala  Asp  Ile  Val  Ser  Lys  Tyr  Leu  His
225                 230                 235                      240

Phe  Asp  Thr  Tyr  Glu  Gly  Met  Ala  Arg  Asn  Lys  Leu  Gln  Cys  Val  Ala
                    245                 250                      255

Thr  Ala  Gly  Ser  His  Leu  Gly  Glu  Ala  Lys  Arg  Gln  Asp  Asn  Lys  Met
               260                 265                      270

Arg  Val  Tyr  Tyr  Gly  Leu  Leu  Lys  Glu  Val  Asp  Phe  Gln  Thr  Leu  Thr
               275            280                 285

Thr  Pro  Ala  Pro  Ala  Pro  Glu  Glu  Asp  Asp  Pro  Asp  Ala  Pro
     290                 295                 300

Asp  Arg  Pro  Lys  Lys  Lys  Pro  Lys  Lys  Asp  Pro  Leu  Leu  Ser  Lys
305                 310                 315                      320

Lys  Ser  Lys  Ser  Asp  Pro  Asn  Ala  Pro  Ser  Ile  Asp  Arg  Ile  Pro  Leu
                325                 330                 335

Pro  Glu  Leu  Lys  Asp  Ser  Asp  Lys  Leu  Lys  Leu  Lys  Ala  Leu  Arg
               340            345                 350

Glu  Ala  Ser  Lys  Arg  Leu  Ala  Leu  Ser  Lys  Asp  Gln  Leu  Pro  Ser  Ala
               355            360                 365

Val  Phe  Tyr  Thr  Val  Leu  Asn  Ser  His  Gln  Gly  Val  Thr  Cys  Ala  Glu
     370            375                 380

Ile  Ser  Asp  Asp  Ser  Thr  Met  Leu  Ala  Cys  Gly  Phe  Gly  Asp  Ser  Ser
385                 390                 395                      400

Val  Arg  Ile  Trp  Ser  Leu  Thr  Pro  Ala  Lys  Leu  Arg  Thr  Leu  Lys  Asp
                405                 410                      415

Ala  Asp  Ser  Leu  Arg  Glu  Leu  Asp  Lys  Glu  Ser  Ala  Asp  Ile  Asn  Val
               420                 425                 430

Arg  Met  Leu  Asp  Asp  Arg  Ser  Gly  Glu  Val  Thr  Arg  Ser  Leu  Met  Gly
          435                 440                 445

His  Thr  Gly  Pro  Val  Tyr  Arg  Cys  Ala  Phe  Ala  Pro  Glu  Met  Asn  Leu
450                      455                 460

Leu  Leu  Ser  Cys  Ser  Glu  Asp  Ser  Thr  Ile  Arg  Leu  Trp  Ser  Leu  Leu
465                 470                 475                      480

Thr  Trp  Ser  Cys  Val  Val  Thr  Tyr  Arg  Gly  His  Val  Tyr  Pro  Val  Trp
                485                 490                 495

Asp  Val  Arg  Phe  Ala  Pro  His  Gly  Tyr  Tyr  Phe  Val  Ser  Cys  Ser  Tyr
               500            505                 510

Asp  Lys  Thr  Ala  Arg  Leu  Trp  Ala  Thr  Asp  Ser  Asn  Gln  Ala  Leu  Arg
          515                 520                 525

Val  Phe  Val  Gly  His  Leu  Ser  Asp  Val  Asp  Cys  Val  Gln  Phe  His  Pro
     530            535                 540

Asn  Ser  Asn  Tyr  Val  Ala  Thr  Gly  Ser  Ser  Asp  Arg  Thr  Val  Arg  Leu
545                 550                 555                      560

Trp  Asp  Asn  Met  Thr  Gly  Gln  Ser  Val  Arg  Leu  Met  Thr  Gly  His  Lys
               565                 570                 575

Gly  Ser  Val  Ser  Ser  Leu  Ala  Phe  Ser  Ala  Cys  Gly  Arg  Tyr  Leu  Ala
               580                 585                 590

Ser  Gly  Ser  Val  Asp  His  Asn  Ile  Ile  Ile  Trp  Asp  Leu  Ser  Asn  Gly
          595                 600                 605

Ser  Leu  Val  Thr  Thr  Leu  Leu  Arg  His  Thr  Ser  Thr  Val  Thr  Thr  Ile
610                 615                 620

Thr  Phe  Ser  Arg  Asp  Gly  Thr  Val  Leu  Ala  Ala  Ala  Gly  Leu  Asp  Asn
625                 630                 635                      640

Asn  Leu  Thr  Leu  Trp  Asp  Phe  His  Lys  Val  Thr  Glu  Asp  Tyr  Ile  Ser
```

|     |     |     |     |     | 645 |     |     |     |     | 650 |     |     |     |     | 655 |     |
|---|---|---|---|---|---|---|---|---|---|---|---|---|---|---|---|---|

```
                        645                         650                         655
Asn His Ile Thr Val Ser His His Gln Asp Glu Asn Asp Glu Asp Val
            660                 665                 670

Tyr Leu Met Arg Thr Phe Pro Ser Lys Asn Ser Pro Phe Val Ser Leu
        675                 680                 685

His Phe Thr Arg Arg Asn Leu Leu Met Cys Val Gly Leu Phe Lys Ser
    690                 695                 700
```

( 2 ) INFORMATION FOR SEQ ID NO:6:

( i ) SEQUENCE CHARACTERISTICS:
        ( A ) LENGTH: 2018 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 70..1842

( x i ) SEQUENCE DESCRIPTION: SEQ ID NO:6:

```
GGAATTCGAG TTGGCCAAAG TGGCGCAATC CGGTATCAAT TGTTCAAACC GAGCAGCCCC        60

TCCAGCAGC ATG CTG TAC GGC TCC AGC ATC TCG GCG GAG TCC ATG AAG          108
          Met Leu Tyr Gly Ser Ser Ile Ser Ala Glu Ser Met Lys
            1               5                  10

GTG ATC GCG GAG AGC ATC GGA GTG GGC TCC CTG TCG GAT GAC GCC GCC        156
Val Ile Ala Glu Ser Ile Gly Val Gly Ser Leu Ser Asp Asp Ala Ala
     15              20                  25

AAG GAA CTA GCG GAG GAT GTG TCC ATC AAG CTG AAG AGG ATT GTA CAG        204
Lys Glu Leu Ala Glu Asp Val Ser Ile Lys Leu Lys Arg Ile Val Gln
 30              35                  40                      45

GAT GCG GCC AAG TTC ATG AAC CAC GCC AAG CGG CAG AAG CTC TCA GTG        252
Asp Ala Ala Lys Phe Met Asn His Ala Lys Arg Gln Lys Leu Ser Val
                 50                  55                  60

CGG GAC ATC GAC ATG TCC CTT AAG GTG CGA AAT GTG GAG CCG CAG TAC        300
Arg Asp Ile Asp Met Ser Leu Lys Val Arg Asn Val Glu Pro Gln Tyr
             65                  70                  75

GGT TTC GTA GCC AAG GAC TTC ATT CCA CTC CGC TTC GCA TCT GGC GGA        348
Gly Phe Val Ala Lys Asp Phe Ile Pro Leu Arg Phe Ala Ser Gly Gly
         80                  85                  90

GGA CGG GAG CTG CAC TTC ACC GAG GAC AAG GAA ATC GAC CTA GGA GAA        396
Gly Arg Glu Leu His Phe Thr Glu Asp Lys Glu Ile Asp Leu Gly Glu
     95                 100                 105

ATC ACA TCC ACC AAC TCT GTA AAA ATT CCC CTG GAT CTC ACC CTG CGC        444
Ile Thr Ser Thr Asn Ser Val Lys Ile Pro Leu Asp Leu Thr Leu Arg
110                 115                 120                 125

TCC CAT TGG TTT GTT GTG GAG GGA GTG CAA CCC ACT GTG CCC GAA AAC        492
Ser His Trp Phe Val Val Glu Gly Val Gln Pro Thr Val Pro Glu Asn
                 130                 135                 140

CCC CCT CCG CTC TCG AAG GAT TCC CAG TTA CTG GAC TCG GTC AAT CCA        540
Pro Pro Pro Leu Ser Lys Asp Ser Gln Leu Leu Asp Ser Val Asn Pro
             145                 150                 155

GTT ATT AAG ATG GAT CAA GGC CTA AAC AAA GAT GCG GCA GGC AAA CCC        588
Val Ile Lys Met Asp Gln Gly Leu Asn Lys Asp Ala Ala Gly Lys Pro
         160                 165                 170

ACC ACC GGC AAG ATA CAC AAG CTG AAA AAC GTG GAG ACC ATT CAT GTC        636
Thr Thr Gly Lys Ile His Lys Leu Lys Asn Val Glu Thr Ile His Val
     175                 180                 185

AAG CAA CTG GCC ACG CAC GAG TTG TCC GTG GAG CAG CAG TTG TAC TAC        684
Lys Gln Leu Ala Thr His Glu Leu Ser Val Glu Gln Gln Leu Tyr Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 190 |     |     |     |     | 195 |     |     |     |     | 200 |     |     |     |     | 205 |      |
| AAG | GAG | ATC | ACC | GAG | GCG | TGC | GTG | GGA | TCT | GAT | GAG | CCG | CGG | CGC | GGG | 732  |
| Lys | Glu | Ile | Thr | Glu | Ala | Cys | Val | Gly | Ser | Asp | Glu | Pro | Arg | Arg | Gly |      |
|     |     |     |     | 210 |     |     |     |     | 215 |     |     |     |     | 220 |     |      |
| GAA | GCG | CTG | CAG | TCG | CTG | GGA | TCC | GAT | CCT | GGC | CTG | CAC | GAA | ATG | CTT | 780  |
| Glu | Ala | Leu | Gln | Ser | Leu | Gly | Ser | Asp | Pro | Gly | Leu | His | Glu | Met | Leu |      |
|     |     |     | 225 |     |     |     |     | 230 |     |     |     |     | 235 |     |     |      |
| CCC | CGC | ATG | TGC | ACC | TTC | ATT | GCC | GAG | GGA | GTT | AAG | GTC | AAT | GTG | GTT | 828  |
| Pro | Arg | Met | Cys | Thr | Phe | Ile | Ala | Glu | Gly | Val | Lys | Val | Asn | Val | Val |      |
|     |     | 240 |     |     |     |     | 245 |     |     |     |     | 250 |     |     |     |      |
| CAG | AAC | AAC | TTG | GCG | TTG | CTT | ATT | TAC | CTC | ATG | CGC | ATG | GTT | CGT | GCG | 876  |
| Gln | Asn | Asn | Leu | Ala | Leu | Leu | Ile | Tyr | Leu | Met | Arg | Met | Val | Arg | Ala |      |
|     | 255 |     |     |     |     | 260 |     |     |     |     | 265 |     |     |     |     |      |
| CTT | CTG | GAT | AAT | CCT | TCG | CTG | TTT | CTG | GAG | AAA | TAC | CTC | CAC | GAA | CTG | 924  |
| Leu | Leu | Asp | Asn | Pro | Ser | Leu | Phe | Leu | Glu | Lys | Tyr | Leu | His | Glu | Leu |      |
| 270 |     |     |     |     | 275 |     |     |     |     | 280 |     |     |     |     | 285 |      |
| ATA | CCC | TCG | GTG | ATG | ACG | TGC | ATT | GTG | TCC | AAA | CAG | CTG | TGT | ATG | CGC | 972  |
| Ile | Pro | Ser | Val | Met | Thr | Cys | Ile | Val | Ser | Lys | Gln | Leu | Cys | Met | Arg |      |
|     |     |     |     | 290 |     |     |     |     | 295 |     |     |     |     | 300 |     |      |
| CCC | GAG | CTG | GAC | AAT | CAC | TGG | GCC | CTG | CGA | GAC | TTT | GCC | TCC | CGA | CTG | 1020 |
| Pro | Glu | Leu | Asp | Asn | His | Trp | Ala | Leu | Arg | Asp | Phe | Ala | Ser | Arg | Leu |      |
|     |     |     | 305 |     |     |     |     | 310 |     |     |     |     | 315 |     |     |      |
| ATG | GCT | CAA | ATC | TGC | AAG | AAC | TTC | AAT | ACC | CTA | ACC | AAC | AAT | CTG | CAA | 1068 |
| Met | Ala | Gln | Ile | Cys | Lys | Asn | Phe | Asn | Thr | Leu | Thr | Asn | Asn | Leu | Gln |      |
|     |     | 320 |     |     |     |     | 325 |     |     |     |     | 330 |     |     |     |      |
| ACC | CGT | GTC | ACC | CGC | ATC | TTC | AGC | AAG | GCC | CTG | CAG | AAC | GAC | AAG | ACC | 1116 |
| Thr | Arg | Val | Thr | Arg | Ile | Phe | Ser | Lys | Ala | Leu | Gln | Asn | Asp | Lys | Thr |      |
|     | 335 |     |     |     |     | 340 |     |     |     |     | 345 |     |     |     |     |      |
| CAC | CTG | TCC | TCG | CTT | TAC | GGC | TCT | ATT | GCG | GGT | CTC | TCG | GAG | CTG | GGG | 1164 |
| His | Leu | Ser | Ser | Leu | Tyr | Gly | Ser | Ile | Ala | Gly | Leu | Ser | Glu | Leu | Gly |      |
| 350 |     |     |     |     | 355 |     |     |     |     | 360 |     |     |     |     | 365 |      |
| GGC | GAA | GTC | ATA | AAG | GTT | TTC | ATC | ATA | CCC | CGC | CTT | AAG | TTC | ATA | TCG | 1212 |
| Gly | Glu | Val | Ile | Lys | Val | Phe | Ile | Ile | Pro | Arg | Leu | Lys | Phe | Ile | Ser |      |
|     |     |     |     | 370 |     |     |     |     | 375 |     |     |     |     | 380 |     |      |
| GAG | CGC | ATT | GAA | CCT | CAC | CTG | CTC | GGC | ACC | TCC | ATC | AGC | AAC | ACT | GAC | 1260 |
| Glu | Arg | Ile | Glu | Pro | His | Leu | Leu | Gly | Thr | Ser | Ile | Ser | Asn | Thr | Asp |      |
|     |     |     | 385 |     |     |     |     | 390 |     |     |     |     | 395 |     |     |      |
| AAG | ACA | GCA | GCA | GGT | CAC | ATC | CGC | GCC | ATG | CTT | CAG | AAG | TGC | TGT | CCC | 1308 |
| Lys | Thr | Ala | Ala | Gly | His | Ile | Arg | Ala | Met | Leu | Gln | Lys | Cys | Cys | Pro |      |
|     |     | 400 |     |     |     |     | 405 |     |     |     |     | 410 |     |     |     |      |
| CCG | ATT | CTC | AGG | CAA | ATG | CTC | AGC | GCC | AGA | TAC | AGC | GGA | GGA | CTA | CAA | 1356 |
| Pro | Ile | Leu | Arg | Gln | Met | Leu | Ser | Ala | Arg | Tyr | Ser | Gly | Gly | Leu | Gln |      |
|     | 415 |     |     |     |     | 420 |     |     |     |     | 425 |     |     |     |     |      |
| GAA | CGA | CTT | TGG | CTT | CCT | GGG | GCC | GTC | GCT | GTG | CCA | GGC | GTA | GTC | AAA | 1404 |
| Glu | Arg | Leu | Trp | Leu | Pro | Gly | Ala | Val | Ala | Val | Pro | Gly | Val | Val | Lys |      |
| 430 |     |     |     |     | 435 |     |     |     |     | 440 |     |     |     |     | 445 |      |
| GTT | CGA | AAT | GCG | CCC | GCC | TCA | AGC | ATT | GTA | ACC | CTG | TCA | TCC | AAC | ACT | 1452 |
| Val | Arg | Asn | Ala | Pro | Ala | Ser | Ser | Ile | Val | Thr | Leu | Ser | Ser | Asn | Thr |      |
|     |     |     |     | 450 |     |     |     |     | 455 |     |     |     |     | 460 |     |      |
| ATC | AAC | ACG | GCA | CCC | ATC | ACG | AGT | GCA | GCA | CAA | ACA | GCA | ACA | ACC | ATC | 1500 |
| Ile | Asn | Thr | Ala | Pro | Ile | Thr | Ser | Ala | Ala | Gln | Thr | Ala | Thr | Thr | Ile |      |
|     |     |     | 465 |     |     |     |     | 470 |     |     |     |     | 475 |     |     |      |
| GGA | CGA | GTG | TCC | ATG | CCC | ACC | ACA | CAG | AGA | CAG | GGA | AGT | CCC | GGA | GTC | 1548 |
| Gly | Arg | Val | Ser | Met | Pro | Thr | Thr | Gln | Arg | Gln | Gly | Ser | Pro | Gly | Val |      |
|     |     | 480 |     |     |     |     | 485 |     |     |     |     | 490 |     |     |     |      |
| TCG | TCC | CTG | CCG | CAA | ATA | AGA | GCC | ATT | CAG | GCC | AAC | CAG | CCG | GCG | CAA | 1596 |
| Ser | Ser | Leu | Pro | Gln | Ile | Arg | Ala | Ile | Gln | Ala | Asn | Gln | Pro | Ala | Gln |      |
|     | 495 |     |     |     |     | 500 |     |     |     |     | 505 |     |     |     |     |      |
| AAG | TTT | GTG | ATA | GTC | ACC | CAG | AAC | TCG | CCG | CAG | CAG | GGC | CAG | GCG | AAG | 1644 |
| Lys | Phe | Val | Ile | Val | Thr | Gln | Asn | Ser | Pro | Gln | Gln | Gly | Gln | Ala | Lys |      |

| | | | | | | | | | | | | | | | | |
|---|---|---|---|---|---|---|---|---|---|---|---|---|---|---|---|---|
| 510 | | | | | 515 | | | | | 520 | | | | | 525 | |
| GTG | GTG | CGG | CGT | GGC | AGC | TCT | CCG | CAC | AGC | GTG | GTC | CTC | TCC | GCG | GCC | 1692 |
| Val | Val | Arg | Arg | Gly | Ser | Ser | Pro | His | Ser | Val | Val | Leu | Ser | Ala | Ala | |
| | | | | 530 | | | | | 535 | | | | | 540 | | |
| TCC | AAC | GCT | GCC | AGT | GCC | TCC | AAT | TCG | AAC | TCA | AGC | TCG | AGC | GGC | AGT | 1740 |
| Ser | Asn | Ala | Ala | Ser | Ala | Ser | Asn | Ser | Asn | Ser | Ser | Ser | Ser | Gly | Ser | |
| | | | 545 | | | | | 550 | | | | | 555 | | | |
| CTA | CTA | GCG | GCT | GCA | CAG | CGG | AGC | AGC | GAG | AAT | GTG | TGT | GTT | ATT | GCC | 1788 |
| Leu | Leu | Ala | Ala | Ala | Gln | Arg | Ser | Ser | Glu | Asn | Val | Cys | Val | Ile | Ala | |
| | | 560 | | | | | 565 | | | | | 570 | | | | |
| GGT | AGC | GAA | GCG | CCA | GCA | GTT | GAT | GGT | ATA | ACA | GTT | CAA | TCT | TTC | AGA | 1836 |
| Gly | Ser | Glu | Ala | Pro | Ala | Val | Asp | Gly | Ile | Thr | Val | Gln | Ser | Phe | Arg | |
| | 575 | | | | | 580 | | | | | 585 | | | | | |
| GCA | TCC | TAGACGCCAA | | CTCGCTGATC | | ATTGAGACGG | | AGATTGTGCG | | CGCACCGGCC | | | | | | 1892 |
| Ala | Ser | | | | | | | | | | | | | | | |
| 590 | | | | | | | | | | | | | | | | |

CGAGCTGGCG GATCTCTCGC ACCTGGAGTA GCCAGCTTAG TTCGTAGTCC ACATTTTGTC  1952

ATATTGTATG CAATAAAATA AAAAATGCGG GTTCCTACCC CAAAAAAATG TAAAAAAAA  2012

AAAAAA  2018

( 2 ) INFORMATION FOR SEQ ID NO:7:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Leu | Tyr | Gly | Ser | Ser | Ile | Ser | Ala | Glu | Ser | Met | Lys | Val | Ile | Ala |
| 1 | | | | 5 | | | | | 10 | | | | | 15 | |
| Glu | Ser | Ile | Gly | Val | Gly | Ser | Leu | Ser | Asp | Asp | Ala | Ala | Lys | Glu | Leu |
| | | | 20 | | | | | 25 | | | | | 30 | | |
| Ala | Glu | Asp | Val | Ser | Ile | Lys | Leu | Lys | Arg | Ile | Val | Gln | Asp | Ala | Ala |
| | | 35 | | | | | 40 | | | | | 45 | | | |
| Lys | Phe | Met | Asn | His | Ala | Lys | Arg | Gln | Lys | Leu | Ser | Val | Arg | Asp | Ile |
| | 50 | | | | | 55 | | | | | 60 | | | | |
| Asp | Met | Ser | Leu | Lys | Val | Arg | Asn | Val | Glu | Pro | Gln | Tyr | Gly | Phe | Val |
| 65 | | | | | 70 | | | | | 75 | | | | | 80 |
| Ala | Lys | Asp | Phe | Ile | Pro | Leu | Arg | Phe | Ala | Ser | Gly | Gly | Gly | Arg | Glu |
| | | | | 85 | | | | | 90 | | | | | 95 | |
| Leu | His | Phe | Thr | Glu | Asp | Lys | Glu | Ile | Asp | Leu | Gly | Glu | Ile | Thr | Ser |
| | | | 100 | | | | | 105 | | | | | 110 | | |
| Thr | Asn | Ser | Val | Lys | Ile | Pro | Leu | Asp | Leu | Thr | Leu | Arg | Ser | His | Trp |
| | | | 115 | | | | | 120 | | | | | 125 | | |
| Phe | Val | Val | Glu | Gly | Val | Gln | Pro | Thr | Val | Pro | Glu | Asn | Pro | Pro | Pro |
| | | 130 | | | | | 135 | | | | | 140 | | | |
| Leu | Ser | Lys | Asp | Ser | Gln | Leu | Leu | Asp | Ser | Val | Asn | Pro | Val | Ile | Lys |
| 145 | | | | | 150 | | | | | 155 | | | | | 160 |
| Met | Asp | Gln | Gly | Leu | Asn | Lys | Asp | Ala | Ala | Gly | Lys | Pro | Thr | Thr | Gly |
| | | | | 165 | | | | | 170 | | | | | 175 | |
| Lys | Ile | His | Lys | Leu | Lys | Asn | Val | Glu | Thr | Ile | His | Val | Lys | Gln | Leu |
| | | | 180 | | | | | 185 | | | | | 190 | | |
| Ala | Thr | His | Glu | Leu | Ser | Val | Glu | Gln | Gln | Leu | Tyr | Tyr | Lys | Glu | Ile |
| | | 195 | | | | | 200 | | | | | 205 | | | |
| Thr | Glu | Ala | Cys | Val | Gly | Ser | Asp | Glu | Pro | Arg | Arg | Gly | Glu | Ala | Leu |

```
         210                      215                      220
Gln  Ser  Leu  Gly  Ser  Asp  Pro  Gly  Leu  His  Glu  Met  Leu  Pro  Arg  Met
225                      230                      235                      240

Cys  Thr  Phe  Ile  Ala  Glu  Gly  Val  Lys  Val  Asn  Val  Val  Gln  Asn  Asn
                    245                      250                      255

Leu  Ala  Leu  Leu  Ile  Tyr  Leu  Met  Arg  Met  Val  Arg  Ala  Leu  Leu  Asp
               260                      265                      270

Asn  Pro  Ser  Leu  Phe  Leu  Glu  Lys  Tyr  Leu  His  Glu  Leu  Ile  Pro  Ser
          275                      280                      285

Val  Met  Thr  Cys  Ile  Val  Ser  Lys  Gln  Leu  Cys  Met  Arg  Pro  Glu  Leu
     290                      295                      300

Asp  Asn  His  Trp  Ala  Leu  Arg  Asp  Phe  Ala  Ser  Arg  Leu  Met  Ala  Gln
305                      310                      315                      320

Ile  Cys  Lys  Asn  Phe  Asn  Thr  Leu  Thr  Asn  Asn  Leu  Gln  Thr  Arg  Val
                    325                      330                      335

Thr  Arg  Ile  Phe  Ser  Lys  Ala  Leu  Gln  Asn  Asp  Lys  Thr  His  Leu  Ser
               340                      345                      350

Ser  Leu  Tyr  Gly  Ser  Ile  Ala  Gly  Leu  Ser  Glu  Leu  Gly  Gly  Glu  Val
          355                      360                      365

Ile  Lys  Val  Phe  Ile  Ile  Pro  Arg  Leu  Lys  Phe  Ile  Ser  Glu  Arg  Ile
     370                      375                      380

Glu  Pro  His  Leu  Leu  Gly  Thr  Ser  Ile  Ser  Asn  Thr  Asp  Lys  Thr  Ala
385                      390                      395                      400

Ala  Gly  His  Ile  Arg  Ala  Met  Leu  Gln  Lys  Cys  Cys  Pro  Pro  Ile  Leu
                    405                      410                      415

Arg  Gln  Met  Leu  Ser  Ala  Arg  Tyr  Ser  Gly  Gly  Leu  Gln  Glu  Arg  Leu
               420                      425                      430

Trp  Leu  Pro  Gly  Ala  Val  Ala  Val  Pro  Gly  Val  Val  Lys  Val  Arg  Asn
          435                      440                      445

Ala  Pro  Ala  Ser  Ser  Ile  Val  Thr  Leu  Ser  Ser  Asn  Thr  Ile  Asn  Thr
     450                      455                      460

Ala  Pro  Ile  Thr  Ser  Ala  Ala  Gln  Thr  Ala  Thr  Thr  Ile  Gly  Arg  Val
465                      470                      475                      480

Ser  Met  Pro  Thr  Thr  Gln  Arg  Gln  Gly  Ser  Pro  Gly  Val  Ser  Ser  Leu
                    485                      490                      495

Pro  Gln  Ile  Arg  Ala  Ile  Gln  Ala  Asn  Gln  Pro  Ala  Gln  Lys  Phe  Val
               500                      505                      510

Ile  Val  Thr  Gln  Asn  Ser  Pro  Gln  Gln  Gly  Gln  Ala  Lys  Val  Val  Arg
          515                      520                      525

Arg  Gly  Ser  Ser  Pro  His  Ser  Val  Val  Leu  Ser  Ala  Ala  Ser  Asn  Ala
     530                      535                      540

Ala  Ser  Ala  Ser  Asn  Ser  Asn  Ser  Ser  Ser  Ser  Gly  Ser  Leu  Leu  Ala
545                      550                      555                      560

Ala  Ala  Gln  Arg  Ser  Ser  Glu  Asn  Val  Cys  Val  Ile  Ala  Gly  Ser  Glu
                    565                      570                      575

Ala  Pro  Ala  Val  Asp  Gly  Ile  Thr  Val  Gln  Ser  Phe  Arg  Ala  Ser
               580                      585                      590
```

( 2 ) INFORMATION FOR SEQ ID NO:8:

( i ) SEQUENCE CHARACTERISTICS:
        ( A ) LENGTH: 1120 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
    ( A ) NAME/KEY: CDS
    ( B ) LOCATION: 80..913

( x i ) SEQUENCE DESCRIPTION: SEQ ID NO:8:

```
GATATGTACG TGCACAATTT CAATGGAATA AACAATCTTC TTGCAGCAAA GCCGACGTAA       60

ACATAATAAC TATAGAAGT ATG AGC GCA GAG AAG TCC GAT AAG GCC AAG ATC       112
                        Met Ser Ala Glu Lys Ser Asp Lys Ala Lys Ile
                         1           5                        10

AGT GCC CAA ATC AAG CAC GTG CCG AAG GAC GCG CAG GTG ATC ATG TCC        160
Ser Ala Gln Ile Lys His Val Pro Lys Asp Ala Gln Val Ile Met Ser
             15                  20                  25

ATC CTG AAG GAG CTG AAT GTC CAG GAG TAC GAG CCG CGC GTG GTC AAC        208
Ile Leu Lys Glu Leu Asn Val Gln Glu Tyr Glu Pro Arg Val Val Asn
         30                  35                  40

CAA CTG CTG GAG TTC ACC TTC CGC TAT GTC ACC TGC ATT CTG GAC GAC        256
Gln Leu Leu Glu Phe Thr Phe Arg Tyr Val Thr Cys Ile Leu Asp Asp
     45                  50                  55

GCC AAG GTA TAC GCC AAC CAT GCG CGC AAG AAG ACC ATC GAC TTG GAC        304
Ala Lys Val Tyr Ala Asn His Ala Arg Lys Lys Thr Ile Asp Leu Asp
 60              65                  70                      75

GAC GTG CGT CTG GCC ACC GAG GTT ACG CTG GAC AAG AGC TTC ACC GGG        352
Asp Val Arg Leu Ala Thr Glu Val Thr Leu Asp Lys Ser Phe Thr Gly
                 80                  85                  90

CCG TTG GAG CGC CAC GTT CTA GCC AAG GTG GCC GAC GTG CGC AAC AGC        400
Pro Leu Glu Arg His Val Leu Ala Lys Val Ala Asp Val Arg Asn Ser
             95                 100                 105

ATG CCC CTG CCA CCC ATT AAG CCG CAC TGC GGT CTC CGA CTG CCG CCC        448
Met Pro Leu Pro Pro Ile Lys Pro His Cys Gly Leu Arg Leu Pro Pro
         110                 115                 120

GAC CGC TAC TGT CTC ACC GGC GTC AAC TAC AAA CTG CGG GCC ACT AAT        496
Asp Arg Tyr Cys Leu Thr Gly Val Asn Tyr Lys Leu Arg Ala Thr Asn
     125                 130                 135

CAG CCC AAG AAA ATG ACC AAG TCG GCG GTG GAG GGC CGT CCA CTG AAG        544
Gln Pro Lys Lys Met Thr Lys Ser Ala Val Glu Gly Arg Pro Leu Lys
140                 145                 150                 155

ACC GTC GTT AAG CCC GTC TCC AGC GCC AAT GGT CCG AAG AGG CCA CAC        592
Thr Val Val Lys Pro Val Ser Ser Ala Asn Gly Pro Lys Arg Pro His
                 160                 165                 170

TCC GTG GTG GCC AAG CAG CAG GTG GTG ACC ATT CCC AAG CCC GTC ATC        640
Ser Val Val Ala Lys Gln Gln Val Val Thr Ile Pro Lys Pro Val Ile
             175                 180                 185

AAG TTT ACC ACC ACT ACG ACA ACG AAA ACG GTG GGC AGC TCC GGC GGA        688
Lys Phe Thr Thr Thr Thr Thr Lys Thr Val Gly Ser Ser Gly Gly
         190                 195                 200

TCT GGG GGC GGC GGT GGT CAG GAG GTT AAG AGC GAG AGC ACC GGC GCC        736
Ser Gly Gly Gly Gly Gly Gln Glu Val Lys Ser Glu Ser Thr Gly Ala
     205                 210                 215

GGC GGA GAT CTC AAG ATG GAG GTG GAC AGC GAT GCG GCG GCC GTG GGC        784
Gly Gly Asp Leu Lys Met Glu Val Asp Ser Asp Ala Ala Ala Val Gly
220                 225                 230                 235

AGC ATC GCT GGC GCA TCC GGT TCG GGA GCA GGA AGT GCC AGC GGA GGA        832
Ser Ile Ala Gly Ala Ser Gly Ser Gly Ala Gly Ser Ala Ser Gly Gly
                 240                 245                 250

GGA GGA GGA GGA GGA TCA TCT GGC GTT GGA GTG GCC GTC AAG CGG GAA        880
Gly Gly Gly Gly Gly Ser Ser Gly Val Gly Val Ala Val Lys Arg Glu
             255                 260                 265

CGT GAG GAG GAG GAG TTT GAG TTT GTG ACC AAC TAGCGAAACG ACATCATTTA      933
Arg Glu Glu Glu Glu Phe Glu Phe Val Thr Asn
```

```
                  270                 275
CCTTAAATTA ATATTCTTAA ATCAGACCAA AGCACTTGCA TTTGGTTGAG CGAACTGGGG    993

GTCTAAATTT CAACTCGAAT GTGAAGTCCC AAAAACCTTA GTATAGATTC GCCCGTTAAT   1053

CATTATGAAA TCTACGTTTT ATACACAAAT ACAACTACCA GATTTTCATA TTAAAAAAAA   1113

AAAAAAA                                                             1120
```

( 2 ) INFORMATION FOR SEQ ID NO:9:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Ser  Ala  Glu  Lys  Ser  Asp  Lys  Ala  Lys  Ile  Ser  Ala  Gln  Ile  Lys
  1              5                        10                       15

His  Val  Pro  Lys  Asp  Ala  Gln  Val  Ile  Met  Ser  Ile  Leu  Lys  Glu  Leu
               20                        25                       30

Asn  Val  Gln  Glu  Tyr  Glu  Pro  Arg  Val  Val  Asn  Gln  Leu  Leu  Glu  Phe
          35                        40                       45

Thr  Phe  Arg  Tyr  Val  Thr  Cys  Ile  Leu  Asp  Asp  Ala  Lys  Val  Tyr  Ala
     50                        55                       60

Asn  His  Ala  Arg  Lys  Lys  Thr  Ile  Asp  Leu  Asp  Asp  Val  Arg  Leu  Ala
 65                       70                       75                       80

Thr  Glu  Val  Thr  Leu  Asp  Lys  Ser  Phe  Thr  Gly  Pro  Leu  Glu  Arg  His
                    85                        90                       95

Val  Leu  Ala  Lys  Val  Ala  Asp  Val  Arg  Asn  Ser  Met  Pro  Leu  Pro  Pro
               100                      105                       110

Ile  Lys  Pro  His  Cys  Gly  Leu  Arg  Leu  Pro  Pro  Asp  Arg  Tyr  Cys  Leu
          115                       120                      125

Thr  Gly  Val  Asn  Tyr  Lys  Leu  Arg  Ala  Thr  Asn  Gln  Pro  Lys  Lys  Met
     130                       135                       140

Thr  Lys  Ser  Ala  Val  Glu  Gly  Arg  Pro  Leu  Lys  Thr  Val  Val  Lys  Pro
145                       150                       155                      160

Val  Ser  Ser  Ala  Asn  Gly  Pro  Lys  Arg  Pro  His  Ser  Val  Val  Ala  Lys
               165                       170                      175

Gln  Gln  Val  Val  Thr  Ile  Pro  Lys  Pro  Val  Ile  Lys  Phe  Thr  Thr  Thr
                    180                       185                      190

Thr  Thr  Thr  Lys  Thr  Val  Gly  Ser  Ser  Gly  Gly  Ser  Gly  Gly  Gly  Gly
          195                       200                       205

Gly  Gln  Glu  Val  Lys  Ser  Glu  Ser  Thr  Gly  Ala  Gly  Gly  Asp  Leu  Lys
     210                       215                       220

Met  Glu  Val  Asp  Ser  Asp  Ala  Ala  Ala  Val  Gly  Ser  Ile  Ala  Gly  Ala
225                       230                       235                      240

Ser  Gly  Ser  Gly  Ala  Gly  Ser  Ala  Ser  Gly  Gly  Gly  Gly  Gly  Gly  Gly
                    245                       250                      255

Ser  Ser  Gly  Val  Gly  Val  Ala  Val  Lys  Arg  Glu  Arg  Glu  Glu  Glu  Glu
               260                       265                      270

Phe  Glu  Phe  Val  Thr  Asn
               275
```

( 2 ) INFORMATION FOR SEQ ID NO:10:

( i ) SEQUENCE CHARACTERISTICS:

5,534,410

( A ) LENGTH: 5962 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 14..5692

( x i ) SEQUENCE DESCRIPTION: SEQ ID NO:10:

```
TTATTTCCGG CAT ATG GGA CCC GGC TGC GAT TTG CTG CTG CGG ACA GCA        49
           Met Gly Pro Gly Cys Asp Leu Leu Leu Arg Thr Ala
            1               5                  10

GCT ACC ATC ACT GCT GCC GCC ATC ATG TCA GAC ACG GAC AGC GAC GAA       97
Ala Thr Ile Thr Ala Ala Ala Ile Met Ser Asp Thr Asp Ser Asp Glu
         15              20                  25

GAT TCC GCT GGA GGC GGC CCA TTT TCT TTA GCG GGT TTC CTT TTC GGC      145
Asp Ser Ala Gly Gly Gly Pro Phe Ser Leu Ala Gly Phe Leu Phe Gly
     30              35                  40

AAC ATC AAT GGA GCC GGG CAG CTG GAG GGG GAA AGC GTC TTG GAT GAT      193
Asn Ile Asn Gly Ala Gly Gln Leu Glu Gly Glu Ser Val Leu Asp Asp
 45              50                  55                  60

GAA TGT AAG AAG CAC TTG GCA GGC TTG GGG GCT TTG GGG CTG GGC AGC      241
Glu Cys Lys Lys His Leu Ala Gly Leu Gly Ala Leu Gly Leu Gly Ser
                 65                  70                  75

CTG ATC ACT GAA CTC ACG GCA AAT GAA GAA TTG ACC GGG ACT GAC GGT      289
Leu Ile Thr Glu Leu Thr Ala Asn Glu Glu Leu Thr Gly Thr Asp Gly
             80                  85                  90

GCC TTG GTA AAT GAT GAA GGG TGG GTT AGG AGT ACA GAA GAT GCT GTG      337
Ala Leu Val Asn Asp Glu Gly Trp Val Arg Ser Thr Glu Asp Ala Val
         95                 100                 105

GAC TAT TCA GAC ATC AAT GAG GTG GCA GAA GAT GAA AGC CGA AGA TAC      385
Asp Tyr Ser Asp Ile Asn Glu Val Ala Glu Asp Glu Ser Arg Arg Tyr
    110                 115                 120

CAG CAG ACG ATG GGG AGC TTG CAG CCC CTT TGC CAC TCA GAT TAT GAT      433
Gln Gln Thr Met Gly Ser Leu Gln Pro Leu Cys His Ser Asp Tyr Asp
125                 130                 135                 140

GAA GAT GAC TAT GAT GCT GAT TGT GAA GAC ATT GAT TGC AAG TTG ATG      481
Glu Asp Asp Tyr Asp Ala Asp Cys Glu Asp Ile Asp Cys Lys Leu Met
                145                 150                 155

CCT CCT CCA CCT CCA CCC CCG GGA CCA ATG AAG AAG GAT AAG GAC CAG      529
Pro Pro Pro Pro Pro Pro Pro Gly Pro Met Lys Lys Asp Lys Asp Gln
            160                 165                 170

GAT TCT ATT ACT GGT GTG TCT GAA AAT GGA GAA GGC ATC ATC TTG CCC      577
Asp Ser Ile Thr Gly Val Ser Glu Asn Gly Glu Gly Ile Ile Leu Pro
        175                 180                 185

TCC ATC ATT GCC CCT TCC TCT TTG GCC TCA GAG AAA GTG GAC TTC AGT      625
Ser Ile Ile Ala Pro Ser Ser Leu Ala Ser Glu Lys Val Asp Phe Ser
    190                 195                 200

AGT TCC TCT GAC TCA GAA TCT GAG ATG GGA CCT CAG GAA GCA ACA CAG      673
Ser Ser Ser Asp Ser Glu Ser Glu Met Gly Pro Gln Glu Ala Thr Gln
205                 210                 215                 220

GCA GAA TCT GAA GAT GGA AAG CTG ACC CTT CCA TTG GCT GGG ATT ATG      721
Ala Glu Ser Glu Asp Gly Lys Leu Thr Leu Pro Leu Ala Gly Ile Met
                225                 230                 235

CAG CAT GAT GCC ACC AAG CTG TTG CCA AGT GTC ACA GAA CTT TTC CCA      769
Gln His Asp Ala Thr Lys Leu Leu Pro Ser Val Thr Glu Leu Phe Pro
            240                 245                 250

GAA TTT CGA CCT GGA AAG GTG TTA CGT TTT CTA CGT CTT TTT GGA CCA      817
Glu Phe Arg Pro Gly Lys Val Leu Arg Phe Leu Arg Leu Phe Gly Pro
        255                 260                 265
```

| | | | | | | | | | | | | | | | | |
|---|---|---|---|---|---|---|---|---|---|---|---|---|---|---|---|---|
| GGG | AAG | AAT | GTC | CCA | TCT | GTT | TGG | CGG | AGT | GCT | CGG | AGA | AAG | AGG | AAG | 865 |
| Gly | Lys 270 | Asn | Val | Pro | Ser | Val 275 | Trp | Arg | Ser | Ala | Arg 280 | Arg | Lys | Arg | Lys | |
| AAG | AAG | CAC | CGT | GAG | CTG | ATA | CAG | GAA | GAG | CAG | ATC | CAG | GAG | GTG | GAG | 913 |
| Lys 285 | Lys | His | Arg | Glu | Leu 290 | Ile | Gln | Glu | Glu | Gln 295 | Ile | Gln | Glu | Val | Glu 300 | |
| TGC | TCA | GTA | GAA | TCA | GAA | GTC | AGC | CAG | AAG | TCT | TTG | TGG | AAC | TAC | GAC | 961 |
| Cys | Ser | Val | Glu | Ser 305 | Glu | Val | Ser | Gln | Lys 310 | Ser | Leu | Trp | Asn | Tyr 315 | Asp | |
| TAC | GCT | CCA | CCA | CCA | CCT | CCA | GAG | CAG | TGT | CTC | TCT | GAT | GAT | GAA | ATC | 1009 |
| Tyr | Ala | Pro | Pro 320 | Pro | Pro | Pro | Glu | Gln 325 | Cys | Leu | Ser | Asp | Asp 330 | Glu | Ile | |
| ACG | ATG | ATG | GCT | CCT | GTG | GAG | TCC | AAA | TTT | TCC | CAA | TCA | ACT | GGA | GAT | 1057 |
| Thr | Met | Met 335 | Ala | Pro | Val | Glu | Ser 340 | Lys | Phe | Ser | Gln | Ser 345 | Thr | Gly | Asp | |
| ATA | GAT | AAA | GTG | ACA | GAT | ACC | AAA | CCA | AGA | GTG | GCT | GAG | TGG | CGT | TAT | 1105 |
| Ile | Asp | Lys 350 | Val | Thr | Asp | Thr | Lys 355 | Pro | Arg | Val | Ala | Glu 360 | Trp | Arg | Tyr | |
| GGG | CCT | GCC | CGA | CTG | TGG | TAT | GAT | ATG | CTG | GGT | GTC | CCT | GAA | GAT | GGC | 1153 |
| Gly | Pro 365 | Ala | Arg | Leu | Trp | Tyr 370 | Asp | Met | Leu | Gly | Val 375 | Pro | Glu | Asp | Gly 380 | |
| AGT | GGG | TTT | GAC | TAT | GGC | TTC | AAA | CTG | AGA | AAG | ACA | GAA | CAT | GAA | CCT | 1201 |
| Ser | Gly | Phe | Asp | Tyr 385 | Gly | Phe | Lys | Leu | Arg 390 | Lys | Thr | Glu | His | Glu 395 | Pro | |
| GTG | ATA | AAA | TCT | AGA | ATG | ATA | GAG | GAA | TTT | AGG | AAA | CTT | GAG | GAA | AAC | 1249 |
| Val | Ile | Lys | Ser 400 | Arg | Met | Ile | Glu | Glu 405 | Phe | Arg | Lys | Leu | Glu 410 | Glu | Asn | |
| AAT | GGC | ACT | GAT | CTT | CTG | GCT | GAT | GAA | AAC | TTC | CTG | ATG | GTG | ACA | CAG | 1297 |
| Asn | Gly | Thr | Asp 415 | Leu | Leu | Ala | Asp | Glu 420 | Asn | Phe | Leu | Met | Val 425 | Thr | Gln | |
| CTG | CAT | TGG | GAG | GAT | GAT | ATC | ATC | TGG | GAT | GGG | GAG | GAT | GTC | AAA | CAC | 1345 |
| Leu | His | Trp 430 | Glu | Asp | Asp | Ile | Ile 435 | Trp | Asp | Gly | Glu | Asp 440 | Val | Lys | His | |
| AAA | GGG | ACA | AAA | CCT | CAG | CGT | GCA | AGC | CTG | GCA | GGC | TGG | CTT | CCT | TCT | 1393 |
| Lys 445 | Gly | Thr | Lys | Pro | Gln 450 | Arg | Ala | Ser | Leu | Ala 455 | Gly | Trp | Leu | Pro | Ser 460 | |
| AGC | ATG | ACT | AGG | AAT | GCG | ATG | GCT | TAC | AAT | GTT | CAG | CAA | GGT | TTT | GCA | 1441 |
| Ser | Met | Thr | Arg | Asn 465 | Ala | Met | Ala | Tyr | Asn 470 | Val | Gln | Gln | Gly | Phe 475 | Ala | |
| GCC | ACT | CTT | GAT | GAT | GAC | AAA | CCT | TGG | TAC | TCC | ATT | TTT | CCC | ATT | GAC | 1489 |
| Ala | Thr | Leu | Asp 480 | Asp | Asp | Lys | Pro | Trp 485 | Tyr | Ser | Ile | Phe | Pro 490 | Ile | Asp | |
| AAT | GAG | GAT | CTG | GTA | TAT | GGA | CGC | TGG | GAG | GAC | AAT | ATC | ATT | TGG | GAT | 1537 |
| Asn | Glu | Asp 495 | Leu | Val | Tyr | Gly | Arg 500 | Trp | Glu | Asp | Asn | Ile 505 | Ile | Trp | Asp | |
| GCT | CAG | GCC | ATG | CCC | CGG | CTG | TTG | GAA | CCT | CCT | GTT | TTG | ACA | CTT | GAT | 1585 |
| Ala | Gln | Ala | Met 510 | Pro | Arg | Leu | Leu | Glu 515 | Pro | Pro | Val | Leu | Thr 520 | Leu | Asp | |
| CCC | AAT | GAT | GAG | AAC | CTC | ATT | TTG | GAA | ATT | CCT | GAT | GAG | AAG | GAA | GAG | 1633 |
| Pro | Asn | Asp | Glu | Asn 525 | Leu | Ile | Leu | Glu | Ile 530 | Pro | Asp | Glu | Lys | Glu 535 | Glu 540 | |
| GCC | ACC | TCT | AAC | TCC | CCC | TCC | AAG | GAG | AGT | AAG | AAG | GAA | TCA | TCT | CTG | 1681 |
| Ala | Thr | Ser | Asn | Ser 545 | Pro | Ser | Lys | Glu | Ser 550 | Lys | Lys | Glu | Ser | Ser 555 | Leu | |
| AAG | AAG | AGT | CGA | ATT | CTC | TTA | GGG | AAA | ACA | GGA | GTC | ATC | AAG | GAG | GAA | 1729 |
| Lys | Lys | Ser | Arg 560 | Ile | Leu | Leu | Gly | Lys 565 | Thr | Gly | Val | Ile | Lys 570 | Glu | Glu | |
| CCA | CAG | CAG | AAC | ATG | TCT | CAG | CCA | GAA | GTG | AAA | GAT | CCA | TGG | AAT | CTC | 1777 |
| Pro | Gln | Gln 575 | Asn | Met | Ser | Gln | Pro 580 | Glu | Val | Lys | Asp | Pro 585 | Trp | Asn | Leu | |

| | | | | | | | | | | | | | | | | |
|---|---|---|---|---|---|---|---|---|---|---|---|---|---|---|---|---|
| TCC | AAT | GAT | GAG | TAT | TAT | TAT | CCC | AAG | CAA | CAG | GGT | CTT | CGA | GGC | ACC | 1825 |
| Ser | Asn | Asp | Glu | Tyr | Tyr | Tyr | Pro | Lys | Gln | Gln | Gly | Leu | Arg | Gly | Thr | |
| | 590 | | | | 595 | | | | | | 600 | | | | | |
| TTT | GGA | GGG | AAT | ATT | ATC | CAG | CAT | TCA | ATT | CCT | GCT | GTG | GAA | TTA | CGG | 1873 |
| Phe | Gly | Gly | Asn | Ile | Ile | Gln | His | Ser | Ile | Pro | Ala | Val | Glu | Leu | Arg | |
| 605 | | | | | 610 | | | | | 615 | | | | | 620 | |
| CAG | CCC | TTC | TTT | CCC | ACC | CAC | ATG | GGG | CCC | ATC | AAA | CTC | CGG | CAG | TTC | 1921 |
| Gln | Pro | Phe | Phe | Pro | Thr | His | Met | Gly | Pro | Ile | Lys | Leu | Arg | Gln | Phe | |
| | | | | 625 | | | | | 630 | | | | | 635 | | |
| CAT | CGC | CCA | CCT | CTG | AAA | AAG | TAC | TCA | TTT | GGT | GCA | CTT | TCT | CAG | CCA | 1969 |
| His | Arg | Pro | Pro | Leu | Lys | Lys | Tyr | Ser | Phe | Gly | Ala | Leu | Ser | Gln | Pro | |
| | | | 640 | | | | | 645 | | | | | 650 | | | |
| GGT | CCC | CAC | TCA | GTC | CAA | CCT | TTG | CTA | AAG | CAC | ATC | AAA | AAA | AAG | GCC | 2017 |
| Gly | Pro | His | Ser | Val | Gln | Pro | Leu | Leu | Lys | His | Ile | Lys | Lys | Lys | Ala | |
| | | 655 | | | | | 660 | | | | | 665 | | | | |
| AAG | ATG | AGA | GAA | CAA | GAG | AGG | CAA | GCT | TCA | GGT | GGT | GGA | GAG | ATG | TTT | 2065 |
| Lys | Met | Arg | Glu | Gln | Glu | Arg | Gln | Ala | Ser | Gly | Gly | Gly | Glu | Met | Phe | |
| | 670 | | | | | 675 | | | | | 680 | | | | | |
| TTT | ATG | CGC | ACA | CCT | CAG | GAC | CTC | ACA | GGC | AAA | GAT | GGT | GAT | CTT | ATT | 2113 |
| Phe | Met | Arg | Thr | Pro | Gln | Asp | Leu | Thr | Gly | Lys | Asp | Gly | Asp | Leu | Ile | |
| 685 | | | | | 690 | | | | | 695 | | | | | 700 | |
| CTT | GCA | GAA | TAT | AGT | GAG | GAA | AAT | GGA | CCC | TTA | ATG | ATG | CAG | GTT | GGC | 2161 |
| Leu | Ala | Glu | Tyr | Ser | Glu | Glu | Asn | Gly | Pro | Leu | Met | Met | Gln | Val | Gly | |
| | | | | 705 | | | | | 710 | | | | | 715 | | |
| ATG | GCA | ACC | AAG | ATA | AAG | AAC | TAT | TAT | AAA | CGG | AAA | CCT | GGA | AAA | GAT | 2209 |
| Met | Ala | Thr | Lys | Ile | Lys | Asn | Tyr | Tyr | Lys | Arg | Lys | Pro | Gly | Lys | Asp | |
| | | | 720 | | | | | 725 | | | | | 730 | | | |
| CCT | GGA | GCA | CCA | GAT | TGT | AAA | TAT | GGG | GAA | ACT | GTT | TAC | TGC | CAT | ACA | 2257 |
| Pro | Gly | Ala | Pro | Asp | Cys | Lys | Tyr | Gly | Glu | Thr | Val | Tyr | Cys | His | Thr | |
| | | 735 | | | | | 740 | | | | | 745 | | | | |
| TCT | CCT | TTC | CTG | GGT | TCT | CTC | CAT | CCT | GGC | CAA | TTG | CTG | CAA | GCA | TTT | 2305 |
| Ser | Pro | Phe | Leu | Gly | Ser | Leu | His | Pro | Gly | Gln | Leu | Leu | Gln | Ala | Phe | |
| | 750 | | | | | 755 | | | | | 760 | | | | | |
| GAG | AAC | AAC | CTT | TTT | CGT | GCT | CCA | ATT | TAT | CTT | CAT | AAG | ATG | CCA | GAA | 2353 |
| Glu | Asn | Asn | Leu | Phe | Arg | Ala | Pro | Ile | Tyr | Leu | His | Lys | Met | Pro | Glu | |
| 765 | | | | | 770 | | | | | 775 | | | | | 780 | |
| ACT | GAT | TTC | TTG | ATC | ATT | CGG | ACA | AGA | CAG | GGT | TAC | TAT | ATT | CGG | GAA | 2401 |
| Thr | Asp | Phe | Leu | Ile | Ile | Arg | Thr | Arg | Gln | Gly | Tyr | Tyr | Ile | Arg | Glu | |
| | | | | 785 | | | | | 790 | | | | | 795 | | |
| TTA | GTG | GAT | ATT | TTT | GTG | GTT | GGC | CAG | CAG | TGT | CCC | TTG | TTT | GAA | GTT | 2449 |
| Leu | Val | Asp | Ile | Phe | Val | Val | Gly | Gln | Gln | Cys | Pro | Leu | Phe | Glu | Val | |
| | | | 800 | | | | | 805 | | | | | 810 | | | |
| CCT | GGG | CCT | AAC | TCC | AAA | AGG | GCC | AAT | ACG | CAT | ATT | CGA | GAC | TTT | CTA | 2497 |
| Pro | Gly | Pro | Asn | Ser | Lys | Arg | Ala | Asn | Thr | His | Ile | Arg | Asp | Phe | Leu | |
| | | 815 | | | | | 820 | | | | | 825 | | | | |
| CAG | GTT | TTT | ATT | TAC | CGC | CTT | TTC | TGG | AAA | AGT | AAA | GAT | CGG | CCA | CGG | 2545 |
| Gln | Val | Phe | Ile | Tyr | Arg | Leu | Phe | Trp | Lys | Ser | Lys | Asp | Arg | Pro | Arg | |
| | 830 | | | | | 835 | | | | | 840 | | | | | |
| AGG | ATA | CGA | ATG | GAA | GAT | ATA | AAA | AAA | GCC | TTT | CCT | TCC | CAT | TCA | GAA | 2593 |
| Arg | Ile | Arg | Met | Glu | Asp | Ile | Lys | Lys | Ala | Phe | Pro | Ser | His | Ser | Glu | |
| 845 | | | | | 850 | | | | | 855 | | | | | 860 | |
| AGC | AGC | ATC | CGG | AAG | AGG | CTA | AAG | CTC | TGC | GCT | GAC | TTC | AAA | CGC | ACA | 2641 |
| Ser | Ser | Ile | Arg | Lys | Arg | Leu | Lys | Leu | Cys | Ala | Asp | Phe | Lys | Arg | Thr | |
| | | | | 865 | | | | | 870 | | | | | 875 | | |
| GGG | ATG | GAC | TCA | AAC | TGG | TGG | GTG | CTT | AAG | TCT | GAT | TTT | CGT | TTA | CCA | 2689 |
| Gly | Met | Asp | Ser | Asn | Trp | Trp | Val | Leu | Lys | Ser | Asp | Phe | Arg | Leu | Pro | |
| | | | 880 | | | | | 885 | | | | | 890 | | | |
| ACG | GAA | GAA | GAG | ATC | AGA | GCT | ATG | GTG | TCA | CCA | GAG | CAG | TGC | TGT | GCT | 2737 |
| Thr | Glu | Glu | Glu | Ile | Arg | Ala | Met | Val | Ser | Pro | Glu | Gln | Cys | Cys | Ala | |
| | | 895 | | | | | 900 | | | | | 905 | | | | |

| | | | | | | | | | | | | | | | | |
|---|---|---|---|---|---|---|---|---|---|---|---|---|---|---|---|---|
| TAT | TAT | AGC | ATG | ATA | GCT | GCA | GAG | CAA | CGA | CTG | AAG | GAT | GCT | GGC | TAT | 2785 |
| Tyr | Tyr 910 | Ser | Met | Ile | Ala | Ala 915 | Glu | Gln | Arg | Leu | Lys 920 | Asp | Ala | Gly | Tyr | |
| GGT | GAG | AAA | TCC | TTT | TTT | GCT | CCA | GAA | GAA | GAA | AAT | GAG | GAA | GAT | TTC | 2833 |
| Gly 925 | Glu | Lys | Ser | Phe | Phe 930 | Ala | Pro | Glu | Glu | Glu 935 | Asn | Glu | Glu | Asp | Phe 940 | |
| CAG | ATG | AAG | ATT | GAT | GAT | GAA | GTT | CGC | ACT | GCC | CCT | TGG | AAC | ACC | ACA | 2881 |
| Gln | Met | Lys | Ile | Asp 945 | Asp | Glu | Val | Arg | Thr 950 | Ala | Pro | Trp | Asn | Thr 955 | Thr | |
| AGG | GCC | TTC | ATT | GCT | GCC | ATG | AAG | GGC | AAG | TGT | CTG | CTA | GAG | GTG | ACT | 2929 |
| Arg | Ala | Phe | Ile 960 | Ala | Ala | Met | Lys | Gly 965 | Lys | Cys | Leu | Leu | Glu 970 | Val | Thr | |
| GGG | GTG | GCA | GAT | CCC | ACG | GGG | TGT | GGT | GAA | GGA | TTC | TCC | TAT | GTG | AAG | 2977 |
| Gly | Val | Ala 975 | Asp | Pro | Thr | Gly | Cys 980 | Gly | Glu | Gly | Phe | Ser 985 | Tyr | Val | Lys | |
| ATT | CCA | AAC | AAA | CCA | ACA | CAG | CAG | AAG | GAT | GAT | AAA | GAA | CCG | CAG | CCA | 3025 |
| Ile | Pro | Asn 990 | Lys | Pro | Thr | Gln | Gln 995 | Lys | Asp | Asp | Lys | Glu 1000 | Pro | Gln | Pro | |
| GTG | AAG | AAG | ACA | GTG | ACA | GGA | ACA | GAT | GCA | GAC | CTT | CGT | CGC | CTT | TCC | 3073 |
| Val | Lys 1005 | Lys | Thr | Val | Thr 1010 | Gly | Thr | Asp | Ala | Asp 1015 | Leu | Arg | Arg | Leu | Ser 1020 | |
| CTG | AAA | AAT | GCC | AAG | CAA | CTT | CTA | CGT | AAA | TTT | GGT | GTG | CCT | GAG | GAA | 3121 |
| Leu | Lys | Asn | Ala | Lys 1025 | Gln | Leu | Leu | Arg | Lys 1030 | Phe | Gly | Val | Pro | Glu 1035 | Glu | |
| GAG | ATT | AAA | AAG | TTG | TCC | CGC | TGG | GAA | GTG | ATT | GAT | GTG | GTG | CGC | ACA | 3169 |
| Glu | Ile | Lys | Lys 1040 | Leu | Ser | Arg | Trp | Glu 1045 | Val | Ile | Asp | Val | Val 1050 | Arg | Thr | |
| ATG | TCA | ACA | GAA | CAG | GCT | CGT | TCT | GGA | GAG | GGG | CCC | ATG | AGT | AAA | TTT | 3217 |
| Met | Ser | Thr 1055 | Glu | Gln | Ala | Arg | Ser 1060 | Gly | Glu | Gly | Pro | Met 1065 | Ser | Lys | Phe | |
| GCC | CGT | GGA | TCA | AGG | TTT | TCT | GTG | GCT | GAG | CAT | CAA | GAG | CGT | TAC | AAA | 3265 |
| Ala | Arg 1070 | Gly | Ser | Arg | Phe | Ser 1075 | Val | Ala | Glu | His | Gln 1080 | Glu | Arg | Tyr | Lys | |
| GAG | GAA | TGT | CAG | CGC | ATC | TTT | GAC | CTA | CAG | AAC | AAG | GTT | CTG | TCA | TCA | 3313 |
| Glu | Glu 1085 | Cys | Gln | Arg | Ile | Phe 1090 | Asp | Leu | Gln | Asn | Lys 1095 | Val | Leu | Ser | Ser 1100 | |
| ACT | GAA | GTC | TTA | TCA | ACT | GAC | ACA | GAC | AGC | AGC | TCA | GCT | GAA | GAT | AGT | 3361 |
| Thr | Glu | Val | Leu | Ser 1105 | Thr | Asp | Thr | Asp | Ser 1110 | Ser | Ser | Ala | Glu | Asp 1115 | Ser | |
| GAC | TTT | GAA | GAA | ATG | GGA | AAG | AAC | ATT | GAG | AAC | ATG | TTG | CAG | AAC | AAG | 3409 |
| Asp | Phe | Glu | Glu | Met 1120 | Gly | Lys | Asn | Ile | Glu 1125 | Asn | Met | Leu | Gln | Asn 1130 | Lys | |
| AAA | ACC | AGC | TCT | CAG | CTT | TCA | CGT | GAA | CGG | GAG | GAA | CAG | GAG | CGG | AAG | 3457 |
| Lys | Thr | Ser | Ser 1135 | Gln | Leu | Ser | Arg | Glu 1140 | Arg | Glu | Glu | Gln | Glu 1145 | Arg | Lys | |
| GAA | CTA | CAG | CGA | ATG | CTA | CTG | GCA | GCA | GGC | TCA | GCA | GCA | TCC | GGA | AAC | 3505 |
| Glu | Leu | Gln | Arg 1150 | Met | Leu | Leu | Ala | Ala 1155 | Gly | Ser | Ala | Ala | Ser 1160 | Gly | Asn | |
| AAT | CAC | AGA | GAT | GAT | GAC | ACA | GCT | TCC | GTG | ACT | AGC | CTT | AAC | TCT | TCT | 3553 |
| Asn | His | Arg 1165 | Asp | Asp | Asp | Thr | Ala 1170 | Ser | Val | Thr | Ser | Leu 1175 | Asn | Ser | Ser 1180 | |
| GCC | ACT | GGA | CGC | TGT | CTC | AAG | ATT | TAT | CGC | ACG | TTT | CGA | GAT | GAA | GAG | 3601 |
| Ala | Thr | Gly | Arg | Cys 1185 | Leu | Lys | Ile | Tyr | Arg 1190 | Thr | Phe | Arg | Asp | Glu 1195 | Glu | |
| GGG | AAA | GAG | TAT | GTT | CGC | TGT | GAG | ACA | GTC | CGA | AAA | CCA | GCT | GTC | ATT | 3649 |
| Gly | Lys | Glu | Tyr 1200 | Val | Arg | Cys | Glu | Thr 1205 | Val | Arg | Lys | Pro | Ala 1210 | Val | Ile | |
| GAT | GCC | TAT | GTG | CGC | ATA | CGG | ACT | ACA | AAA | GAT | GAG | GAA | TTC | ATT | CGA | 3697 |
| Asp | Ala | Tyr 1215 | Val | Arg | Ile | Arg | Thr 1220 | Thr | Lys | Asp | Glu | Glu 1225 | Phe | Ile | Arg | |

| | | | | | | | | | | | | | | | | |
|---|---|---|---|---|---|---|---|---|---|---|---|---|---|---|---|---|
| AAA | TTT | GCC | CTT | TTT | GAT | GAA | CAA | CAT | CGG | GAA | GAG | ATG | CGA | AAA | GAA | 3745 |
| Lys | Phe | Ala | Leu | Phe | Asp | Glu | Gln | His | Arg | Glu | Glu | Met | Arg | Lys | Glu | |
| | | 1230 | | | | 1235 | | | | | 1240 | | | | | |
| CGG | CGG | AGG | ATT | CAA | GAG | CAA | CTG | AGG | CGG | CTT | AAG | AGG | AAC | CAG | GAA | 3793 |
| Arg | Arg | Arg | Ile | Gln | Glu | Gln | Leu | Arg | Arg | Leu | Lys | Arg | Asn | Gln | Glu | |
| 1245 | | | | | 1250 | | | | | 1255 | | | | | 1260 | |
| AAG | GAG | AAG | CTT | AAG | GGT | CCT | CCT | GAG | AAG | AAG | CCC | AAG | AAA | ATG | AAG | 3841 |
| Lys | Glu | Lys | Leu | Lys | Gly | Pro | Pro | Glu | Lys | Lys | Pro | Lys | Lys | Met | Lys | |
| | | | | | 1265 | | | | 1270 | | | | | 1275 | | |
| GAG | CGT | CCT | GAC | CTA | AAA | CTG | AAA | TGT | GGG | GCA | TGT | GGT | GCC | ATT | GGA | 3889 |
| Glu | Arg | Pro | Asp | Leu | Lys | Leu | Lys | Cys | Gly | Ala | Cys | Gly | Ala | Ile | Gly | |
| | | | 1280 | | | | 1285 | | | | | 1290 | | | | |
| CAC | ATG | AGG | ACT | AAC | AAA | TTC | TGC | CCC | CTC | TAT | TAT | CAA | ACA | AAT | GCG | 3937 |
| His | Met | Arg | Thr | Asn | Lys | Phe | Cys | Pro | Leu | Tyr | Tyr | Gln | Thr | Asn | Ala | |
| | | 1295 | | | | 1300 | | | | | 1305 | | | | | |
| CCA | CCT | TCC | AAC | CCT | GTT | GCC | ATG | ACA | GAA | GAA | CAG | GAG | GAG | GAG | TTG | 3985 |
| Pro | Pro | Ser | Asn | Pro | Val | Ala | Met | Thr | Glu | Glu | Gln | Glu | Glu | Glu | Leu | |
| | | 1310 | | | | 1315 | | | | | 1320 | | | | | |
| GAA | AAG | ACA | GTC | ATT | CAT | AAT | GAT | AAT | GAA | GAA | CTT | ATC | AAG | GTT | GAA | 4033 |
| Glu | Lys | Thr | Val | Ile | His | Asn | Asp | Asn | Glu | Glu | Leu | Ile | Lys | Val | Glu | |
| 1325 | | | | | 1330 | | | | | 1335 | | | | | 1340 | |
| GGG | ACC | AAA | ATT | GTC | TTG | GGG | AAA | CAG | CTA | ATT | GAG | AGT | GCG | GAT | GAG | 4081 |
| Gly | Thr | Lys | Ile | Val | Leu | Gly | Lys | Gln | Leu | Ile | Glu | Ser | Ala | Asp | Glu | |
| | | | | 1345 | | | | | 1350 | | | | | 1355 | | |
| GTT | CGC | AGA | AAA | TCT | CTG | GTT | CTC | AAG | TTT | CCT | AAA | CAG | CAG | CTT | CCT | 4129 |
| Val | Arg | Arg | Lys | Ser | Leu | Val | Leu | Lys | Phe | Pro | Lys | Gln | Gln | Leu | Pro | |
| | | | | 1360 | | | | | 1365 | | | | | 1370 | | |
| CCA | AAG | AAG | AAA | CGG | CGA | GTT | GGA | ACC | ACT | GTT | CAC | TGT | GAC | TAT | TTG | 4177 |
| Pro | Lys | Lys | Lys | Arg | Arg | Val | Gly | Thr | Thr | Val | His | Cys | Asp | Tyr | Leu | |
| | | 1375 | | | | 1380 | | | | | 1385 | | | | | |
| AAT | AGA | CCT | CAT | AAG | TCC | ATC | CAC | CGG | CGC | CGC | ACA | GAC | CCT | ATG | GTG | 4225 |
| Asn | Arg | Pro | His | Lys | Ser | Ile | His | Arg | Arg | Arg | Thr | Asp | Pro | Met | Val | |
| | | 1390 | | | | 1395 | | | | | 1400 | | | | | |
| ACG | CTG | TCG | TCC | ATC | TTG | GAG | TCT | ATC | ATC | AAT | GAC | ATG | AGA | GAT | CTT | 4273 |
| Thr | Leu | Ser | Ser | Ile | Leu | Glu | Ser | Ile | Ile | Asn | Asp | Met | Arg | Asp | Leu | |
| 1405 | | | | | 1410 | | | | | 1415 | | | | | 1420 | |
| CCA | AAT | ACA | TAC | CCT | TTC | CAC | ACT | CCA | GTC | AAT | GCA | AAG | GTT | GTA | AAG | 4321 |
| Pro | Asn | Thr | Tyr | Pro | Phe | His | Thr | Pro | Val | Asn | Ala | Lys | Val | Val | Lys | |
| | | | | 1425 | | | | | 1430 | | | | | 1435 | | |
| GAC | TAC | TAC | AAA | ATC | ATC | ACT | CGG | CCA | ATG | GAC | CTA | CAA | ACA | CTC | CGC | 4369 |
| Asp | Tyr | Tyr | Lys | Ile | Ile | Thr | Arg | Pro | Met | Asp | Leu | Gln | Thr | Leu | Arg | |
| | | | 1440 | | | | 1445 | | | | | 1450 | | | | |
| GAA | AAC | GTG | CGT | AAA | CGC | CTC | TAC | CCA | TCT | CGG | GAA | GAG | TTC | AGA | GAG | 4417 |
| Glu | Asn | Val | Arg | Lys | Arg | Leu | Tyr | Pro | Ser | Arg | Glu | Glu | Phe | Arg | Glu | |
| | | | 1455 | | | | 1460 | | | | | 1465 | | | | |
| CAT | CTG | GAG | CTA | ATT | GTG | AAA | AAT | AGT | GCA | ACC | TAC | AAT | GGG | CCA | AAA | 4465 |
| His | Leu | Glu | Leu | Ile | Val | Lys | Asn | Ser | Ala | Thr | Tyr | Asn | Gly | Pro | Lys | |
| | | 1470 | | | | 1475 | | | | | 1480 | | | | | |
| CAC | TCA | TTG | ACT | CAG | ATC | TCT | CAA | TCC | ATG | CTG | GAT | CTC | TGT | GAT | GAA | 4513 |
| His | Ser | Leu | Thr | Gln | Ile | Ser | Gln | Ser | Met | Leu | Asp | Leu | Cys | Asp | Glu | |
| 1485 | | | | | 1490 | | | | | 1495 | | | | | 1500 | |
| AAA | CTC | AAA | GAG | AAA | GAA | GAC | AAA | TTA | GCT | CGC | TTA | GAG | AAA | GCT | ATC | 4561 |
| Lys | Leu | Lys | Glu | Lys | Glu | Asp | Lys | Leu | Ala | Arg | Leu | Glu | Lys | Ala | Ile | |
| | | | | 1505 | | | | | 1510 | | | | | 1515 | | |
| AAC | CCC | TTG | CTG | GAT | GAT | GAT | GAC | CAA | GTG | GCG | TTT | TCT | TTC | ATT | CTG | 4609 |
| Asn | Pro | Leu | Leu | Asp | Asp | Asp | Asp | Gln | Val | Ala | Phe | Ser | Phe | Ile | Leu | |
| | | | | 1520 | | | | | 1525 | | | | | 1530 | | |
| GAC | AAC | ATT | GTC | ACC | CAG | AAA | ATG | ATG | GCA | GTT | CCA | GAT | TCT | TGG | CCA | 4657 |
| Asp | Asn | Ile | Val | Thr | Gln | Lys | Met | Met | Ala | Val | Pro | Asp | Ser | Trp | Pro | |
| | | | | 1535 | | | | | 1540 | | | | | 1545 | | |

| | |
|---|---|
| TTT CAT CAC CCA GTT AAT AAG AAA TTT GTT CCA GAT TAT TAC AAA GTG<br>Phe His His Pro Val Asn Lys Lys Phe Val Pro Asp Tyr Tyr Lys Val<br>1550                     1555                     1560 | 4705 |
| ATT GTC AAT CCA ATG GAT TTA GAG ACC ATA CGT AAG AAC ATC TCC AAG<br>Ile Val Asn Pro Met Asp Leu Glu Thr Ile Arg Lys Asn Ile Ser Lys<br>1565                     1570                     1575                     1580 | 4753 |
| CAC AAG TAT CAG AGT CGG GAG AGC TTT CTG GAT GAT GTA AAC CTT ATT<br>His Lys Tyr Gln Ser Arg Glu Ser Phe Leu Asp Asp Val Asn Leu Ile<br>1585                     1590                     1595 | 4801 |
| CTG GCC AAC AGT GTT AAG TAT AAT GGA CCT GAG AGT CAG TAT ACT AAG<br>Leu Ala Asn Ser Val Lys Tyr Asn Gly Pro Glu Ser Gln Tyr Thr Lys<br>1600                     1605                     1610 | 4849 |
| ACT GCC CAG GAG ATT GTG AAC GTC TGT TAC CAG ACA TTG ACT GAG TAT<br>Thr Ala Gln Glu Ile Val Asn Val Cys Tyr Gln Thr Leu Thr Glu Tyr<br>1615                     1620                     1625 | 4897 |
| GAT GAA CAT TTG ACT CAA CTT GAG AAG GAT ATT TGT ACT GCT AAA GAA<br>Asp Glu His Leu Thr Gln Leu Glu Lys Asp Ile Cys Thr Ala Lys Glu<br>1630                     1635                     1640 | 4945 |
| GCA GCT TTG GAG GAA GCA GAA TTA GAA AGC CTG GAC CCA ATG ACC CCA<br>Ala Ala Leu Glu Glu Ala Glu Leu Glu Ser Leu Asp Pro Met Thr Pro<br>1645                     1650                     1655                     1660 | 4993 |
| GGG CCC TAC ACG CCT CAG CCT CCT GAT TTG TAT GAT ACC AAC ACA TCC<br>Gly Pro Tyr Thr Pro Gln Pro Pro Asp Leu Tyr Asp Thr Asn Thr Ser<br>                     1665                     1670                     1675 | 5041 |
| CTC AGT ATG TCT CGA GAT GCC TCT GTA TTT CAA GAT GAG AGC AAT ATG<br>Leu Ser Met Ser Arg Asp Ala Ser Val Phe Gln Asp Glu Ser Asn Met<br>                     1680                     1685                     1690 | 5089 |
| TCT GTC TTG GAT ATC CCC AGT GCC ACT CCA GAA AAG CAG GTA ACA CAG<br>Ser Val Leu Asp Ile Pro Ser Ala Thr Pro Glu Lys Gln Val Thr Gln<br>                     1695                     1700                     1705 | 5137 |
| GAA GGT GAA GAT GGA GAT GGT GAT CTT GCA GAT GAA GAG GAA GGA ACT<br>Glu Gly Glu Asp Gly Asp Gly Asp Leu Ala Asp Glu Glu Glu Gly Thr<br>1710                     1715                     1720 | 5185 |
| GTA CAA CAG CCT CAA GCC AGT GTC CTG TAT GAG GAT TTG CTT ATG TCT<br>Val Gln Gln Pro Gln Ala Ser Val Leu Tyr Glu Asp Leu Leu Met Ser<br>1725                     1730                     1735                     1740 | 5233 |
| GAA GGA GAA GAT GAT GAG GAA GAT GCT GGG AGT GAT GAA GAA GGA GAC<br>Glu Gly Glu Asp Asp Glu Glu Asp Ala Gly Ser Asp Glu Glu Gly Asp<br>                     1745                     1750                     1755 | 5281 |
| AAT CCT TTC TCT GCT ATC CAG CTG AGT GAA AGT GGA AGT GAC TCT GAT<br>Asn Pro Phe Ser Ala Ile Gln Leu Ser Glu Ser Gly Ser Asp Ser Asp<br>                     1760                     1765                     1770 | 5329 |
| GTG GGA TCT GGT GGA ATA AGA CCC AAA CAA CCC CGC ATG CTT CAG GAG<br>Val Gly Ser Gly Gly Ile Arg Pro Lys Gln Pro Arg Met Leu Gln Glu<br>                     1775                     1780                     1785 | 5377 |
| AAC ACA AGG ATG GAC ATG GAA AAT GAA GAA AGC ATG ATG TCC TAT GAG<br>Asn Thr Arg Met Asp Met Glu Asn Glu Glu Ser Met Met Ser Tyr Glu<br>1790                     1795                     1800 | 5425 |
| GGA GAC GGT GGG GAG GCT TCC CAT GGT TTG GAG GAT AGC AAC ATC AGT<br>Gly Asp Gly Gly Glu Ala Ser His Gly Leu Glu Asp Ser Asn Ile Ser<br>1805                     1810                     1815                     1820 | 5473 |
| TAT GGG AGC TAT GAG GAG CCT GAT CCC AAG TCG AAC ACC CAA GAC ACA<br>Tyr Gly Ser Tyr Glu Glu Pro Asp Pro Lys Ser Asn Thr Gln Asp Thr<br>                     1825                     1830                     1835 | 5521 |
| AGC TTC AGC AGC ATC GGT GGG TAT GAG GTA TCA GAG GAG GAA GAT<br>Ser Phe Ser Ser Ile Gly Gly Tyr Glu Val Ser Glu Glu Glu Asp<br>                     1840                     1845                     1850 | 5569 |
| GAG GAG GAG GAA GAG CAG CGC TCT GGG CCG AGC GTA CTA AGC CAG GTC<br>Glu Glu Glu Glu Glu Gln Arg Ser Gly Pro Ser Val Leu Ser Gln Val<br>                     1855                     1860                     1865 | 5617 |

```
CAC CTG TCA GAG GAC GAG GAG GAC AGT GAG GAT TTC CAC TCC ATT GCT      5665
His Leu Ser Glu Asp Glu Glu Asp Ser Glu Asp Phe His Ser Ile Ala
    1870                1875                1880

GGG GAC AGT GAC TTG GAC TCT GAT GAA TGAGGCTTCC TTTGGGCCTC            5712
Gly Asp Ser Asp Leu Asp Ser Asp Glu
1885                1890

CTTGGTCAGC CTTCCCTGTT CTCCAGCCTA GGTGGTTCAC CTTTCCCCAA TTTGTTCATA    5772

TTTGTACAGT ATCTGATCCT GAAATCATGA AATTAACTAA CACCTTAGCC TTTTTAAAAG    5832

TAGTAAGTAA ATGATAATAA ATCACCTCTC CTAATCTTCC TGGGGCAATG TCACCCTTTG    5892

ATTTAAAACA AAGCAACCCC CTTTCCCCTA CCACTACGGA AAAGAGCAAG CTCATTTTTC    5952

CGTGTCCTCC                                                           5962
```

( 2 ) INFORMATION FOR SEQ ID NO:11:

( i ) SEQUENCE CHARACTERISTICS:
        ( A ) LENGTH: 1893 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Gly Pro Gly Cys Asp Leu Leu Leu Arg Thr Ala Ala Thr Ile Thr
 1               5                  10                  15

Ala Ala Ala Ile Met Ser Asp Thr Asp Ser Asp Glu Asp Ser Ala Gly
            20                  25                  30

Gly Gly Pro Phe Ser Leu Ala Gly Phe Leu Phe Gly Asn Ile Asn Gly
        35                  40                  45

Ala Gly Gln Leu Glu Gly Glu Ser Val Leu Asp Asp Glu Cys Lys Lys
    50                  55                  60

His Leu Ala Gly Leu Gly Ala Leu Gly Leu Gly Ser Leu Ile Thr Glu
65                  70                  75                  80

Leu Thr Ala Asn Glu Glu Leu Thr Gly Thr Asp Gly Ala Leu Val Asn
                85                  90                  95

Asp Glu Gly Trp Val Arg Ser Thr Glu Asp Ala Val Asp Tyr Ser Asp
            100                 105                 110

Ile Asn Glu Val Ala Glu Asp Glu Ser Arg Arg Tyr Gln Gln Thr Met
        115                 120                 125

Gly Ser Leu Gln Pro Leu Cys His Ser Asp Tyr Asp Glu Asp Asp Tyr
    130                 135                 140

Asp Ala Asp Cys Glu Asp Ile Asp Cys Lys Leu Met Pro Pro Pro Pro
145                 150                 155                 160

Pro Pro Pro Gly Pro Met Lys Lys Asp Lys Asp Gln Asp Ser Ile Thr
                165                 170                 175

Gly Val Ser Glu Asn Gly Glu Gly Ile Ile Leu Pro Ser Ile Ile Ala
            180                 185                 190

Pro Ser Ser Leu Ala Ser Glu Lys Val Asp Phe Ser Ser Ser Ser Asp
        195                 200                 205

Ser Glu Ser Glu Met Gly Pro Gln Glu Ala Thr Gln Ala Glu Ser Glu
    210                 215                 220

Asp Gly Lys Leu Thr Leu Pro Leu Ala Gly Ile Met Gln His Asp Ala
225                 230                 235                 240

Thr Lys Leu Leu Pro Ser Val Thr Glu Leu Phe Pro Glu Phe Arg Pro
                245                 250                 255

Gly Lys Val Leu Arg Phe Leu Arg Leu Phe Gly Pro Gly Lys Asn Val
```

|   |   |   |   |   | 260 |   |   |   |   | 265 |   |   |   |   | 270 |   |   |
|---|---|---|---|---|---|---|---|---|---|---|---|---|---|---|---|---|---|

Pro Ser Val Trp Arg Ser Ala Arg Arg Lys Arg Lys Lys Lys His Arg
275 280 285

Glu Leu Ile Gln Glu Glu Gln Ile Gln Glu Val Glu Cys Ser Val Glu
290 295 300

Ser Glu Val Ser Gln Lys Ser Leu Trp Asn Tyr Asp Tyr Ala Pro Pro
305 310 315 320

Pro Pro Pro Glu Gln Cys Leu Ser Asp Asp Glu Ile Thr Met Met Ala
325 330 335

Pro Val Glu Ser Lys Phe Ser Gln Ser Thr Gly Asp Ile Asp Lys Val
340 345 350

Thr Asp Thr Lys Pro Arg Val Ala Glu Trp Arg Tyr Gly Pro Ala Arg
355 360 365

Leu Trp Tyr Asp Met Leu Gly Val Pro Glu Asp Gly Ser Gly Phe Asp
370 375 380

Tyr Gly Phe Lys Leu Arg Lys Thr Glu His Glu Pro Val Ile Lys Ser
385 390 395 400

Arg Met Ile Glu Glu Phe Arg Lys Leu Glu Glu Asn Asn Gly Thr Asp
405 410 415

Leu Leu Ala Asp Glu Asn Phe Leu Met Val Thr Gln Leu His Trp Glu
420 425 430

Asp Asp Ile Ile Trp Asp Gly Glu Asp Val Lys His Lys Gly Thr Lys
435 440 445

Pro Gln Arg Ala Ser Leu Ala Gly Trp Leu Pro Ser Ser Met Thr Arg
450 455 460

Asn Ala Met Ala Tyr Asn Val Gln Gln Gly Phe Ala Ala Thr Leu Asp
465 470 475 480

Asp Asp Lys Pro Trp Tyr Ser Ile Phe Pro Ile Asp Asn Glu Asp Leu
485 490 495

Val Tyr Gly Arg Trp Glu Asp Asn Ile Ile Trp Asp Ala Gln Ala Met
500 505 510

Pro Arg Leu Leu Glu Pro Pro Val Leu Thr Leu Asp Pro Asn Asp Glu
515 520 525

Asn Leu Ile Leu Glu Ile Pro Asp Glu Lys Glu Glu Ala Thr Ser Asn
530 535 540

Ser Pro Ser Lys Glu Ser Lys Lys Glu Ser Ser Leu Lys Lys Ser Arg
545 550 555 560

Ile Leu Leu Gly Lys Thr Gly Val Ile Lys Glu Glu Pro Gln Gln Asn
565 570 575

Met Ser Gln Pro Glu Val Lys Asp Pro Trp Asn Leu Ser Asn Asp Glu
580 585 590

Tyr Tyr Tyr Pro Lys Gln Gln Gly Leu Arg Gly Thr Phe Gly Gly Asn
595 600 605

Ile Ile Gln His Ser Ile Pro Ala Val Glu Leu Arg Gln Pro Phe Phe
610 615 620

Pro Thr His Met Gly Pro Ile Lys Leu Arg Gln Phe His Arg Pro Pro
625 630 635 640

Leu Lys Lys Tyr Ser Phe Gly Ala Leu Ser Gln Pro Gly Pro His Ser
645 650 655

Val Gln Pro Leu Leu Lys His Ile Lys Lys Ala Lys Met Arg Glu
660 665 670

Gln Glu Arg Gln Ala Ser Gly Gly Glu Met Phe Phe Met Arg Thr
675 680 685

| | | | | | | | | | | | | | | |
|---|---|---|---|---|---|---|---|---|---|---|---|---|---|---|
| Pro | Gln | Asp | Leu | Thr | Gly | Lys | Asp | Gly | Asp | Leu | Ile | Leu | Ala | Glu | Tyr |
| | 690 | | | | | 695 | | | | 700 | | | | | |
| Ser | Glu | Glu | Asn | Gly | Pro | Leu | Met | Met | Gln | Val | Gly | Met | Ala | Thr | Lys |
| 705 | | | | | 710 | | | | 715 | | | | | 720 | |
| Ile | Lys | Asn | Tyr | Tyr | Lys | Arg | Lys | Pro | Gly | Lys | Asp | Pro | Gly | Ala | Pro |
| | | | | 725 | | | | 730 | | | | | 735 | | |
| Asp | Cys | Lys | Tyr | Gly | Glu | Thr | Val | Tyr | Cys | His | Thr | Ser | Pro | Phe | Leu |
| | | | 740 | | | | 745 | | | | | 750 | | | |
| Gly | Ser | Leu | His | Pro | Gly | Gln | Leu | Leu | Gln | Ala | Phe | Glu | Asn | Asn | Leu |
| | | 755 | | | | 760 | | | | | 765 | | | | |
| Phe | Arg | Ala | Pro | Ile | Tyr | Leu | His | Lys | Met | Pro | Glu | Thr | Asp | Phe | Leu |
| | 770 | | | | 775 | | | | 780 | | | | | | |
| Ile | Ile | Arg | Thr | Arg | Gln | Gly | Tyr | Tyr | Ile | Arg | Glu | Leu | Val | Asp | Ile |
| 785 | | | | | 790 | | | | 795 | | | | | 800 | |
| Phe | Val | Val | Gly | Gln | Gln | Cys | Pro | Leu | Phe | Glu | Val | Pro | Gly | Pro | Asn |
| | | | 805 | | | | | 810 | | | | | 815 | | |
| Ser | Lys | Arg | Ala | Asn | Thr | His | Ile | Arg | Asp | Phe | Leu | Gln | Val | Phe | Ile |
| | | | 820 | | | | 825 | | | | | 830 | | | |
| Tyr | Arg | Leu | Phe | Trp | Lys | Ser | Lys | Asp | Arg | Pro | Arg | Arg | Ile | Arg | Met |
| | 835 | | | | | 840 | | | | 845 | | | | | |
| Glu | Asp | Ile | Lys | Lys | Ala | Phe | Pro | Ser | His | Ser | Glu | Ser | Ser | Ile | Arg |
| 850 | | | | | 855 | | | | | 860 | | | | | |
| Lys | Arg | Leu | Lys | Leu | Cys | Ala | Asp | Phe | Lys | Arg | Thr | Gly | Met | Asp | Ser |
| 865 | | | | | 870 | | | | 875 | | | | | 880 | |
| Asn | Trp | Trp | Val | Leu | Lys | Ser | Asp | Phe | Arg | Leu | Pro | Thr | Glu | Glu | Glu |
| | | | | 885 | | | | | 890 | | | | | 895 | |
| Ile | Arg | Ala | Met | Val | Ser | Pro | Glu | Gln | Cys | Cys | Ala | Tyr | Tyr | Ser | Met |
| | | | 900 | | | | 905 | | | | | 910 | | | |
| Ile | Ala | Ala | Glu | Gln | Arg | Leu | Lys | Asp | Ala | Gly | Tyr | Gly | Glu | Lys | Ser |
| | | | 915 | | | | 920 | | | | | 925 | | | |
| Phe | Phe | Ala | Pro | Glu | Glu | Glu | Asn | Glu | Glu | Asp | Phe | Gln | Met | Lys | Ile |
| | 930 | | | | | 935 | | | | | 940 | | | | |
| Asp | Asp | Glu | Val | Arg | Thr | Ala | Pro | Trp | Asn | Thr | Thr | Arg | Ala | Phe | Ile |
| 945 | | | | | 950 | | | | 955 | | | | | | 960 |
| Ala | Ala | Met | Lys | Gly | Lys | Cys | Leu | Leu | Glu | Val | Thr | Gly | Val | Ala | Asp |
| | | | | 965 | | | | | 970 | | | | | 975 | |
| Pro | Thr | Gly | Cys | Gly | Glu | Gly | Phe | Ser | Tyr | Val | Lys | Ile | Pro | Asn | Lys |
| | | | 980 | | | | | 985 | | | | | 990 | | |
| Pro | Thr | Gln | Gln | Lys | Asp | Asp | Lys | Glu | Pro | Gln | Pro | Val | Lys | Lys | Thr |
| | | 995 | | | | | 1000 | | | | | 1005 | | | |
| Val | Thr | Gly | Thr | Asp | Ala | Asp | Leu | Arg | Arg | Leu | Ser | Leu | Lys | Asn | Ala |
| | 1010 | | | | | 1015 | | | | | 1020 | | | | |
| Lys | Gln | Leu | Leu | Arg | Lys | Phe | Gly | Val | Pro | Glu | Glu | Glu | Ile | Lys | Lys |
| 1025 | | | | | 1030 | | | | | 1035 | | | | | 1040 |
| Leu | Ser | Arg | Trp | Glu | Val | Ile | Asp | Val | Val | Arg | Thr | Met | Ser | Thr | Glu |
| | | | | 1045 | | | | | 1050 | | | | | 1055 | |
| Gln | Ala | Arg | Ser | Gly | Glu | Gly | Pro | Met | Ser | Lys | Phe | Ala | Arg | Gly | Ser |
| | | | 1060 | | | | | 1065 | | | | | 1070 | | |
| Arg | Phe | Ser | Val | Ala | Glu | His | Gln | Glu | Arg | Tyr | Lys | Glu | Glu | Cys | Gln |
| | | 1075 | | | | | 1080 | | | | | 1085 | | | |
| Arg | Ile | Phe | Asp | Leu | Gln | Asn | Lys | Val | Leu | Ser | Ser | Thr | Glu | Val | Leu |
| | 1090 | | | | | 1095 | | | | | 1100 | | | | |
| Ser | Thr | Asp | Thr | Asp | Ser | Ser | Ser | Ala | Glu | Asp | Ser | Asp | Phe | Glu | Glu |
| 1105 | | | | | 1110 | | | | | 1115 | | | | | 1120 |

```
Met Gly Lys Asn Ile Glu Asn Met Leu Gln Asn Lys Lys Thr Ser Ser
            1125                1130                1135
Gln Leu Ser Arg Glu Arg Glu Glu Glu Arg Lys Glu Leu Gln Arg
            1140                1145                1150
Met Leu Leu Ala Ala Gly Ser Ala Ala Ser Gly Asn Asn His Arg Asp
            1155                1160                1165
Asp Asp Thr Ala Ser Val Thr Ser Leu Asn Ser Ser Ala Thr Gly Arg
    1170                1175                1180
Cys Leu Lys Ile Tyr Arg Thr Phe Arg Asp Glu Glu Gly Lys Glu Tyr
1185                1190                1195                1200
Val Arg Cys Glu Thr Val Arg Lys Pro Ala Val Ile Asp Ala Tyr Val
            1205                1210                1215
Arg Ile Arg Thr Thr Lys Asp Glu Glu Phe Ile Arg Lys Phe Ala Leu
            1220                1225                1230
Phe Asp Glu Gln His Arg Glu Glu Met Arg Lys Glu Arg Arg Arg Ile
            1235                1240                1245
Gln Glu Gln Leu Arg Arg Leu Lys Arg Asn Gln Glu Lys Glu Lys Leu
            1250                1255                1260
Lys Gly Pro Pro Glu Lys Lys Pro Lys Lys Met Lys Glu Arg Pro Asp
1265                1270                1275                1280
Leu Lys Leu Lys Cys Gly Ala Cys Gly Ala Ile Gly His Met Arg Thr
            1285                1290                1295
Asn Lys Phe Cys Pro Leu Tyr Tyr Gln Thr Asn Ala Pro Pro Ser Asn
            1300                1305                1310
Pro Val Ala Met Thr Glu Glu Gln Glu Glu Glu Leu Glu Lys Thr Val
            1315                1320                1325
Ile His Asn Asp Asn Glu Glu Leu Ile Lys Val Glu Gly Thr Lys Ile
            1330                1335                1340
Val Leu Gly Lys Gln Leu Ile Glu Ser Ala Asp Glu Val Arg Arg Lys
1345                1350                1355                1360
Ser Leu Val Leu Lys Phe Pro Lys Gln Gln Leu Pro Pro Lys Lys Lys
            1365                1370                1375
Arg Arg Val Gly Thr Thr Val His Cys Asp Tyr Leu Asn Arg Pro His
            1380                1385                1390
Lys Ser Ile His Arg Arg Arg Thr Asp Pro Met Val Thr Leu Ser Ser
            1395                1400                1405
Ile Leu Glu Ser Ile Ile Asn Asp Met Arg Asp Leu Pro Asn Thr Tyr
            1410                1415                1420
Pro Phe His Thr Pro Val Asn Ala Lys Val Val Lys Asp Tyr Tyr Lys
1425                1430                1435                1440
Ile Ile Thr Arg Pro Met Asp Leu Gln Thr Leu Arg Glu Asn Val Arg
            1445                1450                1455
Lys Arg Leu Tyr Pro Ser Arg Glu Glu Phe Arg Glu His Leu Glu Leu
            1460                1465                1470
Ile Val Lys Asn Ser Ala Thr Tyr Asn Gly Pro Lys His Ser Leu Thr
            1475                1480                1485
Gln Ile Ser Gln Ser Met Leu Asp Leu Cys Asp Glu Lys Leu Lys Glu
            1490                1495                1500
Lys Glu Asp Lys Leu Ala Arg Leu Glu Lys Ala Ile Asn Pro Leu Leu
1505                1510                1515                1520
Asp Asp Asp Asp Gln Val Ala Phe Ser Phe Ile Leu Asp Asn Ile Val
            1525                1530                1535
Thr Gln Lys Met Met Ala Val Pro Asp Ser Trp Pro Phe His His Pro
```

```
                    1540                    1545                    1550

Val  Asn  Lys  Lys  Phe  Val  Pro  Asp  Tyr  Tyr  Lys  Val  Ile  Val  Asn  Pro
               1555                    1560                    1565

Met  Asp  Leu  Glu  Thr  Ile  Arg  Lys  Asn  Ile  Ser  Lys  His  Lys  Tyr  Gln
     1570                    1575                    1580

Ser  Arg  Glu  Ser  Phe  Leu  Asp  Asp  Val  Asn  Leu  Ile  Leu  Ala  Asn  Ser
1585                    1590                    1595                         1600

Val  Lys  Tyr  Asn  Gly  Pro  Glu  Ser  Gln  Tyr  Thr  Lys  Thr  Ala  Gln  Glu
               1605                    1610                    1615

Ile  Val  Asn  Val  Cys  Tyr  Gln  Thr  Leu  Thr  Glu  Tyr  Asp  Glu  His  Leu
               1620                    1625                    1630

Thr  Gln  Leu  Glu  Lys  Asp  Ile  Cys  Thr  Ala  Lys  Glu  Ala  Ala  Leu  Glu
               1635                    1640                    1645

Glu  Ala  Glu  Leu  Glu  Ser  Leu  Asp  Pro  Met  Thr  Pro  Gly  Pro  Tyr  Thr
     1650                    1655                    1660

Pro  Gln  Pro  Pro  Asp  Leu  Tyr  Asp  Thr  Asn  Thr  Ser  Leu  Ser  Met  Ser
1665                    1670                    1675                         1680

Arg  Asp  Ala  Ser  Val  Phe  Gln  Asp  Glu  Ser  Asn  Met  Ser  Val  Leu  Asp
               1685                    1690                    1695

Ile  Pro  Ser  Ala  Thr  Pro  Glu  Lys  Gln  Val  Thr  Gln  Glu  Gly  Glu  Asp
               1700                    1705                    1710

Gly  Asp  Gly  Asp  Leu  Ala  Asp  Glu  Glu  Glu  Gly  Thr  Val  Gln  Gln  Pro
               1715                    1720                    1725

Gln  Ala  Ser  Val  Leu  Tyr  Glu  Asp  Leu  Leu  Met  Ser  Glu  Gly  Glu  Asp
     1730                    1735                    1740

Asp  Glu  Glu  Asp  Ala  Gly  Ser  Asp  Glu  Glu  Gly  Asp  Asn  Pro  Phe  Ser
1745                    1750                    1755                         1760

Ala  Ile  Gln  Leu  Ser  Glu  Ser  Gly  Ser  Asp  Ser  Asp  Val  Gly  Ser  Gly
               1765                    1770                    1775

Gly  Ile  Arg  Pro  Lys  Gln  Pro  Arg  Met  Leu  Gln  Glu  Asn  Thr  Arg  Met
               1780                    1785                    1790

Asp  Met  Glu  Asn  Glu  Glu  Ser  Met  Met  Ser  Tyr  Glu  Gly  Asp  Gly  Gly
               1795                    1800                    1805

Glu  Ala  Ser  His  Gly  Leu  Glu  Asp  Ser  Asn  Ile  Ser  Tyr  Gly  Ser  Tyr
     1810                    1815                    1820

Glu  Glu  Pro  Asp  Pro  Lys  Ser  Asn  Thr  Gln  Asp  Thr  Ser  Phe  Ser  Ser
1825                    1830                    1835                         1840

Ile  Gly  Gly  Tyr  Glu  Val  Ser  Glu  Glu  Glu  Asp  Glu  Glu  Glu
               1845                    1850                    1855

Glu  Gln  Arg  Ser  Gly  Pro  Ser  Val  Leu  Ser  Gln  Val  His  Leu  Ser  Glu
               1860                    1865                    1870

Asp  Glu  Glu  Asp  Ser  Glu  Asp  Phe  His  Ser  Ile  Ala  Gly  Asp  Ser  Asp
               1875                    1880                    1885

Leu  Asp  Ser  Asp  Glu
     1890
```

( 2 ) INFORMATION FOR SEQ ID NO:12:

( i ) SEQUENCE CHARACTERISTICS:
    ( A ) LENGTH: 3182 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:

( A ) NAME/KEY: CDS
( B ) LOCATION: 972..3002

( x i ) SEQUENCE DESCRIPTION: SEQ ID NO:12:

| | | | | | |
|---|---|---|---|---|---|
| CGAGTTTTTT | TTTTTTTTT | TTTTACAAGA | GCACAAATCC | ACATTTATTT | ATTGATTTTT | 60 |
| CGTTAGTTTA | AATCCTTGAG | GGGTACAGCA | TCACTCGGAT | TCTGTGTCCA | ATGGCCTTAG | 120 |
| CAGGAAGATT | GCTTCGGAAT | TTGGCACGAA | CCATGCCACT | GTTTCCATGG | GCCCGAGTTA | 180 |
| CTTTTCCCCA | GATGACTCTG | GTTTTGTTTG | GTTTGCCGCC | AGGAGTGACT | GTGTTGTTCT | 240 |
| TTGCTTTATA | TACATAAGCG | CATCTCTTGC | CCAAATAGAA | TTCTGTTTCA | TCTCGGGCGT | 300 |
| AAACACCTTC | AATTTTAAGA | AGAGCTGTGT | GCTCCCTTTG | GTTCCGGAGA | CCCCGCTTAT | 360 |
| AGCCAGCAAA | AATGGCCTTG | GACCACAGCC | TTCCAGACAT | AGTTCCTTTT | AGAAGTCCCG | 420 |
| TTCCAGCAG | GCCTCCACAG | GAGCCAAGAT | GGCGCCGAGC | CGGGTGAGCA | GCGTCTCGGC | 480 |
| TGCCGCTAGA | GTTTTCCTGC | TCCCCGCGCT | CGGGTGGCGG | GGGCGGGTCT | GAGTGGTACC | 540 |
| CCGGAGGAGA | CCCTTTGAAG | GTCCCTTGTG | GGGACTGGAA | AGAGGACGGT | TGGTTGTGTG | 600 |
| TCTGTGCTCG | TGGGGACCCC | GTGTGTGTGC | CTGCATTGGA | GAGATGTTGC | AGGAGATGGG | 660 |
| GTGGGCTCTC | TGAACCTCCT | TTCGCGCTGC | CCGGGGATCT | TCGACCTGCT | TCTCTGCTGG | 720 |
| GATCTCGCTT | AAGTTAACCC | TTCCCTGGGA | CGCCTTCCTG | CCGCCTCCAC | TGATCTGAGG | 780 |
| AGATCCTGTG | ACTGTAGCGT | GTTTTATGAG | CCTTTACTGG | CAGAGGGTAC | CGCCGGGTAT | 840 |
| TGAAGGATTC | GTAGGAGTTC | GCCAGGGAAG | TGGACACGA | CCCCCTCTTG | TAAACCCGGC | 900 |
| GCCAGGCACA | GAGGTCTCCG | TCTCTCCACC | GGGGGCTTCA | TCCTTCCAGG | GAGGAGAAGA | 960 |

```
GGGACTCCAG A ATG GCT GAG GAG AAG AAG CTG AAG CTT AGC AAC ACT GTG          1010
           Met Ala Glu Glu Lys Lys Leu Lys Leu Ser Asn Thr Val
             1               5                      10

CTG CCC TCG GAG TCC ATG AAG GTG GTG GCT GAA TCC ATG GGC ATC GCC          1058
Leu Pro Ser Glu Ser Met Lys Val Val Ala Glu Ser Met Gly Ile Ala
     15                  20                  25

CAG ATT CAG GAG GAG ACC TGC CAG CTG CTA ACG GAT GAG GTC AGC TAC          1106
Gln Ile Gln Glu Glu Thr Cys Gln Leu Leu Thr Asp Glu Val Ser Tyr
 30              35                  40                  45

CGC ATC AAA GAG ATC GCA CAG GAT GCC TTG AAG TTC ATG CAC ATG GGG          1154
Arg Ile Lys Glu Ile Ala Gln Asp Ala Leu Lys Phe Met His Met Gly
             50                  55                  60

AAG CGG CAG AAG CTC ACC ACC AGT GAC ATT GAC TAC GCC TTG AAG CTA          1202
Lys Arg Gln Lys Leu Thr Thr Ser Asp Ile Asp Tyr Ala Leu Lys Leu
         65                  70                  75

AAG AAT GTC GAG CCA CTC TAT GGC TTC CAC GCC CAG GAG TTC ATT CCT          1250
Lys Asn Val Glu Pro Leu Tyr Gly Phe His Ala Gln Glu Phe Ile Pro
             80                  85                  90

TTC CGC TTC GCC TCT GGT GGG GGC CGG GAG CTT TAC TTC TAT GAG GAG          1298
Phe Arg Phe Ala Ser Gly Gly Gly Arg Glu Leu Tyr Phe Tyr Glu Glu
 95                 100                 105

AAG GAG GTT GAT CTG AGC GAC ATC ATC AAT ACC CCT CTG CCC CGG GTG          1346
Lys Glu Val Asp Leu Ser Asp Ile Ile Asn Thr Pro Leu Pro Arg Val
110                 115                 120                 125

CCC CTG GAC GTC TGC CTC AAA GCT CAT TGG CTG AGC ATC GAG GGC TGC          1394
Pro Leu Asp Val Cys Leu Lys Ala His Trp Leu Ser Ile Glu Gly Cys
                130                 135                 140

CAG CCA GCT ATC CCC GAG AAC CCG CCC CCA GCT CCC AAA GAG CAA CAG          1442
Gln Pro Ala Ile Pro Glu Asn Pro Pro Pro Ala Pro Lys Glu Gln Gln
                145                 150                 155

AAG GCT GAA GCC ACA GAA CCC CTG AAG TCA GCC AAG CCA GGC CAG GAG          1490
Lys Ala Glu Ala Thr Glu Pro Leu Lys Ser Ala Lys Pro Gly Gln Glu
160                 165                 170
```

| | | | | | | | | | | | | | | | | |
|---|---|---|---|---|---|---|---|---|---|---|---|---|---|---|---|---|
| GAA | GAC | GGA | CCC | CTG | AAG | GGC | AAA | GGT | CAA | GGG | GCC | ACC | ACA | GCC | GAC | 1538 |
| Glu | Asp | Gly | Pro | Leu | Lys | Gly | Lys | Gly | Gln | Gly | Ala | Thr | Thr | Ala | Asp | |
| | 175 | | | | 180 | | | | | 185 | | | | | | |
| GGC | AAA | GGG | AAA | GAG | AAG | AAG | GCG | CCG | CCC | TTG | CTG | GAG | GGG | GCC | CCC | 1586 |
| Gly | Lys | Gly | Lys | Glu | Lys | Lys | Ala | Pro | Pro | Leu | Leu | Glu | Gly | Ala | Pro | |
| 190 | | | | | 195 | | | | 200 | | | | | 205 | | |
| TTG | CGA | CTG | AAG | CCC | CGG | AGC | ATC | CAC | GAG | TTG | TCT | GTG | GAG | CAG | CAG | 1634 |
| Leu | Arg | Leu | Lys | Pro | Arg | Ser | Ile | His | Glu | Leu | Ser | Val | Glu | Gln | Gln | |
| | | | | 210 | | | | 215 | | | | | 220 | | | |
| CTC | TAC | TAC | AAG | GAG | ATC | ACC | GAG | GCC | TGC | GTG | GGC | TCC | TGC | GAG | GCC | 1682 |
| Leu | Tyr | Tyr | Lys | Glu | Ile | Thr | Glu | Ala | Cys | Val | Gly | Ser | Cys | Glu | Ala | |
| | | | 225 | | | | 230 | | | | | 235 | | | | |
| AAG | AGG | GCG | GAA | GCC | CTG | CAA | AGC | ATT | GCC | ACG | GAC | CCT | GGA | CTG | TAT | 1730 |
| Lys | Arg | Ala | Glu | Ala | Leu | Gln | Ser | Ile | Ala | Thr | Asp | Pro | Gly | Leu | Tyr | |
| | | 240 | | | | 245 | | | | | 250 | | | | | |
| CAG | ATG | CTG | CCA | CGG | TTC | AGT | ACC | TTT | ATC | TCG | GAG | GGG | GTC | CGT | GTG | 1778 |
| Gln | Met | Leu | Pro | Arg | Phe | Ser | Thr | Phe | Ile | Ser | Glu | Gly | Val | Arg | Val | |
| | 255 | | | | | 260 | | | | | 265 | | | | | |
| AAC | GTG | GTT | CAG | AAC | AAC | CTG | GCC | CTA | CTC | ATC | TAC | CTG | ATG | CGT | ATG | 1826 |
| Asn | Val | Val | Gln | Asn | Asn | Leu | Ala | Leu | Leu | Ile | Tyr | Leu | Met | Arg | Met | |
| 270 | | | | | 275 | | | | | 280 | | | | | 285 | |
| GTG | AAA | GCG | CTG | ATG | GAC | AAC | CCC | ACG | CTC | TAT | CTA | GAA | AAA | TAC | GTC | 1874 |
| Val | Lys | Ala | Leu | Met | Asp | Asn | Pro | Thr | Leu | Tyr | Leu | Glu | Lys | Tyr | Val | |
| | | | | 290 | | | | | 295 | | | | | 300 | | |
| CAT | GAG | CTG | ATT | CCA | GCT | GTG | ATG | ACC | TGC | ATC | GTG | AGC | AGA | CAG | TTG | 1922 |
| His | Glu | Leu | Ile | Pro | Ala | Val | Met | Thr | Cys | Ile | Val | Ser | Arg | Gln | Leu | |
| | | | 305 | | | | | 310 | | | | | 315 | | | |
| TGC | CTG | CGA | CCA | GAT | GTG | GAC | AAT | CAC | TGG | GCA | CTC | CGA | GAC | TTT | GCT | 1970 |
| Cys | Leu | Arg | Pro | Asp | Val | Asp | Asn | His | Trp | Ala | Leu | Arg | Asp | Phe | Ala | |
| | | 320 | | | | | 325 | | | | | 330 | | | | |
| GCC | CGC | CTG | GTG | GCC | CAG | ATC | TGC | AAG | CAT | TTT | AGC | ACA | ACC | ACT | AAC | 2018 |
| Ala | Arg | Leu | Val | Ala | Gln | Ile | Cys | Lys | His | Phe | Ser | Thr | Thr | Thr | Asn | |
| | 335 | | | | | 340 | | | | | 345 | | | | | |
| AAC | ATC | CAG | TCC | CGG | ATC | ACC | AAG | ACC | TTC | ACC | AAG | AGC | TGG | GTG | GAC | 2066 |
| Asn | Ile | Gln | Ser | Arg | Ile | Thr | Lys | Thr | Phe | Thr | Lys | Ser | Trp | Val | Asp | |
| 350 | | | | | 355 | | | | | 360 | | | | | 365 | |
| GAG | AAG | ACG | CCC | TGG | ACG | ACT | CGT | TAT | GGC | TCC | ATC | GCA | GGC | TTG | GCT | 2114 |
| Glu | Lys | Thr | Pro | Trp | Thr | Thr | Arg | Tyr | Gly | Ser | Ile | Ala | Gly | Leu | Ala | |
| | | | | 370 | | | | | 375 | | | | | 380 | | |
| GAG | CTG | GGA | CAC | GAT | GTT | ATC | AAG | ACT | CTG | ATT | CTG | CCC | CGG | CTG | CAG | 2162 |
| Glu | Leu | Gly | His | Asp | Val | Ile | Lys | Thr | Leu | Ile | Leu | Pro | Arg | Leu | Gln | |
| | | | 385 | | | | | 390 | | | | | 395 | | | |
| CAG | GAA | GGG | GAG | CGG | ATC | CGC | AGT | GTG | CTG | GAC | GGC | CCT | GTG | CTG | AGC | 2210 |
| Gln | Glu | Gly | Glu | Arg | Ile | Arg | Ser | Val | Leu | Asp | Gly | Pro | Val | Leu | Ser | |
| | | 400 | | | | | 405 | | | | | 410 | | | | |
| AAC | ATT | GAC | CGG | ATT | GGA | GCA | GAC | CAT | GTG | CAG | AGC | CTC | CTG | CTG | AAA | 2258 |
| Asn | Ile | Asp | Arg | Ile | Gly | Ala | Asp | His | Val | Gln | Ser | Leu | Leu | Leu | Lys | |
| | 415 | | | | | 420 | | | | | 425 | | | | | |
| CAC | TGT | GCT | CCT | GTT | CTG | GCA | AAG | CTG | CGC | CCA | CCG | CCT | GAC | AAT | CAG | 2306 |
| His | Cys | Ala | Pro | Val | Leu | Ala | Lys | Leu | Arg | Pro | Pro | Pro | Asp | Asn | Gln | |
| 430 | | | | | 435 | | | | | 440 | | | | | 445 | |
| GAC | GCC | TAT | CGG | GCA | GAA | TTC | GGG | TCC | CTT | GGG | CCC | CTC | CTC | TGC | TCC | 2354 |
| Asp | Ala | Tyr | Arg | Ala | Glu | Phe | Gly | Ser | Leu | Gly | Pro | Leu | Leu | Cys | Ser | |
| | | | | 450 | | | | | 455 | | | | | 460 | | |
| CAG | GTG | GTC | AAG | GCT | CGG | GCC | CAG | GCT | GCT | CTG | CAG | GCT | CAG | CAG | GTC | 2402 |
| Gln | Val | Val | Lys | Ala | Arg | Ala | Gln | Ala | Ala | Leu | Gln | Ala | Gln | Gln | Val | |
| | | | 465 | | | | | 470 | | | | | 475 | | | |
| AAC | AGG | ACC | ACT | CTG | ACC | ATC | ACG | CAG | CCC | CGG | CCC | ACG | CTG | ACC | CTC | 2450 |
| Asn | Arg | Thr | Thr | Leu | Thr | Ile | Thr | Gln | Pro | Arg | Pro | Thr | Leu | Thr | Leu | |
| | | 480 | | | | | 485 | | | | | 490 | | | | |

| | | | | | | | | | | | | | | | | |
|---|---|---|---|---|---|---|---|---|---|---|---|---|---|---|---|---|
|TCG|CAG|GCC|CCA|CAG|CCT|GGC|CCT|CGC|ACC|CCT|GGC|TTG|CTG|AAG|GTT|2498|
|Ser|Gln|Ala|Pro|Gln|Pro|Gly|Pro|Arg|Thr|Pro|Gly|Leu|Leu|Lys|Val| |
| |495| | | |500| | | | |505| | | | | | |

| | | | | | | | | | | | | | | | | |
|---|---|---|---|---|---|---|---|---|---|---|---|---|---|---|---|---|
|CCT|GGC|TCC|ATC|GCA|CTT|CCT|GTC|CAG|ACA|CTG|GTG|TCT|GCA|CGA|GCG|2546|
|Pro|Gly|Ser|Ile|Ala|Leu|Pro|Val|Gln|Thr|Leu|Val|Ser|Ala|Arg|Ala| |
|510| | | | |515| | | | |520| | | | |525| |

| | | | | | | | | | | | | | | | | |
|---|---|---|---|---|---|---|---|---|---|---|---|---|---|---|---|---|
|GCT|GCC|CCA|CCA|CAG|CCT|TCC|CCT|CCT|CCA|ACC|AAG|TTT|ATT|GTA|ATG|2594|
|Ala|Ala|Pro|Pro|Gln|Pro|Ser|Pro|Pro|Pro|Thr|Lys|Phe|Ile|Val|Met| |
| | | | |530| | | | |535| | | | |540| | |

| | | | | | | | | | | | | | | | | |
|---|---|---|---|---|---|---|---|---|---|---|---|---|---|---|---|---|
|TCA|TCG|TCC|TCC|AGC|GCC|CCA|TCC|ACC|CAG|CAG|GTC|CTG|TCC|CTC|AGC|2642|
|Ser|Ser|Ser|Ser|Ser|Ala|Pro|Ser|Thr|Gln|Gln|Val|Leu|Ser|Leu|Ser| |
| | | | |545| | | | |550| | | | |555| | |

| | | | | | | | | | | | | | | | | |
|---|---|---|---|---|---|---|---|---|---|---|---|---|---|---|---|---|
|ACC|TCG|GCC|CCC|GGC|TCA|GGT|TCC|ACC|ACC|ACT|TCG|CCC|GTC|ACC|ACC|2690|
|Thr|Ser|Ala|Pro|Gly|Ser|Gly|Ser|Thr|Thr|Thr|Ser|Pro|Val|Thr|Thr| |
| | | |560| | | | |565| | | | |570| | | |

| | | | | | | | | | | | | | | | | |
|---|---|---|---|---|---|---|---|---|---|---|---|---|---|---|---|---|
|ACC|GTC|CCC|AGC|GTG|CAG|CCC|ATC|GTC|AAG|TTG|GTC|TCC|ACC|GCC|ACC|2738|
|Thr|Val|Pro|Ser|Val|Gln|Pro|Ile|Val|Lys|Leu|Val|Ser|Thr|Ala|Thr| |
| |575| | | | |580| | | | |585| | | | | |

| | | | | | | | | | | | | | | | | |
|---|---|---|---|---|---|---|---|---|---|---|---|---|---|---|---|---|
|ACC|GCA|CCC|CCC|AGC|ACT|GCT|CCC|TCT|GGT|CCT|GGG|AGT|GTC|CAG|AAG|2786|
|Thr|Ala|Pro|Pro|Ser|Thr|Ala|Pro|Ser|Gly|Pro|Gly|Ser|Val|Gln|Lys| |
|590| | | | |595| | | | |600| | | | |605| |

| | | | | | | | | | | | | | | | | |
|---|---|---|---|---|---|---|---|---|---|---|---|---|---|---|---|---|
|TAC|ATC|GTG|GTC|TCA|CTT|CCC|CCA|ACA|GGG|GAG|GGC|AAA|GGA|GGC|CCC|2834|
|Tyr|Ile|Val|Val|Ser|Leu|Pro|Pro|Thr|Gly|Glu|Gly|Lys|Gly|Gly|Pro| |
| | | | |610| | | | |615| | | | |620| | |

| | | | | | | | | | | | | | | | | |
|---|---|---|---|---|---|---|---|---|---|---|---|---|---|---|---|---|
|ACC|TCC|CAT|CCT|TCT|CCA|GTT|CCT|CCC|CCG|GCA|TCG|TCC|CCG|TCC|CCA|2882|
|Thr|Ser|His|Pro|Ser|Pro|Val|Pro|Pro|Pro|Ala|Ser|Ser|Pro|Ser|Pro| |
| | |625| | | | |630| | | | |635| | | | |

| | | | | | | | | | | | | | | | | |
|---|---|---|---|---|---|---|---|---|---|---|---|---|---|---|---|---|
|CTC|AGC|GGC|AGT|GCC|CTT|TGT|GGG|GGG|AAG|CAG|GAG|GCT|GGG|GAC|AGT|2930|
|Leu|Ser|Gly|Ser|Ala|Leu|Cys|Gly|Gly|Lys|Gln|Glu|Ala|Gly|Asp|Ser| |
| | |640| | | | |645| | | | |650| | | | |

| | | | | | | | | | | | | | | | | |
|---|---|---|---|---|---|---|---|---|---|---|---|---|---|---|---|---|
|CCC|CCT|CCA|GCT|CCA|GGG|ACT|CCA|AAA|GCC|AAT|GGC|TCC|CAG|CCC|AAC|2978|
|Pro|Pro|Pro|Ala|Pro|Gly|Thr|Pro|Lys|Ala|Asn|Gly|Ser|Gln|Pro|Asn| |
|655| | | | |660| | | | |665| | | | | | |

| | | | | | | | | |
|---|---|---|---|---|---|---|---|---|
|TCC|GGC|TCC|CCT|CAG|CCT|GCT|CCG|TGATGCTCCA CCTGCCAGCC CCCGGATTCC|3032|
|Ser|Gly|Ser|Pro|Gln|Pro|Ala|Pro| |
|670| | | |675| | | | |

CACACATGCA GACATGTACA CACGTGCACG TACACACATG CATGCTCGCT AAGCGGAAGG    3092

AAGTTGTAGA TTGCTTCCTT CATGTCACTT TCTTTTTAGA TATTGTACAG CCAGTTTCTC    3152

AGAATAAAAG TTTGGTTTGT AAAAAAAAAA    3182

( 2 ) INFORMATION FOR SEQ ID NO:13:

( i ) SEQUENCE CHARACTERISTICS:
        ( A ) LENGTH: 677 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
|Met|Ala|Glu|Glu|Lys|Lys|Leu|Lys|Leu|Ser|Asn|Thr|Val|Leu|Pro|Ser|
|1| | | |5| | | | |10| | | | |15|

| | | | | | | | | | | | | | | |
|---|---|---|---|---|---|---|---|---|---|---|---|---|---|---|
|Glu|Ser|Met|Lys|Val|Val|Ala|Glu|Ser|Met|Gly|Ile|Ala|Gln|Ile|Gln|
| | | |20| | | | |25| | | | |30| | |

| | | | | | | | | | | | | | | |
|---|---|---|---|---|---|---|---|---|---|---|---|---|---|---|
|Glu|Glu|Thr|Cys|Gln|Leu|Leu|Thr|Asp|Glu|Val|Ser|Tyr|Arg|Ile|Lys|
| | |35| | | | |40| | | | |45| | | |

| | | | | | | | | | | | | | | |
|---|---|---|---|---|---|---|---|---|---|---|---|---|---|---|
|Glu|Ile|Ala|Gln|Asp|Ala|Leu|Lys|Phe|Met|His|Met|Gly|Lys|Arg|Gln|
| |50| | | | |55| | | | |60| | | | |

| | | | | | | | | | | | | | | |
|---|---|---|---|---|---|---|---|---|---|---|---|---|---|---|
|Lys|Leu|Thr|Thr|Ser|Asp|Ile|Asp|Tyr|Ala|Leu|Lys|Leu|Lys|Asn|Val|

| | | | | 65 | | | | | 70 | | | | | 75 | | | | | 80 |
|---|---|---|---|---|---|---|---|---|---|---|---|---|---|---|---|---|---|---|---|

Glu Pro Leu Tyr Gly Phe His Ala Gln Glu Phe Ile Pro Phe Arg Phe
                    85                    90                    95

Ala Ser Gly Gly Gly Arg Glu Leu Tyr Phe Tyr Glu Glu Lys Glu Val
            100                   105                110

Asp Leu Ser Asp Ile Ile Asn Thr Pro Leu Pro Arg Val Pro Leu Asp
            115                   120                125

Val Cys Leu Lys Ala His Trp Leu Ser Ile Glu Gly Cys Gln Pro Ala
    130                   135                140

Ile Pro Glu Asn Pro Pro Pro Ala Pro Lys Glu Gln Gln Lys Ala Glu
145                 150                   155                   160

Ala Thr Glu Pro Leu Lys Ser Ala Lys Pro Gly Gln Glu Glu Asp Gly
                165                   170                   175

Pro Leu Lys Gly Lys Gly Gln Gly Ala Thr Thr Ala Asp Gly Lys Gly
            180                   185                   190

Lys Glu Lys Lys Ala Pro Pro Leu Leu Glu Gly Ala Pro Leu Arg Leu
        195                   200                   205

Lys Pro Arg Ser Ile His Glu Leu Ser Val Glu Gln Gln Leu Tyr Tyr
    210                   215                   220

Lys Glu Ile Thr Glu Ala Cys Val Gly Ser Cys Glu Ala Lys Arg Ala
225                   230                   235                   240

Glu Ala Leu Gln Ser Ile Ala Thr Asp Pro Gly Leu Tyr Gln Met Leu
                245                   250                   255

Pro Arg Phe Ser Thr Phe Ile Ser Glu Gly Val Arg Val Asn Val Val
                260                   265                   270

Gln Asn Asn Leu Ala Leu Leu Ile Tyr Leu Met Arg Met Val Lys Ala
            275                   280                   285

Leu Met Asp Asn Pro Thr Leu Tyr Leu Glu Lys Tyr Val His Glu Leu
    290                   295                   300

Ile Pro Ala Val Met Thr Cys Ile Val Ser Arg Gln Leu Cys Leu Arg
305                   310                   315                   320

Pro Asp Val Asp Asn His Trp Ala Leu Arg Asp Phe Ala Ala Arg Leu
                325                   330                   335

Val Ala Gln Ile Cys Lys His Phe Ser Thr Thr Thr Asn Asn Ile Gln
            340                   345                   350

Ser Arg Ile Thr Lys Thr Phe Thr Lys Ser Trp Val Asp Glu Lys Thr
        355                   360                   365

Pro Trp Thr Thr Arg Tyr Gly Ser Ile Ala Gly Leu Ala Glu Leu Gly
    370                   375                   380

His Asp Val Ile Lys Thr Leu Ile Leu Pro Arg Leu Gln Gln Glu Gly
385                   390                   395                   400

Glu Arg Ile Arg Ser Val Leu Asp Gly Pro Val Leu Ser Asn Ile Asp
                405                   410                   415

Arg Ile Gly Ala Asp His Val Gln Ser Leu Leu Leu Lys His Cys Ala
            420                   425                   430

Pro Val Leu Ala Lys Leu Arg Pro Pro Asp Asn Gln Asp Ala Tyr
        435                   440                   445

Arg Ala Glu Phe Gly Ser Leu Gly Pro Leu Leu Cys Ser Gln Val Val
    450                   455                   460

Lys Ala Arg Ala Gln Ala Ala Leu Gln Ala Gln Gln Val Asn Arg Thr
465                   470                   475                   480

Thr Leu Thr Ile Thr Gln Pro Arg Pro Thr Leu Thr Leu Ser Gln Ala
                485                   490                   495

```
Pro  Gln  Pro  Gly  Pro  Arg  Thr  Pro  Gly  Leu  Leu  Lys  Val  Pro  Gly  Ser
               500                 505                      510

Ile  Ala  Leu  Pro  Val  Gln  Thr  Leu  Val  Ser  Ala  Arg  Ala  Ala  Ala  Pro
               515                 520                 525

Pro  Gln  Pro  Ser  Pro  Pro  Pro  Thr  Lys  Phe  Ile  Val  Met  Ser  Ser  Ser
          530                 535                      540

Ser  Ser  Ala  Pro  Ser  Thr  Gln  Gln  Val  Leu  Ser  Leu  Ser  Thr  Ser  Ala
545                           550                 555                      560

Pro  Gly  Ser  Gly  Ser  Thr  Thr  Thr  Ser  Pro  Val  Thr  Thr  Thr  Val  Pro
                    565                      570                      575

Ser  Val  Gln  Pro  Ile  Val  Lys  Leu  Val  Ser  Thr  Ala  Thr  Thr  Ala  Pro
               580                 585                      590

Pro  Ser  Thr  Ala  Pro  Ser  Gly  Pro  Gly  Ser  Val  Gln  Lys  Tyr  Ile  Val
          595                      600                      605

Val  Ser  Leu  Pro  Pro  Thr  Gly  Glu  Gly  Lys  Gly  Gly  Pro  Thr  Ser  His
     610                      615                      620

Pro  Ser  Pro  Val  Pro  Pro  Pro  Ala  Ser  Ser  Pro  Ser  Pro  Leu  Ser  Gly
625                      630                      635                      640

Ser  Ala  Leu  Cys  Gly  Gly  Lys  Gln  Glu  Ala  Gly  Asp  Ser  Pro  Pro  Pro
                    645                      650                      655

Ala  Pro  Gly  Thr  Pro  Lys  Ala  Asn  Gly  Ser  Gln  Pro  Asn  Ser  Gly  Ser
               660                      665                      670

Pro  Gln  Pro  Ala  Pro
               675
```

(2) INFORMATION FOR SEQ ID NO:14:

(i) SEQUENCE CHARACTERISTICS:
        (A) LENGTH: 1872 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met  Gly  Pro  Gly  Cys  Asp  Leu  Leu  Leu  Arg  Thr  Ala  Ala  Thr  Ile  Thr
1                   5                        10                       15

Ala  Ala  Ala  Ile  Met  Ser  Asp  Thr  Asp  Ser  Asp  Glu  Asp  Ser  Ala  Gly
               20                  25                       30

Gly  Gly  Pro  Phe  Ser  Leu  Ala  Gly  Phe  Leu  Phe  Gly  Asn  Ile  Asn  Gly
          35                      40                       45

Ala  Gly  Gln  Leu  Glu  Gly  Glu  Ser  Val  Leu  Asp  Glu  Cys  Lys  Lys
     50                       55                       60

His  Leu  Ala  Gly  Leu  Gly  Ala  Leu  Gly  Leu  Gly  Ser  Leu  Ile  Thr  Glu
65                            70                       75                  80

Leu  Thr  Ala  Asn  Glu  Glu  Leu  Thr  Gly  Thr  Asp  Gly  Ala  Leu  Val  Asn
                    85                       90                       95

Asp  Glu  Gly  Trp  Val  Arg  Ser  Thr  Glu  Asp  Ala  Val  Asp  Tyr  Ser  Asp
                    100                      105                      110

Ile  Asn  Glu  Val  Ala  Glu  Asp  Glu  Ser  Arg  Arg  Tyr  Gln  Gln  Thr  Met
          115                      120                      125

Gly  Ser  Leu  Gln  Pro  Leu  Cys  His  Ser  Asp  Tyr  Asp  Glu  Asp  Asp  Tyr
     130                      135                      140

Asp  Ala  Asp  Cys  Glu  Asp  Ile  Asp  Cys  Lys  Leu  Met  Pro  Pro  Pro  Pro
145                      150                      155                      160

Pro  Pro  Pro  Gly  Pro  Met  Lys  Lys  Asp  Lys  Asp  Gln  Asp  Ser  Ile  Thr
```

|     |     |     |     |     |     |     | 165 |     |     |     | 170 |     |     |     | 175 |
| --- | --- | --- | --- | --- | --- | --- | --- | --- | --- | --- | --- | --- | --- | --- | --- |

Gly Glu Lys Val Asp Phe Ser Ser Ser Ser Asp Ser Glu Ser Glu Met
            180                 185             190

Gly Pro Gln Glu Ala Thr Gln Ala Glu Ser Glu Asp Gly Lys Leu Thr
        195                 200             205

Leu Pro Leu Ala Gly Ile Met Gln His Asp Ala Thr Lys Leu Leu Pro
        210             215             220

Ser Val Thr Glu Leu Phe Pro Glu Phe Arg Pro Gly Lys Val Leu Arg
225                 230             235                         240

Phe Leu Arg Leu Phe Gly Pro Gly Lys Asn Val Pro Ser Val Trp Arg
                245                 250                 255

Ser Ala Arg Arg Lys Arg Lys Lys Lys His Arg Glu Leu Ile Gln Glu
            260                 265             270

Glu Gln Ile Gln Glu Val Glu Cys Ser Val Glu Ser Glu Val Ser Gln
        275                 280             285

Lys Ser Leu Trp Asn Tyr Asp Tyr Ala Pro Pro Pro Pro Glu Gln
    290                 295             300

Cys Leu Ser Asp Asp Glu Ile Thr Met Met Ala Pro Val Glu Ser Lys
305                 310             315                         320

Phe Ser Gln Ser Thr Gly Asp Ile Asp Lys Val Thr Asp Thr Lys Pro
                325             330             335

Arg Val Ala Glu Trp Arg Tyr Gly Pro Ala Arg Leu Trp Tyr Asp Met
            340                 345             350

Leu Gly Val Pro Glu Asp Gly Ser Gly Phe Asp Tyr Gly Phe Lys Leu
        355                 360             365

Arg Lys Thr Glu His Glu Pro Val Ile Lys Ser Arg Met Ile Glu Glu
370                 375             380

Phe Arg Lys Leu Glu Glu Asn Asn Gly Thr Asp Leu Leu Ala Asp Glu
385                 390             395                         400

Asn Phe Leu Met Val Thr Gln Leu His Trp Glu Asp Asp Ile Ile Trp
            405                 410             415

Asp Gly Glu Asp Val Lys His Lys Gly Thr Lys Pro Gln Arg Ala Ser
            420                 425             430

Leu Ala Gly Trp Leu Pro Ser Ser Met Thr Arg Asn Ala Met Ala Tyr
            435             440             445

Asn Val Gln Gln Gly Phe Ala Ala Thr Leu Asp Asp Lys Pro Trp
450                 455             460

Tyr Ser Ile Phe Pro Ile Asp Asn Glu Asp Leu Val Tyr Gly Arg Trp
465                 470             475                         480

Glu Asp Asn Ile Ile Trp Asp Ala Gln Ala Met Pro Arg Leu Leu Glu
            485             490             495

Pro Pro Val Leu Thr Leu Asp Pro Asn Asp Glu Asn Leu Ile Leu Glu
            500             505             510

Ile Pro Asp Glu Lys Glu Glu Ala Thr Ser Asn Ser Pro Ser Lys Glu
        515             520             525

Ser Lys Lys Glu Ser Ser Leu Lys Lys Ser Arg Ile Leu Leu Gly Lys
        530             535             540

Thr Gly Val Ile Lys Glu Glu Pro Gln Gln Asn Met Ser Gln Pro Glu
545             550             555                         560

Val Lys Asp Pro Trp Asn Leu Ser Asn Asp Glu Tyr Tyr Tyr Pro Lys
            565                 570             575

Gln Gln Gly Leu Arg Gly Thr Phe Gly Gly Asn Ile Ile Gln His Ser
        580             585             590

```
Ile  Pro  Ala  Val  Glu  Leu  Arg  Gln  Pro  Phe  Phe  Pro  Thr  His  Met  Gly
     595                 600                      605

Pro  Ile  Lys  Leu  Arg  Gln  Phe  His  Arg  Pro  Pro  Leu  Lys  Lys  Tyr  Ser
     610                 615                      620

Phe  Gly  Ala  Leu  Ser  Gln  Pro  Gly  Pro  His  Ser  Val  Gln  Pro  Leu  Leu
625                      630                 635                           640

Lys  His  Ile  Lys  Lys  Lys  Ala  Lys  Met  Arg  Glu  Gln  Glu  Arg  Gln  Ala
               645                      650                           655

Ser  Gly  Gly  Gly  Glu  Met  Phe  Phe  Met  Arg  Thr  Pro  Gln  Asp  Leu  Thr
               660                 665                      670

Gly  Lys  Asp  Gly  Asp  Leu  Ile  Leu  Ala  Glu  Tyr  Ser  Glu  Glu  Asn  Gly
          675                 680                      685

Pro  Leu  Met  Met  Gln  Val  Gly  Met  Ala  Thr  Lys  Ile  Lys  Asn  Tyr  Tyr
     690                 695                      700

Lys  Arg  Lys  Pro  Gly  Lys  Asp  Pro  Gly  Ala  Pro  Asp  Cys  Lys  Tyr  Gly
705                      710                 715                           720

Glu  Thr  Val  Tyr  Cys  His  Thr  Ser  Pro  Phe  Leu  Gly  Ser  Leu  His  Pro
               725                 730                           735

Gly  Gln  Leu  Leu  Gln  Ala  Phe  Glu  Asn  Asn  Leu  Phe  Arg  Ala  Pro  Ile
               740                 745                      750

Tyr  Leu  His  Lys  Met  Pro  Glu  Thr  Asp  Phe  Leu  Ile  Ile  Arg  Thr  Arg
          755                 760                      765

Gln  Gly  Tyr  Tyr  Ile  Arg  Glu  Leu  Val  Asp  Ile  Phe  Val  Val  Gly  Gln
     770                 775                      780

Gln  Cys  Pro  Leu  Phe  Glu  Val  Pro  Gly  Pro  Asn  Ser  Lys  Arg  Ala  Asn
785                      790                 795                           800

Thr  His  Ile  Arg  Asp  Phe  Leu  Gln  Val  Phe  Ile  Tyr  Arg  Leu  Phe  Trp
                    805                 810                      815

Lys  Ser  Lys  Asp  Arg  Pro  Arg  Arg  Ile  Arg  Met  Glu  Asp  Ile  Lys  Lys
               820                 825                      830

Ala  Phe  Pro  Ser  His  Ser  Glu  Ser  Ser  Ile  Arg  Lys  Arg  Leu  Lys  Leu
          835                 840                      845

Cys  Ala  Asp  Phe  Lys  Arg  Thr  Gly  Met  Asp  Ser  Asn  Trp  Trp  Val  Leu
850                      855                 860

Lys  Ser  Asp  Phe  Arg  Leu  Pro  Thr  Glu  Glu  Ile  Arg  Ala  Met  Val
865                      870                 875                           880

Ser  Pro  Glu  Gln  Cys  Cys  Ala  Tyr  Tyr  Ser  Met  Ile  Ala  Ala  Glu  Gln
                    885                 890                      895

Arg  Leu  Lys  Asp  Ala  Gly  Tyr  Gly  Glu  Lys  Ser  Phe  Phe  Ala  Pro  Glu
               900                 905                      910

Glu  Glu  Asn  Glu  Glu  Asp  Phe  Gln  Met  Lys  Ile  Asp  Asp  Glu  Val  Arg
               915                 920                      925

Thr  Ala  Pro  Trp  Asn  Thr  Thr  Arg  Ala  Phe  Ile  Ala  Ala  Met  Lys  Gly
          930                 935                      940

Lys  Cys  Leu  Leu  Glu  Val  Thr  Gly  Val  Ala  Asp  Pro  Thr  Gly  Cys  Gly
945                      950                 955                           960

Glu  Gly  Phe  Ser  Tyr  Val  Lys  Ile  Pro  Asn  Lys  Pro  Thr  Gln  Gln  Lys
               965                 970                           975

Asp  Asp  Lys  Glu  Pro  Gln  Pro  Val  Lys  Lys  Thr  Val  Thr  Gly  Thr  Asp
               980                 985                      990

Ala  Asp  Leu  Arg  Arg  Leu  Ser  Leu  Lys  Asn  Ala  Lys  Gln  Leu  Leu  Arg
               995                 1000                     1005

Lys  Phe  Gly  Val  Pro  Glu  Glu  Glu  Ile  Lys  Lys  Leu  Ser  Arg  Trp  Glu
     1010                1015                     1020
```

-continued

| | | | | | | | | | | | | | | |
|---|---|---|---|---|---|---|---|---|---|---|---|---|---|---|
Val | Ile | Asp | Val | Val | Arg | Thr | Met | Ser | Thr | Glu | Gln | Ala | Arg | Ser | Gly
1025 | | | | 1030 | | | | | 1035 | | | | | 1040

Glu Gly Pro Met Ser Lys Phe Ala Arg Gly Ser Arg Phe Ser Val Ala
                  1045                      1050                      1055

Glu His Gln Glu Arg Tyr Lys Glu Glu Cys Gln Arg Ile Phe Asp Leu
                1060                    1065                        1070

Gln Asn Lys Val Leu Ser Ser Thr Glu Val Leu Ser Thr Asp Thr Asp
            1075                    1080                    1085

Ser Ser Ser Ala Glu Asp Ser Asp Phe Glu Glu Met Gly Lys Asn Ile
        1090                    1095                    1100

Glu Asn Met Leu Gln Asn Lys Lys Thr Ser Ser Gln Leu Ser Arg Glu
1105                  1110                    1115                1120

Arg Glu Glu Gln Glu Arg Lys Glu Leu Gln Arg Met Leu Leu Ala Ala
                1125                    1130                    1135

Gly Ser Ala Ala Ser Gly Asn Asn His Arg Asp Asp Asp Thr Ala Ser
        1140                    1145                    1150

Val Thr Ser Leu Asn Ser Ser Ala Thr Gly Arg Cys Leu Lys Ile Tyr
            1155                    1160                    1165

Arg Thr Phe Arg Asp Glu Glu Gly Lys Glu Tyr Val Arg Cys Glu Thr
            1170                    1175                    1180

Val Arg Lys Pro Ala Val Ile Asp Ala Tyr Val Arg Ile Arg Thr Thr
1185                  1190                    1195                1200

Lys Asp Glu Glu Phe Ile Arg Lys Phe Ala Leu Phe Asp Glu Gln His
                1205                    1210                    1215

Arg Glu Glu Met Arg Lys Glu Arg Arg Arg Ile Gln Glu Gln Leu Arg
            1220                    1225                    1230

Arg Leu Lys Arg Asn Gln Glu Lys Glu Lys Leu Lys Gly Pro Pro Glu
            1235                    1240                    1245

Lys Lys Pro Lys Lys Met Lys Glu Arg Pro Asp Leu Lys Leu Lys Cys
        1250                    1255                    1260

Gly Ala Cys Gly Ala Ile Gly His Met Arg Thr Asn Lys Phe Cys Pro
1265                  1270                    1275                1280

Leu Tyr Tyr Gln Thr Asn Ala Pro Pro Ser Asn Pro Val Ala Met Thr
                1285                    1290                    1295

Glu Glu Gln Glu Glu Glu Leu Glu Lys Thr Val Ile His Asn Asp Asn
            1300                    1305                    1310

Glu Glu Leu Ile Lys Val Glu Gly Thr Lys Ile Val Leu Gly Lys Gln
            1315                    1320                    1325

Leu Ile Glu Ser Ala Asp Glu Val Arg Arg Lys Ser Leu Val Leu Lys
        1330                    1335                    1340

Phe Pro Lys Gln Gln Leu Pro Pro Lys Lys Lys Arg Arg Val Gly Thr
1345                  1350                    1355                1360

Thr Val His Cys Asp Tyr Leu Asn Arg Pro His Lys Ser Ile His Arg
                1365                    1370                    1375

Arg Arg Thr Asp Pro Met Val Thr Leu Ser Ser Ile Leu Glu Ser Ile
            1380                    1385                    1390

Ile Asn Asp Met Arg Asp Leu Pro Asn Thr Tyr Pro Phe His Thr Pro
        1395                    1400                    1405

Val Asn Ala Lys Val Val Lys Asp Tyr Tyr Lys Ile Ile Thr Arg Pro
        1410                    1415                    1420

Met Asp Leu Gln Thr Leu Arg Glu Asn Val Arg Lys Arg Leu Tyr Pro
1425                  1430                    1435                1440

Ser Arg Glu Glu Phe Arg Glu His Leu Glu Leu Ile Val Lys Asn Ser

```
                         1445                    1450                    1455

Ala Thr Tyr Asn Gly Pro Lys His Ser Leu Thr Gln Ile Ser Gln Ser
                    1460                    1465                1470

Met Leu Asp Leu Cys Asp Glu Lys Leu Lys Glu Lys Glu Asp Lys Leu
                    1475                    1480                1485

Ala Arg Leu Glu Lys Ala Ile Asn Pro Leu Leu Asp Asp Asp Asp Gln
                    1490                    1495                1500

Val Ala Phe Ser Phe Ile Leu Asp Asn Ile Val Thr Gln Lys Met Met
    1505                1510                1515                1520

Ala Val Pro Asp Ser Trp Pro Phe His His Pro Val Asn Lys Lys Phe
                    1525                    1530                1535

Val Pro Asp Tyr Tyr Lys Val Ile Val Asn Pro Met Asp Leu Glu Thr
                    1540                    1545                1550

Ile Arg Lys Asn Ile Ser Lys His Lys Tyr Gln Ser Arg Glu Ser Phe
                1555                    1560                1565

Leu Asp Asp Val Asn Leu Ile Leu Ala Asn Ser Val Lys Tyr Asn Gly
                1570                    1575                1580

Pro Glu Ser Gln Tyr Thr Lys Thr Ala Gln Glu Ile Val Asn Val Cys
    1585                1590                1595                1600

Tyr Gln Thr Leu Thr Glu Tyr Asp Glu His Leu Thr Gln Leu Glu Lys
                    1605                    1610                1615

Asp Ile Cys Thr Ala Lys Glu Ala Ala Leu Glu Glu Ala Glu Leu Glu
                    1620                    1625                1630

Ser Leu Asp Pro Met Thr Pro Gly Pro Tyr Thr Pro Gln Pro Pro Asp
                    1635                    1640                1645

Leu Tyr Asp Thr Asn Thr Ser Leu Ser Met Ser Arg Asp Ala Ser Val
                    1650                    1655                1660

Phe Gln Asp Glu Ser Asn Met Ser Val Leu Asp Ile Pro Ser Ala Thr
    1665                1670                1675                1680

Pro Glu Lys Gln Val Thr Gln Glu Gly Glu Asp Gly Asp Gly Asp Leu
                    1685                    1690                1695

Ala Asp Glu Glu Glu Gly Thr Val Gln Gln Pro Gln Ala Ser Val Leu
                    1700                    1705                1710

Tyr Glu Asp Leu Leu Met Ser Glu Gly Glu Asp Asp Glu Glu Asp Ala
                    1715                    1720                1725

Gly Ser Asp Glu Glu Gly Asp Asn Pro Phe Ser Ala Ile Gln Leu Ser
                1730                    1735                1740

Glu Ser Gly Ser Asp Ser Asp Val Gly Ser Gly Gly Ile Arg Pro Lys
    1745                1750                1755                1760

Gln Pro Arg Met Leu Gln Glu Asn Thr Arg Met Asp Met Glu Asn Glu
                    1765                    1770                1775

Glu Ser Met Met Ser Tyr Glu Gly Asp Gly Gly Glu Ala Ser His Gly
                    1780                    1785                1790

Leu Glu Asp Ser Asn Ile Ser Tyr Gly Ser Tyr Glu Glu Pro Asp Pro
                    1795                    1800                1805

Lys Ser Asn Thr Gln Asp Thr Ser Phe Ser Ser Ile Gly Gly Tyr Glu
                1810                    1815                1820

Val Ser Glu Glu Glu Glu Asp Glu Glu Glu Glu Gln Arg Ser Gly
    1825                1830                1835                1840

Pro Ser Val Leu Ser Gln Val His Leu Ser Glu Asp Glu Glu Asp Ser
                    1845                    1850                1855

Glu Asp Phe His Ser Ile Ala Gly Asp Ser Asp Leu Asp Ser Asp Glu
                    1860                    1865                1870
```

( 2 ) INFORMATION FOR SEQ ID NO:15:

( i ) SEQUENCE CHARACTERISTICS:
        ( A ) LENGTH: 3603 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2214

( x i ) SEQUENCE DESCRIPTION: SEQ ID NO:15:

```
AGA  GGT  GGT  GCA  GGC  GGC  GCC  CCC  GGC  GGC  GCA  GAC  CCT  GGC  GCC  AGC         48
Arg  Gly  Gly  Ala  Gly  Gly  Ala  Pro  Gly  Gly  Ala  Asp  Pro  Gly  Ala  Ser
  1                  5                           10                          15

GGC  CCG  GCC  AGC  ACG  GCG  GCC  AGC  ATG  GTC  ATC  GGG  CCA  ACT  ATG  CAA         96
Gly  Pro  Ala  Ser  Thr  Ala  Ala  Ser  Met  Val  Ile  Gly  Pro  Thr  Met  Gln
                20                          25                          30

GGG  CGC  TGC  CCA  GCC  CGG  CCG  CCG  TCC  CGC  CGC  CCG  CCC  CCG  GGA  CCC        144
Gly  Arg  Cys  Pro  Ala  Arg  Pro  Pro  Ser  Arg  Arg  Pro  Pro  Pro  Gly  Pro
            35                          40                          45

CCA  CCG  GGC  TGC  CCA  AAA  GGC  GCG  GCC  GGC  GCA  GTG  ACC  CAG  AGC  CTG        192
Pro  Pro  Gly  Cys  Pro  Lys  Gly  Ala  Ala  Gly  Ala  Val  Thr  Gln  Ser  Leu
       50                          55                          60

TCC  CGG  ACG  CCC  ACG  GCC  ACC  ACC  AGC  GGG  ATT  CGG  GCC  ACC  CTG  ACG        240
Ser  Arg  Thr  Pro  Thr  Ala  Thr  Thr  Ser  Gly  Ile  Arg  Ala  Thr  Leu  Thr
 65                          70                          75                  80

CCC  ACC  GTG  CTG  GCC  CCC  CGC  TTG  CCG  CAG  CCG  CCT  CAG  AAC  CCG  ACC        288
Pro  Thr  Val  Leu  Ala  Pro  Arg  Leu  Pro  Gln  Pro  Pro  Gln  Asn  Pro  Thr
                          85                          90                          95

AAC  ATC  CAG  AAC  TTC  CAG  CTG  CCC  CCA  GGA  ATG  GTC  CTC  GTC  CGA  AGT        336
Asn  Ile  Gln  Asn  Phe  Gln  Leu  Pro  Pro  Gly  Met  Val  Leu  Val  Arg  Ser
                100                         105                         110

GAG  AAT  GGG  CAG  TTG  TTA  ATG  ATT  CCT  CAG  CAG  GCC  TTG  GCC  CAG  ATG        384
Glu  Asn  Gly  Gln  Leu  Leu  Met  Ile  Pro  Gln  Gln  Ala  Leu  Ala  Gln  Met
            115                         120                         125

CAG  GCG  CAG  GCC  CAT  GCC  CAG  CCT  CAG  ACC  ACC  ATG  GCG  CCT  CGC  CCT        432
Gln  Ala  Gln  Ala  His  Ala  Gln  Pro  Gln  Thr  Thr  Met  Ala  Pro  Arg  Pro
       130                         135                         140

GCC  ACC  CCC  ACA  AGT  GCC  CCT  CCC  GTC  CAG  ATC  TCC  ACC  GTA  CAG  GCA        480
Ala  Thr  Pro  Thr  Ser  Ala  Pro  Pro  Val  Gln  Ile  Ser  Thr  Val  Gln  Ala
145                         150                         155                         160

CCT  GGA  ACA  CCT  ATC  ATT  GCA  CGG  CAG  GTG  ACC  CCA  ACT  ACC  ATA  ATT        528
Pro  Gly  Thr  Pro  Ile  Ile  Ala  Arg  Gln  Val  Thr  Pro  Thr  Thr  Ile  Ile
                     165                         170                         175

AAG  CAA  GTG  TCT  CAG  GCC  CAG  ACA  ACG  GTG  CAG  CCC  AGT  GCA  ACC  CTG        576
Lys  Gln  Val  Ser  Gln  Ala  Gln  Thr  Thr  Val  Gln  Pro  Ser  Ala  Thr  Leu
                180                         185                         190

CAG  CGC  TCG  CCC  GGC  GTC  CAG  CCT  CAG  CTC  GTT  CTG  GGT  GGC  GCT  GCC        624
Gln  Arg  Ser  Pro  Gly  Val  Gln  Pro  Gln  Leu  Val  Leu  Gly  Gly  Ala  Ala
            195                         200                         205

CAG  ACG  GCT  TCA  CTT  GGG  ACG  GCG  ACG  GCT  GTT  CAG  ACG  GGG  ACT  CCT        672
Gln  Thr  Ala  Ser  Leu  Gly  Thr  Ala  Thr  Ala  Val  Gln  Thr  Gly  Thr  Pro
       210                         215                         220

CAG  CGC  ACG  GTA  CCA  GGG  GCG  ACC  ACC  ACT  TCC  TCA  GCT  GCC  ACG  GAA        720
Gln  Arg  Thr  Val  Pro  Gly  Ala  Thr  Thr  Thr  Ser  Ser  Ala  Ala  Thr  Glu
225                         230                         235                         240

ACT  ATG  GAA  AAC  GTG  AAG  AAA  TGT  AAA  AAT  TTC  CTA  TCT  ACG  TTA  ATA        768
Thr  Met  Glu  Asn  Val  Lys  Lys  Cys  Lys  Asn  Phe  Leu  Ser  Thr  Leu  Ile
                     245                         250                         255
```

| | | | | | | | | | | | | | | | | |
|---|---|---|---|---|---|---|---|---|---|---|---|---|---|---|---|---|
| AAA | CTG | GCT | TCA | TCT | GGC | AAG | CAG | TCT | ACA | GAG | ACA | GCA | GCT | AAT | GTG | 816 |
| Lys | Leu | Ala | Ser | Ser | Gly | Lys | Gln | Ser | Thr | Glu | Thr | Ala | Ala | Asn | Val | |
| | | | 260 | | | | 265 | | | | | 270 | | | | |
| AAA | GAG | CTC | GTG | CAG | AAT | TTA | CTG | GAT | GGA | AAA | ATA | GAA | GCA | GAA | GAT | 864 |
| Lys | Glu | Leu | Val | Gln | Asn | Leu | Leu | Asp | Gly | Lys | Ile | Glu | Ala | Glu | Asp | |
| | | 275 | | | | 280 | | | | 285 | | | | | | |
| TTC | ACA | AGC | AGG | TTA | TAC | CGA | GAA | CTT | AAT | TCT | TCA | CCT | CAA | CCT | TAC | 912 |
| Phe | Thr | Ser | Arg | Leu | Tyr | Arg | Glu | Leu | Asn | Ser | Ser | Pro | Gln | Pro | Tyr | |
| | 290 | | | | | 295 | | | | 300 | | | | | | |
| CTT | GTG | CCT | TTC | CTG | AAG | AGG | AGC | TTA | CCC | GCC | TTG | AGA | CAG | CTG | ACC | 960 |
| Leu | Val | Pro | Phe | Leu | Lys | Arg | Ser | Leu | Pro | Ala | Leu | Arg | Gln | Leu | Thr | |
| 305 | | | | | 310 | | | | 315 | | | | | 320 | | |
| CCC | GAC | TCC | GCG | GCC | TTC | ATC | CAG | CAG | AGC | CAG | CAG | CCG | CCA | CCG | | 1008 |
| Pro | Asp | Ser | Ala | Ala | Phe | Ile | Gln | Gln | Ser | Gln | Gln | Pro | Pro | Pro | | |
| | | | | 325 | | | | | 330 | | | | 335 | | | |
| CCC | ACC | TCG | CAG | GCC | ACC | ACT | GCG | CTC | ACG | GCC | GTG | GTG | CTG | AGT | AGC | 1056 |
| Pro | Thr | Ser | Gln | Ala | Thr | Thr | Ala | Leu | Thr | Ala | Val | Val | Leu | Ser | Ser | |
| | | | 340 | | | | | 345 | | | | | 350 | | | |
| TCG | GTC | CAG | CGC | ACG | GCC | GGG | AAG | ACG | GCG | GCC | ACC | GTG | ACC | AGT | GCC | 1104 |
| Ser | Val | Gln | Arg | Thr | Ala | Gly | Lys | Thr | Ala | Ala | Thr | Val | Thr | Ser | Ala | |
| | | 355 | | | | 360 | | | | | 365 | | | | | |
| CTC | CAG | CCC | CCT | GTG | CTC | AGC | CTC | ACG | CAG | CCC | ACG | CAG | GTC | GGC | GTC | 1152 |
| Leu | Gln | Pro | Pro | Val | Leu | Ser | Leu | Thr | Gln | Pro | Thr | Gln | Val | Gly | Val | |
| | 370 | | | | | 375 | | | | | 380 | | | | | |
| GGC | AAG | CAG | GGG | CAA | CCC | ACA | CCG | CTG | GTC | ATC | CAG | CAG | CCT | CCG | AAG | 1200 |
| Gly | Lys | Gln | Gly | Gln | Pro | Thr | Pro | Leu | Val | Ile | Gln | Gln | Pro | Pro | Lys | |
| 385 | | | | | 390 | | | | 395 | | | | | 400 | | |
| CCA | GGA | GCC | CTG | ATC | CGG | CCC | CCG | CAG | GTG | ACG | TTG | ACG | CAG | ACA | CCC | 1248 |
| Pro | Gly | Ala | Leu | Ile | Arg | Pro | Pro | Gln | Val | Thr | Leu | Thr | Gln | Thr | Pro | |
| | | | | 405 | | | | | 410 | | | | 415 | | | |
| ATG | GTC | GCC | CTG | CGG | CAG | CCT | CAC | AAC | CGG | ATC | ATG | CTC | ACC | ACG | CCT | 1296 |
| Met | Val | Ala | Leu | Arg | Gln | Pro | His | Asn | Arg | Ile | Met | Leu | Thr | Thr | Pro | |
| | | | 420 | | | | | 425 | | | | | 430 | | | |
| CAG | CAG | ATC | CAG | CTG | AAC | CCA | CTG | CAG | CCA | GTC | CCT | GTG | GTG | AAA | CCC | 1344 |
| Gln | Gln | Ile | Gln | Leu | Asn | Pro | Leu | Gln | Pro | Val | Pro | Val | Val | Lys | Pro | |
| | | 435 | | | | 440 | | | | | 445 | | | | | |
| GCC | GTG | TTA | CCT | GGA | ACC | AAA | GCC | CTT | TCT | GCT | GTC | TCG | GCA | CAA | GCA | 1392 |
| Ala | Val | Leu | Pro | Gly | Thr | Lys | Ala | Leu | Ser | Ala | Val | Ser | Ala | Gln | Ala | |
| | 450 | | | | | 455 | | | | | 460 | | | | | |
| GCT | GCT | GCA | CAG | AAA | AAT | AAA | CTC | AAG | GAG | CCT | GGG | GGA | GGT | TCG | TTT | 1440 |
| Ala | Ala | Ala | Gln | Lys | Asn | Lys | Leu | Lys | Glu | Pro | Gly | Gly | Gly | Ser | Phe | |
| 465 | | | | | 470 | | | | 475 | | | | | 480 | | |
| CGG | GAC | GAT | GAT | GAC | ATT | AAT | GAT | GTT | GCA | TCG | ATG | GCT | GGA | GTA | AAC | 1488 |
| Arg | Asp | Asp | Asp | Asp | Ile | Asn | Asp | Val | Ala | Ser | Met | Ala | Gly | Val | Asn | |
| | | | | 485 | | | | | 490 | | | | | 495 | | |
| TTG | TCA | GAA | GAA | AGT | GCA | AGA | ATA | TTA | GCC | ACG | AAC | TCT | GAA | TTG | GTG | 1536 |
| Leu | Ser | Glu | Glu | Ser | Ala | Arg | Ile | Leu | Ala | Thr | Asn | Ser | Glu | Leu | Val | |
| | | | 500 | | | | 505 | | | | | 510 | | | | |
| GGC | ACG | CTA | ACG | CGG | TCC | TGT | AAA | GAT | GAA | ACC | TTC | CTC | CTC | CAA | GCG | 1584 |
| Gly | Thr | Leu | Thr | Arg | Ser | Cys | Lys | Asp | Glu | Thr | Phe | Leu | Leu | Gln | Ala | |
| | | 515 | | | | 520 | | | | | 525 | | | | | |
| CCT | TTG | CAG | AGA | AGA | ATA | TTA | GAA | ATA | GGT | AAA | AAA | CAT | GGT | ATA | ACG | 1632 |
| Pro | Leu | Gln | Arg | Arg | Ile | Leu | Glu | Ile | Gly | Lys | Lys | His | Gly | Ile | Thr | |
| | 530 | | | | | 535 | | | | 540 | | | | | | |
| GAA | TTA | CAT | CCA | GAT | GTA | GTA | AGT | TAT | GTA | TCA | CAT | GCC | ACG | CAA | CAA | 1680 |
| Glu | Leu | His | Pro | Asp | Val | Val | Ser | Tyr | Val | Ser | His | Ala | Thr | Gln | Gln | |
| 545 | | | | | 550 | | | | 555 | | | | | 560 | | |
| AGG | CTA | CAG | AAT | CTT | GTA | GAG | AAA | ATA | TCA | GAA | ACA | GCT | CAG | CAG | AAG | 1728 |
| Arg | Leu | Gln | Asn | Leu | Val | Glu | Lys | Ile | Ser | Glu | Thr | Ala | Gln | Gln | Lys | |
| | | | | 565 | | | | | 570 | | | | 575 | | | |

```
AAC TTT TCT TAC AAG GAT GAC GAC AGA TAT GAG CAG GCG AGT GAC GTC    1776
Asn Phe Ser Tyr Lys Asp Asp Asp Arg Tyr Glu Gln Ala Ser Asp Val
            580                 585                 590

CGG GCA CAG CTC AAG TTT TTT GAA CAG CTT GAT CAA ATC GAA AAG CAG    1824
Arg Ala Gln Leu Lys Phe Phe Glu Gln Leu Asp Gln Ile Glu Lys Gln
        595                 600                 605

AGG AAG GAT GAG CAG GAG CGG GAG ATC CTG ATG AGG GCA GCA AAG TCT    1872
Arg Lys Asp Glu Gln Glu Arg Glu Ile Leu Met Arg Ala Ala Lys Ser
    610                 615                 620

CGG TCA AGA CAA GAA GAT CCA GAA CAG TTA AGG CTG AAA CAG AAG GCA    1920
Arg Ser Arg Gln Glu Asp Pro Glu Gln Leu Arg Leu Lys Gln Lys Ala
625                 630                 635                 640

AAG GAG ATG CAG CAA CAG GAA CTG GCA CAA ATG AGA CAG CGG GAC GCC    1968
Lys Glu Met Gln Gln Gln Glu Leu Ala Gln Met Arg Gln Arg Asp Ala
                645                 650                 655

AAC CTC ACA GCA CTA GCA GCG ATC GGG CCC AGG AAA AAG AGG AAA GTG    2016
Asn Leu Thr Ala Leu Ala Ala Ile Gly Pro Arg Lys Lys Arg Lys Val
            660                 665                 670

GAC TGT CCG GGG CCG GGC TCA GGA GCA GAG GGG TCG GGC CCC GGC TCA    2064
Asp Cys Pro Gly Pro Gly Ser Gly Ala Glu Gly Ser Gly Pro Gly Ser
        675                 680                 685

GTG GTC CCA GGC AGC TCG GGT GTC GGA ACC CCC AGA CAG TTC ACG CGA    2112
Val Val Pro Gly Ser Ser Gly Val Gly Thr Pro Arg Gln Phe Thr Arg
    690                 695                 700

CAA AGA ATC ACG CGG GTC AAC CTC AGG GAC CTC ATA TTT TGT TTA GAA    2160
Gln Arg Ile Thr Arg Val Asn Leu Arg Asp Leu Ile Phe Cys Leu Glu
705                 710                 715                 720

AAT GAA CGT GAG ACA AGC CAT TCA CTG CTG CTC TAC AAA GCA TTC CTT    2208
Asn Glu Arg Glu Thr Ser His Ser Leu Leu Leu Tyr Lys Ala Phe Leu
                725                 730                 735

AAG TGACACAGGA GGACGCCTGG GGACTTTTTA TATATTTGCA GATTACGCCT         2261
Lys

TTTTGTAACG AGCAAATGGG ATATTGTTTA AAAAACAGCC ACCTCTTTAC AATGGAACAG   2321
TTTTATATTC CTGTTTCTAA ATCAGCTCTT CAGTGTGAAA GAAAACACGT TCTGTAACA    2381
GAGAGAACAC AAAGGCCTGT GGATACTCTT AAAGGACAAT TAAATCTTAA CTCATCTTGA   2441
TTGAGTGGCC TTCCTGCCAA ACAAGCCATA TATAAAGACT GATGGAATCG TTAGCAAATA   2501
ATTAGCTGCC CTCTGTCAAC TCATAGCAGT TTCTGCATTA TTTGTGCATT TTGGTTTAGT   2561
TCTACCTAAC TTACTATGTA GGTGTATGTC TACAGCCGAT GACCTCATTT CGTTTATTTT   2621
ATTTTTGTAA TAGTCAGTTG GCAAAGCAAA CTGATTTTTT AGACTATTTA TCTTCCTTCC   2681
CTTCCCCTCC CACCCCGCTC TCCTCTCTGC CCCCTGCCCT CCCCTCCCCT CCCTTCCCCT   2741
CCACTCCGCT GAGAATCCTG GAGGAATACA CAATTCATCG TTGCACCCCC ACCTCAGAGT   2801
GTAATCGCAT TTCTGCTTGG TAGAGGCCGA GCCCAGCAAA GGTGGCTCCT TCTGAATGTG   2861
TGGTCAGCAT CTGTACAAAT GCATTTATT TGCTATAGTT TGTAAAGCTG TAAAGTTAAA   2921
AGAGATGAAA ACCTTTTCAG CATAAATATA TTTTACTTGC ACTGTGTTTT TTAGCTAAAA   2981
GTGAAAACCT AGATTAAATA AAATCAAAGT TGAGAAGAAT CATCAAAAGA CTGTTTCTCG   3041
GTGTGAATCA AGTGTTGAAA AATGGTTGGT GTATTTTGTC AGTAATTGTA CATAACTTTT   3101
GGCACATGAC ATAGAAATGG CTATGTAAAC TATAATTATT TTGCTAAGAG ACTGTATGCA   3161
AGCCTTGGGC CGACTTTACA GACGTCCAGA GCAAAGCCCC TTCTTTGTAC CTATTTTTTT   3221
ATTACAAATA TACTAATTGG TTCTTTCTAT TTTCAGAGGT TATTGTATGA AATTGTCTAT   3281
TGATAGTACT TTTATGACTG TAAATACTCT GGCTTTCTCC GTGTGAATTC TCACATTAGA   3341
```

```
CTTTAATTCG AGCGCGTGTG AACTGAACGC TGATCAGTAT TTTTTATCAA CACCTGAGAA   3401

CTGTTACACC TTTTATTTTG TCTTTTAGGA AATCCCTGTC TTTCCATTTT TTCATGTAAA   3461

TTTTGCACAG TTACTTGTTC ATATGTAAAT ATTTTACTTT CAGAAATGAA GTTTTTAATT   3521

GCTATTGTTT TATATAGGAT TGAAAGAAAA TTAACTCCTT TATTAAAAAC AAATTTATCT   3581

GTAAAAAAAA AAAAAAAAA AA                                            3603
```

(2) INFORMATION FOR SEQ ID NO:16:

(i) SEQUENCE CHARACTERISTICS:
        (A) LENGTH: 737 amino acids
        (B) TYPE: amino acid
        (D) TOPOLOGY: linear (ii) MOLECULE TYPE: protein (xi) SEQUENCE DESCRIPTION: SEQ ID NO:16:

```
Arg Gly Gly Ala Gly Gly Ala Pro Gly Gly Ala Asp Pro Gly Ala Ser
 1               5                  10                  15

Gly Pro Ala Ser Thr Ala Ala Ser Met Val Ile Gly Pro Thr Met Gln
            20                  25                  30

Gly Arg Cys Pro Ala Arg Pro Pro Ser Arg Arg Pro Pro Pro Gly Pro
        35                  40                  45

Pro Pro Gly Cys Pro Lys Gly Ala Ala Gly Ala Val Thr Gln Ser Leu
50                  55                  60

Ser Arg Thr Pro Thr Ala Thr Thr Ser Gly Ile Arg Ala Thr Leu Thr
65                  70                  75                  80

Pro Thr Val Leu Ala Pro Arg Leu Pro Gln Pro Pro Gln Asn Pro Thr
                85                  90                  95

Asn Ile Gln Asn Phe Gln Leu Pro Pro Gly Met Val Leu Val Arg Ser
            100                 105                 110

Glu Asn Gly Gln Leu Leu Met Ile Pro Gln Gln Ala Leu Ala Gln Met
        115                 120                 125

Gln Ala Gln Ala His Ala Gln Pro Gln Thr Thr Met Ala Pro Arg Pro
    130                 135                 140

Ala Thr Pro Thr Ser Ala Pro Pro Val Gln Ile Ser Thr Val Gln Ala
145                 150                 155                 160

Pro Gly Thr Pro Ile Ile Ala Arg Gln Val Thr Pro Thr Thr Ile Ile
                165                 170                 175

Lys Gln Val Ser Gln Ala Gln Thr Thr Val Gln Pro Ser Ala Thr Leu
            180                 185                 190

Gln Arg Ser Pro Gly Val Gln Pro Gln Leu Val Leu Gly Gly Ala Ala
        195                 200                 205

Gln Thr Ala Ser Leu Gly Thr Ala Thr Ala Val Gln Thr Gly Thr Pro
    210                 215                 220

Gln Arg Thr Val Pro Gly Ala Thr Thr Thr Ser Ser Ala Ala Thr Glu
225                 230                 235                 240

Thr Met Glu Asn Val Lys Lys Cys Lys Asn Phe Leu Ser Thr Leu Ile
                245                 250                 255

Lys Leu Ala Ser Ser Gly Lys Gln Ser Thr Glu Thr Ala Ala Asn Val
            260                 265                 270

Lys Glu Leu Val Gln Asn Leu Leu Asp Gly Lys Ile Glu Ala Glu Asp
        275                 280                 285

Phe Thr Ser Arg Leu Tyr Arg Glu Leu Asn Ser Ser Pro Gln Pro Tyr
    290                 295                 300

Leu Val Pro Phe Leu Lys Arg Ser Leu Pro Ala Leu Arg Gln Leu Thr
```

|     |     |     |     |     |     |     |     |     |     |     |     |     |     |     |     |
|---|---|---|---|---|---|---|---|---|---|---|---|---|---|---|---|
| 305 | | | | | | 310 | | | | | 315 | | | | 320 |

Pro Asp Ser Ala Ala Phe Ile Gln Gln Ser Gln Gln Gln Pro Pro Pro
                       325                          330                  335

Pro Thr Ser Gln Ala Thr Thr Ala Leu Thr Ala Val Val Leu Ser Ser
             340                    345                   350

Ser Val Gln Arg Thr Ala Gly Lys Thr Ala Ala Thr Val Thr Ser Ala
           355                      360                 365

Leu Gln Pro Pro Val Leu Ser Leu Thr Gln Pro Thr Gln Val Gly Val
   370                    375                 380

Gly Lys Gln Gly Gln Pro Thr Pro Leu Val Ile Gln Gln Pro Pro Lys
385                    390                  395                 400

Pro Gly Ala Leu Ile Arg Pro Pro Gln Val Thr Leu Thr Gln Thr Pro
             405                    410                 415

Met Val Ala Leu Arg Gln Pro His Asn Arg Ile Met Leu Thr Thr Pro
             420                    425                430

Gln Gln Ile Gln Leu Asn Pro Leu Gln Pro Val Pro Val Val Lys Pro
             435             440                  445

Ala Val Leu Pro Gly Thr Lys Ala Leu Ser Ala Val Ser Ala Gln Ala
450                    455                  460

Ala Ala Ala Gln Lys Asn Lys Leu Lys Glu Pro Gly Gly Gly Ser Phe
465                    470                  475                 480

Arg Asp Asp Asp Ile Asn Asp Val Ala Ser Met Ala Gly Val Asn
                485                   490              495

Leu Ser Glu Glu Ser Ala Arg Ile Leu Ala Thr Asn Ser Glu Leu Val
            500                   505              510

Gly Thr Leu Thr Arg Ser Cys Lys Asp Glu Thr Phe Leu Leu Gln Ala
             515              520                525

Pro Leu Gln Arg Arg Ile Leu Glu Ile Gly Lys Lys His Gly Ile Thr
        530                    535              540

Glu Leu His Pro Asp Val Val Ser Tyr Val Ser His Ala Thr Gln Gln
545                    550                 555                560

Arg Leu Gln Asn Leu Val Glu Lys Ile Ser Glu Thr Ala Gln Gln Lys
            565                   570              575

Asn Phe Ser Tyr Lys Asp Asp Arg Tyr Glu Gln Ala Ser Asp Val
                580                   585              590

Arg Ala Gln Leu Lys Phe Phe Glu Gln Leu Asp Gln Ile Glu Lys Gln
           595                     600                605

Arg Lys Asp Glu Gln Glu Arg Glu Ile Leu Met Arg Ala Ala Lys Ser
      610                   615                  620

Arg Ser Arg Gln Glu Asp Pro Glu Gln Leu Arg Leu Lys Gln Lys Ala
625                    630                 635                 640

Lys Glu Met Gln Gln Gln Glu Leu Ala Gln Met Arg Gln Arg Asp Ala
             645                    650                655

Asn Leu Thr Ala Leu Ala Ala Ile Gly Pro Arg Lys Lys Arg Lys Val
             660                    665                670

Asp Cys Pro Gly Pro Gly Ser Gly Ala Glu Gly Ser Gly Pro Gly Ser
           675                     680                685

Val Val Pro Gly Ser Ser Gly Val Gly Thr Pro Arg Gln Phe Thr Arg
           690                     695                700

Gln Arg Ile Thr Arg Val Asn Leu Arg Asp Leu Ile Phe Cys Leu Glu
705                    710                 715                 720

Asn Glu Arg Glu Thr Ser His Ser Leu Leu Leu Tyr Lys Ala Phe Leu
             725                    730                735

Lys ( 2 ) INFORMATION FOR SEQ ID NO:17:

( i ) SEQUENCE CHARACTERISTICS:
        ( A ) LENGTH: 2152 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2112

( x i ) SEQUENCE DESCRIPTION: SEQ ID NO:17:

```
CTA CTG GCC GTG CTG CAG TTC CTA CGG CAG AGC AAA CTC CGC GAG GCC        48
Leu Leu Ala Val Leu Gln Phe Leu Arg Gln Ser Lys Leu Arg Glu Ala
 1               5                  10                  15

GAA GAG GCG CTG CGC CGT GAG GCC GGG CTG CTG GAG GAG GCA GTG GCG        96
Glu Glu Ala Leu Arg Arg Glu Ala Gly Leu Leu Glu Glu Ala Val Ala
             20                  25                  30

GGC TCC GGA GCC CCG GGA GAG GTG GAC AGC GCC GGC GCT GAG GTG ACC       144
Gly Ser Gly Ala Pro Gly Glu Val Asp Ser Ala Gly Ala Glu Val Thr
         35                  40                  45

AGC GCG CTT CTC AGC CGG GTG ACC GCC TCG GCC CCT GGC CCT GCG GCC       192
Ser Ala Leu Leu Ser Arg Val Thr Ala Ser Ala Pro Gly Pro Ala Ala
     50                  55                  60

CCC GAC CCT CCG GGC ACT GGC GCT TCG GGG GCC ACG GTC GTC TCA GGT       240
Pro Asp Pro Pro Gly Thr Gly Ala Ser Gly Ala Thr Val Val Ser Gly
 65                  70                  75                  80

TCA GCC TCA GGT CCT GCG GCT CCG GGT AAA GTT GGA AGT GTT GCT GTG       288
Ser Ala Ser Gly Pro Ala Ala Pro Gly Lys Val Gly Ser Val Ala Val
                 85                  90                  95

GAA GAC CAG CCA GAT GTC AGT GCC GTG TTG TCA GCC TAC AAC CAA CAA       336
Glu Asp Gln Pro Asp Val Ser Ala Val Leu Ser Ala Tyr Asn Gln Gln
            100                 105                 110

GGA GAT CCC ACA ATG TAT GAA GAA TAC TAT AGT GGA CTG AAA CAC TTC       384
Gly Asp Pro Thr Met Tyr Glu Glu Tyr Tyr Ser Gly Leu Lys His Phe
        115                 120                 125

ATT GAA TGT TCC CTG GAC TGC CAT CGG GCA GAG TTG TCC CAA CTT TTT       432
Ile Glu Cys Ser Leu Asp Cys His Arg Ala Glu Leu Ser Gln Leu Phe
    130                 135                 140

TAT CCT CTG TTT GTG CAC ATG TAC TTG GAG CTA GTC TAC AAT CAA CAT       480
Tyr Pro Leu Phe Val His Met Tyr Leu Glu Leu Val Tyr Asn Gln His
145                 150                 155                 160

GAG AAT GAA GCA AAG TCA TTC TTT GAG AAG TTC CAT GGA GAT CAG GAA       528
Glu Asn Glu Ala Lys Ser Phe Phe Glu Lys Phe His Gly Asp Gln Glu
                165                 170                 175

TGT TAT TAC CAG GAT GAC CTA CGA GTA TTA TCT AGT CTT ACC AAA AAG       576
Cys Tyr Tyr Gln Asp Asp Leu Arg Val Leu Ser Ser Leu Thr Lys Lys
            180                 185                 190

GAA CAC ATG AAA GGG AAT GAG ACC ATG TTG GAT TTT CGA ACA AGT AAA       624
Glu His Met Lys Gly Asn Glu Thr Met Leu Asp Phe Arg Thr Ser Lys
        195                 200                 205

TTT GTT CTG CGT ATT TCC CGT GAC TCG TAC CAA CTC TTG AAG AGG CAT       672
Phe Val Leu Arg Ile Ser Arg Asp Ser Tyr Gln Leu Leu Lys Arg His
    210                 215                 220

CTT CAG GAG AAA CAG AAC AAT CAG ATA TGG AAC ATA GTT CAG GAG CAC       720
Leu Gln Glu Lys Gln Asn Asn Gln Ile Trp Asn Ile Val Gln Glu His
225                 230                 235                 240

CTC TAC ATT GAC ATC TTT GAT GGG ATG CCG CGT AGT AAG CAA CAG ATA       768
```

```
            Leu  Tyr  Ile  Asp  Ile  Phe  Asp  Gly  Met  Pro  Arg  Ser  Lys  Gln  Gln  Ile
                           245                     250                          255

GAT  GCG  ATG  GTG  GGA  AGT  TTG  GCA  GGA  GAG  GCT  AAA  CGA  GAG  GCA  AAC                816
Asp  Ala  Met  Val  Gly  Ser  Leu  Ala  Gly  Glu  Ala  Lys  Arg  Glu  Ala  Asn
               260                    265                         270

AAA  TCA  AAG  GTA  TTT  TTT  GGT  TTA  TTA  AAA  GAA  CCA  GAA  ATT  GAG  GTA                864
Lys  Ser  Lys  Val  Phe  Phe  Gly  Leu  Leu  Lys  Glu  Pro  Glu  Ile  Glu  Val
          275                         280                    285

CCT  TTG  GAT  GAC  GAG  GAT  GAA  GAG  GGA  GAA  AAT  GAA  GAA  GGA  AAA  CCT                912
Pro  Leu  Asp  Asp  Glu  Asp  Glu  Glu  Gly  Glu  Asn  Glu  Glu  Gly  Lys  Pro
     290                    295                    300

AAA  AAG  AAG  AAG  CCT  AAA  AAA  GAT  AGT  ATT  GGA  TCC  AAA  AGC  AAA  AAA                960
Lys  Lys  Lys  Lys  Pro  Lys  Lys  Asp  Ser  Ile  Gly  Ser  Lys  Ser  Lys  Lys
305                      310                    315                         320

CAA  GAT  CCC  AAT  GCT  CCA  CCT  CAG  AAC  AGA  ATC  CCT  CTT  CCT  GAG  TTG               1008
Gln  Asp  Pro  Asn  Ala  Pro  Pro  Gln  Asn  Arg  Ile  Pro  Leu  Pro  Glu  Leu
                    325                         330                    335

AAA  GAT  TCA  GAT  AAG  TTG  GAT  AAG  ATA  ATG  AAT  ATG  AAA  GAA  ACC  ACC               1056
Lys  Asp  Ser  Asp  Lys  Leu  Asp  Lys  Ile  Met  Asn  Met  Lys  Glu  Thr  Thr
               340                         345                    350

AAA  CGA  GTA  CGC  CTT  GGG  CCG  GAC  TGC  TTA  CCC  TCC  ATT  TGT  TTC  TAT               1104
Lys  Arg  Val  Arg  Leu  Gly  Pro  Asp  Cys  Leu  Pro  Ser  Ile  Cys  Phe  Tyr
          355                         360                    365

ACA  TTT  CTC  AAT  GCT  TAC  CAG  GGT  CTC  ACT  GCA  GTG  GAT  GTC  ACT  GAT               1152
Thr  Phe  Leu  Asn  Ala  Tyr  Gln  Gly  Leu  Thr  Ala  Val  Asp  Val  Thr  Asp
     370                         375                    380

GAT  TCT  AGT  CTG  ATT  GCT  GGA  GGT  TTT  GCA  GAT  TCA  ACT  GTC  AGA  GTG               1200
Asp  Ser  Ser  Leu  Ile  Ala  Gly  Gly  Phe  Ala  Asp  Ser  Thr  Val  Arg  Val
385                      390                    395                         400

TGG  TCG  GTA  ACA  CCC  AAA  AAG  CTT  CGT  AGT  GTC  AAA  CAA  GCA  TCA  GAT               1248
Trp  Ser  Val  Thr  Pro  Lys  Lys  Leu  Arg  Ser  Val  Lys  Gln  Ala  Ser  Asp
                    405                    410                         415

CTT  AGT  CTT  ATA  GAC  AAA  GAA  TCA  GAT  GAT  GTC  TTA  GAA  AGA  ATC  ATG               1296
Leu  Ser  Leu  Ile  Asp  Lys  Glu  Ser  Asp  Asp  Val  Leu  Glu  Arg  Ile  Met
               420                         425                    430

GAT  GAG  AAA  ACA  GCA  AGT  GAG  TTG  AAG  ATT  TTG  TAT  GGT  CAC  AGT  GGG               1344
Asp  Glu  Lys  Thr  Ala  Ser  Glu  Leu  Lys  Ile  Leu  Tyr  Gly  His  Ser  Gly
          435                         440                    445

CCT  GTC  TAC  GGA  GCC  AGC  TTC  AGT  CCG  GAT  AGG  AAC  TAT  CTG  CTT  TCC               1392
Pro  Val  Tyr  Gly  Ala  Ser  Phe  Ser  Pro  Asp  Arg  Asn  Tyr  Leu  Leu  Ser
     450                         455                    460

TCT  TCA  GAG  GAC  GGA  ACT  GTT  AGA  TTG  TGG  AGC  CTT  CAA  ACA  TTT  ACT               1440
Ser  Ser  Glu  Asp  Gly  Thr  Val  Arg  Leu  Trp  Ser  Leu  Gln  Thr  Phe  Thr
465                      470                    475                         480

TGT  TTG  GTG  GGA  TAT  AAA  GGA  CAC  AAC  TAT  CCA  GTA  TGG  GAC  ACA  CAA               1488
Cys  Leu  Val  Gly  Tyr  Lys  Gly  His  Asn  Tyr  Pro  Val  Trp  Asp  Thr  Gln
                    485                    490                         495

TTT  TCT  CCA  TAT  GGA  TAT  TAT  TTT  GTG  TCA  GGG  GGC  CAT  GAC  CGA  GTA               1536
Phe  Ser  Pro  Tyr  Gly  Tyr  Tyr  Phe  Val  Ser  Gly  Gly  His  Asp  Arg  Val
               500                         505                    510

GCT  CGG  CTC  TGG  GCT  ACA  GAC  CAC  TAT  CAG  CCT  TTA  AGA  ATA  TTT  GCC               1584
Ala  Arg  Leu  Trp  Ala  Thr  Asp  His  Tyr  Gln  Pro  Leu  Arg  Ile  Phe  Ala
          515                         520                    525

GGC  CAT  CTT  GCT  GAT  GTG  AAT  TGT  ACC  AGA  TTC  CAT  CCA  AAT  TCT  AAT               1632
Gly  His  Leu  Ala  Asp  Val  Asn  Cys  Thr  Arg  Phe  His  Pro  Asn  Ser  Asn
     530                         535                    540

TAT  GTT  GCT  ACG  GGC  TCT  GCA  GAC  AGA  ACT  GTG  CGG  CTC  TGG  GAC  GTC               1680
Tyr  Val  Ala  Thr  Gly  Ser  Ala  Asp  Arg  Thr  Val  Arg  Leu  Trp  Asp  Val
545                      550                    555                         560

CTG  AAT  GGT  AAC  TGT  GTA  AGG  ATC  TTC  ACT  GGA  CAC  AAG  GGA  CCA  ATT               1728
```

```
Leu Asn Gly Asn Cys Val Arg Ile Phe Thr Gly His Lys Gly Pro Ile
         565                 570                 575

CAT TCC TTG ACA TTT TCT CCC AAT GGG AGA TTC CTG GCT ACA GGA GCA          1776
His Ser Leu Thr Phe Ser Pro Asn Gly Arg Phe Leu Ala Thr Gly Ala
            580                 585                 590

ACA GAT GGC AGA GTG CTT CTT TGG GAT ATT GGA CAT GGT TTG ATG GTT          1824
Thr Asp Gly Arg Val Leu Leu Trp Asp Ile Gly His Gly Leu Met Val
        595                 600                 605

GGA GAA TTA AAA GGC CAC ACT GAT ACA GTC TGT TCA CTT AGG TTT AGT          1872
Gly Glu Leu Lys Gly His Thr Asp Thr Val Cys Ser Leu Arg Phe Ser
610                 615                 620

AGA GAT GGT GAA ATT TTG GCA TCA GGT TCA ATG GAT AAT ACA GTT CGA          1920
Arg Asp Gly Glu Ile Leu Ala Ser Gly Ser Met Asp Asn Thr Val Arg
625                 630                 635                 640

TTA TGG GAT GCT ATC AAA GCC TTT GAA GAT TTA GAG ACC GAT GAC TTT          1968
Leu Trp Asp Ala Ile Lys Ala Phe Glu Asp Leu Glu Thr Asp Asp Phe
                645                 650                 655

ACT ACA GCC ACT GGG CAT ATA AAT TTA CCT GAG AAT TCA CAG GAG TTA          2016
Thr Thr Ala Thr Gly His Ile Asn Leu Pro Glu Asn Ser Gln Glu Leu
            660                 665                 670

TTG TTG GGA ACA TAT ATG ACC AAA TCA ACA CCA GTT GTA CAC CTT CAT          2064
Leu Leu Gly Thr Tyr Met Thr Lys Ser Thr Pro Val Val His Leu His
        675                 680                 685

TTT ACT CGA AGA AAC CTG GTT CTA GCT GCA GGA GCT TAT AGT CCA CAA          2112
Phe Thr Arg Arg Asn Leu Val Leu Ala Ala Gly Ala Tyr Ser Pro Gln
690                 695                 700

TAAACCATCG GTATTAAAGA CCAAAAAAAA AAAAAAAAA                                2152
```

( 2 ) INFORMATION FOR SEQ ID NO:18:

( i ) SEQUENCE CHARACTERISTICS:
        ( A ) LENGTH: 704 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Leu Leu Ala Val Leu Gln Phe Leu Arg Gln Ser Lys Leu Arg Glu Ala
 1               5                  10                  15

Glu Glu Ala Leu Arg Arg Glu Ala Gly Leu Leu Glu Glu Ala Val Ala
            20                  25                  30

Gly Ser Gly Ala Pro Gly Glu Val Asp Ser Ala Gly Ala Glu Val Thr
        35                  40                  45

Ser Ala Leu Leu Ser Arg Val Thr Ala Ser Ala Pro Gly Pro Ala Ala
    50                  55                  60

Pro Asp Pro Pro Gly Thr Gly Ala Ser Gly Ala Thr Val Val Ser Gly
65                  70                  75                  80

Ser Ala Ser Gly Pro Ala Ala Pro Gly Lys Val Gly Ser Val Ala Val
                85                  90                  95

Glu Asp Gln Pro Asp Val Ser Ala Val Leu Ser Ala Tyr Asn Gln Gln
            100                 105                 110

Gly Asp Pro Thr Met Tyr Glu Glu Tyr Tyr Ser Gly Leu Lys His Phe
        115                 120                 125

Ile Glu Cys Ser Leu Asp Cys His Arg Ala Glu Leu Ser Gln Leu Phe
    130                 135                 140

Tyr Pro Leu Phe Val His Met Tyr Leu Glu Leu Val Tyr Asn Gln His
145                 150                 155                 160

Glu Asn Glu Ala Lys Ser Phe Phe Glu Lys Phe His Gly Asp Gln Glu
```

```
                        165                           170                           175
Cys  Tyr  Tyr  Gln  Asp  Asp  Leu  Arg  Val  Leu  Ser  Ser  Leu  Thr  Lys  Lys
               180                      185                      190
Glu  His  Met  Lys  Gly  Asn  Glu  Thr  Met  Leu  Asp  Phe  Arg  Thr  Ser  Lys
          195                      200                      205
Phe  Val  Leu  Arg  Ile  Ser  Arg  Asp  Ser  Tyr  Gln  Leu  Leu  Lys  Arg  His
     210                      215                           220
Leu  Gln  Glu  Lys  Gln  Asn  Asn  Gln  Ile  Trp  Asn  Ile  Val  Gln  Glu  His
225                      230                      235                           240
Leu  Tyr  Ile  Asp  Ile  Phe  Asp  Gly  Met  Pro  Arg  Ser  Lys  Gln  Gln  Ile
                    245                      250                           255
Asp  Ala  Met  Val  Gly  Ser  Leu  Ala  Gly  Glu  Ala  Lys  Arg  Glu  Ala  Asn
               260                      265                      270
Lys  Ser  Lys  Val  Phe  Phe  Gly  Leu  Leu  Lys  Glu  Pro  Glu  Ile  Glu  Val
          275                      280                      285
Pro  Leu  Asp  Asp  Glu  Asp  Glu  Glu  Gly  Glu  Asn  Glu  Glu  Gly  Lys  Pro
     290                      295                      300
Lys  Lys  Lys  Lys  Pro  Lys  Lys  Asp  Ser  Ile  Gly  Ser  Lys  Ser  Lys  Lys
305                      310                      315                           320
Gln  Asp  Pro  Asn  Ala  Pro  Pro  Gln  Asn  Arg  Ile  Pro  Leu  Pro  Glu  Leu
                    325                      330                      335
Lys  Asp  Ser  Asp  Lys  Leu  Asp  Lys  Ile  Met  Asn  Met  Lys  Glu  Thr  Thr
               340                      345                      350
Lys  Arg  Val  Arg  Leu  Gly  Pro  Asp  Cys  Leu  Pro  Ser  Ile  Cys  Phe  Tyr
          355                      360                      365
Thr  Phe  Leu  Asn  Ala  Tyr  Gln  Gly  Leu  Thr  Ala  Val  Asp  Val  Thr  Asp
     370                      375                      380
Asp  Ser  Ser  Leu  Ile  Ala  Gly  Gly  Phe  Ala  Asp  Ser  Thr  Val  Arg  Val
385                      390                      395                           400
Trp  Ser  Val  Thr  Pro  Lys  Lys  Leu  Arg  Ser  Val  Lys  Gln  Ala  Ser  Asp
                    405                      410                      415
Leu  Ser  Leu  Ile  Asp  Lys  Glu  Ser  Asp  Asp  Val  Leu  Glu  Arg  Ile  Met
               420                      425                      430
Asp  Glu  Lys  Thr  Ala  Ser  Glu  Leu  Lys  Ile  Leu  Tyr  Gly  His  Ser  Gly
          435                      440                      445
Pro  Val  Tyr  Gly  Ala  Ser  Phe  Ser  Pro  Asp  Arg  Asn  Tyr  Leu  Leu  Ser
     450                      455                      460
Ser  Ser  Glu  Asp  Gly  Thr  Val  Arg  Leu  Trp  Ser  Leu  Gln  Thr  Phe  Thr
465                      470                      475                           480
Cys  Leu  Val  Gly  Tyr  Lys  Gly  His  Asn  Tyr  Pro  Val  Trp  Asp  Thr  Gln
                    485                      490                      495
Phe  Ser  Pro  Tyr  Gly  Tyr  Tyr  Phe  Val  Ser  Gly  Gly  His  Asp  Arg  Val
               500                      505                      510
Ala  Arg  Leu  Trp  Ala  Thr  Asp  His  Tyr  Gln  Pro  Leu  Arg  Ile  Phe  Ala
          515                      520                      525
Gly  His  Leu  Ala  Asp  Val  Asn  Cys  Thr  Arg  Phe  His  Pro  Asn  Ser  Asn
     530                      535                      540
Tyr  Val  Ala  Thr  Gly  Ser  Ala  Asp  Arg  Thr  Val  Arg  Leu  Trp  Asp  Val
545                      550                      555                           560
Leu  Asn  Gly  Asn  Cys  Val  Arg  Ile  Phe  Thr  Gly  His  Lys  Gly  Pro  Ile
                    565                      570                      575
His  Ser  Leu  Thr  Phe  Ser  Pro  Asn  Gly  Arg  Phe  Leu  Ala  Thr  Gly  Ala
               580                      585                      590
```

```
Thr Asp Gly Arg Val Leu Leu Trp Asp Ile Gly His Gly Leu Met Val
    595                 600                 605
Gly Glu Leu Lys Gly His Thr Asp Thr Val Cys Ser Leu Arg Phe Ser
        610                 615                 620
Arg Asp Gly Glu Ile Leu Ala Ser Gly Ser Met Asp Asn Thr Val Arg
625                 630                 635                 640
Leu Trp Asp Ala Ile Lys Ala Phe Glu Leu Glu Thr Asp Asp Phe
                645                 650                 655
Thr Thr Ala Thr Gly His Ile Asn Leu Pro Glu Asn Ser Gln Glu Leu
            660                 665                 670
Leu Leu Gly Thr Tyr Met Thr Lys Ser Thr Pro Val Val His Leu His
        675                 680                 685
Phe Thr Arg Arg Asn Leu Val Leu Ala Ala Gly Ala Tyr Ser Pro Gln
690                 695                 700
```

(2) INFORMATION FOR SEQ ID NO:19:

(i) SEQUENCE CHARACTERISTICS:
        (A) LENGTH: 3812 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 60..3701

(xi) SEQUENCE DESCRIPTION: SEQ ID NO:19:

```
TTTTTTATAA CAAACGCAAA TTAGTTAATA AATTCTGGCG CAGAACCGGC ATTTGAGCG          59

ATG GAA ACG CAA CCT GAG GTG CCC GAG GTG CCG CTG CGA CCG TTT AAA         107
Met Glu Thr Gln Pro Glu Val Pro Glu Val Pro Leu Arg Pro Phe Lys
1               5                   10                  15

TTG GCG CAT CAG GTT GTG AGC CTC ACG GGC ATC AGT TTC GAG CGG AGG         155
Leu Ala His Gln Val Val Ser Leu Thr Gly Ile Ser Phe Glu Arg Arg
                20                  25                  30

AGC ATA ATC GGC GTG GTC GAG CTG ACC ATT GTG CCG AAC AGC GAG AAT         203
Ser Ile Ile Gly Val Val Glu Leu Thr Ile Val Pro Asn Ser Glu Asn
            35                  40                  45

CTG CGC CTG ATA AGC CTG AAT GCC AAG CAG CTG AGA ATC TAC AGC GTC         251
Leu Arg Leu Ile Ser Leu Asn Ala Lys Gln Leu Arg Ile Tyr Ser Val
        50                  55                  60

GTT TTG AAC GAT GTC TGC CAG GCG GAT TTC ACG TAC TTC GAT CCC TTC         299
Val Leu Asn Asp Val Cys Gln Ala Asp Phe Thr Tyr Phe Asp Pro Phe
65                  70                  75                  80

CAG AAC ATC TGC TAC AAG GAG CCC AAG AGC CGC GCT CTG GAG GTC TAC         347
Gln Asn Ile Cys Tyr Lys Glu Pro Lys Ser Arg Ala Leu Glu Val Tyr
                85                  90                  95

TCC AAG CAT CAT CTG ACC GCC GCT CAG TAC ACC GAT CCC GAT GTG AAC         395
Ser Lys His His Leu Thr Ala Ala Gln Tyr Thr Asp Pro Asp Val Asn
            100                 105                 110

AAC GGC GAA CTG CTC ATC CAG GTT CCG CCC GAG GGC TAC TCT ATG ATC         443
Asn Gly Glu Leu Leu Ile Gln Val Pro Pro Glu Gly Tyr Ser Met Ile
        115                 120                 125

CAG GAG GGT CAG GGT CTG CGC ATC CGC ATT GAG TTC TCG TTG GAG AAT         491
Gln Glu Gly Gln Gly Leu Arg Ile Arg Ile Glu Phe Ser Leu Glu Asn
130                 135                 140

CCC AAA TGC GGC GTA CAT TTT GTC ATA CCA CCC GCT TCA ACG GAC GAG         539
Pro Lys Cys Gly Val His Phe Val Ile Pro Pro Ala Ser Thr Asp Glu
                150                 155                 160
```

| | | | | | | | | | | | | | | | | |
|---|---|---|---|---|---|---|---|---|---|---|---|---|---|---|---|---|
| GAG | ACA | CAG | ATG | AAC | AGC | TCG | CAT | ATG | TTC | ACC | AAT | TGC | TAT | GAA | AAC | 587 |
| Glu | Thr | Gln | Met | Asn | Ser | Ser | His | Met | Phe | Thr | Asn | Cys | Tyr | Glu | Asn | |
| | | | 165 | | | | | 170 | | | | | | 175 | | |
| TCG | TCG | AGA | TTG | TGG | TTT | CCC | TGC | GTG | GAC | AGT | TTC | GCC | GAT | CCC | TGC | 635 |
| Ser | Ser | Arg | Leu | Trp | Phe | Pro | Cys | Val | Asp | Ser | Phe | Ala | Asp | Pro | Cys | |
| | | | 180 | | | | | 185 | | | | | 190 | | | |
| ACC | TGG | CGG | CTG | GAG | TTC | ACT | GTC | GAC | AAA | AAT | ATG | ACC | GCC | GTT | TCG | 683 |
| Thr | Trp | Arg | Leu | Glu | Phe | Thr | Val | Asp | Lys | Asn | Met | Thr | Ala | Val | Ser | |
| | | 195 | | | | | 200 | | | | | 205 | | | | |
| TGT | GGA | GAA | CTT | CTA | GAA | GTC | ATT | ATG | ACC | CCA | GAT | CTG | CGA | AAG | AAA | 731 |
| Cys | Gly | Glu | Leu | Leu | Glu | Val | Ile | Met | Thr | Pro | Asp | Leu | Arg | Lys | Lys | |
| | 210 | | | | | 215 | | | | | 220 | | | | | |
| ACC | TTC | CAC | TAT | TCG | GTT | AGC | ACA | CCA | GTA | TGT | GCA | CCA | AAT | ATT | GCG | 779 |
| Thr | Phe | His | Tyr | Ser | Val | Ser | Thr | Pro | Val | Cys | Ala | Pro | Asn | Ile | Ala | |
| 225 | | | | | 230 | | | | | 235 | | | | | 240 | |
| CTG | GCT | GTG | GGT | CAG | TTT | GAG | ATC | TAC | GTG | GAT | CCG | CAC | ATG | CAT | GAA | 827 |
| Leu | Ala | Val | Gly | Gln | Phe | Glu | Ile | Tyr | Val | Asp | Pro | His | Met | His | Glu | |
| | | | | 245 | | | | | 250 | | | | | 255 | | |
| GTG | ACC | CAC | TTT | TGT | CTG | CCC | GGA | TTG | TTG | CCG | CTG | TTA | AAA | AAT | ACG | 875 |
| Val | Thr | His | Phe | Cys | Leu | Pro | Gly | Leu | Leu | Pro | Leu | Leu | Lys | Asn | Thr | |
| | | | 260 | | | | | 265 | | | | | 270 | | | |
| GTT | CGC | TAT | TTG | CAC | GAG | GCA | TTT | GAA | TTT | TAC | GAG | GAG | ACC | TTA | TCT | 923 |
| Val | Arg | Tyr | Leu | His | Glu | Ala | Phe | Glu | Phe | Tyr | Glu | Glu | Thr | Leu | Ser | |
| | | 275 | | | | | 280 | | | | | 285 | | | | |
| ACG | CGC | TAC | CCA | TTC | AGT | TGC | TAC | AAA | CAA | GTG | TTT | GTA | GAC | GAA | TTG | 971 |
| Thr | Arg | Tyr | Pro | Phe | Ser | Cys | Tyr | Lys | Gln | Val | Phe | Val | Asp | Glu | Leu | |
| | 290 | | | | | 295 | | | | | 300 | | | | | |
| GAC | ACG | GAC | ATA | AGT | GCC | TAT | GCC | ACT | ATG | AGC | ATT | GCT | TCG | GTG | AAC | 1019 |
| Asp | Thr | Asp | Ile | Ser | Ala | Tyr | Ala | Thr | Met | Ser | Ile | Ala | Ser | Val | Asn | |
| 305 | | | | | 310 | | | | | 315 | | | | | 320 | |
| CTG | CTG | CAC | TCC | ATA | GCT | ATC | ATC | GAT | CAG | ACC | TAT | ATA | TCT | CGA | ACC | 1067 |
| Leu | Leu | His | Ser | Ile | Ala | Ile | Ile | Asp | Gln | Thr | Tyr | Ile | Ser | Arg | Thr | |
| | | | | 325 | | | | | 330 | | | | | 335 | | |
| TTT | ATG | TCG | CGC | GCT | GTG | GCT | GAG | CAA | TTC | TTC | GGC | TGC | TTT | ATT | ACA | 1115 |
| Phe | Met | Ser | Arg | Ala | Val | Ala | Glu | Gln | Phe | Phe | Gly | Cys | Phe | Ile | Thr | |
| | | | 340 | | | | | 345 | | | | | 350 | | | |
| TCG | CAT | CAT | TGG | TCG | GAC | ACC | TGG | CTG | GCC | AAG | GGC | ATT | GCG | GAG | TAC | 1163 |
| Ser | His | His | Trp | Ser | Asp | Thr | Trp | Leu | Ala | Lys | Gly | Ile | Ala | Glu | Tyr | |
| | | 355 | | | | | 360 | | | | | 365 | | | | |
| CTG | TGT | GGA | TTG | TAT | TCC | AGG | AAG | TGC | TTC | GGC | AAC | AAC | GAG | TAC | CGT | 1211 |
| Leu | Cys | Gly | Leu | Tyr | Ser | Arg | Lys | Cys | Phe | Gly | Asn | Asn | Glu | Tyr | Arg | |
| | 370 | | | | | 375 | | | | | 380 | | | | | |
| GCT | TGG | GTG | CAA | TCT | GAA | CTG | GCG | CGT | GTC | GTT | CGC | TAC | GAG | GAG | CAG | 1259 |
| Ala | Trp | Val | Gln | Ser | Glu | Leu | Ala | Arg | Val | Val | Arg | Tyr | Glu | Glu | Gln | |
| 385 | | | | | 390 | | | | | 395 | | | | | 400 | |
| TAT | GGC | GGC | ATT | ATT | CTC | GAT | TGC | AGT | CAG | CCG | CCA | GCA | CCT | TTG | CCT | 1307 |
| Tyr | Gly | Gly | Ile | Ile | Leu | Asp | Cys | Ser | Gln | Pro | Pro | Ala | Pro | Leu | Pro | |
| | | | | 405 | | | | | 410 | | | | | 415 | | |
| GTT | TCG | GGC | ACA | AAT | CAA | TCG | GCT | GCT | TCC | AGC | AAA | CAG | CAG | GAG | ATT | 1355 |
| Val | Ser | Gly | Thr | Asn | Gln | Ser | Ala | Ala | Ser | Ser | Lys | Gln | Gln | Glu | Ile | |
| | | | 420 | | | | | 425 | | | | | 430 | | | |
| GTC | CAC | TAT | TTT | CCC | ATC | AAG | AGT | TTG | CAC | ACC | GTA | TCG | CCG | AAG | TAT | 1403 |
| Val | His | Tyr | Phe | Pro | Ile | Lys | Ser | Leu | His | Thr | Val | Ser | Pro | Lys | Tyr | |
| | | 435 | | | | | 440 | | | | | 445 | | | | |
| GTG | GAG | GCG | ATG | CGA | AGG | AAA | GCG | CAT | TTC | GTA | ATC | CGA | ATG | CTG | GAG | 1451 |
| Val | Glu | Ala | Met | Arg | Arg | Lys | Ala | His | Phe | Val | Ile | Arg | Met | Leu | Glu | |
| | 450 | | | | | 455 | | | | | 460 | | | | | |
| AAC | CGC | ATC | GGG | CAG | GAG | CTG | CTG | ATT | CAG | GTG | TTC | AAT | AAG | CAA | TTG | 1499 |
| Asn | Arg | Ile | Gly | Gln | Glu | Leu | Leu | Ile | Gln | Val | Phe | Asn | Lys | Gln | Leu | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| GCT | TTG | GCT | TCT | AGT | GCG | GCA | ACG | ACG | AAG | ATC | GGT | GCA | GGA | CTC | TGG | 1547 |
| Ala | Leu | Ala | Ser | Ser | Ala | Ala | Thr | Thr | Lys | Ile | Gly | Ala | Gly | Leu | Trp | |
| | | | | 485 | | | | | 490 | | | | | 495 | | |
| TCT | CAG | CTG | CTC | ATC | TCG | ACC | AAC | ATT | TTT | ATC | AAG | GCC | ATC | TTC | ACC | 1595 |
| Ser | Gln | Leu | Leu | Ile | Ser | Thr | Asn | Ile | Phe | Ile | Lys | Ala | Ile | Phe | Thr | |
| | | | 500 | | | | | 505 | | | | | 510 | | | |
| GTA | ACC | GGA | AAA | GAT | ATG | TCT | GTC | TTC | ATG | GAC | CAG | TGG | GTG | CGC | ACT | 1643 |
| Val | Thr | Gly | Lys | Asp | Met | Ser | Val | Phe | Met | Asp | Gln | Trp | Val | Arg | Thr | |
| | | 515 | | | | 520 | | | | | 525 | | | | | |
| GGA | GGG | CAC | GCC | AAG | TTT | TCG | CTC | ACA | TCT | GTG | TTC | AAT | CGC | AAG | AGA | 1691 |
| Gly | Gly | His | Ala | Lys | Phe | Ser | Leu | Thr | Ser | Val | Phe | Asn | Arg | Lys | Arg | |
| | 530 | | | | | 535 | | | | 540 | | | | | | |
| AAC | ACG | ATT | GAA | CTG | GAA | ATC | CGC | CAG | GAC | TAT | GTT | AAT | CAG | CGG | GGA | 1739 |
| Asn | Thr | Ile | Glu | Leu | Glu | Ile | Arg | Gln | Asp | Tyr | Val | Asn | Gln | Arg | Gly | |
| 545 | | | | | 550 | | | | | 555 | | | | | 560 | |
| ATT | AGA | AAA | TAC | AAT | GGT | CCA | TTG | ATG | GTG | CAG | CTG | CAG | GAG | TTG | GAT | 1787 |
| Ile | Arg | Lys | Tyr | Asn | Gly | Pro | Leu | Met | Val | Gln | Leu | Gln | Glu | Leu | Asp | |
| | | | | 565 | | | | | 570 | | | | | 575 | | |
| GGA | ACG | TTT | AAG | CAC | ACA | TTG | CAG | ATT | GAG | AGT | ACC | CTG | GTA | AAG | TCC | 1835 |
| Gly | Thr | Phe | Lys | His | Thr | Leu | Gln | Ile | Glu | Ser | Thr | Leu | Val | Lys | Ser | |
| | | | 580 | | | | | 585 | | | | | 590 | | | |
| GAT | ATC | ACT | TGT | CAC | TCG | AAG | AGC | AGG | CGT | AAC | AAA | AAG | AAG | AAG | ATC | 1883 |
| Asp | Ile | Thr | Cys | His | Ser | Lys | Ser | Arg | Arg | Asn | Lys | Lys | Lys | Lys | Ile | |
| | | 595 | | | | 600 | | | | | 605 | | | | | |
| CCC | TTG | TGC | ACC | GGT | GAG | GAA | GTG | GAT | ATG | GAT | TTA | TCA | GCC | ATG | GAC | 1931 |
| Pro | Leu | Cys | Thr | Gly | Glu | Glu | Val | Asp | Met | Asp | Leu | Ser | Ala | Met | Asp | |
| | 610 | | | | | 615 | | | | | 620 | | | | | |
| GAC | TCA | CCT | GTG | CTT | TGG | ATC | CGC | CTC | GAT | CCC | GAA | ATG | ATT | CTG | CTG | 1979 |
| Asp | Ser | Pro | Val | Leu | Trp | Ile | Arg | Leu | Asp | Pro | Glu | Met | Ile | Leu | Leu | |
| 625 | | | | | 630 | | | | | 635 | | | | | 640 | |
| CGC | GAC | CTC | ATA | ATC | GAA | CAG | CCC | GAC | TTC | CAG | TGG | CAG | TAT | CAG | CTT | 2027 |
| Arg | Asp | Leu | Ile | Ile | Glu | Gln | Pro | Asp | Phe | Gln | Trp | Gln | Tyr | Gln | Leu | |
| | | | | 645 | | | | | 650 | | | | | 655 | | |
| CGG | CAT | GAA | CGT | GAT | GTT | ACT | GCT | CAA | TTT | CAG | GCG | ATT | CAA | GCC | CTG | 2075 |
| Arg | His | Glu | Arg | Asp | Val | Thr | Ala | Gln | Phe | Gln | Ala | Ile | Gln | Ala | Leu | |
| | | | 660 | | | | | 665 | | | | | 670 | | | |
| CAA | AAG | TAC | CCC | ACG | AAT | GCC | ACC | AGG | CTT | GCT | TTA | ACC | GAC | ACC | ATA | 2123 |
| Gln | Lys | Tyr | Pro | Thr | Asn | Ala | Thr | Arg | Leu | Ala | Leu | Thr | Asp | Thr | Ile | |
| | | 675 | | | | 680 | | | | | 685 | | | | | |
| GAA | AGC | GAA | CGT | TGC | TTC | TAT | CAG | GTG | CGC | TGC | GAG | GCA | GCC | CAC | AGC | 2171 |
| Glu | Ser | Glu | Arg | Cys | Phe | Tyr | Gln | Val | Arg | Cys | Glu | Ala | Ala | His | Ser | |
| | 690 | | | | | 695 | | | | | 700 | | | | | |
| TTG | ACC | AAA | GTG | GCC | AAC | CAG | ATG | GTG | GCC | TCC | TGG | AGT | GGA | CCG | CCC | 2219 |
| Leu | Thr | Lys | Val | Ala | Asn | Gln | Met | Val | Ala | Ser | Trp | Ser | Gly | Pro | Pro | |
| 705 | | | | | 710 | | | | | 715 | | | | | 720 | |
| GCC | ATG | CTG | AAC | ATA | TTT | AGG | AAG | TTT | TTC | GGC | TCA | TTT | AGT | GCT | CCG | 2267 |
| Ala | Met | Leu | Asn | Ile | Phe | Arg | Lys | Phe | Phe | Gly | Ser | Phe | Ser | Ala | Pro | |
| | | | | 725 | | | | | 730 | | | | | 735 | | |
| CAC | ATT | ATC | AAA | CTG | AAC | AAC | TTC | TCC | AAC | TTT | CAG | CTG | TAC | TTC | CTG | 2315 |
| His | Ile | Ile | Lys | Leu | Asn | Asn | Phe | Ser | Asn | Phe | Gln | Leu | Tyr | Phe | Leu | |
| | | | 740 | | | | | 745 | | | | | 750 | | | |
| CAG | AAG | GCT | ATT | CCC | GTA | GCC | ATG | GCA | GGT | CTG | CGC | ACA | TCT | CAT | GGT | 2363 |
| Gln | Lys | Ala | Ile | Pro | Val | Ala | Met | Ala | Gly | Leu | Arg | Thr | Ser | His | Gly | |
| | | 755 | | | | 760 | | | | | 765 | | | | | |
| ATT | TGC | CCG | CCG | GAA | GTG | ATG | CGT | TTT | CTT | TTC | GAT | CTC | TTC | AAG | TAC | 2411 |
| Ile | Cys | Pro | Pro | Glu | Val | Met | Arg | Phe | Leu | Phe | Asp | Leu | Phe | Lys | Tyr | |
| | 770 | | | | | 775 | | | | | 780 | | | | | |
| AAC | GAG | AAT | TCG | CGT | AAC | CAT | TAC | ACG | GAT | GCA | TAC | TAC | AGG | GCA | GCT | 2459 |
| Asn | Glu | Asn | Ser | Arg | Asn | His | Tyr | Thr | Asp | Ala | Tyr | Tyr | Arg | Ala | Ala | |
| 785 | | | | | 790 | | | | | 795 | | | | | 800 | |

| | | | | | | | | | | | | | | | | |
|---|---|---|---|---|---|---|---|---|---|---|---|---|---|---|---|---|
| TTG | GTA | GAA | GCT | CTA | GGC | GAA | ACC | TTA | ACA | CCT | GTG | GTC | TCC | GTT | GCT | 2507 |
| Leu | Val | Glu | Ala | Leu | Gly | Glu | Thr | Leu | Thr | Pro | Val | Val | Ser | Val | Ala | |
| | | | | 805 | | | | 810 | | | | | 815 | | | |
| ATC | CAT | GGC | ACA | CAA | ATC | ACT | ACG | GAC | AGT | CTA | TCC | ACG | GAT | GCG | AAA | 2555 |
| Ile | His | Gly | Thr | Gln | Ile | Thr | Thr | Asp | Ser | Leu | Ser | Thr | Asp | Ala | Lys | |
| | | | 820 | | | | | 825 | | | | | 830 | | | |
| CTT | GTG | CTA | GAT | GAA | GTT | ACA | CGT | CTG | CTG | AAC | ATG | GAG | AAA | CAT | CTA | 2603 |
| Leu | Val | Leu | Asp | Glu | Val | Thr | Arg | Leu | Leu | Asn | Met | Glu | Lys | His | Leu | |
| | | 835 | | | | | 840 | | | | | 845 | | | | |
| CCC | TCG | TAC | AAG | TAC | ATG | GTG | TCC | GTG | TCG | TGT | CTG | AAG | GTC | ATC | CGG | 2651 |
| Pro | Ser | Tyr | Lys | Tyr | Met | Val | Ser | Val | Ser | Cys | Leu | Lys | Val | Ile | Arg | |
| | 850 | | | | | 855 | | | | | 860 | | | | | |
| AAG | CTG | CAA | AAA | TTC | GGT | CAT | CTG | CCC | TCA | CTG | CCG | CAC | ATT | TAC | CGC | 2699 |
| Lys | Leu | Gln | Lys | Phe | Gly | His | Leu | Pro | Ser | Leu | Pro | His | Ile | Tyr | Arg | |
| 865 | | | | | 870 | | | | | 875 | | | | | 880 | |
| AGC | TAT | GCC | GAA | TAT | GGA | ATA | TAT | CTC | GAT | CTC | CGC | ATT | GCT | GCT | ATG | 2747 |
| Ser | Tyr | Ala | Glu | Tyr | Gly | Ile | Tyr | Leu | Asp | Leu | Arg | Ile | Ala | Ala | Met | |
| | | | | 885 | | | | | 890 | | | | | 895 | | |
| GAG | TGT | CTC | GTG | GAC | TTT | GTG | AAA | GTG | GAT | GGG | CGC | AGC | GAG | GAT | TTG | 2795 |
| Glu | Cys | Leu | Val | Asp | Phe | Val | Lys | Val | Asp | Gly | Arg | Ser | Glu | Asp | Leu | |
| | | | 900 | | | | | 905 | | | | | 910 | | | |
| GAA | CAT | TTG | ATT | ACT | CTG | CTG | GAA | ACT | GAT | CCG | GAT | CCG | GCT | GCT | CGC | 2843 |
| Glu | His | Leu | Ile | Thr | Leu | Leu | Glu | Thr | Asp | Pro | Asp | Pro | Ala | Ala | Arg | |
| | | 915 | | | | | 920 | | | | | 925 | | | | |
| CAT | GCA | CTG | GCC | CAA | CTG | CTG | ATC | GAT | AAT | CCG | CCT | TTC | ACA | CGC | GAA | 2891 |
| His | Ala | Leu | Ala | Gln | Leu | Leu | Ile | Asp | Asn | Pro | Pro | Phe | Thr | Arg | Glu | |
| | 930 | | | | | 935 | | | | | 940 | | | | | |
| TCT | CGC | AGC | CGT | CTG | GAT | AAA | CCC | AAT | CTC | GTG | GAT | CGT | CTA | TGG | TTC | 2939 |
| Ser | Arg | Ser | Arg | Leu | Asp | Lys | Pro | Asn | Leu | Val | Asp | Arg | Leu | Trp | Phe | |
| 945 | | | | | 950 | | | | | 955 | | | | | 960 | |
| AGT | ATT | AAC | CGC | TTG | CCC | TAC | GAT | ACC | AAG | CTG | CGC | TGC | GAT | ATT | GTC | 2987 |
| Ser | Ile | Asn | Arg | Leu | Pro | Tyr | Asp | Thr | Lys | Leu | Arg | Cys | Asp | Ile | Val | |
| | | | | 965 | | | | | 970 | | | | | 975 | | |
| GAT | CTG | TAC | TAC | GCA | CTG | TAC | GGA | ACT | AAG | CGT | CCG | AAT | TGC | TTG | CAG | 3035 |
| Asp | Leu | Tyr | Tyr | Ala | Leu | Tyr | Gly | Thr | Lys | Arg | Pro | Asn | Cys | Leu | Gln | |
| | | | 980 | | | | | 985 | | | | | 990 | | | |
| GCC | GGC | GAG | AAC | CAA | AGC | TTC | TAC | AAG | GAT | TTG | ATG | AAG | GAC | AAT | AAT | 3083 |
| Ala | Gly | Glu | Asn | Gln | Ser | Phe | Tyr | Lys | Asp | Leu | Met | Lys | Asp | Asn | Asn | |
| | | 995 | | | | | 1000 | | | | | 1005 | | | | |
| AGC | AGT | GTA | GGC | AGC | GTA | ACC | GGC | AGC | TTC | AAG | AAG | ACC | AGT | GAT | TCA | 3131 |
| Ser | Ser | Val | Gly | Ser | Val | Thr | Gly | Ser | Phe | Lys | Lys | Thr | Ser | Asp | Ser | |
| | 1010 | | | | | 1015 | | | | | 1020 | | | | | |
| AAG | TCA | CAT | TTG | CCA | ACA | CCA | ACG | AAT | ACT | TTG | GAC | AAT | GAG | CCA | CAG | 3179 |
| Lys | Ser | His | Leu | Pro | Thr | Pro | Thr | Asn | Thr | Leu | Asp | Asn | Glu | Pro | Gln | |
| 1025 | | | | | 1030 | | | | | 1035 | | | | | 1040 | |
| GAG | CGG | CAA | AAG | CCG | GCA | ATG | GTT | ACC | ATC | AAG | CGA | ACG | GCC | ACA | GAA | 3227 |
| Glu | Arg | Gln | Lys | Pro | Ala | Met | Val | Thr | Ile | Lys | Arg | Thr | Ala | Thr | Glu | |
| | | | | 1045 | | | | | 1050 | | | | | 1055 | | |
| GCA | TTT | GAG | GTG | GGC | GAT | GAG | ATT | ATC | AAG | CTG | GAA | CGC | AGC | GAG | GAG | 3275 |
| Ala | Phe | Glu | Val | Gly | Asp | Glu | Ile | Ile | Lys | Leu | Glu | Arg | Ser | Glu | Glu | |
| | | | 1060 | | | | | 1065 | | | | | 1070 | | | |
| ATC | ACC | GTG | CTA | GAT | GAA | CCA | GTT | AAC | GTG | CAG | GCC | TAT | GAC | AGT | GAG | 3323 |
| Ile | Thr | Val | Leu | Asp | Glu | Pro | Val | Asn | Val | Gln | Ala | Tyr | Asp | Ser | Glu | |
| | | | | 1075 | | | | | 1080 | | | | | 1085 | | |
| ACC | AAA | GTG | AAT | GCC | CTG | CAG | GCA | GAT | GAA | GAA | GCA | CGT | GAT | ACC | CAT | 3371 |
| Thr | Lys | Val | Asn | Ala | Leu | Gln | Ala | Asp | Glu | Glu | Ala | Arg | Asp | Thr | His | |
| | 1090 | | | | | 1095 | | | | | 1100 | | | | | |
| CAG | GCT | GCC | AAG | CGC | CTT | AAG | AAC | GAA | ATG | TAC | GCC | GAG | GAT | GAT | AAC | 3419 |
| Gln | Ala | Ala | Lys | Arg | Leu | Lys | Asn | Glu | Met | Tyr | Ala | Glu | Asp | Asp | Asn | |
| 1105 | | | | | 1110 | | | | | 1115 | | | | | 1120 | |

| | | | | | | | | | | | | | | | | |
|---|---|---|---|---|---|---|---|---|---|---|---|---|---|---|---|---|
| TCA | TCC | ACA | ATG | CTC | GAC | GTG | GGC | GAC | TCC | ACC | AGA | TAT | GAG | AGT | AGC | 3467 |
| Ser | Ser | Thr | Met | Leu | Asp | Val | Gly | Asp | Ser | Thr | Arg | Tyr | Glu | Ser | Ser | |
| | | | 1125 | | | | | 1130 | | | | | | 1135 | | |
| CAC | GAG | GAG | GGC | AAA | TTG | AAG | TCC | GGC | GAT | GGT | GGG | CTC | AAG | AAG | AAA | 3515 |
| His | Glu | Glu | Gly | Lys | Leu | Lys | Ser | Gly | Asp | Gly | Gly | Leu | Lys | Lys | Lys | |
| | | | 1140 | | | | | 1145 | | | | | | 1150 | | |
| AAG | AAG | AAG | GAG | AAG | AAG | AAG | CAT | AAG | CAC | AAA | CAC | AAG | CAT | AGG | CAC | 3563 |
| Lys | Lys | Lys | Glu | Lys | Lys | Lys | His | Lys | His | Lys | His | Lys | His | Arg | His | |
| | | | 1155 | | | | | 1160 | | | | | | 1165 | | |
| AGC | AAG | GAC | AAG | GAC | AAG | GAG | CGA | AAG | GAT | AAG | GAC | AAG | CGT | GAC | CCG | 3611 |
| Ser | Lys | Asp | Lys | Asp | Lys | Glu | Arg | Lys | Asp | Lys | Asp | Lys | Arg | Asp | Pro | |
| | | 1170 | | | | | 1175 | | | | | 1180 | | | | |
| CAT | ATA | TCA | CGC | CTG | CAG | GCC | GCG | AGA | CAG | CCA | CTC | CGG | ACA | CTC | TCA | 3659 |
| His | Ile | Ser | Arg | Leu | Gln | Ala | Ala | Arg | Gln | Pro | Leu | Arg | Thr | Leu | Ser | |
| 1185 | | | | | 1190 | | | | | 1195 | | | | | 1200 | |
| GCT | CGG | AGG | ACA | GTA | GCA | ACA | GCA | ATA | GCC | TGC | CGC | CCA | TGAACCTTAA | | | 3708 |
| Ala | Arg | Arg | Thr | Val | Ala | Thr | Ala | Ile | Ala | Cys | Arg | Pro | | | | |
| | | | | 1205 | | | | | 1210 | | | | | | | |

CTAAGTGAGG GTTCCTACAG GTGGGGAAAT TGCAATGTTT GGGGGATAGA TGACAGAATA  3768

AAGGTATAAT ACCTTAAAAA AAAAAAAAAA AAAAAAAAA AAAA  3812

( 2 ) INFORMATION FOR SEQ ID NO:20:

( i ) SEQUENCE CHARACTERISTICS:
        ( A ) LENGTH: 1213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| | | | | | | | | | | | | | | |
|---|---|---|---|---|---|---|---|---|---|---|---|---|---|---|
| Met | Glu | Thr | Gln | Pro | Glu | Val | Pro | Glu | Val | Pro | Leu | Arg | Pro | Phe | Lys |
| 1 | | | | 5 | | | | | 10 | | | | | 15 | |
| Leu | Ala | His | Gln | Val | Val | Ser | Leu | Thr | Gly | Ile | Ser | Phe | Glu | Arg | Arg |
| | | | 20 | | | | | 25 | | | | | 30 | | |
| Ser | Ile | Ile | Gly | Val | Val | Glu | Leu | Thr | Ile | Val | Pro | Asn | Ser | Glu | Asn |
| | | | 35 | | | | | 40 | | | | | 45 | | |
| Leu | Arg | Leu | Ile | Ser | Leu | Asn | Ala | Lys | Gln | Leu | Arg | Ile | Tyr | Ser | Val |
| | | 50 | | | | | 55 | | | | | 60 | | | |
| Val | Leu | Asn | Asp | Val | Cys | Gln | Ala | Asp | Phe | Thr | Tyr | Phe | Asp | Pro | Phe |
| 65 | | | | | 70 | | | | | 75 | | | | | 80 |
| Gln | Asn | Ile | Cys | Tyr | Lys | Glu | Pro | Lys | Ser | Arg | Ala | Leu | Glu | Val | Tyr |
| | | | | 85 | | | | | 90 | | | | | 95 | |
| Ser | Lys | His | His | Leu | Thr | Ala | Ala | Gln | Tyr | Thr | Asp | Pro | Asp | Val | Asn |
| | | | 100 | | | | | 105 | | | | | 110 | | |
| Asn | Gly | Glu | Leu | Leu | Ile | Gln | Val | Pro | Pro | Glu | Gly | Tyr | Ser | Met | Ile |
| | | | 115 | | | | | 120 | | | | | 125 | | |
| Gln | Glu | Gly | Gln | Gly | Leu | Arg | Ile | Arg | Ile | Glu | Phe | Ser | Leu | Glu | Asn |
| | | 130 | | | | | 135 | | | | | 140 | | | |
| Pro | Lys | Cys | Gly | Val | His | Phe | Val | Ile | Pro | Pro | Ala | Ser | Thr | Asp | Glu |
| 145 | | | | | 150 | | | | | 155 | | | | | 160 |
| Glu | Thr | Gln | Met | Asn | Ser | Ser | His | Met | Phe | Thr | Asn | Cys | Tyr | Glu | Asn |
| | | | | 165 | | | | | 170 | | | | | 175 | |
| Ser | Ser | Arg | Leu | Trp | Phe | Pro | Cys | Val | Asp | Ser | Phe | Ala | Asp | Pro | Cys |
| | | | 180 | | | | | 185 | | | | | 190 | | |
| Thr | Trp | Arg | Leu | Glu | Phe | Thr | Val | Asp | Lys | Asn | Met | Thr | Ala | Val | Ser |
| | | | 195 | | | | | 200 | | | | | 205 | | |
| Cys | Gly | Glu | Leu | Leu | Glu | Val | Ile | Met | Thr | Pro | Asp | Leu | Arg | Lys | Lys |

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |
| Thr | Phe | His | Tyr | Ser | Val | Ser | Thr | Pro | Val | Cys | Ala | Pro | Asn | Ile | Ala |
| 225 |     |     |     |     | 230 |     |     |     |     | 235 |     |     |     |     | 240 |
| Leu | Ala | Val | Gly | Gln | Phe | Glu | Ile | Tyr | Val | Asp | Pro | His | Met | His | Glu |
|     |     |     |     | 245 |     |     |     |     | 250 |     |     |     |     | 255 |     |
| Val | Thr | His | Phe | Cys | Leu | Pro | Gly | Leu | Leu | Pro | Leu | Leu | Lys | Asn | Thr |
|     |     |     | 260 |     |     |     |     | 265 |     |     |     |     | 270 |     |     |
| Val | Arg | Tyr | Leu | His | Glu | Ala | Phe | Glu | Phe | Tyr | Glu | Glu | Thr | Leu | Ser |
|     |     | 275 |     |     |     |     | 280 |     |     |     |     | 285 |     |     |     |
| Thr | Arg | Tyr | Pro | Phe | Ser | Cys | Tyr | Lys | Gln | Val | Phe | Val | Asp | Glu | Leu |
|     | 290 |     |     |     |     | 295 |     |     |     |     | 300 |     |     |     |     |
| Asp | Thr | Asp | Ile | Ser | Ala | Tyr | Ala | Thr | Met | Ser | Ile | Ala | Ser | Val | Asn |
| 305 |     |     |     |     | 310 |     |     |     |     | 315 |     |     |     |     | 320 |
| Leu | Leu | His | Ser | Ile | Ala | Ile | Ile | Asp | Gln | Thr | Tyr | Ile | Ser | Arg | Thr |
|     |     |     |     | 325 |     |     |     |     | 330 |     |     |     |     | 335 |     |
| Phe | Met | Ser | Arg | Ala | Val | Ala | Glu | Gln | Phe | Phe | Gly | Cys | Phe | Ile | Thr |
|     |     |     | 340 |     |     |     |     | 345 |     |     |     |     | 350 |     |     |
| Ser | His | His | Trp | Ser | Asp | Thr | Trp | Leu | Ala | Lys | Gly | Ile | Ala | Glu | Tyr |
|     |     | 355 |     |     |     |     | 360 |     |     |     |     | 365 |     |     |     |
| Leu | Cys | Gly | Leu | Tyr | Ser | Arg | Lys | Cys | Phe | Gly | Asn | Asn | Glu | Tyr | Arg |
|     | 370 |     |     |     |     | 375 |     |     |     |     | 380 |     |     |     |     |
| Ala | Trp | Val | Gln | Ser | Glu | Leu | Ala | Arg | Val | Val | Arg | Tyr | Glu | Glu | Gln |
| 385 |     |     |     |     | 390 |     |     |     |     | 395 |     |     |     |     | 400 |
| Tyr | Gly | Gly | Ile | Ile | Leu | Asp | Cys | Ser | Gln | Pro | Pro | Ala | Pro | Leu | Pro |
|     |     |     |     | 405 |     |     |     |     | 410 |     |     |     |     | 415 |     |
| Val | Ser | Gly | Thr | Asn | Gln | Ser | Ala | Ala | Ser | Ser | Lys | Gln | Gln | Glu | Ile |
|     |     |     | 420 |     |     |     |     | 425 |     |     |     |     | 430 |     |     |
| Val | His | Tyr | Phe | Pro | Ile | Lys | Ser | Leu | His | Thr | Val | Ser | Pro | Lys | Tyr |
|     |     | 435 |     |     |     |     | 440 |     |     |     |     | 445 |     |     |     |
| Val | Glu | Ala | Met | Arg | Arg | Lys | Ala | His | Phe | Val | Ile | Arg | Met | Leu | Glu |
|     | 450 |     |     |     |     | 455 |     |     |     |     | 460 |     |     |     |     |
| Asn | Arg | Ile | Gly | Gln | Glu | Leu | Leu | Ile | Gln | Val | Phe | Asn | Lys | Gln | Leu |
| 465 |     |     |     |     | 470 |     |     |     |     | 475 |     |     |     |     | 480 |
| Ala | Leu | Ala | Ser | Ser | Ala | Ala | Thr | Thr | Lys | Ile | Gly | Ala | Gly | Leu | Trp |
|     |     |     |     | 485 |     |     |     |     | 490 |     |     |     |     | 495 |     |
| Ser | Gln | Leu | Leu | Ile | Ser | Thr | Asn | Ile | Phe | Ile | Lys | Ala | Ile | Phe | Thr |
|     |     |     | 500 |     |     |     |     | 505 |     |     |     |     | 510 |     |     |
| Val | Thr | Gly | Lys | Asp | Met | Ser | Val | Phe | Met | Asp | Gln | Trp | Val | Arg | Thr |
|     |     | 515 |     |     |     |     | 520 |     |     |     |     | 525 |     |     |     |
| Gly | Gly | His | Ala | Lys | Phe | Ser | Leu | Thr | Ser | Val | Phe | Asn | Arg | Lys | Arg |
|     | 530 |     |     |     |     | 535 |     |     |     |     | 540 |     |     |     |     |
| Asn | Thr | Ile | Glu | Leu | Glu | Ile | Arg | Gln | Asp | Tyr | Val | Asn | Gln | Arg | Gly |
| 545 |     |     |     |     | 550 |     |     |     |     | 555 |     |     |     |     | 560 |
| Ile | Arg | Lys | Tyr | Asn | Gly | Pro | Leu | Met | Val | Gln | Leu | Gln | Glu | Leu | Asp |
|     |     |     |     | 565 |     |     |     |     | 570 |     |     |     |     | 575 |     |
| Gly | Thr | Phe | Lys | His | Thr | Leu | Gln | Ile | Glu | Ser | Thr | Leu | Val | Lys | Ser |
|     |     |     | 580 |     |     |     |     | 585 |     |     |     |     | 590 |     |     |
| Asp | Ile | Thr | Cys | His | Ser | Lys | Ser | Arg | Arg | Asn | Lys | Lys | Lys | Lys | Ile |
|     |     | 595 |     |     |     |     | 600 |     |     |     |     | 605 |     |     |     |
| Pro | Leu | Cys | Thr | Gly | Glu | Glu | Val | Asp | Met | Asp | Leu | Ser | Ala | Met | Asp |
|     | 610 |     |     |     |     | 615 |     |     |     |     | 620 |     |     |     |     |
| Asp | Ser | Pro | Val | Leu | Trp | Ile | Arg | Leu | Asp | Pro | Glu | Met | Ile | Leu | Leu |
| 625 |     |     |     |     | 630 |     |     |     |     | 635 |     |     |     |     | 640 |

```
Arg Asp Leu Ile Ile Glu Gln Pro Asp Phe Gln Trp Gln Tyr Gln Leu
            645                 650                 655

Arg His Glu Arg Asp Val Thr Ala Gln Phe Gln Ala Ile Gln Ala Leu
            660                 665                 670

Gln Lys Tyr Pro Thr Asn Ala Thr Arg Leu Ala Leu Thr Asp Thr Ile
            675                 680                 685

Glu Ser Glu Arg Cys Phe Tyr Gln Val Arg Cys Glu Ala Ala His Ser
            690                 695                 700

Leu Thr Lys Val Ala Asn Gln Met Val Ala Ser Trp Ser Gly Pro Pro
705                 710                 715                 720

Ala Met Leu Asn Ile Phe Arg Lys Phe Phe Gly Ser Phe Ser Ala Pro
                725                 730                 735

His Ile Ile Lys Leu Asn Asn Phe Ser Asn Phe Gln Leu Tyr Phe Leu
            740                 745                 750

Gln Lys Ala Ile Pro Val Ala Met Ala Gly Leu Arg Thr Ser His Gly
            755                 760                 765

Ile Cys Pro Pro Glu Val Met Arg Phe Leu Phe Asp Leu Phe Lys Tyr
770                 775                 780

Asn Glu Asn Ser Arg Asn His Tyr Thr Asp Ala Tyr Tyr Arg Ala Ala
785                 790                 795                 800

Leu Val Glu Ala Leu Gly Glu Thr Leu Thr Pro Val Val Ser Val Ala
                805                 810                 815

Ile His Gly Thr Gln Ile Thr Thr Asp Ser Leu Ser Thr Asp Ala Lys
            820                 825                 830

Leu Val Leu Asp Glu Val Thr Arg Leu Leu Asn Met Glu Lys His Leu
            835                 840                 845

Pro Ser Tyr Lys Tyr Met Val Ser Val Ser Cys Leu Lys Val Ile Arg
    850                 855                 860

Lys Leu Gln Lys Phe Gly His Leu Pro Ser Leu Pro His Ile Tyr Arg
865                 870                 875                 880

Ser Tyr Ala Glu Tyr Gly Ile Tyr Leu Asp Leu Arg Ile Ala Ala Met
                885                 890                 895

Glu Cys Leu Val Asp Phe Val Lys Val Asp Gly Arg Ser Glu Asp Leu
            900                 905                 910

Glu His Leu Ile Thr Leu Leu Glu Thr Asp Pro Asp Pro Ala Ala Arg
    915                 920                 925

His Ala Leu Ala Gln Leu Leu Ile Asp Asn Pro Pro Phe Thr Arg Glu
930                 935                 940

Ser Arg Ser Arg Leu Asp Lys Pro Asn Leu Val Asp Arg Leu Trp Phe
945                 950                 955                 960

Ser Ile Asn Arg Leu Pro Tyr Asp Thr Lys Leu Arg Cys Asp Ile Val
            965                 970                 975

Asp Leu Tyr Tyr Ala Leu Tyr Gly Thr Lys Arg Pro Asn Cys Leu Gln
            980                 985                 990

Ala Gly Glu Asn Gln Ser Phe Tyr Lys Asp Leu Met Lys Asp Asn Asn
            995                 1000                1005

Ser Ser Val Gly Ser Val Thr Gly Ser Phe Lys Lys Thr Ser Asp Ser
    1010                1015                1020

Lys Ser His Leu Pro Thr Pro Thr Asn Thr Leu Asp Asn Glu Pro Gln
1025                1030                1035                1040

Glu Arg Gln Lys Pro Ala Met Val Thr Ile Lys Arg Thr Ala Thr Glu
            1045                1050                1055

Ala Phe Glu Val Gly Asp Glu Ile Ile Lys Leu Glu Arg Ser Glu Glu
            1060                1065                1070
```

| | | | | | | | | | | | | | | |
|---|---|---|---|---|---|---|---|---|---|---|---|---|---|---|
| Ile | Thr | Val | Leu | Asp | Glu | Pro | Val | Asn | Val | Gln | Ala | Tyr | Asp | Ser | Glu |
| | | | 1075 | | | | 1080 | | | | 1085 | | | | |
| Thr | Lys | Val | Asn | Ala | Leu | Gln | Ala | Asp | Glu | Glu | Ala | Arg | Asp | Thr | His |
| | | | 1090 | | | | 1095 | | | | 1100 | | | | |
| Gln | Ala | Ala | Lys | Arg | Leu | Lys | Asn | Glu | Met | Tyr | Ala | Glu | Asp | Asp | Asn |
| 1105 | | | | | 1110 | | | | 1115 | | | | | | 1120 |
| Ser | Ser | Thr | Met | Leu | Asp | Val | Gly | Asp | Ser | Thr | Arg | Tyr | Glu | Ser | Ser |
| | | | | 1125 | | | | | 1130 | | | | | 1135 | |
| His | Glu | Glu | Gly | Lys | Leu | Lys | Ser | Gly | Asp | Gly | Leu | Lys | Lys | Lys |
| | | | | 1140 | | | | 1145 | | | | 1150 | | |
| Lys | Lys | Lys | Glu | Lys | Lys | Lys | His | Lys | His | Lys | His | Lys | His | Arg | His |
| | | | 1155 | | | | 1160 | | | | 1165 | | | | |
| Ser | Lys | Asp | Lys | Asp | Lys | Glu | Arg | Lys | Asp | Lys | Asp | Lys | Arg | Asp | Pro |
| | 1170 | | | | | 1175 | | | | | 1180 | | | | |
| His | Ile | Ser | Arg | Leu | Gln | Ala | Ala | Arg | Gln | Pro | Leu | Arg | Thr | Leu | Ser |
| 1185 | | | | | 1190 | | | | | 1195 | | | | | 1200 |
| Ala | Arg | Arg | Thr | Val | Ala | Thr | Ala | Ile | Ala | Cys | Arg | Pro |
| | | | | 1205 | | | | | 1210 | | | |

(2) INFORMATION FOR SEQ ID NO:21:

(i) SEQUENCE CHARACTERISTICS:
        (A) LENGTH: 872 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 96..686

(xi) SEQUENCE DESCRIPTION: SEQ ID NO:21:

```
CCAAAAATCC GCCCAACTTA CTGTACTTTC CCCAAACACT TCCAACCAAC CGACCTACCA          60

CCCACTTGAT TTGACTCTGA AGAAACCCAA AAGCA ATG TCG GAT CTC TTT ACC           113
                                      Met Ser Asp Leu Phe Thr
                                       1               5

ACT TTC GAT AGC AAC GGC GTC GCG AGG CAC CAC CTG CAC CAC AAC CAC          161
Thr Phe Asp Ser Asn Gly Val Ala Arg His His Leu His His Asn His
         10                  15                  20

AAC TCC ACA TCG TCC GCC AGC GGA CTG CTC CAC GAC CCA CCC ATG GCC          209
Asn Ser Thr Ser Ser Ala Ser Gly Leu Leu His Asp Pro Pro Met Ala
     25                  30                  35

TCG CCC TCC CAG CAC AGT CCG ATG ACC AAC AAC AGC AAC TCA TCC TCG          257
Ser Pro Ser Gln His Ser Pro Met Thr Asn Asn Ser Asn Ser Ser Ser
 40                  45                  50

CAG AAC GGC GGA CCG GTT TCC GGT TTG GGT ACG GGA ACG GGC CCC ATA          305
Gln Asn Gly Gly Pro Val Ser Gly Leu Gly Thr Gly Thr Gly Pro Ile
 55                  60                  65                  70

TCT GGT GGT AGC AAG TCA TCC AAT CAC ACA TCA TCC GCC GCC GGT TCC          353
Ser Gly Gly Ser Lys Ser Ser Asn His Thr Ser Ser Ala Ala Gly Ser
             75                  80                  85

GAG AAC ACT CCC ATG CTT ACC AAA CCG CGT CTC ACA GAG CTC GTC CGA          401
Glu Asn Thr Pro Met Leu Thr Lys Pro Arg Leu Thr Glu Leu Val Arg
                 90                  95                 100

GAG GTG GAT ACC ACC ACG CAG CTG GAC GAG GAT GTT GAG GAG CTT CTG          449
Glu Val Asp Thr Thr Thr Gln Leu Asp Glu Asp Val Glu Glu Leu Leu
            105                 110                 115

CTT CAG ATC ATC GAC GAC TTT GTG AGG GAC ACC GTC AAG TCG ACG AGC          497
```

| | | | | | | | | | | | | | | | |
|---|---|---|---|---|---|---|---|---|---|---|---|---|---|---|---|
| Leu | Gln | Ile | Ile | Asp | Asp | Phe | Val | Arg | Asp | Thr | Val | Lys | Ser | Thr | Ser |
| | 120 | | | | 125 | | | | | 130 | | | | | |

| | | | | | | | | | | | | | | | | |
|---|---|---|---|---|---|---|---|---|---|---|---|---|---|---|---|---|
| GCC | TTC | GCC | AAG | CAC | CGA | AAG | TCT | AAC | AAG | ATC | GAG | GTG | CGC | GAC | GTG | 545 |
| Ala | Phe | Ala | Lys | His | Arg | Lys | Ser | Asn | Lys | Ile | Glu | Val | Arg | Asp | Val | |
| 135 | | | | | 140 | | | | 145 | | | | | 150 | | |

| | | | | | | | | | | | | | | | | |
|---|---|---|---|---|---|---|---|---|---|---|---|---|---|---|---|---|
| CAG | CTG | CAC | TTT | GAG | CGG | AAG | TAC | AAC | ATG | TGG | ATA | CCC | GGC | TTC | GGT | 593 |
| Gln | Leu | His | Phe | Glu | Arg | Lys | Tyr | Asn | Met | Trp | Ile | Pro | Gly | Phe | Gly | |
| | | | | 155 | | | | | 160 | | | | | 165 | | |

| | | | | | | | | | | | | | | | | |
|---|---|---|---|---|---|---|---|---|---|---|---|---|---|---|---|---|
| ACG | GAC | GAA | CTG | CGT | CCC | TAC | AAG | CGG | GCA | GCT | GTC | ACG | GAG | GCG | CAC | 641 |
| Thr | Asp | Glu | Leu | Arg | Pro | Tyr | Lys | Arg | Ala | Ala | Val | Thr | Glu | Ala | His | |
| | | | 170 | | | | | 175 | | | | 180 | | | | |

| | | | | | | | | | | | | | |
|---|---|---|---|---|---|---|---|---|---|---|---|---|---|
| AAA | CAG | CGC | CTT | GCC | CTC | ATA | CGG | AAA | ACG | ATC | AAG | AAA | TAC | TAGAGGATTG | 693 |
| Lys | Gln | Arg | Leu | Ala | Leu | Ile | Arg | Lys | Thr | Ile | Lys | Lys | Tyr | | |
| | | 185 | | | | | 190 | | | | | 195 | | | |

GATCTAATCG GGTCGAGGCT CTGTTTCGGT TTGCCGGATT TCGCGTATGC TAAACGTGCA 753

CACGCCACAA ACTAATTTAA GCTCCAATTT AGATTAAATA ACAAATTATC GTCGCTCTAT 813

TGTAGATTTA TTGTAATAAA AGTGCACTAT TGATTTCACA TTCAAAAAAA AAAAAAAA 872

( 2 ) INFORMATION FOR SEQ ID NO:22:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| | | | | | | | | | | | | | | |
|---|---|---|---|---|---|---|---|---|---|---|---|---|---|---|
| Met | Ser | Asp | Leu | Phe | Thr | Thr | Phe | Asp | Ser | Asn | Gly | Val | Ala | Arg | His |
| 1 | | | | 5 | | | | | 10 | | | | | 15 |

| | | | | | | | | | | | | | | |
|---|---|---|---|---|---|---|---|---|---|---|---|---|---|---|
| His | Leu | His | His | Asn | His | Asn | Ser | Thr | Ser | Ser | Ala | Ser | Gly | Leu | Leu |
| | | | 20 | | | | | 25 | | | | | 30 | |

| | | | | | | | | | | | | | | |
|---|---|---|---|---|---|---|---|---|---|---|---|---|---|---|
| His | Asp | Pro | Pro | Met | Ala | Ser | Pro | Ser | Gln | His | Ser | Pro | Met | Thr | Asn |
| | | 35 | | | | | 40 | | | | | 45 | | |

| | | | | | | | | | | | | | |
|---|---|---|---|---|---|---|---|---|---|---|---|---|---|
| Asn | Ser | Asn | Ser | Ser | Ser | Gln | Asn | Gly | Gly | Pro | Val | Ser | Gly | Leu | Gly |
| | 50 | | | | | 55 | | | | | 60 | | | |

| | | | | | | | | | | | | | | |
|---|---|---|---|---|---|---|---|---|---|---|---|---|---|---|
| Thr | Gly | Thr | Gly | Pro | Ile | Ser | Gly | Gly | Ser | Lys | Ser | Ser | Asn | His | Thr |
| 65 | | | | | 70 | | | | | 75 | | | | | 80 |

| | | | | | | | | | | | | | | |
|---|---|---|---|---|---|---|---|---|---|---|---|---|---|---|
| Ser | Ser | Ala | Ala | Gly | Ser | Glu | Asn | Thr | Pro | Met | Leu | Thr | Lys | Pro | Arg |
| | | | | 85 | | | | | 90 | | | | | 95 |

| | | | | | | | | | | | | | | |
|---|---|---|---|---|---|---|---|---|---|---|---|---|---|---|
| Leu | Thr | Glu | Leu | Val | Arg | Glu | Val | Asp | Thr | Thr | Thr | Gln | Leu | Asp | Glu |
| | | | 100 | | | | | 105 | | | | | 110 | |

| | | | | | | | | | | | | | | |
|---|---|---|---|---|---|---|---|---|---|---|---|---|---|---|
| Asp | Val | Glu | Glu | Leu | Leu | Leu | Gln | Ile | Ile | Asp | Asp | Phe | Val | Arg | Asp |
| | | 115 | | | | | 120 | | | | | 125 | | |

| | | | | | | | | | | | | | | |
|---|---|---|---|---|---|---|---|---|---|---|---|---|---|---|
| Thr | Val | Lys | Ser | Thr | Ser | Ala | Phe | Ala | Lys | His | Arg | Lys | Ser | Asn | Lys |
| | 130 | | | | | 135 | | | | | 140 | | | |

| | | | | | | | | | | | | | | |
|---|---|---|---|---|---|---|---|---|---|---|---|---|---|---|
| Ile | Glu | Val | Arg | Asp | Val | Gln | Leu | His | Phe | Glu | Arg | Lys | Tyr | Asn | Met |
| 145 | | | | | 150 | | | | | 155 | | | | | 160 |

| | | | | | | | | | | | | | | |
|---|---|---|---|---|---|---|---|---|---|---|---|---|---|---|
| Trp | Ile | Pro | Gly | Phe | Gly | Thr | Asp | Glu | Leu | Arg | Pro | Tyr | Lys | Arg | Ala |
| | | | | 165 | | | | | 170 | | | | | 175 |

| | | | | | | | | | | | | | | |
|---|---|---|---|---|---|---|---|---|---|---|---|---|---|---|
| Ala | Val | Thr | Glu | Ala | His | Lys | Gln | Arg | Leu | Ala | Leu | Ile | Arg | Lys | Thr |
| | | | 180 | | | | | 185 | | | | | 190 | |

| | | | |
|---|---|---|---|
| Ile | Lys | Lys | Tyr |
| | | 195 | |

( 2 ) INFORMATION FOR SEQ ID NO:23:

( i ) SEQUENCE CHARACTERISTICS:

(A) LENGTH: 738 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 31..624

(xi) SEQUENCE DESCRIPTION: SEQ ID NO:23:

| | | | | | | | | | | | | | | | | |
|---|---|---|---|---|---|---|---|---|---|---|---|---|---|---|---|---|
| CCCCCCCCCC | CCCCCCCGA | TTTTTTTAA | ATG | GAC | GAA | ATC | CTC | TTT | CCC | ACG | | | | | | 54 |
| | | | Met | Asp | Glu | Ile | Leu | Phe | Pro | Thr | | | | | | |
| | | | 1 | | | | 5 | | | | | | | | | |
| CAG | CAA | AAG | AGC | AAC | TCC | CTA | AGC | GAC | GGC | GAC | GAT | GTC | GAC | CTG | AAA | 102 |
| Gln | Gln | Lys | Ser | Asn | Ser | Leu | Ser | Asp | Gly | Asp | Asp | Val | Asp | Leu | Lys | |
| | 10 | | | | 15 | | | | | 20 | | | | | | |
| TTC | TTC | CAG | TCG | GGC | CTC | CGG | GGG | AGG | CGA | AAG | GAC | AGC | GAC | ACC | TCG | 150 |
| Phe | Phe | Gln | Ser | Gly | Leu | Arg | Gly | Arg | Arg | Lys | Asp | Ser | Asp | Thr | Ser | |
| 25 | | | | | 30 | | | | | 35 | | | | | 40 | |
| GAT | CCG | GGA | AAC | GAT | GCG | GAT | CGT | GAT | GGC | AAA | GAT | GCG | GAT | GGG | GAC | 198 |
| Asp | Pro | Gly | Asn | Asp | Ala | Asp | Arg | Asp | Gly | Lys | Asp | Ala | Asp | Gly | Asp | |
| | | | | 45 | | | | | 50 | | | | | 55 | | |
| AAC | GAC | AAC | AAG | AAC | ACG | GAC | GGA | GAT | GGT | GAC | TCT | GGC | GAG | CCG | GCG | 246 |
| Asn | Asp | Asn | Lys | Asn | Thr | Asp | Gly | Asp | Gly | Asp | Ser | Gly | Glu | Pro | Ala | |
| | | | 60 | | | | | 65 | | | | | 70 | | | |
| CAC | AAA | AAG | CTC | AAA | ACC | AAG | AAG | GAA | CTG | GAG | GAG | GAG | GAG | CGC | GAA | 294 |
| His | Lys | Lys | Leu | Lys | Thr | Lys | Lys | Glu | Leu | Glu | Glu | Glu | Glu | Arg | Glu | |
| | | 75 | | | | | 80 | | | | | 85 | | | | |
| CGA | ATG | CAG | GTT | CTC | GTT | TCC | AAC | TTT | ACT | GAA | GAA | CAG | CTG | GAT | CGC | 342 |
| Arg | Met | Gln | Val | Leu | Val | Ser | Asn | Phe | Thr | Glu | Glu | Gln | Leu | Asp | Arg | |
| | 90 | | | | | 95 | | | | | 100 | | | | | |
| TAC | GAA | ATG | TAT | CGT | CGC | TCA | GCC | TTT | CCC | AAG | GCC | GCC | GTC | AAG | CGT | 390 |
| Tyr | Glu | Met | Tyr | Arg | Arg | Ser | Ala | Phe | Pro | Lys | Ala | Ala | Val | Lys | Arg | |
| 105 | | | | | 110 | | | | | 115 | | | | | 120 | |
| CTA | ATG | CAA | ACT | ATC | ACC | GGC | TGT | TCC | GTG | TCC | CAA | AAT | GTT | GTG | ATA | 438 |
| Leu | Met | Gln | Thr | Ile | Thr | Gly | Cys | Ser | Val | Ser | Gln | Asn | Val | Val | Ile | |
| | | | | 125 | | | | | 130 | | | | | 135 | | |
| GCC | ATG | TCC | GGC | ATT | GCG | AAG | GTC | TTC | GTC | GGC | GAG | GTT | GTG | GAG | GAA | 486 |
| Ala | Met | Ser | Gly | Ile | Ala | Lys | Val | Phe | Val | Gly | Glu | Val | Val | Glu | Glu | |
| | | | 140 | | | | | 145 | | | | | 150 | | | |
| GCC | CTC | GAC | GTG | ATG | GAG | GCC | CAA | GGT | GAA | TCC | GGT | GCC | CTG | CAG | CCC | 534 |
| Ala | Leu | Asp | Val | Met | Glu | Ala | Gln | Gly | Glu | Ser | Gly | Ala | Leu | Gln | Pro | |
| | | 155 | | | | | 160 | | | | | 165 | | | | |
| AAA | TTC | ATA | CGA | GAG | GCA | GTG | CGA | CGA | CTG | AGG | ACC | AAG | GAT | CGG | ATG | 582 |
| Lys | Phe | Ile | Arg | Glu | Ala | Val | Arg | Arg | Leu | Arg | Thr | Lys | Asp | Arg | Met | |
| | 170 | | | | | 175 | | | | | 180 | | | | | |
| CCC | ATA | GGC | AGA | TAC | CAG | CAG | CCC | TAT | TTC | AGA | CTG | AAC | TAGCGAGTCG | | | 631 |
| Pro | Ile | Gly | Arg | Tyr | Gln | Gln | Pro | Tyr | Phe | Arg | Leu | Asn | | | | |
| 185 | | | | | 190 | | | | | 195 | | | | | | |

AGACATTAAG AAATATAGTT TGTAAATCTG TTAGTGAATA TAAAAATACA TAAACAAGTA     691

AAAAGTAAAT AAATATAAAG ATTTTTTCAA GAAAAAAAAA AAAAAA                   738

(2) INFORMATION FOR SEQ ID NO:24:

(i) SEQUENCE CHARACTERISTICS:
(A) LENGTH: 197 amino acids
(B) TYPE: amino acid
(D) TOPOLOGY: linear (ii) MOLECULE TYPE: protein (xi) SEQUENCE DESCRIPTION: SEQ ID NO:24:

```
Met  Asp  Glu  Ile  Leu  Phe  Pro  Thr  Gln  Gln  Lys  Ser  Asn  Ser  Leu  Ser
 1                    5                        10                        15

Asp  Gly  Asp  Asp  Val  Asp  Leu  Lys  Phe  Phe  Gln  Ser  Gly  Leu  Arg  Gly
               20                        25                        30

Arg  Arg  Lys  Asp  Ser  Asp  Thr  Ser  Asp  Pro  Gly  Asn  Asp  Ala  Asp  Arg
          35                        40                        45

Asp  Gly  Lys  Asp  Ala  Asp  Gly  Asp  Asn  Asp  Asn  Lys  Asn  Thr  Asp  Gly
     50                        55                        60

Asp  Gly  Asp  Ser  Gly  Glu  Pro  Ala  His  Lys  Lys  Leu  Lys  Thr  Lys  Lys
65                        70                        75                        80

Glu  Leu  Glu  Glu  Glu  Glu  Arg  Glu  Arg  Met  Gln  Val  Leu  Val  Ser  Asn
                    85                        90                        95

Phe  Thr  Glu  Glu  Gln  Leu  Asp  Arg  Tyr  Glu  Met  Tyr  Arg  Arg  Ser  Ala
               100                       105                       110

Phe  Pro  Lys  Ala  Ala  Val  Lys  Arg  Leu  Met  Gln  Thr  Ile  Thr  Gly  Cys
          115                       120                       125

Ser  Val  Ser  Gln  Asn  Val  Val  Ile  Ala  Met  Ser  Gly  Ile  Ala  Lys  Val
     130                       135                       140

Phe  Val  Gly  Glu  Val  Val  Glu  Glu  Ala  Leu  Asp  Val  Met  Glu  Ala  Gln
145                       150                       155                       160

Gly  Glu  Ser  Gly  Ala  Leu  Gln  Pro  Lys  Phe  Ile  Arg  Glu  Ala  Val  Arg
                    165                       170                       175

Arg  Leu  Arg  Thr  Lys  Asp  Arg  Met  Pro  Ile  Gly  Arg  Tyr  Gln  Gln  Pro
               180                       185                       190

Tyr  Phe  Arg  Leu  Asn
               195
```

( 2 ) INFORMATION FOR SEQ ID NO:25:

( i ) SEQUENCE CHARACTERISTICS:
     ( A ) LENGTH: 1183 base pairs
     ( B ) TYPE: nucleic acid
     ( C ) STRANDEDNESS: double
     ( D ) TOPOLOGY: linear ( i i ) MOLECULE TYPE: cDNA ( i x ) FEATURE:
     ( A ) NAME/KEY: CDS
     ( B ) LOCATION: 161..952

( x i ) SEQUENCE DESCRIPTION: SEQ ID NO:25:

```
GAATTCGCGG  CCGCCGGGGA  CCATGTTGCT  TCCGAACATC  CTGCTCACCG  GTACACCAGG      60

GGTTGGAAAA  ACCACACTAG  GCAAAGAACT  TGCGTCAAAA  TCAGGACTGA  AATACATTAA     120

TGTGGGTGAT  TTAGCTCGAG  AAGTCTGATC  ATCGGATATC  ATG GAG TCT GGC AAG       175
                                                  Met Glu Ser Gly Lys
                                                   1               5

ACG GCT TCT CCC AAG AGC ATG CCG AAA GAT GCA CAG ATG ATG GCA CAA           223
Thr Ala Ser Pro Lys Ser Met Pro Lys Asp Ala Gln Met Met Ala Gln
             10                      15                      20

ATC CTG AAG GAT ATG GGG ATT ACA GAA TAT GAG CCA AGA GTT ATA AAT           271
Ile Leu Lys Asp Met Gly Ile Thr Glu Tyr Glu Pro Arg Val Ile Asn
         25                      30                      35

CAG ATG TTG GAG TTT GCC TTC CGA TAT GTG ACC ACA ATT CTA GAT GAT           319
Gln Met Leu Glu Phe Ala Phe Arg Tyr Val Thr Thr Ile Leu Asp Asp
             40                      45                      50

GCA AAA ATT TAT TCA AGC CAT GCT AAG AAA GCT ACT GTT GAT GCA GAT           367
Ala Lys Ile Tyr Ser Ser His Ala Lys Lys Ala Thr Val Asp Ala Asp
     55                      60                      65
```

| | | | | | | | | | | | | | | | | |
|---|---|---|---|---|---|---|---|---|---|---|---|---|---|---|---|---|
| GAT | GTG | CGA | TTG | GCA | ATC | CAG | TGC | CGC | GCT | GAT | CAG | TCT | TTT | ACC | TCT | 415 |
| Asp | Val | Arg | Leu | Ala | Ile | Gln | Cys | Arg | Ala | Asp | Gln | Ser | Phe | Thr | Ser | |
| 70 | | | | | 75 | | | | | 80 | | | | | 85 | |
| CCT | CCC | CCA | AGA | GAT | TTT | TTA | TTA | GAT | ATT | GCA | AGG | CAA | AGA | AAT | CAA | 463 |
| Pro | Pro | Pro | Arg | Asp | Phe | Leu | Leu | Asp | Ile | Ala | Arg | Gln | Arg | Asn | Gln | |
| | | | | 90 | | | | | 95 | | | | | 100 | | |
| ACC | CCT | TTG | CCA | TTG | ATC | AAG | CCA | TAT | TCA | GGT | CCT | AGG | TTG | CCA | CCT | 511 |
| Thr | Pro | Leu | Pro | Leu | Ile | Lys | Pro | Tyr | Ser | Gly | Pro | Arg | Leu | Pro | Pro | |
| | | | 105 | | | | | 110 | | | | | 115 | | | |
| GAT | AGA | TAC | TGC | TTA | ACA | GCT | CCA | AAC | TAT | AGG | CTG | AAA | TCT | TTA | CAG | 559 |
| Asp | Arg | Tyr | Cys | Leu | Thr | Ala | Pro | Asn | Tyr | Arg | Leu | Lys | Ser | Leu | Gln | |
| | | 120 | | | | | 125 | | | | | 130 | | | | |
| AAA | AAG | GCA | TCA | ACT | TCT | GCG | GGA | AGA | ATA | ACA | GTC | CCG | CGG | TTA | AGT | 607 |
| Lys | Lys | Ala | Ser | Thr | Ser | Ala | Gly | Arg | Ile | Thr | Val | Pro | Arg | Leu | Ser | |
| 135 | | | | | 140 | | | | | 145 | | | | | | |
| GTT | GGT | TCA | GTT | ACT | AGC | AGA | CCA | AGT | ACT | CCC | ACA | CTA | GGC | ACA | CCA | 655 |
| Val | Gly | Ser | Val | Thr | Ser | Arg | Pro | Ser | Thr | Pro | Thr | Leu | Gly | Thr | Pro | |
| 150 | | | | | 155 | | | | | 160 | | | | | 165 | |
| ACC | CCA | CAG | ACC | ATG | TCT | GTT | TCA | ACT | AAA | GTA | GGG | ACT | CCC | ATG | TCC | 703 |
| Thr | Pro | Gln | Thr | Met | Ser | Val | Ser | Thr | Lys | Val | Gly | Thr | Pro | Met | Ser | |
| | | | | 170 | | | | | 175 | | | | | 180 | | |
| CTC | ACA | GGT | CAA | AGG | TTT | ACA | GTA | CAG | ATG | CCT | ACT | TCT | CAG | TCT | CCA | 751 |
| Leu | Thr | Gly | Gln | Arg | Phe | Thr | Val | Gln | Met | Pro | Thr | Ser | Gln | Ser | Pro | |
| | | | | 185 | | | | | 190 | | | | | 195 | | |
| GCT | GTA | AAA | GCT | TCA | ATT | CCT | GCA | ACC | TCA | GCA | GTT | CAG | AAT | GTT | CTG | 799 |
| Ala | Val | Lys | Ala | Ser | Ile | Pro | Ala | Thr | Ser | Ala | Val | Gln | Asn | Val | Leu | |
| | | 200 | | | | | 205 | | | | | 210 | | | | |
| ATT | AAT | CCA | TCA | TTA | ATC | GGG | TCC | AAA | AAC | ATT | CTT | ATT | ACC | ACT | AAT | 847 |
| Ile | Asn | Pro | Ser | Leu | Ile | Gly | Ser | Lys | Asn | Ile | Leu | Ile | Thr | Thr | Asn | |
| | | 215 | | | | | 220 | | | | | 225 | | | | |
| ATG | ATG | TCA | TCA | CAA | AAT | ACT | GCC | AAT | GAA | TCA | TCA | AAT | GCA | TTG | AAA | 895 |
| Met | Met | Ser | Ser | Gln | Asn | Thr | Ala | Asn | Glu | Ser | Ser | Asn | Ala | Leu | Lys | |
| 230 | | | | | 235 | | | | | 240 | | | | | 245 | |
| AGA | AAA | CGT | GAA | GAT | GAT | GAT | GAT | GAC | GAT | GAT | GAT | GAT | GAT | GAC | TAT | 943 |
| Arg | Lys | Arg | Glu | Asp | Asp | Asp | Asp | Asp | Asp | Asp | Asp | Asp | Asp | Asp | Tyr | |
| | | | | 250 | | | | | 255 | | | | | 260 | | |

| | | | | |
|---|---|---|---|---|
| GAT AAT CTG | TAATCTAGCC | TTGCTGAATG | TAACATGTAT | ACTTGGTCTT | 992 |
| Asp Asn Leu | | | | |
| GAATTCATTG | TACTGATATT | AAACATGCAT | GCTGGATGTT | TTCAAGTTGT GTTTTAGAAA | 1052 |
| ACTAATAATA | ATGAGTAAAC | ACAGTTACCA | TACTTTTCAA | TTGAAATGAA GGTTTTTCAT | 1112 |
| CAGCCTTAAA | AGTGTAAGAA | AAATAAAGTT | GTCATTCATT | CGATAAAAAA AAAAAAAGCG | 1172 |
| GCCGCGAATT | C | | | | 1183 |

( 2 ) INFORMATION FOR SEQ ID NO:26:

( i ) SEQUENCE CHARACTERISTICS:
      ( A ) LENGTH: 264 amino acids
      ( B ) TYPE: amino acid
      ( D ) TOPOLOGY: linear ( i i ) MOLECULE TYPE: protein ( x i ) SEQUENCE DESCRIPTION: SEQ ID NO:26:

| | | | | | | | | | | | | | | |
|---|---|---|---|---|---|---|---|---|---|---|---|---|---|---|
| Met | Glu | Ser | Gly | Lys | Thr | Ala | Ser | Pro | Lys | Ser | Met | Pro | Lys | Asp | Ala |
| 1 | | | | 5 | | | | | 10 | | | | | 15 | |
| Gln | Met | Met | Ala | Gln | Ile | Leu | Lys | Asp | Met | Gly | Ile | Thr | Glu | Tyr | Glu |
| | | | 20 | | | | | 25 | | | | | 30 | | |
| Pro | Arg | Val | Ile | Asn | Gln | Met | Leu | Glu | Phe | Ala | Phe | Arg | Tyr | Val | Thr |
| | | 35 | | | | | 40 | | | | | 45 | | | |

```
Thr  Ile  Leu  Asp  Asp  Ala  Lys  Ile  Tyr  Ser  Ser  His  Ala  Lys  Lys  Ala
     50                  55                      60

Thr  Val  Asp  Ala  Asp  Asp  Val  Arg  Leu  Ala  Ile  Gln  Cys  Arg  Ala  Asp
65                       70                      75                           80

Gln  Ser  Phe  Thr  Ser  Pro  Pro  Pro  Arg  Asp  Phe  Leu  Leu  Asp  Ile  Ala
               85                       90                           95

Arg  Gln  Arg  Asn  Gln  Thr  Pro  Leu  Pro  Leu  Ile  Lys  Pro  Tyr  Ser  Gly
               100                      105                     110

Pro  Arg  Leu  Pro  Pro  Asp  Arg  Tyr  Cys  Leu  Thr  Ala  Pro  Asn  Tyr  Arg
          115                      120                     125

Leu  Lys  Ser  Leu  Gln  Lys  Lys  Ala  Ser  Thr  Ser  Ala  Gly  Arg  Ile  Thr
     130                 135                     140

Val  Pro  Arg  Leu  Ser  Val  Gly  Ser  Val  Thr  Ser  Arg  Pro  Ser  Thr  Pro
145                      150                     155                          160

Thr  Leu  Gly  Thr  Pro  Thr  Pro  Gln  Thr  Met  Ser  Val  Ser  Thr  Lys  Val
               165                      170                     175

Gly  Thr  Pro  Met  Ser  Leu  Thr  Gly  Gln  Arg  Phe  Thr  Val  Gln  Met  Pro
               180                      185                     190

Thr  Ser  Gln  Ser  Pro  Ala  Val  Lys  Ala  Ser  Ile  Pro  Ala  Thr  Ser  Ala
          195                      200                     205

Val  Gln  Asn  Val  Leu  Ile  Asn  Pro  Ser  Leu  Ile  Gly  Ser  Lys  Asn  Ile
210                      215                     220

Leu  Ile  Thr  Thr  Asn  Met  Met  Ser  Ser  Gln  Asn  Thr  Ala  Asn  Glu  Ser
225                      230                     235                          240

Ser  Asn  Ala  Leu  Lys  Arg  Lys  Arg  Glu  Asp  Asp  Asp  Asp  Asp  Asp  Asp
               245                      250                     255

Asp  Asp  Asp  Asp  Tyr  Asp  Asn  Leu
               260
```

( 2 ) INFORMATION FOR SEQ ID NO:27:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Asp  Val  Gln  Leu  His  Leu  Glu  Arg  Gln  Asn  Met  Ile  Pro  Gly  Phe  Gly
1                  5                      10                          15

Ser  Glu  Glu  Ile  Pro  Tyr  Lys
               20
```

( 2 ) INFORMATION FOR SEQ ID NO:28:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Val  Phe  Val  Gly  Glu  Val  Val  Glu  Glu  Ala  Leu  Asp  Val  Glu  Glu  Lys
1                  5                      10                          15

Pro
```

( 2 ) INFORMATION FOR SEQ ID NO:29:

( i ) SEQUENCE CHARACTERISTICS:
        ( A ) LENGTH: 1578 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 25..1377

( x i ) SEQUENCE DESCRIPTION: SEQ ID NO:29:

```
ATTCCAAGCT AAATTTAGGC GGGT ATG AGT GAT TTC AGT GAA GAA TTA AAA         51
                          Met Ser Asp Phe Ser Glu Glu Leu Lys
                           1               5

GGG CCT GTG ACA GAT GAT GAA GAA GTG GAA ACA TCT GTG CTC AGT GGT        99
Gly Pro Val Thr Asp Asp Glu Glu Val Glu Thr Ser Val Leu Ser Gly
 10              15                  20                      25

GCA GGA ATG CAT TTT CCT TGG CTT CAA ACA TAC GTA GAA ACT GTG GCC       147
Ala Gly Met His Phe Pro Trp Leu Gln Thr Tyr Val Glu Thr Val Ala
             30                  35                  40

ATT GGA GGG AAA AGG AGG AAG GAT TTT GCT CAG ACA ACA AGT GCT TGT       195
Ile Gly Gly Lys Arg Arg Lys Asp Phe Ala Gln Thr Thr Ser Ala Cys
         45                  50                  55

TTA AGT TTT ATC CAA GAA GCT CTG CTG AAG CAC CAA TGG CAG CAA GCT       243
Leu Ser Phe Ile Gln Glu Ala Leu Leu Lys His Gln Trp Gln Gln Ala
     60                  65                  70

GCA GAA TAC ATG TAC AGT TAT TTT CAG ACC TTG GAA GAT TCA GAT AGC       291
Ala Glu Tyr Met Tyr Ser Tyr Phe Gln Thr Leu Glu Asp Ser Asp Ser
 75                  80                  85

TAC AAA AGG CAG GCT GCA CCT GAG ATT ATT TGG AAG CTC GGA AGT GAA       339
Tyr Lys Arg Gln Ala Ala Pro Glu Ile Ile Trp Lys Leu Gly Ser Glu
 90                  95                 100                 105

ATT CTA TTT TAT CAT CCC AAA AGC AAC ATG GAG AGT TTC AAT ACT TTT       387
Ile Leu Phe Tyr His Pro Lys Ser Asn Met Glu Ser Phe Asn Thr Phe
             110                 115                 120

GCT AAC CGG ATG AAA AAT ATT GGC GTC ATG AAT TAT TTA AAG ATC TCC       435
Ala Asn Arg Met Lys Asn Ile Gly Val Met Asn Tyr Leu Lys Ile Ser
         125                 130                 135

TTA CAA CAT GCA TTA TAC CTT CTG CAT CAT GGA ATG CTT AAA GAT GCT       483
Leu Gln His Ala Leu Tyr Leu Leu His His Gly Met Leu Lys Asp Ala
     140                 145                 150

AAG AGA AAT CTG AGT GAG GCA GAG ACA TGG AGA CAT GGT GAA AAT ACG       531
Lys Arg Asn Leu Ser Glu Ala Glu Thr Trp Arg His Gly Glu Asn Thr
 155                 160                 165

TCT TCC CGG GAA ATA TTA ATC AAC CTT ATT CAG GCC TAT AAA GGG CTT       579
Ser Ser Arg Glu Ile Leu Ile Asn Leu Ile Gln Ala Tyr Lys Gly Leu
170                 175                 180                 185

TTA CAG TAT TAT ACC TGG TCT GAA AAG AAG ATG GAA TTG TCA AAG CTT       627
Leu Gln Tyr Tyr Thr Trp Ser Glu Lys Lys Met Glu Leu Ser Lys Leu
             190                 195                 200

GAT AAG GAT GAT TAT GCT TAC AAT GCA GTA GCC CAG GAT GTG TTC AAC       675
Asp Lys Asp Asp Tyr Ala Tyr Asn Ala Val Ala Gln Asp Val Phe Asn
         205                 210                 215

CAC AGC TGG AAG ACA TCT GCA AAT ATT TCT GCA TTG ATT AAA ATT CCT       723
His Ser Trp Lys Thr Ser Ala Asn Ile Ser Ala Leu Ile Lys Ile Pro
     220                 225                 230

GGA GTT TGG GAC CCT TTT GTG AAG AGT TAT GTA GAA ATG CTG GAA TTC       771
Gly Val Trp Asp Pro Phe Val Lys Ser Tyr Val Glu Met Leu Glu Phe
 235                 240                 245
```

| | | | | | | | | | | | | | | | | |
|---|---|---|---|---|---|---|---|---|---|---|---|---|---|---|---|---|
| TAT | GGG | GAT | CGA | GAT | GGA | GCC | CAA | GAG | GTA | CTC | ACC | AAT | TAT | GCA | TAT | 819 |
| Tyr | Gly | Asp | Arg | Asp | Gly | Ala | Gln | Glu | Val | Leu | Thr | Asn | Tyr | Ala | Tyr | |
| 250 | | | | | 255 | | | | 260 | | | | | | 265 | |
| GAT | GAA | AAG | TTT | CCA | TCA | AAT | CCA | AAT | GCC | CAT | ATC | TAC | TTA | TAC | AAC | 867 |
| Asp | Glu | Lys | Phe | Pro | Ser | Asn | Pro | Asn | Ala | His | Ile | Tyr | Leu | Tyr | Asn | |
| | | | | 270 | | | | 275 | | | | | | 280 | | |
| TTT | CTA | AAG | AGA | CAG | AAG | GCA | CCA | AGA | TCA | AAA | TTG | ATA | AGT | GTG | CTT | 915 |
| Phe | Leu | Lys | Arg | Gln | Lys | Ala | Pro | Arg | Ser | Lys | Leu | Ile | Ser | Val | Leu | |
| | | | 285 | | | | | 290 | | | | | 295 | | | |
| AAG | ATT | TTG | TAT | CAG | ATT | GTA | CCA | TCT | CAT | AAA | TTG | ATG | TTG | GAA | TTC | 963 |
| Lys | Ile | Leu | Tyr | Gln | Ile | Val | Pro | Ser | His | Lys | Leu | Met | Leu | Glu | Phe | |
| | | 300 | | | | | 305 | | | | | 310 | | | | |
| CAT | ACA | TTA | CTT | AGA | AAA | TCA | GAA | AAA | GAA | GAA | CAC | CGT | AAA | CTG | GGG | 1011 |
| His | Thr | Leu | Leu | Arg | Lys | Ser | Glu | Lys | Glu | Glu | His | Arg | Lys | Leu | Gly | |
| 315 | | | | | 320 | | | | | 325 | | | | | | |
| TTG | GAG | GTA | TTA | TTT | GGA | GTC | TTA | GAT | TTT | GCC | GGA | TGC | ACT | AAG | AAT | 1059 |
| Leu | Glu | Val | Leu | Phe | Gly | Val | Leu | Asp | Phe | Ala | Gly | Cys | Thr | Lys | Asn | |
| 330 | | | | | 335 | | | | 340 | | | | | | 345 | |
| ATA | ACT | GCT | TGG | AAA | TAC | TTG | GCA | AAA | TAT | CTG | AAA | AAT | ATC | TTA | ATG | 1107 |
| Ile | Thr | Ala | Trp | Lys | Tyr | Leu | Ala | Lys | Tyr | Leu | Lys | Asn | Ile | Leu | Met | |
| | | | | 350 | | | | | 355 | | | | | 360 | | |
| GGA | AAC | CAC | CTT | GCG | TGG | GTT | CAA | GAA | GAG | TGG | AAC | TCC | AGG | AAA | AAC | 1155 |
| Gly | Asn | His | Leu | Ala | Trp | Val | Gln | Glu | Glu | Trp | Asn | Ser | Arg | Lys | Asn | |
| | | | 365 | | | | | 370 | | | | | 375 | | | |
| TGG | TGG | CCA | GGG | TTT | CAT | TTC | AGC | TAC | TTT | TGG | GCA | AAA | AGT | GAT | TGG | 1203 |
| Trp | Trp | Pro | Gly | Phe | His | Phe | Ser | Tyr | Phe | Trp | Ala | Lys | Ser | Asp | Trp | |
| | | | 380 | | | | | 385 | | | | | 390 | | | |
| AAG | GAA | GAT | ACA | GCT | TTG | GCC | TGT | GAG | AAA | GCT | TTT | GTG | GCT | GGT | TTA | 1251 |
| Lys | Glu | Asp | Thr | Ala | Leu | Ala | Cys | Glu | Lys | Ala | Phe | Val | Ala | Gly | Leu | |
| 395 | | | | | 400 | | | | | 405 | | | | | | |
| CTG | TTA | GGA | AAA | GGT | TGT | AGA | TAT | TTC | CGG | TAT | ATT | TTA | AAG | CAA | GAT | 1299 |
| Leu | Leu | Gly | Lys | Gly | Cys | Arg | Tyr | Phe | Arg | Tyr | Ile | Leu | Lys | Gln | Asp | |
| 410 | | | | | 415 | | | | | 420 | | | | | 425 | |
| CAC | CAA | ATC | TTA | GGG | AAG | AAA | ATT | AAG | CGG | ATG | AAG | AGA | TCT | GTG | AAA | 1347 |
| His | Gln | Ile | Leu | Gly | Lys | Lys | Ile | Lys | Arg | Met | Lys | Arg | Ser | Val | Lys | |
| | | | | 430 | | | | | 435 | | | | | 440 | | |
| AAA | TAC | AGT | ATT | GTA | AAT | CCA | AGA | CTC | TGATACTGAA | | TTTTAGTTAT | | | | | 1394 |
| Lys | Tyr | Ser | Ile | Val | Asn | Pro | Arg | Leu | | | | | | | | |
| | | | 445 | | | | 450 | | | | | | | | | |

| | |
|---|---|
| TTCACAGTTG TAGCTACACA GTAAGTAGCT TGGTAGATAG TTATTGAATG TATTTATGTA | 1454 |
| GTGTATTAAG AAGCTTATAT TACTACAAAA AACTTATTTT TATATATTTT TATATTTTTG | 1514 |
| TATTATTTAT AGCTAGAGAA ACAATATTAC TGCCTTTGCT CTTTGTAACT ATGTCTGTTT | 1574 |
| TCTT | 1578 |

( 2 ) INFORMATION FOR SEQ ID NO:30:

( i ) SEQUENCE CHARACTERISTICS:
        ( A ) LENGTH: 450 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | | |
|---|---|---|---|---|---|---|---|---|---|---|---|---|---|---|---|
| Met | Ser | Asp | Phe | Ser | Glu | Glu | Leu | Lys | Gly | Pro | Val | Thr | Asp | Asp | Glu |
| 1 | | | | 5 | | | | 10 | | | | | 15 | | |
| Glu | Val | Glu | Thr | Ser | Val | Leu | Ser | Gly | Ala | Gly | Met | His | Phe | Pro | Trp |
| | | | 20 | | | | 25 | | | | 30 | | | | |
| Leu | Gln | Thr | Tyr | Val | Glu | Thr | Val | Ala | Ile | Gly | Gly | Lys | Arg | Arg | Lys |

```
                    35                              40                              45
Asp  Phe  Ala  Gln  Thr  Thr  Ser  Ala  Cys  Leu  Ser  Phe  Ile  Gln  Glu  Ala
     50                  55                       60

Leu  Leu  Lys  His  Gln  Trp  Gln  Ala  Ala  Glu  Tyr  Met  Tyr  Ser  Tyr
65                  70                       75                             80

Phe  Gln  Thr  Leu  Glu  Asp  Ser  Asp  Ser  Tyr  Lys  Arg  Gln  Ala  Ala  Pro
                    85                       90                       95

Glu  Ile  Ile  Trp  Lys  Leu  Gly  Ser  Glu  Ile  Leu  Phe  Tyr  His  Pro  Lys
               100                      105                      110

Ser  Asn  Met  Glu  Ser  Phe  Asn  Thr  Phe  Ala  Asn  Arg  Met  Lys  Asn  Ile
          115                      120                      125

Gly  Val  Met  Asn  Tyr  Leu  Lys  Ile  Ser  Leu  Gln  His  Ala  Leu  Tyr  Leu
     130                      135                      140

Leu  His  His  Gly  Met  Leu  Lys  Asp  Ala  Lys  Arg  Asn  Leu  Ser  Glu  Ala
145                      150                      155                      160

Glu  Thr  Trp  Arg  His  Gly  Glu  Asn  Thr  Ser  Ser  Arg  Glu  Ile  Leu  Ile
               165                      170                      175

Asn  Leu  Ile  Gln  Ala  Tyr  Lys  Gly  Leu  Leu  Gln  Tyr  Tyr  Thr  Trp  Ser
               180                      185                      190

Glu  Lys  Lys  Met  Glu  Leu  Ser  Lys  Leu  Asp  Lys  Asp  Tyr  Ala  Tyr
          195                      200                      205

Asn  Ala  Val  Ala  Gln  Asp  Val  Phe  Asn  His  Ser  Trp  Lys  Thr  Ser  Ala
     210                      215                      220

Asn  Ile  Ser  Ala  Leu  Ile  Lys  Ile  Pro  Gly  Val  Trp  Asp  Pro  Phe  Val
225                      230                      235                      240

Lys  Ser  Tyr  Val  Glu  Met  Leu  Glu  Phe  Tyr  Gly  Asp  Arg  Asp  Gly  Ala
                    245                      250                      255

Gln  Glu  Val  Leu  Thr  Asn  Tyr  Ala  Tyr  Asp  Glu  Lys  Phe  Pro  Ser  Asn
               260                      265                      270

Pro  Asn  Ala  His  Ile  Tyr  Leu  Tyr  Asn  Phe  Leu  Lys  Arg  Gln  Lys  Ala
          275                      280                      285

Pro  Arg  Ser  Lys  Leu  Ile  Ser  Val  Leu  Lys  Ile  Leu  Tyr  Gln  Ile  Val
     290                      295                      300

Pro  Ser  His  Lys  Leu  Met  Leu  Glu  Phe  His  Thr  Leu  Leu  Arg  Lys  Ser
305                      310                      315                      320

Glu  Lys  Glu  Glu  His  Arg  Lys  Leu  Gly  Leu  Glu  Val  Leu  Phe  Gly  Val
                    325                      330                      335

Leu  Asp  Phe  Ala  Gly  Cys  Thr  Lys  Asn  Ile  Thr  Ala  Trp  Lys  Tyr  Leu
               340                      345                      350

Ala  Lys  Tyr  Leu  Lys  Asn  Ile  Leu  Met  Gly  Asn  His  Leu  Ala  Trp  Val
          355                      360                      365

Gln  Glu  Glu  Trp  Asn  Ser  Arg  Lys  Asn  Trp  Trp  Pro  Gly  Phe  His  Phe
     370                      375                      380

Ser  Tyr  Phe  Trp  Ala  Lys  Ser  Asp  Trp  Lys  Glu  Asp  Thr  Ala  Leu  Ala
385                      390                      395                      400

Cys  Glu  Lys  Ala  Phe  Val  Ala  Gly  Leu  Leu  Leu  Gly  Lys  Gly  Cys  Arg
                    405                      410                      415

Tyr  Phe  Arg  Tyr  Ile  Leu  Lys  Gln  Asp  His  Gln  Ile  Leu  Gly  Lys  Lys
               420                      425                      430

Ile  Lys  Arg  Met  Lys  Arg  Ser  Val  Lys  Lys  Tyr  Ser  Ile  Val  Asn  Pro
          435                      440                      445

Arg  Leu
     450
```

( 2 ) INFORMATION FOR SEQ ID NO:31:

( i ) SEQUENCE CHARACTERISTICS:
        ( A ) LENGTH: 3901 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 185..2791

( x i ) SEQUENCE DESCRIPTION: SEQ ID NO:31:

```
GCTCGAGTGC  CAAAGCTGGG  GTTCTACTTG  AGATTTCCCT  CGTGGTGCCA  GGGTCCGGCG     60

AGCATCACGC  CGAGGCCCAT  TTTCCAGACG  ACCACGACGA  GGCCGGGGTC  ACGAACTCTG    120

GCGCCCCTTA  CCAGCTTCCA  GTCTCTCGAG  GTGGCCAGTG  TGGTGCTTGG  TCCTTGTTTC    180

CAGG ATG GAC TTC CCC AGC TCC CTC CGC CCT GCG TTG TTT CTG ACC GGC          229
     Met Asp Phe Pro Ser Ser Leu Arg Pro Ala Leu Phe Leu Thr Gly
     1               5                  10                  15

CCC CTT GGT CTG AGC GAC GTC CCT GAC CTC TCT TTC ATG TGC AGC TGG          277
Pro Leu Gly Leu Ser Asp Val Pro Asp Leu Ser Phe Met Cys Ser Trp
            20                  25                  30

CGA GAC GCA CTG ACT CTG CCA GAG GCC CAG CCC CAG AAC TCA GAG AAT          325
Arg Asp Ala Leu Thr Leu Pro Glu Ala Gln Pro Gln Asn Ser Glu Asn
                35                  40                  45

GGG GCA CTG CAT GTG ACC AAG GAC CTG CTG TGG GAG CCG GCA ACC CCT          373
Gly Ala Leu His Val Thr Lys Asp Leu Leu Trp Glu Pro Ala Thr Pro
            50                  55                  60

GGG CCT CTC CCC ATG CTG CCT CCC CTC ATC GAT CCC TGG GAC CCT GGC          421
Gly Pro Leu Pro Met Leu Pro Pro Leu Ile Asp Pro Trp Asp Pro Gly
65                  70                  75

CTG ACT GCC CGG GAC CTG CTT TTC CGC GGA GGG TAC CGG TAT CGG AAG          469
Leu Thr Ala Arg Asp Leu Leu Phe Arg Gly Gly Tyr Arg Tyr Arg Lys
80                  85                  90                  95

CGG CCC CGA GTC GTG CTG GAT GTG ACT GAG CAG ATC AGC CGG TTC CTC          517
Arg Pro Arg Val Val Leu Asp Val Thr Glu Gln Ile Ser Arg Phe Leu
                100                 105                 110

TTG GAT CAT GGA GAC GTA GCC TTT GCG CCC CTG GGG AAG CTG ATG CTG          565
Leu Asp His Gly Asp Val Ala Phe Ala Pro Leu Gly Lys Leu Met Leu
            115                 120                 125

GAG AAT TTC AAG CTG GAG GGA GCG GGG AGC CGC ACT AAG AAG AAG ACA          613
Glu Asn Phe Lys Leu Glu Gly Ala Gly Ser Arg Thr Lys Lys Lys Thr
        130                 135                 140

GTG GTC AGT GTG AAG AAG CTG CTC CAG GAC CTC GGT GGA CAC CAG CCC          661
Val Val Ser Val Lys Lys Leu Leu Gln Asp Leu Gly Gly His Gln Pro
145                 150                 155

TGG GGG TGT CCC TGG GCT TAC CTC AGC AAC CGA CAG CGC CGC TTC TCT          709
Trp Gly Cys Pro Trp Ala Tyr Leu Ser Asn Arg Gln Arg Arg Phe Ser
160                 165                 170                 175

ATC CTC GGG GGC CCC ATC CTG GGC ACG TCG GTG GCG AGC CAC TTG GCA          757
Ile Leu Gly Gly Pro Ile Leu Gly Thr Ser Val Ala Ser His Leu Ala
                180                 185                 190

GAG CTG CTG CAC GAG GAG CTG GTG CTG CGG TGG GAG CAG CTG CTT CTG          805
Glu Leu Leu His Glu Glu Leu Val Leu Arg Trp Glu Gln Leu Leu Leu
            195                 200                 205

GAT GAG GCC TGC ACT GGG GGC GCG CTG GCC TGG GTT CCT GGA AGG ACA          853
Asp Glu Ala Cys Thr Gly Gly Ala Leu Ala Trp Val Pro Gly Arg Thr
        210                 215                 220

CCC CAG TTC GGG CAG CTG GTC TAC CCT GCT GGA GGC GCC CAG GAC AGG          901
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| Pro | Gln | Phe | Gly | Gln | Leu | Val | Tyr | Pro | Ala | Gly | Gly | Ala | Gln | Asp | Arg |      |
|     | 225 |     |     |     | 230 |     |     |     |     | 235 |     |     |     |     |     |      |
| CTG | CAT | TTC | CAA | GAG | GTC | GTT | CTG | ACC | CCA | GGT | GAC | AAT | CCC | CAA | TTC | 949  |
| Leu | His | Phe | Gln | Glu | Val | Val | Leu | Thr | Pro | Gly | Asp | Asn | Pro | Gln | Phe |      |
| 240 |     |     |     |     | 245 |     |     |     | 250 |     |     |     |     |     | 255 |      |
| CTT | GGG | AAA | CCT | GGA | CGC | ATC | CAG | CTC | CAG | GGA | CCT | GTC | CGG | CAA | GTG | 997  |
| Leu | Gly | Lys | Pro | Gly | Arg | Ile | Gln | Leu | Gln | Gly | Pro | Val | Arg | Gln | Val |      |
|     |     |     |     | 260 |     |     |     |     | 265 |     |     |     |     | 270 |     |      |
| GTG | ACA | TGC | ACC | GTC | CAG | GGA | GAA | AGT | AAG | GCC | CTT | ATA | TAC | ACT | TTC | 1045 |
| Val | Thr | Cys | Thr | Val | Gln | Gly | Glu | Ser | Lys | Ala | Leu | Ile | Tyr | Thr | Phe |      |
|     |     |     | 275 |     |     |     |     | 280 |     |     |     |     | 285 |     |     |      |
| CTC | CCT | CAC | TGG | CTG | ACC | TGC | TAC | CTG | ACC | CCT | GGC | CCT | TTC | CAT | CCC | 1093 |
| Leu | Pro | His | Trp | Leu | Thr | Cys | Tyr | Leu | Thr | Pro | Gly | Pro | Phe | His | Pro |      |
|     |     | 290 |     |     |     |     | 295 |     |     |     |     | 300 |     |     |     |      |
| TCC | TCA | GCT | CTG | CTG | GCC | GTC | CGC | TCT | GAC | TAC | CAC | TGT | GCC | GTG | TGG | 1141 |
| Ser | Ser | Ala | Leu | Leu | Ala | Val | Arg | Ser | Asp | Tyr | His | Cys | Ala | Val | Trp |      |
| 305 |     |     |     |     | 310 |     |     |     |     | 315 |     |     |     |     |     |      |
| AAG | TTT | GGT | AAA | CAG | TGG | CAG | CCA | ACC | CTT | CTG | CAG | GCG | ATG | CAG | GTG | 1189 |
| Lys | Phe | Gly | Lys | Gln | Trp | Gln | Pro | Thr | Leu | Leu | Gln | Ala | Met | Gln | Val |      |
| 320 |     |     |     |     | 325 |     |     |     |     | 330 |     |     |     |     | 335 |      |
| GAG | AAA | GGG | GCC | ACG | GGG | ATC | AGC | CTC | AGC | CCT | CAC | CTG | CCC | GGG | GAG | 1237 |
| Glu | Lys | Gly | Ala | Thr | Gly | Ile | Ser | Leu | Ser | Pro | His | Leu | Pro | Gly | Glu |      |
|     |     |     |     | 340 |     |     |     |     | 345 |     |     |     |     | 350 |     |      |
| CTG | GCC | ATC | TGC | AGC | CGC | TCG | GGA | GCC | GTC | TGC | CTG | TGG | AGC | CCT | GAG | 1285 |
| Leu | Ala | Ile | Cys | Ser | Arg | Ser | Gly | Ala | Val | Cys | Leu | Trp | Ser | Pro | Glu |      |
|     |     |     |     | 355 |     |     |     |     | 360 |     |     |     |     | 365 |     |      |
| GAT | GGG | CTG | CGG | CAA | ATC | TAC | AGG | GAC | CCT | GAG | ACC | CTC | GTG | TTC | CGG | 1333 |
| Asp | Gly | Leu | Arg | Gln | Ile | Tyr | Arg | Asp | Pro | Glu | Thr | Leu | Val | Phe | Arg |      |
|     |     | 370 |     |     |     |     | 375 |     |     |     |     | 380 |     |     |     |      |
| GAC | TCC | TCT | TCG | TGG | CGT | TGG | GCA | GAC | TTC | ACT | GCG | CAC | CCT | CGG | GTG | 1381 |
| Asp | Ser | Ser | Ser | Trp | Arg | Trp | Ala | Asp | Phe | Thr | Ala | His | Pro | Arg | Val |      |
| 385 |     |     |     |     | 390 |     |     |     |     | 395 |     |     |     |     |     |      |
| CTG | ACC | GTG | GGT | GAC | CGC | ACC | GGA | GTG | AAG | ATG | CTG | GAC | ACT | CAG | GGC | 1429 |
| Leu | Thr | Val | Gly | Asp | Arg | Thr | Gly | Val | Lys | Met | Leu | Asp | Thr | Gln | Gly |      |
| 400 |     |     |     |     | 405 |     |     |     |     | 410 |     |     |     |     | 415 |      |
| CCG | CCG | GGC | TGT | GGT | CTG | TTG | CTT | TTT | CGT | TTG | GGG | GCA | GAG | GCT | TCG | 1477 |
| Pro | Pro | Gly | Cys | Gly | Leu | Leu | Leu | Phe | Arg | Leu | Gly | Ala | Glu | Ala | Ser |      |
|     |     |     |     | 420 |     |     |     |     | 425 |     |     |     |     | 430 |     |      |
| TGC | CAG | AAA | GGG | GAA | CGT | GTC | CTG | CTT | ACC | CAG | TAC | CTG | GGG | CAC | TCC | 1525 |
| Cys | Gln | Lys | Gly | Glu | Arg | Val | Leu | Leu | Thr | Gln | Tyr | Leu | Gly | His | Ser |      |
|     |     |     | 435 |     |     |     |     | 440 |     |     |     |     | 445 |     |     |      |
| AGC | CCC | AAA | TGC | CTC | CCC | CCT | ACT | CTT | CAT | CTC | GTC | TGT | ACC | CAG | TTC | 1573 |
| Ser | Pro | Lys | Cys | Leu | Pro | Pro | Thr | Leu | His | Leu | Val | Cys | Thr | Gln | Phe |      |
|     |     | 450 |     |     |     |     | 455 |     |     |     |     | 460 |     |     |     |      |
| TCT | CTC | TAC | CTA | GTG | GAC | GAG | CGC | CTT | CCC | CTG | GTG | CCG | ATG | CTG | AAG | 1621 |
| Ser | Leu | Tyr | Leu | Val | Asp | Glu | Arg | Leu | Pro | Leu | Val | Pro | Met | Leu | Lys |      |
| 465 |     |     |     |     | 470 |     |     |     |     | 475 |     |     |     |     |     |      |
| TGG | AAC | CAT | GGC | CTC | CCC | TCC | CCG | CTC | CTG | CTG | GCC | CGA | CTG | CTG | CCT | 1669 |
| Trp | Asn | His | Gly | Leu | Pro | Ser | Pro | Leu | Leu | Leu | Ala | Arg | Leu | Leu | Pro |      |
| 480 |     |     |     |     | 485 |     |     |     |     | 490 |     |     |     |     | 495 |      |
| CCG | CCC | CGG | CCC | AGC | TGC | GTG | CAG | CCC | CTG | CTC | CTC | GGA | GGC | CAG | GGT | 1717 |
| Pro | Pro | Arg | Pro | Ser | Cys | Val | Gln | Pro | Leu | Leu | Leu | Gly | Gly | Gln | Gly |      |
|     |     |     |     | 500 |     |     |     |     | 505 |     |     |     |     | 510 |     |      |
| GGG | CAG | CTG | CAG | CTG | CTG | CAC | CTG | GCA | GGA | GAA | GGG | GCG | TCG | GTG | CCC | 1765 |
| Gly | Gln | Leu | Gln | Leu | Leu | His | Leu | Ala | Gly | Glu | Gly | Ala | Ser | Val | Pro |      |
|     |     |     | 515 |     |     |     |     | 520 |     |     |     |     | 525 |     |     |      |
| CGC | CTG | GCA | GGC | CCC | CCC | CAG | TCT | CTT | CCT | TCC | AGG | ATC | GAC | TCC | CTC | 1813 |
| Arg | Leu | Ala | Gly | Pro | Pro | Gln | Ser | Leu | Pro | Ser | Arg | Ile | Asp | Ser | Leu |      |
|     |     | 530 |     |     |     |     | 535 |     |     |     |     | 540 |     |     |     |      |
| CCT | GCA | TTT | CCT | CTG | CTG | GAG | CCT | AAG | ATC | AGG | TGG | CGG | CTG | CAG | GAG | 1861 |

```
Pro Ala Phe Pro Leu Leu Glu Pro Lys Ile Gln Trp Arg Leu Gln Glu
545                 550                 555

CGC CTG AAA GCA CCG ACC ATA GGT CTG GCT GCC GTC GTC CCG CCC TTG    1909
Arg Leu Lys Ala Pro Thr Ile Gly Leu Ala Ala Val Val Pro Pro Leu
560                 565                 570                 575

CCC TCA GCG CCC ACA CCA GGC CTG GTG CTC TTC CAG CTC TCG GCG GCG    1957
Pro Ser Ala Pro Thr Pro Gly Leu Val Leu Phe Gln Leu Ser Ala Ala
                580                 585                 590

GGA GAT GTC TTC TAC CAG CAG CTC CGC CCC CAG GTG GAC TCC AGC CTC    2005
Gly Asp Val Phe Tyr Gln Gln Leu Arg Pro Gln Val Asp Ser Ser Leu
            595                 600                 605

CGC AGA GAT GCT GGG CCT CCT GGC GAC ACC CAA CCT GAC TGC CAT GCC    2053
Arg Arg Asp Ala Gly Pro Pro Gly Asp Thr Gln Pro Asp Cys His Ala
        610                 615                 620

CCC ACA GCT TCC TGG ACC TCC CAG GAC ACT GCC GGC TGC AGC CAG TGG    2101
Pro Thr Ala Ser Trp Thr Ser Gln Asp Thr Ala Gly Cys Ser Gln Trp
    625                 630                 635

CTG AAG GCC CTG CTA AAA GTG CCC CTG GCT CCT CCT GTG TGG ACA GCA    2149
Leu Lys Ala Leu Leu Lys Val Pro Leu Ala Pro Pro Val Trp Thr Ala
640                 645                 650                 655

CCC ACC TTC ACC CAC CGC CAG ATG CTG GGC AGC ACA GAG CTG CGG AGG    2197
Pro Thr Phe Thr His Arg Gln Met Leu Gly Ser Thr Glu Leu Arg Arg
                660                 665                 670

GAG GAA GAG GAA GGG CAG CGG CTG GGT GTG CTC CGC AAG GCC ATG GCC    2245
Glu Glu Glu Glu Gly Gln Arg Leu Gly Val Leu Arg Lys Ala Met Ala
            675                 680                 685

CGA GGG CAG CTC CTG CTG CAG AGA GAC CTG GGC TCC CTC CCT GCG GCA    2293
Arg Gly Gln Leu Leu Leu Gln Arg Asp Leu Gly Ser Leu Pro Ala Ala
        690                 695                 700

GAG CCA CCC CCT GCA CCC GAG TCA GGC CTA GAG GAC AAG CTC AGT GAG    2341
Glu Pro Pro Pro Ala Pro Glu Ser Gly Leu Glu Asp Lys Leu Ser Glu
    705                 710                 715

CGC CTG GGG GAA GCC TGG GCA GGC CGA GGG GCT GCC TGG TGG GAG AGG    2389
Arg Leu Gly Glu Ala Trp Ala Gly Arg Gly Ala Ala Trp Trp Glu Arg
720                 725                 730                 735

CAG CAG GGC AGG ACC TCG GAG CCC GGG AGA CAG ACC AGG CGG CCC AAG    2437
Gln Gln Gly Arg Thr Ser Glu Pro Gly Arg Gln Thr Arg Arg Pro Lys
                740                 745                 750

CGC CGG ACC CAG CTG TCC AGC AGC TTT TCG CTC AGT GGC CAT GTG GAT    2485
Arg Arg Thr Gln Leu Ser Ser Ser Phe Ser Leu Ser Gly His Val Asp
            755                 760                 765

CCG TCA GAG GAC ACC AGC TCC CCT CAT AGC CCT GAG TGG CCA CCT GCT    2533
Pro Ser Glu Asp Thr Ser Ser Pro His Ser Pro Glu Trp Pro Pro Ala
        770                 775                 780

GAT GCT CTG CCC CTG CCC CCC ACG ACC CCG CCC TCC CAG GAG TTG ACT    2581
Asp Ala Leu Pro Leu Pro Pro Thr Thr Pro Pro Ser Gln Glu Leu Thr
    785                 790                 795

CCG GAT GCA TGC GCC CAG GGC GTC CCA TCA GAG CAG CGG CAG ATG CTC    2629
Pro Asp Ala Cys Ala Gln Gly Val Pro Ser Glu Gln Arg Gln Met Leu
800                 805                 810                 815

CGT GAC TAC ATG GCC AAG CTA CCA CCC CAG AGG GAC ACC CCA GGC TGT    2677
Arg Asp Tyr Met Ala Lys Leu Pro Pro Gln Arg Asp Thr Pro Gly Cys
                820                 825                 830

GCC ACC ACA CCT CCC CAC TCC CAG GCC TCC AGC GTC CGG GCC ACT CGC    2725
Ala Thr Thr Pro Pro His Ser Gln Ala Ser Ser Val Arg Ala Thr Arg
            835                 840                 845

TCC CAG CAG CAC ACA CCC GTC CTC TCT AGC TCT CAG CCC CTC CGG AAG    2773
Ser Gln Gln His Thr Pro Val Leu Ser Ser Ser Gln Pro Leu Arg Lys
        850                 855                 860

AAG CCT CGA ATG GGC TTC TGAGGACACA AGGTGGGCTG CCCTCAAGCC           2821
Lys Pro Arg Met Gly Phe
```

Lys Pro Arg Met Gly Phe
    865

| | | | | | |
|---|---|---|---|---|---|
| CCAGAGAGCC | CCTCATCCTT | CCTCTGGGAC | CAGATGTGCC | TTCCACAGTT | GAAACTTGAG | 2881
| AAGCAGAGCT | CGCCACCTTC | TGGAGGCCAC | TGTGATGATG | AGCCAAGCAA | TTTGGAGCCA | 2941
| AGTTGAAGGG | ACAGGGCAAC | AAAATACAGT | AGTAGTTTCT | TTTGTATTTT | GTATATTCGC | 3001
| CTGAAGATCA | TCCCGCAAGG | CAGGCTGGAG | GTGCCGGTGG | GCCTGTGTTG | CTGGGATTTT | 3061
| AGTCTGTGCT | GGGAGGCAGG | GCTCCGTGCG | CCTCAGCTGT | GGGGGCCTCA | GGCAGGTCCC | 3121
| TCAGTTCTCA | CGCCTTCCTG | TCCAGTGGAA | TGGGGGCCAG | GAGTGCTGGC | TCCTCGTGTT | 3181
| TGGTGAGGGT | GGAGTGAGGC | CCCTGCAGAG | CTGCTGATGA | GGTGGGCACA | GCGGCCGTTG | 3241
| GCAGCTGCTG | TTGTGGGTTG | CTTTGTCAAT | CTCTGCCCCG | GTCTGATGTT | TCCTACAGGG | 3301
| AGATGCCGTG | GATCCAGGTT | CAGGGACTAA | ATACACTTGG | CAGCTGAAGA | TGAATTGGAA | 3361
| TGGTCACGTT | TTTTAGGCTG | GACAGCGTCC | CGCCACAGCT | ACTACCTGAC | ACTGAGCTCA | 3421
| TGCAGAGAGA | TGATGGCTGA | TGTTCCTTCT | CCCTTGGGAC | ATGGGTCTGG | CACCTGTGGG | 3481
| CTGTCGATAG | TGCCCTCTGA | GCAGAGGGTC | ACGGTCATGT | CAGTTTGGGG | GAATTCTCTG | 3541
| TTGTGCCTCA | GAGACTCCCC | CCTTTCTTTC | CTCCCTCCCC | TTCTCATTTT | GATGTCTAAA | 3601
| GCATCAAGTC | CCTCTTCCTC | AGAGTTTCTC | TAGCTGCAGT | GGAAGATTCT | GTTTTCCTGT | 3661
| GGGGAAAATG | CTCACTTGAG | ATTTTGCAGG | GACCCGGGTC | TGTCTGGTTT | CTGATGACAT | 3721
| AGTAAGAGAA | AGGTCTTTTT | TCAGGTTGGC | TGGTGAAAGG | AATTGCATGT | GACTCACACA | 3781
| AACAGGAGCT | AGCCCAATCA | TACACTGACT | CGCGTGGGTG | TTTAAATGTT | TATCATGCCT | 3841
| AAGGGAGACA | TTTATAATTA | AACCATTTAT | GCTACATAAA | AAAAAAAAA | AAAAAAAAA | 3901

( 2 ) INFORMATION FOR SEQ ID NO:32:

( i ) SEQUENCE CHARACTERISTICS:
        ( A ) LENGTH: 869 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

Met Asp Phe Pro Ser Ser Leu Arg Pro Ala Leu Phe Leu Thr Gly Pro
  1               5                  10                  15

Leu Gly Leu Ser Asp Val Pro Asp Leu Ser Phe Met Cys Ser Trp Arg
             20                  25                  30

Asp Ala Leu Thr Leu Pro Glu Ala Gln Pro Gln Asn Ser Glu Asn Gly
         35                  40                  45

Ala Leu His Val Thr Lys Asp Leu Leu Trp Glu Pro Ala Thr Pro Gly
     50                  55                  60

Pro Leu Pro Met Leu Pro Pro Leu Ile Asp Pro Trp Asp Pro Gly Leu
 65                  70                  75                  80

Thr Ala Arg Asp Leu Leu Phe Arg Gly Gly Tyr Arg Tyr Arg Lys Arg
                 85                  90                  95

Pro Arg Val Val Leu Asp Val Thr Glu Gln Ile Ser Arg Phe Leu Leu
                100                 105                 110

Asp His Gly Asp Val Ala Phe Ala Pro Leu Gly Lys Leu Met Leu Glu
            115                 120                 125

Asn Phe Lys Leu Glu Gly Ala Gly Ser Arg Thr Lys Lys Lys Thr Val
    130                 135                 140

Val Ser Val Lys Lys Leu Leu Gln Asp Leu Gly Gly His Gln Pro Trp
145                 150                 155                 160

```
Gly  Cys  Pro  Trp  Ala  Tyr  Leu  Ser  Asn  Arg  Gln  Arg  Arg  Phe  Ser  Ile
               165                      170                      175

Leu  Gly  Gly  Pro  Ile  Leu  Gly  Thr  Ser  Val  Ala  Ser  His  Leu  Ala  Glu
               180                      185                      190

Leu  Leu  His  Glu  Glu  Leu  Val  Leu  Arg  Trp  Glu  Gln  Leu  Leu  Leu  Asp
          195                      200                      205

Glu  Ala  Cys  Thr  Gly  Gly  Ala  Leu  Ala  Trp  Val  Pro  Gly  Arg  Thr  Pro
     210                      215                      220

Gln  Phe  Gly  Gln  Leu  Val  Tyr  Pro  Ala  Gly  Gly  Ala  Gln  Asp  Arg  Leu
225                      230                      235                      240

His  Phe  Gln  Glu  Val  Val  Leu  Thr  Pro  Gly  Asp  Asn  Pro  Gln  Phe  Leu
                    245                      250                      255

Gly  Lys  Pro  Gly  Arg  Ile  Gln  Leu  Gln  Gly  Pro  Val  Arg  Gln  Val  Val
               260                      265                      270

Thr  Cys  Thr  Val  Gln  Gly  Glu  Ser  Lys  Ala  Leu  Ile  Tyr  Thr  Phe  Leu
          275                      280                      285

Pro  His  Trp  Leu  Thr  Cys  Tyr  Leu  Thr  Pro  Gly  Pro  Phe  His  Pro  Ser
     290                      295                      300

Ser  Ala  Leu  Leu  Ala  Val  Arg  Ser  Asp  Tyr  His  Cys  Ala  Val  Trp  Lys
305                      310                      315                      320

Phe  Gly  Lys  Gln  Trp  Gln  Pro  Thr  Leu  Leu  Gln  Ala  Met  Gln  Val  Glu
                    325                      330                      335

Lys  Gly  Ala  Thr  Gly  Ile  Ser  Leu  Ser  Pro  His  Leu  Pro  Gly  Glu  Leu
               340                      345                      350

Ala  Ile  Cys  Ser  Arg  Ser  Gly  Ala  Val  Cys  Leu  Trp  Ser  Pro  Glu  Asp
          355                      360                      365

Gly  Leu  Arg  Gln  Ile  Tyr  Arg  Asp  Pro  Glu  Thr  Leu  Val  Phe  Arg  Asp
     370                      375                      380

Ser  Ser  Ser  Trp  Arg  Trp  Ala  Asp  Phe  Thr  Ala  His  Pro  Arg  Val  Leu
385                      390                      395                      400

Thr  Val  Gly  Asp  Arg  Thr  Gly  Val  Lys  Met  Leu  Asp  Thr  Gln  Gly  Pro
                    405                      410                      415

Pro  Gly  Cys  Gly  Leu  Leu  Leu  Phe  Arg  Leu  Gly  Ala  Glu  Ala  Ser  Cys
               420                      425                      430

Gln  Lys  Gly  Glu  Arg  Val  Leu  Leu  Thr  Gln  Tyr  Leu  Gly  His  Ser  Ser
          435                      440                      445

Pro  Lys  Cys  Leu  Pro  Pro  Thr  Leu  His  Leu  Val  Cys  Thr  Gln  Phe  Ser
     450                      455                      460

Leu  Tyr  Leu  Val  Asp  Glu  Arg  Leu  Pro  Leu  Val  Pro  Met  Leu  Lys  Trp
465                      470                      475                      480

Asn  His  Gly  Leu  Pro  Ser  Pro  Leu  Leu  Ala  Arg  Leu  Leu  Pro  Pro
                    485                      490                      495

Pro  Arg  Pro  Ser  Cys  Val  Gln  Pro  Leu  Leu  Gly  Gly  Gln  Gly  Gly
               500                      505                      510

Gln  Leu  Gln  Leu  Leu  His  Leu  Ala  Gly  Glu  Gly  Ala  Ser  Val  Pro  Arg
          515                      520                      525

Leu  Ala  Gly  Pro  Pro  Gln  Ser  Leu  Pro  Ser  Arg  Ile  Asp  Ser  Leu  Pro
     530                      535                      540

Ala  Phe  Pro  Leu  Leu  Glu  Pro  Lys  Ile  Gln  Trp  Arg  Leu  Gln  Glu  Arg
545                      550                      555                      560

Leu  Lys  Ala  Pro  Thr  Ile  Gly  Leu  Ala  Ala  Val  Val  Pro  Pro  Leu  Pro
                    565                      570                      575

Ser  Ala  Pro  Thr  Pro  Gly  Leu  Val  Leu  Phe  Gln  Leu  Ser  Ala  Ala  Gly
```

|     |     |     |     |     | 580 |     |     |     |     | 585 |     |     |     |     | 590 |     |     |     |
|-----|-----|-----|-----|-----|-----|-----|-----|-----|-----|-----|-----|-----|-----|-----|-----|-----|-----|-----|

Asp Val Phe Tyr Gln Gln Leu Arg Pro Gln Val Asp Ser Ser Leu Arg
          595                 600                 605

Arg Asp Ala Gly Pro Pro Gly Asp Thr Gln Pro Asp Cys His Ala Pro
    610             615                 620

Thr Ala Ser Trp Thr Ser Gln Asp Thr Ala Gly Cys Ser Gln Trp Leu
625                 630                 635                     640

Lys Ala Leu Leu Lys Val Pro Leu Ala Pro Pro Val Trp Thr Ala Pro
                645             650                     655

Thr Phe Thr His Arg Gln Met Leu Gly Ser Thr Glu Leu Arg Arg Glu
            660                 665                 670

Glu Glu Glu Gly Gln Arg Leu Gly Val Leu Arg Lys Ala Met Ala Arg
        675                 680             685

Gly Gln Leu Leu Leu Gln Arg Asp Leu Gly Ser Leu Pro Ala Ala Glu
    690                 695                 700

Pro Pro Pro Ala Pro Glu Ser Gly Leu Glu Asp Lys Leu Ser Glu Arg
705             710                 715                     720

Leu Gly Glu Ala Trp Ala Gly Arg Gly Ala Ala Trp Trp Glu Arg Gln
                725             730                 735

Gln Gly Arg Thr Ser Glu Pro Gly Arg Gln Thr Arg Arg Pro Lys Arg
            740                 745                 750

Arg Thr Gln Leu Ser Ser Ser Phe Ser Leu Ser Gly His Val Asp Pro
        755                 760                 765

Ser Glu Asp Thr Ser Ser Pro His Ser Pro Glu Trp Pro Pro Ala Asp
    770                 775                 780

Ala Leu Pro Leu Pro Pro Thr Thr Pro Pro Ser Gln Glu Leu Thr Pro
785             790                 795                     800

Asp Ala Cys Ala Gln Gly Val Pro Ser Glu Gln Arg Gln Met Leu Arg
                805             810                 815

Asp Tyr Met Ala Lys Leu Pro Pro Gln Arg Asp Thr Pro Gly Cys Ala
            820                 825                 830

Thr Thr Pro Pro His Ser Gln Ala Ser Ser Val Arg Ala Thr Arg Ser
        835                 840                 845

Gln Gln His Thr Pro Val Leu Ser Ser Ser Gln Pro Leu Arg Lys Lys
    850                 855                 860

Pro Arg Met Gly Phe
865

( 2 ) INFORMATION FOR SEQ ID NO:33:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Lys Lys Leu Gln Asp Leu Val Arg Glu Val Asp Pro Asn Glu Gln Leu
1               5                   10                      15

Asp Glu Asp Val Glu Met Leu Leu Gln Ile Ala Asp Asp
            20                  25

( 2 ) INFORMATION FOR SEQ ID NO:34:

( i ) SEQUENCE CHARACTERISTICS:
        ( A ) LENGTH: 11 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Leu Gln Asp Leu Val Arg Glu Val Asp Pro Asn
1               5                   10

(2) INFORMATION FOR SEQ ID NO:35:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

His Met Arg Glu Ala Val Arg Arg Leu Lys
1               5                   10

(2) INFORMATION FOR SEQ ID NO:36:

(i) SEQUENCE CHARACTERISTICS:
    (A) LENGTH: 24 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:36:

Met Gln Ile Leu Val Ser Ser Phe Glu Glu Glu Gln Leu Asn Tyr Glu
1               5                   10                  15

Met Tyr Asn Lys Ala Tyr Gly Gln
                20

TATA-BINDING PROTEIN ASSOCIATED FACTORS DRUG SCREENS

CROSS-REFERENCE TO RELATED APPLICATIONS

This application is a continuation-in-part of application Ser. No. 08/087,119 filed Jun. 30,1993, now abandoned, which is a continuation-in-part of application Ser. No. 08/013,412 filed Jan. 28, 1993, now abandoned.

The research carried out in the subject application was supported in part by grants from the National Institutes of Health. The government may have rights in any patent issuing on this application.

INTRODUCTION

1. Technical Field

The technical field of this invention concerns TATA-binding protein associated factors, proteins involved in gene transcription.

2. Background

Gene transcription requires the concerted action of a number of molecules. DNA provides regulatory sequences and a coding sequence, or template, from which an RNA polymerase synthesizes corresponding RNA. Regulatory sequences generally include sites for sequence-specific transcriptional control, including promoters, enhancers, suppressors, etc; and also a site for transcription initiation. For review, see Mitchell and Tjian (1989), Science 245,371–378.

RNA polymerases alone appear incapable of initiating transcription. However, in vitro transcriptional activity of RNA polymerases can be restored by the addition of nuclear extracts or fractions thereof. For example, under certain conditions, in vitro transcription by RNA polymerase II (Pol II) can be at least partially restored by the addition of what have variously been reported to be four, five, six or seven nuclear fractions [See e.g. Matsui et al. (1980), Biol Chem 255, 1192], herein referred to as TFIIA, TFIIB, TFIID, TFIIE, TFIIF, TFIIH and TFIIJ. Pol I and Pol III appear to require at least two fractions, called respectively SL1 and UBF, and TFIIIA and TFIIIB.

Many of these transcription fractions remain only partially characterized. For example, all but one of the Pol II fractions remain incompletely characterized or comprise multiple components. The fractions TFIID, SL1 and TFIIB have been reported to contain a TATA binding component, henceforth, TATA-binding protein, or TBP. Groups of the present Applicants have reported anti-TBP antibodies capable of immunoprecipitating TBP from TFIID, SL1, and TFIIIB.

TFIID, SL1 and TFIIIB immunoprecipitates have revealed TBP and numerous associated factors, tentatively called TBP-associated factors, or TAFs. Furthermore, preliminary experiments indicated that the TBP and non-TBP (TAF) fractions, when combined, facilitated at least some sequence-specific transcription activation.

Unfortunately, it is not clear from the above art that there is any transcriptional activity in the non-TBP fractions of TFIID, SL1 or TFIIB immunoprecipitates. For example, the reported apparent functional complementarity of the TBP and non-TBP fractions might result from the influence of antirepressors, inhibitor inhibition, etc. Furthermore, the coactivator transcriptional activity attributed to the non-TBP fractions could result from one or more components unrelated to the electrophoretically resolved TAF components. Nor does the literature provide any suggestion as to which, if any, of the electrophoretically resolved components of the non-TBP fraction provide(s) transcriptional activity, nor means for identifying bands resolvable from the non-TBP fractions.

Relevant Literature

Pugh and Tjian (1990), Cell 61:1187–1197; Tanese et al. (1991), Genes and Devel 5:2212–2224; Pugh and Tjian (1991), Genes and Devel 5:1935–1945; Dynlacht et al. (1991), Cell 66:563–576; Timmers et al. (1991), Genes and Devel 5:1946–1956; Zhou et al. (1992), Genes and Devel 6:1964–1974; and Takada et al. (1992), Proc Natl Acad Sci USA 89:11809–11813, relate to factors associated with Pol II transcription. Comai et al. (1992) Cell 68:965–976 relates to factors associated with Pol I transcription. Lobo et al. (1991), Genes and Devel, 5:1477–1489; Margotin et al. (1991), Science 251:424–426; Simmen et al. (1991), EMBO J 10:1853–1862; and Taggart et al. (1992), Cell 71:1015; Lobo et al. (1992), Cell 71:1029; and White and Jackson (1992), Cell 71:1041 relate to factors associated with Pol III transcription. Sekiguchi et al. (1988), EMBO J 7:1683–1687 and Sekiguchi et al. (1991), Mol and Cellular Biol 11:3317–3325 disclose the cloning of the CCG1 gene encoding a protein reported to be involved in cell cycle progression.

SUMMARY OF THE INVENTION

Substantially pure and biologically active TATA-binding protein associated factors (TAFs), eukaryotic nuclear proteins involved in RNA polymerase I, II, and III transcription, nucleic acids encoding TAFs, and methods of using TAFs and TAF-encoding nucleic acids are provided. Recombinant TAFs, anti-TAF antibodies and TAF-fusion products find use in drug screening, diagnositcs and therapeutics. In particular, the disclosed TAFs provide valuable reagents in developing specific biochemical assays for screening compounds that agonize or antagonize selected transcription factors involved in regulating gene expression associated with human pathology.

DESCRIPTION OF SPECIFIC EMBODIMENTS

Substantially pure and biologically active TATA-binding protein associated factors (TAFs) and portions thereof, nucleic acids encoding TAFs and portions thereof, and methods of use are provided.

As used herein, a given TAF refers to the TAF protein, recombinant or purified from a natural source, and functional and xenogeneic analogs thereof. For example "dTAFII110" refers to a Pol II TAF, derivable from Drosophila, with an apparent molecular weight of about 110 kD, generally as determined by SDS-PAGE under conditions described herein, in Dynlacht et al. (1991), Comai et al. (1992), or otherwise identified by functional, sequence, etc. data herein. It is understood that these molecular weight designations are for the convenience of nomenclature and may not necessarily correspond to actual or predicted molecular weight. Other TAFs are analogously identified herein.

A "portion" of a given TAF is a peptide comprising at least about a six, preferably at least about an eighteen, more preferably at least about a thirty-six amino acid sequence of the TAF. Of particular interest are portions of the TAF that facilitate functional or structural interaction with activators, TAFs, TBP, Pol I, II or III, the TATA box and surrounding DNA sequences, etc. Methods for identifying such preferred portions are described below.

By substantially full-length is meant a polypeptide or polynucleotide that comprises at least 50%, preferably at least 70% and more preferably at least 90% of the natural TAF polypeptide or polynucleotide length.

"Xenogeneic" TAF analogs are nonhuman-, nonDrosophila-derived proteins with substantial functional or sequence identity to human and Drosophila TAFs. Of particular interest are xenogeneic TAF analogs derived from rodents, primates, and livestock animals including bovine, ovine, equine and avian species "Functional" analogs of a given TAF or proteins with "substantial functional identity" to a given TAF are compounds that exhibit one or more biochemical properties specific to such TAF, such as the ability of dTAFII110 to interact with Sp1.

"Modulating transcription" means altering transcription, and includes changing the rate of transcription initiation, the level of transcription, or the responsiveness of transcription/transcription initiation to regulatory controls.

The terms "substantially pure" or "isolated" mean that the TAF, TAF portion, or nucleic acid encoding a TAF or TAF portion is unaccompanied by at least some of the material with which it is normally associated in its natural state. While a composition of a substantially pure TAF or portion thereof is preferably substantially free of polyacrylamide, such composition may contain excipients and additives useful in diagnostic, therapeutic and investigative reagents. A substantially pure TAF composition subject to electrophoresis or reverse phase HPLC provides such TAF as a single discernable proteinaceous band or peak.

Generally, a substantially pure TAF composition is at least about 1% protein weight said TAF; preferably at least about 10%; more preferably at least about 50%; and most preferably at least 90%. Protein weight percentages are determined by dividing the weight of the TAF or TAF portion, including alternative forms and analogs of the TAF such as proteolytic breakdown products, alternatively spliced, differentially phosphorylated or glycosylated, or otherwise post-translationally modified forms of the TAF, present in a fraction by the total protein weight present.

A biologically active TAF or TAF portion retains one or more of the TAF's native function such as the ability to specifically bind TBP, transcription factors (activators), other TAFs or anti-TAF antibodies, or to modulate or facilitate transcription or transcription initiation. Exemplary assays for biological activity are described below and in the working exemplification.

Specific binding is empirically determined by contacting, for example a TAF, with a mixture of components and identifying those components that preferentially bind the TAF. Specific binding may be conveniently shown by competitive binding studies, for example, immobilizing a TAF, on a solid matrix such as a polymer bead or microtiter plate and contacting the immobilized TAF with a mixture. Often, one or more components of the mixture will be labeled. Another useful approach is to displace labeled ligand. Generally, specific binding of a TAF will have binding affinity of $10^{-6}$M, preferably $10^{-8}$M, more preferably $10^{-10}$M under optimized reaction conditions and temperature.

Portions of TAFs find use in screening TAF expression libraries, defining functional domains or TAFs, identifying compounds that bind or associate with TAFs and the like. Accordingly, peptides encoding a portion of a TAF are provided that are capable of modulating transcription including transcription initiation. Typically, such peptides are effective by binding to a TAF, an activator, or TBP or competitively inhibiting a TAF domain's association with another compound, typically a protein like TBP or another TAF, an activator, or DNA. For example, TAF-TAF interactions may be exploited to purify TAFs, e.g. immobilized TAF200 is used to purify TAF110.

Associational domains of TAFs are ascertainable by those skilled in the art using the methods and compositions disclosed herein. Useful methods include in vitro mutagenesis such as deletion mutants, secondary and tertiary structural predictions, antibody and solvent accessibility, etc. For example, peptides derived from highly charged regions find particular use as immunogens and as modulators of TAF-protein interactions. Also, TAF mutants are used to identify regions important for specific protein interactions or otherwise involved in transcription. Here, useful assays include column binding assay and transfection studies.

The invention provides recombinantly produced TAFs, TAF analogs and portions thereof. These recombinant products are readily modified through physical, chemical, and molecular techniques disclosed or cited herein or otherwise known to those skilled in the relevant art. According to a particular embodiment of the invention, portions of the TAF-encoding sequences are spliced with heterologous sequences to produce fusion proteins. Such fusion proteins find particular use in modulating gene transcription in vitro and in vivo.

For example, many eukaryotic sequence-specific transcription factors have separable DNA binding and activation domains. A TAF or domain thereof can be fused to a well-characterized DNA binding domain (see, e.g., Sadowski et al., (1988) Nature 335, 563–564) and the resulting fusion protein can be tested for its ability to modulate transcription or transcriptional initiation. For example, we disclose the fusion of the N-terminal region of TAF110 to the DNA binding domain of the GAL4 protein. Alternatively, an TAF domain can be fused with a domain having endonuclease activity for site-specific DNA cleaving. Other useful TAF fusion partners include GST, Lerner epitope, an epitope recognized by a monoclonal antibody (e.g. hemagglutinin epitope and 12CA5 monoclonal antibody), glutathione S-transferase for immobilization, the SP1 or VP16 activation domains, etc.

TAFs can be further modified by methods known in the art. For example, TAFs may be phosphorylated or dephosphorylated, glycosylated or deglycosylated, with or without radioactive labeling, etc. The disclosed TAF serine residues in particular provide useful phosphorylation sites. See e.g. methods disclosed in Roberts et al. (1991) Science 253, 1022–1026 and in Wegner et al. (1992) Science 256, 370–373. Especially useful are modifications that alter TAF solubility, membrane transportability, stability, and binding specificity and affinity. Some examples include fatty acid-acylation, proteolysis, and mutations in TAF-TAF or TAF-TBP interaction domains that stabilize binding.

TAFs may also be modified with a label capable of providing a detectable signal, for example, at a heart muscle kinase labeling site, either directly or indirectly. Exemplary labels include radioisotopes, fluorescers, etc. Alternatively, a TAF may be expressed in the presence of a labeled amino acid such as $^{35}$S-methionine. Such labeled TAFs and analogs thereof find use, for example, as probes in expression screening assays for proteins that interact with TAFs, or, for example, TAF binding to other transcription factors in drug screening assays.

Specific polyclonal or monoclonal antibodies that can distinguish TAFs from other nuclear proteins are conveniently made using the methods and compositions disclosed in Harlow and Lane, Antibodies, A Laboratory Manual, Cold Spring Harbor Laboratory, 1988, other references cited herein, as well as immunological and hybridoma technologies known to those in the art. In particular, TAFs and analogs and portions thereof also find use in raising anti-TAF antibodies in laboratory animals such as mice and rabbits as well as the production of monoclonal antibodies by cell fusion or transformation.

Anti-TAF antibodies and fragments (Fab, etc) thereof find use in modulating TAF involvement in transcription complexes, screening TAF expression libraries, etc. In addition, these antibodies can be used to identify, isolate, and purify structural analogs of TAFs. Anti-TAF antibodies also find use for subcellular localization of TAFs under various conditions such as infection, during various cell cycle phases, induction with cytokines, protein kinases such as C and A, etc. Other exemplary applications include using TAF-specific antibodies (including monoclonal or TAF-derived peptide specific antibodies) to immuno-deplete in vitro transcription extracts and using immuno-affinity chromatography to purify TAFs, including analogs, or other nuclear factors which interact with TAFs.

Compositions are also provided for therapeutic intervention in disease, for example, by modifying TAFs or TAF encoding nucleic acids. Oligopeptides can be synthesized in pure form and can find many uses in diagnosis and therapy. These oligopeptides can be used, for example, to modulate native TAF interaction with other TAFs, TBP, other transcription factors or DNA. The oligopeptides will generally be more than six and fewer than about 60 amino acids, more usually fewer than about 30 amino acids, although large oligopeptides may be employed. A TAF or a portion thereof may be used in purified form, generally greater than about 50%, usually greater than about 90% pure. Methods for purifying such peptides to such purities include various forms of chromatographic, chemical, and electrophoretic separations disclosed herein or otherwise known to those skilled in the art.

Experimental methods for purifying TAFs are set out briefly below and in detail in the following working exemplification. Generally, TBP-TAF complexes are immunopurified (generally, by immunoprecipitation) using polyclonal or monoclonal antibodies directed against a native TAF or TBP epitope. Alternatively, monoclonal antibodies directed against an epitope-tagged TBP or TAF may be used. See e.g. Zhou, et al. (1992). At least three complementary experimental approaches are employed for isolating cDNAs encoding TAFs: (1) TAF-specific binding proteins (e.g. antibodies directed against TAF proteins, TAF-binding TAFs, TBP, TAF-binding activators, or TAF-binding coactivators) are used for screening expression libraries; (2) cDNA libraries are screened with potentially homologous TAF oligonucleotide sequences (alternatively, a series of degenerate oligonucleotide PCR primers derived from the homologous TAF sequence may be used to amplify probes from cDNA. See Peterson et al. (1990) Science, 248, 1625–1630, FIG. 1.); and, (3) TAF proteins are purified to homogeneity for protein microsequencing.

TAF ENCODING NUCLEIC ACID

The invention provides nucleic acid sequences encoding TAFs and portions of TAFs. By "encoding a portion of a TAF" is meant to include sequences substantially identical to sequences encoding at least a portion of a TAF. Included are DNA and RNA sequences, sense and antisense.

"Substantial sequence identity" means that a portion of the protein or nucleic acid presents at least about 70%, more preferably at least about 80%, and most preferably at least about 90% sequence identity with a TAF sequence portion. Where the sequence diverges from native TAF sequences disclosed herein, the differences are preferably conservative, i.e. an acidic for an acidic amino acid substitution or a nucleotide change providing a redundant codon. Dissimilar sequences are typically aggregated within regions rather than being distributed evenly over the polymer.

A substantially identical sequence hybridizes to a complementary TAF-encoding sequence under low stringency conditions, for example, at 50° C. and 6× SSC (0.9M saline/0.09M sodium citrate) and that remains bound when subject to washing at 55° C. with 1× SSC.

The invention's TAF encoding polynucleotides are isolated; meaning that the claimed sequence is present as other than a naturally occurring chromosome or transcript in its natural environment. Typically isolated sequences are removed from at least some of the nucleotide sequences with which they are normally associated with on a natural chromosome.

A substantially pure or isolated TAF- or TAF portion-encoding nucleic acid is generally at least about 1% nucleic acid weight said TAF-encoding nucleic acid; preferably at least about 10%; more preferably at least about 50%; and most preferably at least 90%. Nucleic acid weight percentages are determined by dividing the weight of the TAF or TAF portion-encoding nucleic acid, including alternative forms and analogs such as alternatively spliced or partially transcribed forms, by the total nucleic acid weight present.

The invention also provides for TAF sequences modified by transitions, transversions, deletions, insertions, or other modifications such as alternative splicing and such alternative forms, genomic TAF sequences, TAF gene flanking sequences, including TAF regulatory sequences and other non-transcribed TAF sequences, TAF mRNA sequences, and RNA and DNA antisense sequences complementary to TAF encoding sequences, sequences encoding xenogeneic TAFs and TAF sequences comprising synthetic nucleotides, e.g., the oxygen of the phosphate group may be replaced with sulfur, methyl, or the like.

For modified TAF-encoding sequences or related sequences encoding proteins with TAF-like functions, there will generally be substantial sequence identity between at least a portion thereof and a portion of a TAF, preferably at least about 40%, more preferably at least 80%, most preferably at least 90%, particularly conservative substitutions, particularly within regulatory regions and regions encoding protein domains involved in protein-protein interactions, particularly TAF-transcription factor interactions.

Typically, the invention's TAF encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein. See for example, Russel Doolittle, Of URFs and ORFs, A Primer on How to Analyze Derived Amino Acid Sequences, University Science Books, Mill Valley Calif.

TAF encoding nucleic acids can be subject to alternative purification, synthesis, modification or use by methods disclosed herein or otherwise known in the art. For example, the nucleic acids can be modified to alter stability, solubility, binding affinity and specificity, methylation, etc. The nucleic acid sequences of the present invention may also be modified with a label capable of providing a detectable signal, either directly or indirectly. Exemplary labels include radioisotopes, fluorescers, biotinylation, etc.

Nucleic acids encoding at least a portion of a TAF are used to identify nuclear factors which interact with that TAF using expression screening in yeast as described in Current Protocols in Molecular Biology. In this example, a yeast cDNA library containing fusion genes of cDNA joined with DNA encoding the activation domain of a transcription factor (e.g. Gal4) are transfected with fusion genes encoding a portion of a TAF and the DNA binding domain of a transcription factor. Clones encoding TAF binding proteins provide for the complementation of the transcription factor and are identified through transcription of a reporter gene. See, e.g. Fields and Song (1989) Nature 340, 245–246 and Chien et al. (1991) Proc Natl Acad Sci USA 88, 9578–9582.

The invention also provides vectors comprising nucleic acids encoding a TAF or portion or analog thereof. A large number of vectors, including plasmid and viral vectors, have been described for expression in a variety of eukaryotic and prokaryotic hosts. Vectors will often include one or more replication systems for cloning or expression, one or more markers for selection in the host, e.g. antibiotic resistance, and one or more expression cassettes. The inserted TAF coding sequences may be synthesized, isolated from natural sources, prepared as hybrids, etc. Ligation of the coding sequences to the transcriptional regulatory sequences may be achieved by known methods. Advantageously, vectors may also include a promotor operably linked to the TAF encoding portion.

Suitable host cells may be transformed/transfected/infected by any suitable method including electropotation, $CaCl_2$ mediated DNA uptake, viral infection, microinjection, microprojectile, or other established methods. Alternatively, nucleic acids encoding one or more TAFs may be introduced into cells by recombination events. For example, a sequence can be microinjected into a cell, and thereby effect homologous recombination at the site of an endogenous gene encoding a TAF, an analog or pseudogene thereof, or a sequence with substantial identity to a TAF-encoding gene. Other recombination-based methods such as nonhomologous recombinations, deletion of endogenous gene by homologous recombination, especially in pluripotent cells, etc., provide additional applications.

Appropriate host cells include bacteria, archebacteria, fungi, especially yeast, and plant and animal cells, especially mammalian cells. Of particular interest are E. coli, B. subtilis, Saccharomyces cerevisiae, SF9 and SF21 cells, C129 cells, 293 cells, Neurospora, and CHO, COS, HeLa cells and immortalized mammalian myeloid and lymphoid cell lines. Preferred replication systems include M13, ColE1, SV40, baculovirus, vaccinia, lambda, adenovirus, AAV, BPV, etc. A large number of transcription initiation and termination regulatory elements/regions have been isolated and shown to be effective in the transcription and translation of heterologous proteins in the various hosts. Examples of these regions, methods of isolation, manner of manipulation, etc. are known in the art. The particular choice of vector/host cell is not critical to the invention.

Under appropriate expression conditions, host cells are used as a source of recombinantly produced TAFs or TAF analogs. Preferred expression systems include E. Coli, vaccinia, or baculovirus; the latter two permitting the recombinant TAFs to be modified, processed and transported within a eukaryotic system.

TAF-encoding oligonucleotides also used to identify other TAFs or transcription factors. For example, $^{32}P$-labeled TAF-encoding nucleic acids are used to screen cDNA libraries at low stringency to identify similar cDNAs that encode proteins with TAF-related domains. Additionally, TAF related proteins are isolated by PCR amplification with degenerate oligonucleotide probes using the sequences disclosed herein. Other experimental methods for cloning TAFs, sequencing DNA encoding TAFs, and expressing recombinant TAFs are also set out in the working exemplification below. Other useful cloning, expression, and genetic manipulation techniques for practicing the inventions disclosed herein are known to those skilled in the art.

The compositions and methods disclosed herein may be used to effect gene therapy. See, e.g. Gutierrez et al. (1992) Lancet 339, 715–721. For example, cells are transfected with TAF sequences operably linked to gene regulatory sequences capable of effecting altered TAF expression or regulation. To modulate TAF translation, cells may be transfected with TAF complementary antisense polynucleotides.

Antisense modulation may employ TAF antisense sequences operably linked to gene regulatory sequences. Cells are transfected with a vector comprising a TAF sequence with a promoter sequence oriented such that transcription of the gene yields an antisense transcript capable of binding to TAF encoding mRNA. Transcription may be constitutive or inducible and the vector may provide for stable extrachromosomal maintenance or integration. Alternatively, single-stranded antisense nucleic acid sequences that bind to genomic DNA or mRNA encoding at least a portion of TAF may be administered to the target cell at a concentration that results in a substantial reduction in TAF expression.

ASSAYS FOR IDENTIFYING TRANSCRIPTION FACTORS AND THERAPEUTIC AGENTS

The invention provides methods and compositions for identifying agents useful in modulating gene transcription. Such agents find use in the diagnosis or treatment of broad range of disease including cancer, cardiovascular diseases, microbial and fungal intactions and particularly viral infections, inflammatory disease, immune disease, etc. The ability to develop rapid and convenient high-throughput biochemical assays for screening compounds that interfere with the process of transcription in human cells opens a new avenue for drug development. An overview of this therapeutic approach is presented in Peterson & Baichwal (1993), Trends in Biotechnology, in press.

Typically, prospective agents are screened from large libraries of synthetic or natural compounds. For example, numerous means are available for random and directed synthesis of saccharide, peptide, and nucleic acid based compounds, see, e.g. Lam et al., (1991) Nature 354, 82–86. Alternatively, libraries of natural compounds in the form of bacterial, fungal, plant and animal extracts are available or readily predicable. Additionally, natural and synthetically produced libraries and compounds are readily modified through conventional chemical, physical, and biochemical means. Examples of such modifications are disclosed herein.

Useful agents are identified with a range of assays employing TAFs or TAF encoding nucleic acids. As examples, protein binding assays, nucleic acid binding assays and gel shift assays are useful approaches. Exemplary assays include assaying labeled TBP binding to immobilized TAF, labeled TAF or TAF peptide binding immobilized TBP, etc. Many appropriate assays are amenable to scaled-up, high throughput usage suitable for volume drug screening. Such screening will typically require the screening of at least about 10, preferably at least about 100, and more preferably at least about 1000 prospective agents per week. The particular assay used will be determined by the particular nature of the TAF interactions. For instance, a prospective agent may modify with the function of a TAF but not with transcription complex assembly. For example, a molecule that binds to a TAF but does not disrupt complex assembly is identified more readily through labeled binding assays than through gel retardation assay. Assays may employ single TAFS, TAF portions, TAF fusion products, partial TAF complexes, or the complete TFIID transcription complex, depending on the associational requirements of the subject transcription factor.

Useful agents are typically those that bind to or modify the association of transcription associated factors, especially TAFs. Preferred agents include those capable of modulating the expression of Pol II genes, particularly oncogenes (including viral oncogenes such as adenovirus EIA, human papilloma E7, and cellular oncogenes such as Rb, P53, E2F, myc, fos/jun (AP1), abl, etc.), genes transcribed during vital infection or activation, and sterol regulated genes. Preferred agents modify, preferably disrupt, TAF-TAF, TAF-activator, TAF-coactivator (coactivators include OCA-B, dTAFII110, etc.) or TAF-TBP binding. An especially preferred useful agent disrupts the association of a disclosed hTAF, with an activator, particularly a viral-specific activator, particularly an HIV-specific activator such as tat.

Useful agents are found within numerous chemical classes, though typically they are organic compounds; preferably small organic compounds. Small organic compounds have a molecular weight of more than 50 yet less than about 2,500, preferably less than about 750, more preferably, less than about 250. Exemplary classes include peptides, saccharides, steroids, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. Alternatively, peptide (and protein and nucleic acid agents) are readily produced by known recombinant technologies.

For therapeutic uses, the compositions and selected agents disclosed herein may be administered by any convenient way that will depend upon the nature of the compound. For small molecular weight agents, oral administration is preferred and enteric coatings may be indicated where the compound is not expected to retain activity after exposure to the stomach environment. Generally the amount administered will be empirically determined, typically in the range of about 1 to 1000 ug/kg of recipient.

Large proteins are preferably administered parenterally, conveniently in a physiologically acceptable carrier, e.g., phosphate buffered saline, saline, deionized water, or the like. Typically, such compositions are added to a retained physiological fluid such as blood or synovial fluid. Generally, the amount administered will be empirically determined, typically in the range of about 10 to 1000 μg/kg of the recipient. Other additives may be included, such as stabilizers, bactericides, etc. These additives will be present in conventional amounts.

The following examples are offered by way of illustration and not by way of limitation.

EXAMPLES

Additional exemplary materials and methods for the purification, cloning and expression of TAFs are described below. Additional exemplary functional assays are described in detail. While exemplified primarily for dTAFII110, the disclosed methods find ready application to other TAFs by those skilled in the art and familiar with the methods hereinor found in standard manuals such as Molecular Cloning, A Laboratory Manual (2nd Ed., Sambrook, Fritsch and Maniatis, Cold Spring Harbor), Current Protocols in Molecular Biology (Eds. Ausubel, Brent, Kingston, Moore, Seidman, Smith and Struhl, Greene Publ. Assoc., Wiley-Interscience, NY, N.Y., 1992)

Immunopurified dTFIID complex is necessary and sufficient to mediate Sp1 activation in vitro.

In order to determine if the TFIID complex is sufficient to substitute for a partially-purified TFIID fraction, we have purified the TBP-TAF complex extensively by using an affinity resin coupled to a specific monoclonal antibody directed against TBP. Transcriptionally active TFIID purified from Drosophila embryos was obtained by eluting the complex from the antibody affinity resin with a low concentration (0.5M) of guanidine hydrochloride in the presence of a synthetic peptide corresponding to the epitope recognized by monoclonal 42A11. The antibody used for the immunopurification remained bound to the protein G-sepharose beads and was found in the pellet. The proteins were electrophoresed on an 8% polyacrylamide-SDS gel and detected by silver staining. The resultant gels reveal seven major TAFs in the complex ranging in size from 30 to over 200 kD.

After dialysis of the purified TFIID complex to remove the peptide and denaturant, in vitro transcription reactions were carried out in the presence of basal factors that were isolated from Drosophila embryo nuclear extracts (Dynlacht et al., 1991; Wampler et al., 1990). Without the TFIID fraction there is no detectable transcription. Purified, recombinant dTBP is able to direct basal but not activated transcription. In contrast, immunopurified TFIID complex is able to mediate basal expression and Sp1 activation. Sp1-dependent activation with the TFIID fraction is shown in lanes 7 and 8. For the in vitro transcription assay, 2 ul of the immunopurified TFIID complex was assayed. Transcription was assayed by primer extension. The results demonstrate that the immunopurified TFIID complex containing TBP and at least 7 specific TAFs is necessary and sufficient for Sp1-dependent activation of transcription in vitro. As expected, the impure TFIID fraction also mediates transcriptional activation by Sp1, while the recombinant TBP protein is only able to direct basal, but not activated transcription.

The immunopurified complex is also able to support activation by other transcription factors such as NTF-1.

Cloning and expression of Drosophila TAF110 cDNAs

Purified TFIID complex was used to immunize a mouse, and monoclonal antibodies were generated against TAF110 (see Experimental Procedures below). The serum from the immunized mouse was also collected and polyclonal antibodies used to screen a λgt11 expression library constructed from Drosophila embryo cDNA (Zinn et al., 1988). One clone was tentatively classified as a TAF110 cDNA because it produced protein that cross-reacted with independently isolated anti-TAF110 monoclonal antibodies. This partial cDNA clone was subsequently used as a probe to isolate full-length cDNAs from a λgt10 library (Poole et al., 1985). The longest clone obtained was 4.6 kb. This cDNA is polyadenylated at the 3' end and appears to be nearly full-length, based on the size of the mRNA, as determined by Northern blot analysis. The 4.6 kb cDNA clone contains a long open reading frame coding for a protein of 921 amino acids (SEQ ID NOS:1 and 2), with a calculated molecular weight of 99.4 kD and an estimated pI of 10.1. Within the predicted amino acid sequence, there are 3 peptides that correspond to amino acid sequences determined from lys C peptides generated from HPLC purified TAF110. For microsequencing, the TFIID complex was immunopurified from fractionated embryo nuclear extract, and the TAFs were separated from TBP and the antibody by elution with 1M guanidine-HCl. The purified TAFs were fractionated on a C4 reverse phase HPLC column. Three adjacent fractions containing TAF 110 as the major species were cleaved with the protease lys-C, and the resulting peptides were purified and sequenced. Three peptide sequences were found that match the predicted amino acid sequence of the TAF110 cDNA We have expressed TAF 110 protein in a variety of cell types. The protein was expressed from the cloned gene in a baculovirus expression system and detected by western blot using a TAF110 monoclonal antibody. The protein encoded by the TAF110 cDNA has the same apparent molecular weight as the endogenous protein in the TFIID fraction derived from Drosophila cells, and the protein produced from the cloned gene cross-reacts with monoclonal antibodies directed against the TAF110 protein isolated from embryos. These results taken together demonstrate that the 4.6 kb cDNA encodes the full-length TAF110 protein.

TAF110 appears to be a single copy gene in Drosophila based on low-stringency Southern blot analysis. The TAF110 gene is located at 72D,4-5 on the left arm of the third chromosome. There are not any previously identified Drosophila genes assigned to this chromosomal location (Lindsley and Zimm, 1992).

Hybridomas producing antibodies against TAF110 were selected by screening cell culture supernatants for those containing antibodies that specifically recognize the 110 kd protein in a western blot. For westerns, approximately 50 ug of the TFIID fraction was immunoprecipitated with antibodies against dTBP or TAF110. The α-TAF110 monoclonal antibody 33G8 was obtained from a hybridoma culture medium and purified by binding to protein G-sepharose. Proteins were eluted from the resin by boiling in sample buffer, electrophoresed on 8% polyacrylamide gel, and silver stained. Several of the a-TAF110 monoclonals that were obtained by this method specifically immunoprecipitate the same set of proteins as a-dTBP antibodies. This demonstrates that at least part of TAF110 is accessible to our antibodies, and therefore exposed in the native TFIID complex and positioned for interaction with activators.

Monoclonal antibodies specific for other Drosophila TAFs can also immunopurify the same TFIID complex as a-TBP and α-TAF110 antibodies. Thus, there appears to be one predominant TBP-containing complex in the TFIID fraction, as opposed to a heterogeneous set of complexes containing different sets of TAFs bound to TBP. Our methods are also used to determine if there are rare, perhaps tissue-specific, TBP-containing complexes that might contain different collections of TAFs or if the activity of the TAFs could be modulated by post-translational modifications. For example, TAF200 does not stain as intensely as the other TAFs and TBP, and, on this basis, might not be present in all complexes. However, this protein seems to be an authentic member of the major TFIID complex since antibodies directed against TAF200 immunopurify a set of proteins that appear to be identical to complexes purified by antibodies directed against TBP or other TAFs. The preparations of the purified TFIID complex contain some polypeptides that are less abundant than the major TAF proteins. Based on western analyses with α-TAF antibodies, these minor species appear to be proteolytic breakdown products of larger TAFs or substoichiometric TAFs.

The TAF110 coding sequence (SEQ ID NO:1, resides 538-3300) contains several regions which are rich in glutamine residues or rich in serine and threonine residues, and the C-terminal third of the protein is highly charged. The C-terminal region of the molecule contains 32% acidic or basic residues. We searched the existing data bases for genes similar to the TAF110 gene, and found that it is not highly homologous to any previously identified genes. In particular, TAF110 did not show any similarity to any DNA binding domains. Interestingly, Sp1 received one of the highest scores in the NBRF protein sequence data base search for similarity to TAF110. The amino terminal third of TAF 110 has an organization similar to the activation domains of Sp1, consisting or glutamine-rich regions flanked by serine-threonine rich domains. The two proteins share 21% amino acid identity and 35% similarity over 260 residues.

This unexpected similarity to Sp1 prompted us to consider a possible functional relationship between Sp1 and TAF110. In particular, whether the amino-terminal region of TAF110 might contain interaction surfaces for activators such as Sp1, especially since the A and B glutamine-rich domains are responsible for mediating Sp1-Sp1 interactions as well as activation. Indeed, one of the unique properties of Sp1 activation domains is their capacity to mediate a phenomenon called superactivation, in which a truncated form of Sp1 lacking the zinc fingers but containing glutamine-rich domains A and B is able to interact directly with DNA-bound full length Sp1. This interaction increases the number of activation domains at the promoter and can greatly enhance expression of a gene regulated by Sp1 binding sites. This type of interaction also appears to be involved in synergistic activation mediated by distally and proximally bound Sp1.

?dTAF110 can function as a target for the Sp1 activation domains

To test for functional homology between the similar domains, we asked if the N-terminal region of TAF110 could function as a target for the Sp1 activation domains in a superactivation assay. The amino terminal 308 residues of TAF110 (SEQ ID NO:2) were fused to the DNA binding domain of the GAL4 protein, G4(1–147), and tested in a transient cotransfection assay in Drosophila Schneider cells. This hybrid construct, by itself, weakly activates (4 fold) a reporter gene which is dependent on GAL4 binding sites. This low level of activity is similar to the modest activation observed with constructs containing the Sp1 B domain fused to GAL4. When this TAF 110 hybrid construct is cotransfected with DNA expressing the gln-rich A and B domains of Sp1, (N539), a 60 fold increase in transcription is observed. This 15 fold superactivation is dependent on the TAF110 sequences since Sp1(N539) is unable to stimulate transcription when cotransfected with G4(1–147) alone. The interaction with Sp1 apparently requires an extended region of TAF110 (SEQ ID NO:2) since GAL4 fusion proteins bearing TAF110 residues 1–137, 138–308, or 87–308 are unable to mediate superactivation by Sp1.

These results indicate that the N-terminal 308 amino acids of TAF110 are sufficient for mediating an interaction with the glutamine-rich activation domains of Sp1 that lead to superactivation. In the positive control for this experiment, a GAL4-Sp1B domain fusion is superactivated approximately 50 fold by the fingerless Sp1 mutant. In a search for other potential targets of Sp1, we have tested some additional members of the TFIID complex for the ability to mediate superactivation by Sp1. For example, GAL4 hybrids containing TAF40, TAF80, or the amino-terminal region of dTBP were found to be inactive in the superactivation assay. This results shows that the interaction between TAF110 and Sp1 in Drosophila cells is quite specific and that other subunits of the TBP-TAF complex that we tested are unable to interact with the glutamine-rich activation domains of Sp1.

dTAF110 and Sp1 interact in yeast

The superactivation assay in Drosophila Schneider cells provided the first hint that TAF110 may serve as a coactivator for Sp1. However, it is difficult to assess in this assay whether TAF110 can interact with Sp1 in the absence of the other TAFs which are present in Drosophila cells. The superactivation assay also imposes certain limitations to the number and types of constructs that can be tested. Moreover, it seemed prudent to establish several independent assays to investigate the relationship between TAF110 and transcription activation domains. Therefore, we carried out two additional types of assays, one in vivo and one in vitro, to test the results obtained in Schneider cells. First, we tested the ability of TAF110 and Sp1 to interact in a versatile assay for protein-protein interaction which is carried out in yeast cells (Fields and Song, 1989). This strategy takes advantage of the modular organization of eukaryotic transcription factors. In this assay, one of the partners to be tested is fused to the DNA binding domain of GAL4 and, in a separate molecule, the other partner is fused to the acidic activation domain (AAD). A functional activation domain is recruited to the target promoter bearing GAL4 binding sites and the lacZ reporter gene is expressed only if there is a protein-protein interaction between the partners being tested.

Full-length TAF 110 as well as a variety of deletion mutants were fused to the DNA binding domain of GAL4, G4(1–147). In contrast to the situation in Drosophila cells, the amino terminal region of TAF110 cannot activate transcription by itself in yeast. This result was anticipated since glutamine-rich activation domains have not been observed to function in yeast. As potential partners for TAF110, the Sp1 activation domains were fused to the acidic activation domain of GAL4. Each of the Sp1 glutamine-rich activation domains A or B can independently interact with full-length TAF110 as judged by activation of the reporter gene. In these experiments, yeast bearing an integrated GAL1:lacZ fusion were transformed with two plasmids: (1) fusions to the DNA binding domain of GAL4 (residues 1–147), and (2) fusions to the acidic activation domain (AAD; residues 768–881 of GAL4), and the resulting β-gal activity was measured (expressed in units/mg or protein). Interestingly, domain A of Sp1 appears to interact more efficiently than domain B, and this correlates well with the previous finding that A is a better activator for transcription than domain B (Courey and Tjian, 1988). As in Drosophila cells, residues 1–308 of TAF110 are sufficient for the interaction, while regions 1–137 and 138–308 are inactive. The full-length TAF110 fusion is more active than the N308 construct in this assay. Although this effect may be due to differential protein expression, it is possible that the C-terminal regions of TAF110 contribute to interactions with Sp1. The protein-protein interaction assay in yeast further supports the idea that TAF110 interacts, directly or indirectly, with the activation domains of Sp1, and the strength of this interaction appears to be correlated with transcriptional function.

The other TAF proteins that have been tested in the superactivation assay or the yeast assay displayed no detectable interaction with Sp1. However, the GAL4 fusion proteins that these assays rely on might not be able to participate in all the correct interactions because some surfaces could be sterically blocked. Therefore, additional strategies, such as the use of full length Sp1, are used to test for other potential interactions.

dTAF110 does not interact with other activators tested

To determine whether the interaction between Sp1 and TAF110 is specific, or whether other types of activators also interact with TAF110, we used the yeast assay to test a variety of other activation domains including the acidic activation domain of GAL4 (Ma and Ptashne, 1987) and the proline-rich activation domain of CTF (Mermod et al. 1989). Neither of these two activators displayed any interaction with TAF 110 in the yeast assay. In addition we tested activation domains from the Drosophila proteins Antennapedia (Antp) and bicoid (bcd), both of which are glutamine-rich. Surprisingly, both of these glutamine-rich domains failed to interact with TAF110 in the yeast assay. Since TAF110 can interact with both Sp1 domains A and B, which have no significant homology other than high glutamine content, but not Antp and bcd which are even more glutamine-rich than Sp1, it appears that glutamine content alone may not be a sufficient criterion for the classification of functionally similar activation domains. In this regard, it may be useful to draw a distinction between the Sp1 activation domains, which are approximately 25% glutamine and flanked by serine/threonine rich sequences, and the bcd and Antp sequences, which are partially composed of uninterrupted stretches of glutamines and lack adjacent serine/threonine sequences.

The N-terminal region of TAF110, containing the glutamine-and serine/threonine-rich sequences, is able to function as a weak activation domain in Drosophila cells, suggesting that this region can interact with a component of the native TFIID complex. To determine whether the N-terminal region of TAF110 is similar to the Sp1 activation domains which can mediate multimerization, we tested for TAF110-TAF110 interactions. We found that the N-terminal region of TAF110 is able to interact with itself as judged by activation of the lacZ reporter gene in the yeast assay (FIG. 6A). This is another example of functional similarity between the Sp1 activation domains and the N-terminal region of TAF110, which can interact with each other as well themselves.

TBP and other TAFs tested do not interact with Sp1 in yeast

Since Sp1 synergistically activates transcription through multiple sites even though it does not bind cooperatively to DNA, we sought to determine whether Sp1 works via interactions with multiple targets or coactivators. We therefore tested two other members of the TFIID complex, TAF40 and TAF80. Similar to the superactivation assay in Drosophila cells, neither TAF40 or TAF80 displayed any ability to interact with Sp1 under the conditions of the yeast assay. In addition, the conserved C-terminal domain of TBP was tested for Sp1 interaction in yeast but no interaction was observed. We were unable to test full-length dTBP in this assay because it functions as an activator in yeast when fused to the GAL4 DNA binding domain. These results show that the interaction between TAF110 and Sp1 is quite specific, and that TAF80, TAF40, and the conserved region of TBP do not appear to be targets for Sp1.

Since the TFIID complex is also required at promoters that lack a TATA box, one of the TAFs might be required for promoter recognition through the initiator element. In addition to communicating with promoter-selective factors, the TAFs interact with each other, at least one TAF interacts with TBP, and one interacts with RNA polymerase II or one of the basal factors.

Sp1 binds dTAF110 in vitro

The superactivation assay in Schneider cells and the yeast experiments are both indirect assays for protein-protein interactions. Therefore, we also determined the ability of Sp1 to bind directly to TAF110 in vitro. Biotinylated oligonucleotides containing Sp1 binding sites were coupled to streptavidin-agarose resin. The resin was incubated with Sp1 that had been over-expressed and purified from HeLa cells infected with a vaccinia virus expression vector (Jackson et al., 1990). After allowing Sp1 to bind DNA on the beads, the unbound Sp1 was washed away. Control resin that lacked Sp1 was also prepared and tested in parallel. These resins were incubated in batch with $^{35}$S-labeled TAF110 synthesized in vitro in a reticulocyte lysate. After incubation with the labeled protein, the beads were extensively washed and the bound proteins were eluted in two steps with buffer containing 0.2M KCl followed by 1.0M KCl. The 1.0M salt incubation elutes Sp1 from the DNA. The input, unbound supernatant, and eluted fractions were subsequently analyzed by SDS-PAGE and autoradiography. Samples from the binding reaction were also analyzed by silver staining to detect non-specific binding of proteins present in the reticulocyte lysate.

$^{35}$S-labeled TAF110 synthesized in vitro in a reticulocyte lysate and incubated with streptavidin-agarose beads with or without DNA-bound Sp1. Protein fractions were run on SDS-PAGE and analyzed by autoradiography or by silver staining. After allowing TAF110 to bind Sp1, the beads were pelleted and the supernatant containing the unbound proteins was collected. The resin was washed 4 time. The specifically bound proteins were eluted by incubating the beads in buffer containing 0.2M KCl followed by 1.0M KCl. The Sp1 protein bound to the DNA is eluted by treatment with 1.0M salt. Labeled TAF110 protein is detectable in the eluted fractions. No detectable TAF110 protein bound to the DNA affinity resin in the absence of Sp1 protein. Quantitation of these results by analysis of the gel in a PhosphorImager (Molecular Dynamics) scintillation gel scanner indicate a 60-fold greater binding by labeled TAF110 to the Sp1-containing resin. The silver stained gel showed that Sp1 is the major species in the eluate indicating that the unlabeled proteins in the extract are not able to bind Sp1.

These data show that TAF110 is selectively retained on the resin containing DNA-bound Sp1, but TAF110 does not bind the control resin that lacks Sp1. Most of the bound TAF110 elutes with the Sp1 at 1.0M KCl with a lower amount eluting at 0.2M KCl. Analysis of the fractions by silver staining indicates that Sp1 is the major protein detectable in the high salt eluate, indicating that the unlabeled proteins present the reticulocyte lysate, which constitute the vast majority of the total protein in tile input, are not non-specifically binding to Sp1 in this assay. To rule out tile possibility that an intermediary protein, perhaps some other TAF or other eukaryotic protein, was required for the Sp1-TAF110 interaction, this experiment was repeated using $^{35}$S-labeled TAF110 synthesized in an in vitro transcription/translation extract derived from E. coli (Skelly et al., 1987). The TAF110 protein synthesized in the prokaryotic system was also specifically retained on the Sp1 affinity resin providing further evidence that Sp1 can bind directly to TAF110.

As an additional test of specificity, we also determined if deletion mutants of TAF110 could bind to Sp1 in this in vitro assay (mutants are expressed from the N-terminal). A 1–137 mutant was not able to bind Sp1 in vitro, while some binding was obtained with a 1–308 mutant. Mutants of 308–921, 447–921, and 571–921 were all effective ill binding Sp1, while C-termina deletions beyond 852 from these mutants eliminated Sp1 binding. These results indicate the importance of a 852–921 region and a 137–308 region of TAF110 in transcription activator interaction.

TAF110 does not directly bind TBP

Our experiments indicate that TAF110 cannot directly bind to TBP by itself and that at least one additional TAF is required to connect TAF110 and TBP. For example, α-TAF110 antibodies fail to coprecipitate both in vitro expressed TAF110 and TBP and similarly with α-TBP antibody.

Exemplary Experimental Procedures

Purification of the TFIID complex

For the in vitro transcription assay, the TFIID complex was immunopurified from tile partially purified TFIID fraction (Q-sepharose fraction, 0.3M KCl eluate) (Dynlacht et al., 1991) using the α-dTBP monoclonal antibody 42A11 coupled to protein G-sepharose (Pharmacia). The immunoprecipitates were washed with 0.1M KCl-HEMG-ND buffer (25 mM HEPES pH 7.6, 0.1 mM EDTA, 12.5 mM MgCl$_2$, 10% glycerol, 0.1.% NP-40, 0.1 mM DTT) and the TFIID complex was eluted from the antibody by addition 10 mg/ml of the peptide mimicking the epitope of 42A11 in HEMG buffer containing 0.5M guanidine-HCl. The eluate was dialyzed against 0.1M KCl-HEMG-ND, and then assayed for transcription activity.

Purification of dTAF110

Nuclear extracts derived from approximately 1 kg of Drosophila embryos were prepared and fractionated as previously described (Dynlacht et al., 1991; Wampler et al., 1990). For protein sequencing, the TFIID complex was purified with polyclonal α-dTBP antibodies as previously described (Dynlacht et al., 1991) or with a monoclonal antibody as described above. The TAFs were separated from TBP by elution of the protein A-antibody resin with 0.1M KCl-HEMG buffer containing 1.5 mM DTT, 0.1% LDAO (lauryl dimethylamineoxide), and 1M Gd-HCl. The TAFs were eluted by batch incubation of the resin with an equal volume of buffer for 25 min at 4° C. This procedure was repeated and the two supernatants were combined. Urea was added to 8M, DTT to 10 mM, and cysteines were modified with 4-vinylpyridine.

Two approaches were used to separate the TAFs: HPLC and PAGE. Under the HPLC approach, the TAFs were fractionated by reverse phase HPLC on a 300 angstrom C4 column (2.1×30 mm). The proteins were eluted with a gradient from 20–70% buffer B (buffer A=0.1% TFA, 1% n-propanol; buffer B=0.1% TFA, 1% n-propanol, 60% isopropanol, 30% acetonitrile). TAF110 consistently eluted at 35% buffer B. Fractions containing TAF110 (approximately 5 µg) were lyophilized, resuspended in 100 mM TRIS, pH 8.0, and 2M urea, and incubated at 55° C. for 10 min. 150 ng of the protease lys C was added and the protein was digested for 20 hr at 37° C. Peptides were chromatographed and sequenced as previously described (Williams et al., 1988).

Under the gel electrophoresis approach, the TAFs were separated by electrophoesis and transferred to membranes. The separated TAFs were digested with LysC or trypsin and the resultant peptides eluted, chromatographed and sequenced. See Fernandez et al., (1992) Analytical Biochemistry 201, 255–264.

In vitro transcription assay

Transcription factor fractions were reconstituted with basal factor fractions derived from 0–12 hr Drosophila embryo nuclear extracts essentially as previously described (Dynlacht et al., 1991) except that TFIIB was separated from TFIIE/TFIIF and pol II was fractionated further on a phosphocellulose column. Each reaction contained 0.5 ug of the TFIIB fraction (S-sepharose 0.5M eluate), 1.5 ug of the TFIIE/TFIIF fraction (S-sepharose 0.25M eluate), and 0.25 mg of the pol II fraction (phosphocellulose 0.4M eluate). Some reactions contained 1.5 ug of the TFIID fraction or 2 ng of purified, recombinant dTBP that had been expressed in E. coli (Hoey et al., 1990). The template for the in vitro transcription reaction was BCAT (Lillie and Green, 1989) containing 3 Sp1 binding sites, and transcription was assayed by primer extension.

Generation of antibodies against the TAFs

Immunopurified TFIID complex (approximately 10 ug/injection) was mixed with Ribi's adjuvant and injected intraperitoneally into a Swiss-Webster mouse at days 0, 7, and 21. The initial immune response was monitored at day 28 and boosted further by two biweekly injections of more antigen. After an intravenous injection of one further dose of antigen the spleen was dissected out and electrofused with myeloma cells. Approximately 600 supernatants from 96-well dishes (each well containing on average 5 independent hybridomas) were assayed on western strip blots for cross-reactivity with immunopurified TFIID complex proteins. Hybridomas from wells producing anti-TAF and/or anti-TBP antibodies were cloned by limited dilution and tested by Western blotting and immunoprecipitation assays.

Cloning of TAF110 cDNAs

The polyclonal antiserum obtained from the immunization scheme described above was used at a 1/1000 dilution to screen approximately $5 \times 10^5$ plaques of a size-selected (>1.8 kb) 9–12 hr lgt 11 Drosophila cDNA library (Zinn et al., 1988). Positive clones were plaque-purified to homogeneity and tested for cross-reactivity against anti-TAF monoclonal antibodies of known specificity. One clone, λ106, cross-reacted strongly with several independent anti-TAF110 hybridomas.

Insert DNA (2.6 kb) from λ106 was purified and labeled using Klenow polymerase and random hexamer priming (Amersham). $10^6$ recombinant phage from a cDNA library (Poole, et al., 1985) prepared from 3–9 hour Drosophila embryos were screened as previously described (Kadonaga et al., 1987). 24 positives were obtained in duplicate on the primary screen; 12 of these were randomly selected for rescreening, and 10 of 12 were positive on the secondary screen. All 10 of these cDNA clones were found to be related to each other on the basis of restriction mapping and cross-hybridization. The largest cDNA clone of 4.6 kb, λ110-5, was completely sequenced, and two other clones of 3.1 kb, λ110-1, and 2.1 kb, λ110-2, were partially sequenced. The inserts were subcloned into pBS-SK (Stratagene) in both orientations, a nested set of deletions was constructed with exonuclease III, and the clones were sequenced by the dideoxy method. The λ110-1 clone was found to be 37 nucleotides longer at the 5' end than the λ110-5 clone and missing 1.5 kb on the 3' end. The SEQ ID NO: 1 is a composite of the λ110-1 and λ110-5 sequence.

Expression of dTAF110 protein

An NdeI site was created at the initiating methionine using a PCR based strategy. A 3.1 kb NdeI-BssHII fragment containing the entire coding sequence was subcloned into the SmaI site of the baculovirus expression vector pVL1392 (Pharmingen). Recombinant baculoviruses were selected by co-transfection of Sf9 cells with the expression vector and linear vital DNA as described by the supplier (Pharmingen). Samples for the western blot were prepared by infecting SF9 cells with recombinant virus obtained from the transfection supernatant. Three days after infection the cells were harvested, washed, resuspended in HEMG buffer, and lysed by sonication. The protein concentration was measured by Bradford assay. After electrophoresis proteins were transferred to nitrocellulose; TAF110 protein was detected using the monoclonal antibody 3E7.

Transfections

Transfection of Schneider cells (line SL2) was carried out as previously described (Courey and Tjian, 1988) except that the transfections were performed in 60 mm dishes. The expression vector for all proteins used in this study was pPac, which contains the Drosophila actin 5c promoter. TAF110 sequences were fused in frame to GAL4 DNA binding domain, residues 1–147. The following restriction fragments of the TAF110 cDNA were used: N137, NdeI-ClaI; N308, NdeI-SalI, 138–308, ClaI-SalI; 87–308, HincII. The constructs were checked by sequencing across the fusion junctions. The amounts of DNA used were as follows: 100 ng of the pPacGAL4 derivatives, 500 ng of the pPacSp1N539, and 2.5 ug of the reporter gene pG5BCAT (Lillie and Green, 1989). CAT assays were performed and quantitated as previously described (Courey and Tjian, 1988).

Yeast Methods

The yeast strain Y153 (a, gal4, gal80, his3, trp1-901, ade2-101, ura3-52, leu2-3, 112, URA3::Gal1:lacZ, LYS2::Gal-His3) was transformed with two plasmids according to the method of Shiestl and Gietz (Schiestl and Gietz, 1989). The Gal4 DNA binding domain hybrids were constructed in the vector pAS1. pAS1 is a 2µ it plasmid with TRP selection that expresses fusions to Gal4(1–147) from the ADH promoter. For expression of GAL4(1–147), an XbaI linker containing stop codons in all three reading frames was inserted in pAS1 immediately downstream of the GAL4(1–147) coding sequence. G4-110 (fl) contains the entire coding region of the TAF110 on an NdeI-BssHII fragment, and the shorter G4-110 fusions contain fragments as described for the Drosophila expression vectors. G4-80 (fl) contains an NdeI-XbaI fragment that includes the entire coding region of Drosophila TAF80. G4-40 (fl) contains an NdeI-EcoRV fragment encoding Drosophila TAF40. G4-dTBP( 191C) contains an NdeI fragment derived from pAR-191C containing the conserved C-terminal domain (Hoey et al., 1990). The reading frame across all fusion junctions was verified by sequencing, and the protein expression was verified by western blot analyses with either α-TAF or α-GAL4 antibodies, with the exception of G4-110(N137).

The acidic activation domain fusions were constructed in the vectors pGAD1F, pGAD2F or pGAD3F which differ only in the reading frame of a unique Bam site (Chien et al., 1991). These 2μ plasmids with LEU2 selection express fusions to activating region II (residues 768–881) of GAL4 from the ADH promoter. Sp1 region A consists of amino acids 83–262 and Sp1 region B consists of residues 263–542; these were cloned as BamHI-BglII fragments from the plasmids pKSABg10 and pKSBG respectively. The C-terminal 100 amino acids of CTF1 (residues 399–499) were cloned as a BglII-EcoRI fragment (Mermod et al., 1989). The Antp construct was made by subcloning a BamHI fragment containing the activation domain (Courey et al., 1989). Bcd residues 249–489 (Driever et al., 1989) were cloned on a SalI fragment derived from pPac-bcd. The reading frame across all fusion junctions was verified by sequencing.

Transformed yeast were assayed qualitatively after growth on media containing X-gal. Quantitative β-galactosidase assays were performed as described (Himmelfarb et al., 1990) except cells were grown to mid log in selective media containing 2% glucose. Assays were performed in triplicate and activity is expressed as units/mg of total protein.

In vitro protein-protein interaction assay

A 3.1 kb NdeI-BssHII fragment containing the entire TAF110 coding region was subcloned into the plasmid pTbSTOP (Jantzen et al., 1992), which contains the b-globin untranslated leader downstream of a T7 promoter. The plasmid was linearized with XbaI, and the gene was transcribed in vitro with T7 RNA polymerase. $^{35}$S-met labeled protein was synthesized in vitro in a rabbit reticulocyte lysate (Promega). Alternatively, TAF110 was synthesized in vitro in an E. coli derived S30 transcription/translation extract (Skelly et al., 1987). Sp1 protein was overexpressed in HeLa cells using a vaccinia virus expression vector (Jackson et al., 1990) and purified by wheat germ agglutinin (WGA) affinity chromatography (Jackson and Tjian 1990), prior to DNA affinity purification as outlined below.

DNA affinity resin was prepared as follows: 5'-biotinylated oligonucleotides containing 4 Sp1 binding sites, and its complement, were annealed and coupled to streptavidin-agarose beads (Pierce) by incubating overnight at room temperature. The beads were incubated with WGA-purified Sp1 in buffer Z' (25 mM HEPES, pH 7.6, 20% glycerol, 0.1% NP-40, 10 mM $ZnSO_4$, 1 mM DTF) containing 0.1M KCl for 2 hours at 4° C. Sp1 was bound to the resin at a concentration of approximately 1 mg/ml of beads. $^{35}$S-labeled TAF110 was incubated in batch with 15 ml of the DNA affinity resin in Z'+50 mM KCl, with or without Sp1, for 4 hours at 4° C. The beads were washed 4 times with 1 ml of the same buffer, and eluted with Z'+0.2M KCl, followed by Z'+1.0M KCl. The eluted proteins were TCA-precipitated and analyzed by SDS-PAGE. Before autoradiography, the gel was fixed and treated with Amplify (Amersham).

Detection of Direct TBP/TAF Interactions on Protein Blots

Immunopurification of the Drosophila TFIID complex using anti-TBP antibodies results in the purification of a large multiprotein complex consisting of TBP and 7 major TAFs. To identify TAFs which can bind directly to TBP we probed a blot containing renatured TAFs with a 32P-labeled TBP-GST fusion protein. After washing off unbound TBP-fusion protein and exposing the blot to X-ray film a strong signal was seen which coincided with the position of dTAFII-250K on the gel. Further experiments revealed that a truncated version of TBP, consisting of the highly conserved C-terminal domain, is sufficient to mediate this interaction. We also tested other fractions containing basal factors (Wampler et al., 1990; Dynlacht et al., 1991), including TFIIB, E/F and RNA polymerase II, and failed to detect specific signals. We conclude that TBP and TAFII-250K interact directly and that TAFII-250K is present in the TFIID fraction but not associated with TFIIB, E, F or RNA polymerase II.

Molecular Cloning and Characterization of the dTAFII-250K Gene

Having identified dTAFII-250K as a candidate for a direct TBP-TAF interaction we decided to clone the corresponding gene. The low abundance and large size of dTAF(II)-250K disfavours cloning strategies based on protein microsequencing. Instead, we were able to obtain monoclonal antibodies which specifically (and exclusively) recognize dTAF(II)-250K on Western blots. To show that dTAF(II)-250K is indeed a genuine component of the TFIID complex, we used two of these monoclonal antibodies, 2B2 and 30H9, to carry out immunoprecipitations from the TFIID fraction. The pattern and stoichiometry of TAFs and TBP is indistinguishable from the ones described previously using either anti-TBP (Dynlacht et al., 1991) or anti-dTAF(II)-110K (Hoey et al., 1993) antibodies. We cloned the gene encoding the Drosophila dTAF(II)-250K by screening a lgt11 expression library prepared from 6–12 hour old embryos (Zinn et al., 1988) with hybridoma supernatants containing either 2B2 and 30H9 anti-dTAF(II)-250K monoclonal antibodies. Five partial cDNA clones were obtained, which all cross-hybridized with each other at high stringency. Restriction mapping and sequence analysis confirmed that they were indeed derived from the same gene. Two of these cDNAs, ID-1 and ID-2, allowed us to establish a composite open reading frame spanning 4.5 kb (FIG. 2). Attempts to isolate additional cDNA clones encoding N-terminal regions of dTAF(II)250 or 5'-RACE experiments have so far been unsuccessful. Genomic DNA sequencing allowed us to extend the open reading frame by approximately 1 kb before encountering noncoding (presumanbly intronic) sequences. Inspection of the open reading frame encoded by the cDNA clones reveals a protein sequence which displays an extensive similarity to the human 'Cell Cycle Gene 1' (CCG1) gene previously described by Sekiguchi et al., 1991. Many of the sequence elements defined in the CCG1 genes are also present in the dTAF-250K encoding sequence. Interestingly, however, we detected a 35 amino acid insertion in the region which Sekiguchi et al. putatively identified as an HMG box. This insertion causes substantial disruption of the spatial alignment with the consensus sequence. We also used the 1D-2 cDNA fragment to map the dTAFII-250K gene to position 32E1-2 (left arm of chromosome II) by in situ hybridization. This location does not contain any previously characterized genes and currently no deletions spanning that regions are available. Since dTAF-250 seems to be present in all or the majority of the TFIID complexes present within cells and seems to provide essential contact points with TBP and TAFs (see below) we expect that a deletion of the 32E1-2 locus would cause a lethal phenotype.

Expression of the C-terminal domain of dTAF(II)-250K in Insect Cells

To study the functional properties of the proteins encoded by these cDNAs we decided to express the protein encoded by the reading frame of our longest cDNA, 1D-1. Because of the expected large size of the protein encoded we chose the baculovirus system. After subcloning of the fragment into expression vector pVL1393 and transfecting the construct into Sf9 cells we detected expression of a 180K protein (subsequently referred to as DN250) which cross-reacted strongly with several anti-TAF250 monoclonal antibodies recognizing a variety of epitopes in different parts of the 250K TAF. We detected no cross-reactivity between our antibodies and any endogenous Spodoptera TAF250 homologs which might be present in Sf9 cells.

The C-terminal Domain of the dTAF(II)250K Is Sufficient for TBP Binding

To study whether DN250 was capable of interacting with TBP we immunopurified the protein from infected cells. Monoclonal antibody 30H9 was bound to protein A or G beads and incubated with extracts from baculovirus infected cells. Under these conditions DN250 is specifically immobilized on the beads. After washing off unbound material we added an extract containing partially purified TBP (also expressed in the baculovirus system). TBP was specifically bound to beads carrying tile immunopurified TAF250-C180 protein whereas beads containing antibody only failed to do so. Further evidence for this direct TBP-TAF interaction by carrying out protein blots. The ability of a protein representing appr. 60% of the full-length 250K protein to bind TBP demonstrates conclusively that the cloned C-terminal part is sufficient for TBP binding.

Gelshift Analysis of the DN250/TBP Complex

TBP is the only component of the general transcriptional machinery capable of sequence-specific binding to the TATA box. We therefore were interested to see how interaction of TBP with TAF250-C180 affected tile specificity and affinity of DNA binding. TBP was added to a 32-P labeled DNA fragment containing the −33 to +55 region of the adenovirus major late promoter and DNA-binding was monitored using a gelshift assay. The intensity of probe DNA shifted by TBP increased substantially in presence of purified TAF250-C 180 whcras TAF250-C 180 alone did not detectably bind to DNA. To investigate whether this enhanced affinity of the TBP/TAF250-C180 complex for DNA was due to additional contacts with DNA provided by the TAF250-C180 protein we carried out footprinting studies, again using the adenovirus major later promoter region as a probe.

TAF250 and TAF110 Specifically Interact With Each Other, even in Absence of TBP

Since we have not observed any of the cloned Drosophila TAFs to bind to TBP we investigated whether they would interact with the TBP/d250KdeltaC180 complex. 35S-labeled 110K protein (Hoey et al., 1993) was synthesized in an in-vitro translation system and incubated with TAF250-C180 protein in presence and absence of TBP. As shown in FIG. 5 we found that the 110K TAF binds specifically to dTAF(II)250K-C180 in the presence and absence of TBP thus indicating that the two proteins bind independently to two distinct domains within the 250K TAF. The affinity and specificity of this interaction is sufficiently high to allow selective purification of TAF110 from a crude baculovirus extract expressing the recombinant protein by using TAF250-C180 immobilized on beads.

Protein Blot Analysis pGEX-2TK was linearized with Sinai, phosphatase-treated and the ligated with gel-purified Ndel fragments of either pARdTFIID or pARdTFIID-191C (Hoey et al., 1990). Generation of 32-P labeled GST fusion protein, protein blotting and hybridization were carried out essentially as described in Kaelin et al., 1992.

Generation of anti-dTAFII-250K Hybridoma Cell Lines

The monoclonal antibodies described in this study were derived as described in Hoey et al. (1993). Briefly, a Swiss-Webster mouse was immunized with intact immunopurified Drosophila TFIID complex. After fusion hybridoma supernatants containing anti-dTAFII-250K antibodies were selected using stripblots containing SDS-gel-separated TBP and TAFs. Two such cell lines, 2B2 and 30H9, were then cloned to homogeneity by limited dilution.

Isolation of dTAFII-250K cDNA and Genomic Clones

Approximately $5\times10^5$ independent plaques of a size-selected (>=1.8 kb) Drosophila lgt11 library prepared from Drosophila embryos (Zinn et al., 19..) were screened with two independent anti-dTAFII-250K monoclonal antibodies, 2B2 and 30H9. All the positives identified cross-hybridized at high stringency with each other on the DNA level. Restriction mapping and sequence analysis showed that all of the clones were derived from the same gene. cDNA clones 1D1 and 1D2 contained inserts of 1.5 and 4.0 kb, respectively, and were sequenced to completion. 1D2 was found to extend 500 bp further towards the 5' end of the gene and was used to isolate genomic clones 1DASH3 and 1DASH4 (Sau3A partially digested DNA cloned into 1DASH).

Sequencing Strategy

We employed the gd transposon-directed sequencing strategy (Gold Biosystems) as described ill Strathmann et al., 1991. DNA fragments of interest were subcloned into tile plasmid vector pMOB1 and electroporated into DPWC cells. After conjugation with the recipient host BW26 the mixture was plated out on kanamycin/carbenicillin plates. Transposon insertion points were mapped by PCR. Clones with the desired transposon locations were then grown up and sequenced using transposon-specific printers with 35S-dATP or the Pharmacia A.L.F. Sequencer.

Expression of a Truncated Version of dTAFII-250K (DN250) in the Baculovirus System cDNA #5 was inserted into the EcoRI site of Baculovirus-expression plasmid pVL1393 (Pharmingen). The resulting construct was co-transfected with 'BaculoGold' vital DNA (Pharmingen) into Sf9 cells. After 3 days cells were harvested and expression or the DN250 protein was monitored by Western blotting using the anti-dTAFII-250K monoclonal antibody 2B2. The recombinant virus-containing supernatant was used to infect large scale cultures of Sf9 cells. We typically prepared whole cell extracts from 1 liter of plate cultures of infected Sf9-cells by sonicating them in HEMG-ND/0.1M KCl (HEMG-ND contains 25 mM HEPES, pH7.6, mM MgCl2 0.1 mM EDTA, 0.1% NP40, 1 mM PMSF, 1.5 mM DTT, 5 mg/ml leupeptin). The supernatant was partially purified (approximately 5 fold) by chromatography over Q-sepharose (Pharmacia) with step gradient elution (HEMG containing 0.1M, 0.2, 0.4 and 1.0M KCl, respectively). dTAFII-250K(C180) eluted in the 0.4M KCl step('Q.4' fraction). After dialysis against HEMG-0.1M KCl the extract was frozen in aliquots and used for the immunopurification/coprecipitation studies.

Coimmunopreciptiation Studies

Protein G-beads were preloabded with monoclonal antibodies and incubated with various cell extracts from Baculovirus-infected cell fractions or 35S-labeled dTAFII110 prepared by in vitro translation. After 45 minutes on ice, unbound protein was removed with several washes with HEMG-ND.

hTAFII250 purification and cloning

We previously reported the isolation of hTFIID by affinity chromatography using antibodies specific to TBP. The purified complex contains at least seven distinct TAFs ranging in molecular weight from 30–250 kD which copurify with TBP. We were particularly interested in characterizing the 250 kD species because this subunit of TFIID appears to bind TBP directly as determined by Far Western analysis. Using affinity-purified TAFs to immunize mice, we generated both polyclonal and monoclonal antibodies that cross-react with different TAFs. We used these antibodies to screen lgt11 expression cDNA libraries and several clones were isolated, including lH1 which contains a 1.1 kb insert. To determine which, if any, TAF is encoded by lH1, we expressed this cDNA as a GST fusion protein, purified the tagged protein by glutathione affinity chromatography, and raised antibodies against this recombinant protein. Antisera directed against GST-lH1 specifically crossreacted with the 250 kD TAF, indicating that a portion of the gene encoding hTAFII250 had been isolated.

Next, we determined the DNA sequence of lH1 and discovered that this open reading frame is related to the previously identified human gene, CCG1, which had been implicated in cell cycle regulation. Specifically, a temperature-sensitive mutant hamster cell line, ts13, is arrested at G1 a few hours before entering S phase at the non-permissive temperature. Expression of human CCG1 in ts13 overcomes this cell cycle block. Since lH1 only encoded a small portion of hTAFII250, we isolated several additional clones from a primary HeLa cDNA library, including lH2, which contained a 5.3 kb insert. The construction of a full-length hTAFII250 cDNA revealed the predominant hTAFII250 RNA species characterized in HeLa cells encodes 21 additional amino acids between residues 177 and 178 relative to CCG1. Interestingly, we sequenced several other cDNAs containing internal insertions or deletions when compared to CCG1. This finding suggests that multiple hTAFII250-related proteins may be generated by alternate splicing of a primary transcript.

Although the finding that a cDNA isolated by antibodies directed against TAFs encodes a cell cycle gone is exciting, it was important to provide some functional evidence that this clone indeed encodes a bona fide TAF which is a subunit of TFIID. We first asked whether the recombinant hTAFII250 expressed in a vaccinia virus system becomes associated with the endogenous TFIID complex in HeLa cells. To distinguish between the recombinant and endogenous protein, we engineered a version containing a hemagglutinin antigen (HA) epitope at the N-terminus of hTAFII250. Antibodies against TBP were used to immunopurify the TFIID complex from HeLa cells infected with either recombinant or control vaccinia virus. The immunopurified complexes were subjected to gel electrophoresis and analyzed by Western blot analysis using either a monoclonal anti-HA antibody to detect the HA-tagged molecule or monoclonal antibody 6B3, raised against the endogenous hTAFII250. The anti-HA antibody crossreacted specifically with a 250 kD protein only in the TFIID complex prepared from recombinant hTAFII250 virus infected HeLa cells but not control infected cells. As expected, 6B3 recognized both the recombinant hTAFII250 and the endogenous protein. Thus, we conclude that the recombinant hTAFII250 associates with TBP in vivo and is part of the TFIID complex.

To test for a direct interaction between hTAFII250 and TBP, we performed a Far Western analysis with radiolabeled TBP and antibody immunopurified HA-tagged hTAFII250. The full-length hTAFII250 is capable of interacting directly with TBP in vitro, even ill the absence of other TAFs or coactivators. These results and the analysis of the independently cloned Drosophila TAFII250 suggest that this largest TAF is responsible for the initial assembly of the TFIID complex by binding directly to TBP and other TAFs.

The important role of hTAFII250 in the formation of a TFIID complex prompted us to define more precisely its interaction with TBP. For these studies we employed the two hybrid system carried out in yeast cells. Using this rapid and convenient assay for protein:protein interactions, we observed that a hybrid construct containing hTAFII250 fused to the DNA binding domain of GAL4, G4(1–147), interacted selectively and efficiently with human TBP attached to the acidic activation domain of GAL4, G4(768–881). Yeast expressing both of these proteins produced high levels or b-galactosidase due to increased transcription of a lacZ reporter construct, containing GAL4 binding sites. Interestingly, hTAFII250 also interacts efficiently with a truncated version of human TBP which contains only the conserved C-terminal 180 amino acids. By contrast, a construct containing the "species-specific" N-terminal domain of human TBP failed to interact with hTAFII250. These results are in agreement with Far Western experiments using radiolabeled cTBP and nTBP as probes and suggest that residues 160 to 339 on the outer surface of TBP may be responsible for hTAFII250 binding.

Our unexpected finding that hTAFII250 is related to CCG1 suggests a rather intriguing link between a subunit of TFIID and expression of genes involved in cell cycle control. Interestingly, CCG1 is a nuclear phosphoprotein with several domains characteristic of transcription factors including a putative HMG-box and a proline-rich cluster. Based on these structural motifs, Sekiguchi et al. suggested that CCG1 might work as a sequence-specific transcription factor needed for regulating genes involved in the progression through G1. However, it now seems clear that CCG1 or a related product is part of the TFIID complex and is not a promoter-specific transcription factor. Therefore, it seems more likely that the G1 arrest in ts13 is due to the failure of a defective TFIID complex to mediate activation by a subset of cellular transcription factors that govern cell cycle genes, e.g. thymidine kinase and dihydrofolate reductase genes. The presence of a putative DNA binding domain, the HMG box, may suggest that once hTAFII250 forms a complex with TBP, some portion of this large subunit of TFIID may contact DNA, perhaps downstream of the initiation site.

Immunoaffinity purified hTFIID complex: Interaction with hTBP and production of hTAFs-specific antibodies A. Immunoprecipitation reactions were carried out according to a modified version of previously described procedures (Tanese et. al.). 0.5 mg of affinity purified a-hTBP antibody was added to 200 mg of hTFIID (phosphocellulose 0.48–1.0M KCl) fraction, and the mixture nutated for 2–4 hrs at 4° C. Protein A Sepharose was then added and nutation continued for an additional 2–4 hrs.

Antibody-antigen complexes were pelleted by low-speed centrifugation, washed four times with 0.1M KCl—HEMG (25mM Hepes, 12.5 mM MgCl2, 0.1 mM EDTA, 10% glycerol) containing 0.1% NP-40 and 1 mM DTT. The immunoprecipitated hTFIID complex was subjected to 8% SDS-PAGE and silver stained. For Far Western analysis, the proteins were blotted onto nitrocellulose membrane and hybridized with 35S-labeled hTBP (Kaelin et al.). pTbhTBP was used to in vitro transcribe hTBP RNA which was in vitro translated using 120 mCi 35S-methionine (>1000 Ci/mMol, Amersham) in reticulocyte lysate (Promega).

B. Antigen used to immunize mice for antibody production was prepared as follows. The immunoprecipitated hTFIID complex, purified from 250 liters of HeLa cells, was eluted from the Protein A Sepharose—antibody complex with 0.1M KCl—HEMG containing 1M guanidine—HCl, 0.1% NP-40, and 1 mM DTT. Under these conditions TBP remained bound to the antibody. The eluted TAFs were dialized against 0.1M KCl—HEMG containing 0.1% NP-40 and 1 mM DTT. The mixture of proteins containing 1–2 mg of each TAF was used to immunize a mouse. Test bleeds were taken and the immune response monitored by Western blot analysis. After a series of five boosts, the mouse was sacrificed and the spleen was used liar the production of monoclonal antibody producing hybridoma cells lines. The identification of hybridoma cell lines producing hTAF specific antibodies was determined by Western blot analysis of eluted TAFs.

Cloning and identification of the 250 kD subunit of hTFIID complex as CCG1

A. An expression screen of 2.4×106 PFU from a lgt 11 HeLa S3 cDNA library (Clontech) was carried out using the a-hTAFs polyclonal serum described above. 38 primary signals were identified of which 6 were plaque purified. 1 phage DNA was prepared and analyzed by EcoRI restriction enzyme digestion. lH1 contained a 1.1 kb insert which was subcloned into the EcoRI site of pGEX1 (Pharmacia) to express a GST-lH1 fusion protein. The resulting construct was transformed into Escherichia coli TG2, and following induction with 0.5 mM IPTG, the induced protein was purified on glutathione Sepharose 4B beads (Pharmacia). 2 mg (per injection) of the fusion protein was used to immunize a mouse. Test bleeds were taken and used for Western blot analyses.

B. Poly(A)+ RNA from HeLa cells was used for construction of a directional cDNA library in lZAPII (Stratagene) as described previously (Ruppert et al. 1992). Using a randomly 32P-labeled probe derived from the lH1 cDNA insert, 15 independent cDNA clones were isolated from 1.2×106 original PFU. The cDNA inserts were rescued by the zapping procedure (Short et al.) and characterized extensively by restriction enzyme analysis and Southern blotting. The longest cDNA clone isolated from lH2 contains a 5.3 kb insert, revealing an extended 3' untranslated region but missing about 1.15 kb of 5' sequences when compared to CCG 1. This 5' region was generated by PCR using conditions described previously (Ruppert et al.). Two set of PCR primers were designed according to the CCG1 cDNA sequencc (Sekiguchi et al). PCR-I, forward primer #1: 5'-TATTTCCGGCATATGGGACCCGGCTG-3' (see SEQ ID NO:10) (position 40 to 65, containing an engineered NdeI restriction site at the translation start codon) and reverse primer #2: 5'-GAAGTCCACTTTCTCACCAG-3' (see SEQ ID NO:10) (position 578 to 597). PCR-II, forward primer #3: 5'-TACCAGCAGCATATGGGGAGCTTGCAG-3' (see SEQ ID NO:10) (position 421 to 447) and reverse primer #4: 5'-GCTCTAAGGAAGCCAGCCTGCCAG-GCTTG-3' (see SEQ ID NO:10 ) (position 1343 to 1371). All PCR products were subcloned into pBluescript KS (Stratagene) and sequenced. The most abundant product of PCR-II, a 1 kb fragment, included a 63 bp in frame insertion, while a minor 330 bp fragment revealed a 618 bp in frame deletion with respect to the CCG1 cDNA. To generate a full-length hTAFII250 cDNA, the product of PCR-I and the 1 kb PCR-II product were joined via the shared SmaI restriction site. Subsequently the 1.2 kb XbaI fragment of the resulting plasmid was cloned into XbaI cut pH2 to generate the full-length cDNA clone phTAFII250.

Analyses of hTAFII250 and hTBP interaction

A. To construct an HA-tagged version of hTAFII250 we generated a plasmid, pSK-HAX, containing the hemagglutinin antigen (HA) epitope, factor X cleavage site, and in frame NdeI cloning site. A 6.3 kb NdeI/Asp718 fragment from phTAFII250 was inserted into pSK-HAX to generate pHAX-hTAFII250. A 6.0 kb SpeI fragment thereof containing the complete coding region of hTAFII250, was inserted into the XbaI site of the vaccinia virus expression vector pAbT4537 (Applied biotechnology Inc.). Extracts from recombinant virus, vhTAFII250, or control virus (New York City Board of Health strain of vaccinia virus) infected HeLa cells (Dynlacht 1989) were fractionated by phosphocellulose chromatography as described (Tanese et al.). hTFIID complexes from the 0.48–1.0M KCl fraction were immunoprecipitated with affinity-purified a-hTBP antibodies, subjected to 8% SDS-PAGE and analyzed by Western blotting.

B. To generate all HA-tagged version of hTAFII250 in the baculovirus expression system, we first generated new baculovirus vectors, pVL1392HAX and pVL1393HAX, derived from pVL1392 and pVL1393 (Pharmingen), respectively. These vectors contain the HA antigen epitope, factor X cleavage site, and unique in frame NcoI and NdeI restriction sites. A 6.0 kb NdeI/SpeI fragment from phTAFII250 was inserted into pVL1392HAX creating pbHAX-hTAFII250. Whole cell extracts from either SF9 cells or SF9 cells infected with recombinant baculovirus were prepared in 0.4M KCl—HEMG (including 0.04% NP-40, 1 mM DTT, 0.2 mM AEBSF, 0.1 mM NaMBS) and used directly for immunoprecipitation with the a-HA antibody. The precipitate was subjected to 8% SDS-PAGE and blotted onto nitrocellulose membrane. The filter was probed first with 35S-labeled hTBP, and subsequently with the monoclonal antibody 6B3.

hTAFII250 interacts with hTBP in yeast hTAFII250, fused to the DNA binding domain of GAL4 (residues 1–147), was constructed by inserting a 6.0 kb NdeI/BamHI fragment derived from pvhTAFII250 into the pASI vector. The activation domain fusions were obtained by cloning inserts into the pGAD1F vector (Chien et al.). The hybird proteins generated included the acidic activation domain of GAL4 (residues 768–881) fused to either full-length, residues 160–339, or residues 1–159 of hTBP. The above described constructs were transformed into the yeast strain Y153 (a, gal4, gal80, his3, trp1-901, ade2-101, ura3-52, leu2-3, 112, URA3::Gal1:lacZ, LYS2::Gal-His3; as described (Chien et al.) and b-galactosidase assays performed according to published procedures (Hoey et al).

Drosophila TBP and dTAFII250 interact with the C-terminal portion of dTAFII150

Radiolabeled in vitro translated dTAFII150 bound efficiently to immobilized HA-dTBP or dTAFII250ΔN (sec Weinzierl et al (1993) Nature 362, 511–517). In contrast, dTAFII110 and other TAFs failed to interact selectively with dTAFII150, showing that dTAFII150 interacts with at least two subunits of the TFIID complex, dTBP and dTAFII250, which also contact each other.

We also carried out in vivo experiments in which insect Sf9 cells were co-infected with two recombinant baculoviruses, one expressing dTAFII150 and the second expressing either TBP or one of the other TAFs. Complexes were subsequently in immunopurified from cellular lysates and analyses by SDS PAGE followed by immunoblotting using antibodies directed against dTAFII150. Coinfection of virus expressing dTAFII150 and either HA-dTBP or dTAFII250ΔN resulted in efficient formation and copurification of heteromeric complexes. Similarly, full-length hTAFII250 bound efficiently to dTAFII150.

Radiolabeled in vitro translated C-terminal 369 residue portion (dTAFII150ΔN) of this protein binds TBP and dTAFII250ΔN with the same effenciency as the full length protein. No significant binding of a N-terminal 786 residue portion (dTAFII150ΔC) was observed: i.e. the interaction interfaces from these proteins are located in the C-terminal portion of dTAFII150.

TSM-1 associates with TBP and TAFII250

Like dTAFII150, TSM1ΔN (C-terminal 920 residue portion) bound efficiently to yTBP as well as HA-dTBP; hence we conclude that yeast contain a TAFII250 and TSM-1 is a TAF.

The activation domain of the Drosophila regulator NTF-1 (Neurogenic Element Binding Transcription Factor-1) interacts with dTAFII150.

NTF-1 immuno-copurifies with dTFIID using anti-dTBP, indicatin that one or more subunits of the dTFIID interacts directly with NTF-1. Using coimmunoprecipitation experiments: dTAFII150 was immunopurified from Sf9 extracts containing dTAFII150, the immobilized TAF was mixed with recombinant NTF-1, the isolated complex was analyzed by SDS-PAGE, and the presence of NTF-1 was detected by protein immunoblot anaysis, showing that NTF-1 directly interacts with dTAFII150.

Next we used a GST-NTF-1 fusion protein containing the N-terminal 284 amino acids of NTF-1 to bind various truncated bersions of dTAFII150, showing that the N-terminal, but not the C-terminal region of dTAFII150 bound to the N-terminal extended activation domain of NTF-1. Neither dTAFII80 nor dTAFII40 bound significantly under these conditions.

Using an affinity resin containing a covalently attached synthetic peptide corresponding to the 56 amino acid minimal activation domain of NTF-1, we showed that this region is sufficient to interact with dTAFII150 and that the activator interface of dTAFII150 is distinct from the C-terminal region with interacts with dTBP and dTAFII250. Hence, the requirement for TAFs during NTF-1 activation is at least in part mediated by NTF-1:dTAFII150 interactions.

TAF Sequence Data

Nucleotide and amino acid sequences of:
dTAFII30α.(SEQ II) NO:21, 22)
dTAFII30β.(SEQ II) NO:23, 24)
dTAFII40 (SEQ ID NO:8, 9)
dTAFII60 (SEQ ID NO:6, 7)
dTAFII80 (SEQ ID NO:4, 5)
dTAFII110 (SEQ ID NO:1, 2)
dTAF150 (SEQ ID NO:19, 20 )
dTAFII250 (SEQ ID NO:3, 14)
hTAFII30α.(SEQ ID NOS:28, 33 and 34)
hTAFII30β.(SEQ ID NOS:27, 35 and 36)
hTAFII40 (SEQ ID NO:25, 26)
hTAFII70 (SEQ ID NO:12, 13)
hTAFII100 (SEQ ID NO:17, 18)
hTAFII130 (SEQ ID NO:15, 16)
hTAFII250 (SEQ ID) NO:10, 11)
hTAFI48 (SEQ ID NO:29, 30)
hTAFI110 (SEQ ID NO:31, 32)
were obtained as described above. Additional methods relating to PolI TAFs may be found in Comai et al. (1992) Cell 68, 965–976.

It is evident from the above results that one can use the methods and compositions disclosed herein for making and identifying diagnostic probes and therapeutic drugs. It win also be clear to one skilled in the art from a reading of this disclosure that advantage call be taken to effect alterations of gene expression: both genes encoding TAF and genes amenable to TAF-mediated transcriptional modulation. Such alterations can be effected for example, using a small molecule drug identified with disclosed TAF-based screening assays.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening for a compound which binds a human TATA-Binding Protein Associated Factor (TAF) protein or peptide, said method comprising the steps of:

contacting an agent with a substantially pure, biologically active polypeptide consisting of a sequence of six or more consecutive amino acids of a human TAF protein or peptide selected from the group consisting of hTAFII30α peptide 1 (SEQ ID NO:28), hTAFII30α peptide 2 (SEQ ID NO:33), hTAFII30α peptide 3 (SEQ ID NO:34), hTAFII30β peptide 1 (SEQ ID NO:27), hTAFII30β peptide 2 (SEQ ID NO:35), hTAFII30β peptide 3 (SEQ ID NO:36), hTAFII40 (SEQ ID NO:26), hTAFII70 (SEQ ID NO:13), hTAFII100 (SEQ ID NO:18), hTAFII130 (SEQ ID NO:16), hTAFII250 (SEQ ID NO:11), hTAFI48 (SEQ ID NO:30), and hTAFI110 (SEQ ID NO:32); and, determining whether said agent specifically binds said polypeptide, wherein specific binding of said agent to said polypeptide identifies said agent as a lead pharmaceutical compound which binds a human TAF.

2. A method according to claim 1 wherein said TAF protein or peptide is hTAFII30α peptide 1 (SEQ ID NO:28), hTAFII30α peptide 2 (SEQ ID NO:33) or hTAFII30α peptide 3 (SEQ ID NO:34).

3. A method according to claim 1 wherein said TAF protein or peptide is hTAFII30β peptide 1 (SEQ ID NO:27), hTAFII30β peptide 2 (SEQ ID NO:35) or hTAFII30β peptide 3 (SEQ ID NO:36).

4. A method according to claim 1 wherein said TAF protein or peptide is hTAFII40 (SEQ ID NO:26).

5. A method according to claim 1 wherein said TAF protein or peptide is hTAFII70 (SEQ ID NO:13).

6. A method according to claim 1 wherein said TAF protein or peptide is hTAFII100 (SEQ ID No:18).

7. A method according to claim 1 wherein said TAF protein or peptide is hTAFII130 (SEQ ID NO:16).

8. A method according to claim 1 wherein said TAF protein or peptide is hTAFII250 (SEQ ID NO:11).

9. A method according to claim 1 wherein said TAF protein or peptide is hTAFI48 (SEQ ID NO:30).

10. A method according to claim 1 wherein said TAF protein or peptide is hTAFI110 (SEQ ID NO:32).

11. A method of screening for a compound which modulates the formation of a transcription complex comprising a human TATA-Binding Protein Associated Factor (TAF), said method comprising the steps of:

adding an agent to a mixture comprising transcription complex components including a substantially pure, biologically active polypeptide consisting of a sequence of six or more consecutive amino acids of a human TAF protein or peptide selected from the group consisting of hTAFII30α peptide 1 (SEQ ID NO:28), hTAFII30α peptide 2 (SEQ ID NO:33), hTAFII30α peptide 3 (SEQ ID NO:34), hTAFII30β peptide 1 (SEQ ID NO:27), hTAFII30β peptide 2 (SEQ ID NO:35), hTAFII30β peptide 3 (SEQ ID NO:36), hTAFII40 (SEQ ID NO:26), hTAFII70 (SEQ ID NO:13), hTAFII100 (SEQ ID NO:18), hTAFII130 (SEQ ID NO:16), hTAFII250 (SEQ ID NO:11), hTAFI48 (SEQ ID NO:30), and hTAFI110 (SEQ ID NO:32); and, comparing the in vitro association of said components before and after said adding step;

wherein a difference between said in vitro association before and after said adding step identifies said agent as a lead pharmaceutical compound which modulates the formation of a transcription complex comprising a human TAF.

12. A method according to claim 11 wherein said TAF protein or peptide is hTAFII30α peptide 1 (SEQ ID NO:28), hTAFII30α peptide 2 (SEQ ID NO:33) or hTAFII30α peptide 3 (SEQ ID NO:34).

13. A method according to claim 11 wherein said TAF protein or peptide is hTAFII30β peptide 1 (SEQ ID NO:27), hTAFII30β peptide 2 (SEQ ID NO:35) or hTAFII30β peptide 3 (SEQ ID NO:36).

14. A method according to claim 11 wherein said TAF protein or peptide is hTAFII40 (SEQ ID NO:26).

15. A method according to claim 11 wherein said TAF protein or peptide is hTAFII70 (SEQ ID NO:13).

16. A method according to claim 11 wherein said TAF protein or peptide is hTAFTII100 (SEQ ID NO:18).

17. A method according to claim 11 wherein said TAF protein or peptide is hTAFII130 (SEQ ID NO:16).

18. A method according to claim 11 wherein said TAF protein or peptide is hTAFII250 (SEQ ID NO:11).

19. A method according to claim 11 wherein said TAF protein or peptide is hTAFI48 (SEQ ID NO:30).

20. A method according to claim 11 wherein said TAF protein or peptide is hTAFI110 (SEQ ID NO:32).

* * * * *